(12) United States Patent
Konishi et al.

(10) Patent No.: US 9,115,107 B2
(45) Date of Patent: Aug. 25, 2015

(54) HETEROARYLCARBOXYLIC ACID ESTER DERIVATIVE

(71) Applicant: AJINOMOTO CO., INC., Tokyo (JP)

(72) Inventors: Atsushi Konishi, Kawasaki (JP); Munetaka Tokumasu, Kawasaki (JP); Tamotsu Suzuki, Kawasaki (JP); Takahiro Koshiba, Kawasaki (JP); Koji Ohsumi, Kawasaki (JP); Osamu Ikehara, Kawasaki (JP); Yuko Kodama, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/496,363

(22) Filed: Sep. 25, 2014

(65) Prior Publication Data

US 2015/0011511 A1  Jan. 8, 2015

Related U.S. Application Data

(63) Continuation of application No. 14/089,040, filed on Nov. 25, 2013, now Pat. No. 8,877,805, which is a continuation of application No. 13/484,822, filed on May 31, 2012, now Pat. No. 8,609,715, which is a continuation of application No. PCT/JP2010/071929, filed on Dec. 7, 2010.

(30) Foreign Application Priority Data

Dec. 7, 2009  (JP) ................................. 2009-277827
Sep. 24, 2010  (JP) ................................. 2010-214406

(51) Int. Cl.
| | | |
|---|---|---|
| C07D 307/68 | (2006.01) | |
| C07D 277/20 | (2006.01) | |
| C07D 277/56 | (2006.01) | |
| C07D 333/38 | (2006.01) | |
| C07D 405/06 | (2006.01) | |
| C07C 53/18 | (2006.01) | |
| C07F 9/655 | (2006.01) | |
| C07F 9/38 | (2006.01) | |

(52) U.S. Cl.
CPC .............. *C07D 307/68* (2013.01); *C07C 53/18* (2013.01); *C07D 277/20* (2013.01); *C07D 277/56* (2013.01); *C07D 333/38* (2013.01); *C07D 405/06* (2013.01); *C07F 9/3808* (2013.01); *C07F 9/65515* (2013.01)

(58) Field of Classification Search
CPC ..................................................... C07D 307/68
USPC .......................................................... 514/99
See application file for complete search history.

(56) References Cited

U.S. PATENT DOCUMENTS

| | | |
|---|---|---|
| 6,358,960 B1 | 3/2002 | Senokuchi et al. |
| 2002/0128315 A1 | 9/2002 | Nakai et al. |
| 2007/0298025 A1 | 12/2007 | Harosh et al. |
| 2008/0009537 A1 | 1/2008 | Sakai |
| 2010/0311690 A1 | 12/2010 | Harosh et al. |
| 2013/0338132 A1 | 12/2013 | Koshiba et al. |
| 2014/0094489 A1 | 4/2014 | Suzuki et al. |

FOREIGN PATENT DOCUMENTS

| | | |
|---|---|---|
| JP | 56-161385 | 12/1981 |
| JP | 2008-266174 | 11/2008 |
| WO | 99-41231 | 8/1999 |
| WO | 2006/050999 | 5/2006 |
| WO | 2006/057152 | 6/2006 |
| WO | 2009/071601 | 6/2009 |

OTHER PUBLICATIONS

U.S. Appl. No. 14/567,506, filed Dec. 11, 2014, Koshiba, et al.
International Search Report issued in PCT/JP2010/071929 on Jan. 18, 2011.
M. Matsushima et al., "Biomedical Research", vol. 22 , No. 5 (2001) pp. 257-260.
T. Yokoyama et al., "Advances in Experimental Medicine and Biology", (1989) 247B pp. 271-276.
King, Med. Chem. Principle and Practice (1994), pp. 206-208.
Combined Chinese Office Action and Search Report issued Feb. 20, 2014, in Chinese Patent Application No. 201080063274.5 with English Translation.
Fengchao Jiang, "Drug Design", Beijing: Chemical Industry Press, Jan. 31, 2007, pp. 91-101.

*Primary Examiner* — Taofiq A Solola
(74) *Attorney, Agent, or Firm* — Oblon, McClelland, Maier & Neustadt, L.L.P.

(57) ABSTRACT

Compounds represented by formula (I):

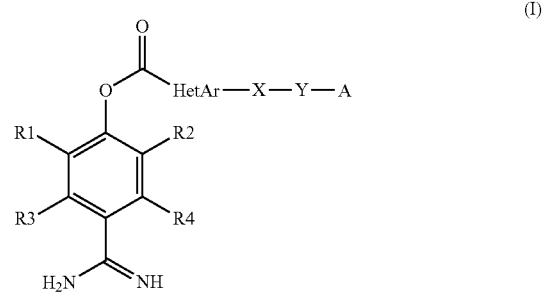

wherein each symbol is as defined in the description, and pharmaceutically acceptable salts thereof are useful as hyperglycemic inhibitors having a serine protease inhibitory action and as prophylactic or therapeutic drugs for diabetes.

9 Claims, No Drawings

HETEROARYLCARBOXYLIC ACID ESTER DERIVATIVE

CROSS REFERENCES TO RELATED APPLICATIONS

This application is a Continuation of U.S. patent application Ser. No. 14/089,040, filed on Nov. 25, 2013, which was a Continuation of U.S. patent application Ser. No. 13/484,822, filed on May 31, 2012, which was a Continuation of International Patent Application No. JP/2010/071929, filed Dec. 7, 2010, and claims priority to Japanese Patent Application No. 2009-277827, filed on Dec. 7, 2009, and Japanese Patent Application No. 2010-214406, filed on Sep. 24, 2010.

BACKGROUND OF THE INVENTION

1. Field of the Invention Description

The present invention relates to novel heteroarylcarboxylic acid ester derivatives having a serine protease (particularly trypsin and enteropeptidase) inhibitory activity. The present invention also relates to pharmaceutical compositions which contain such a heteroarylcarboxylic acid ester derivative and drugs for the treatment or prophylaxis of diabetes. The present invention further relates to methods for the treatment and/or prophylaxis of diabetes by administering such a heteroarylcarboxylic acid ester derivative.

2. Discussion of the Background

At present, insulin secretagogues (sulfonylurea), glucose absorption inhibitors (α-glucosidase inhibitor), insulin sensitizers (biguanide, thiazolidine derivative), and the like are clinically used as therapeutic drugs for diabetes. However, since all of them are accompanied by side effects such as hypoglycemia, diarrhea, lactic acidosis, edema, and the like, show an insufficient effect, and the like, a medicament satisfying clinical needs is still demanded.

In recent years, a benzoic acid ester having a protease inhibitory activity, which is represented by the following compound, has been reported to show a blood glucose elevation suppressing action in diabetes animal model (see WO2006/057152, which is incorporated herein by reference in its entirety). The following compound is considered to show an enzyme inhibitory activity on trypsin, thrombin, pancreatic, and plasma kallikreins, plasmin and the like and a leukotriene receptor antagonistic action. Moreover, an enteropeptidase inhibitory activity of the following compound has also been reported (see Biomedical Research (2001), 22(5) 257-260, which is incorporated herein by reference in its entirety). However, many unclear points remain in the relationship between such actions and a blood glucose elevation suppressing action.

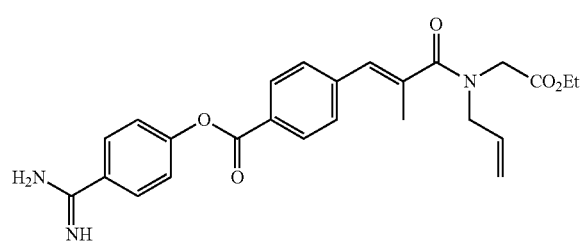 [SMILES: C=CCN(CC(=O)OCC)C(=O)/C(C)=C/c1ccc(C(=O)Oc2ccc(C(=N)N)cc2)cc1]

On the other hand, as for a heteroarylcarboxylic acid ester structure, JP-A-55-161385, which is incorporated herein by reference in its entirety, discloses a compound as a therapeutic drug for pancreatitis. In this document, only heteroarylcarboxylic acid ester compounds wherein the substituent of the heteroarylcarboxylic acid moiety is a methyl group or a methoxy group or unsubstituted compounds are disclosed, as represented by the following formula. While these compounds are disclosed as showing an inhibitory activity on trypsin, chymotrypsin and thrombin, no description is given as to the enteropeptidase inhibitory activity and blood glucose elevation suppressing action.

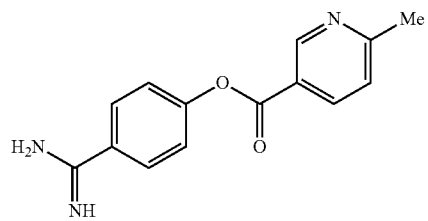 [SMILES: Cc1ccc(C(=O)Oc2ccc(C(=N)N)cc2)cn1]

In addition, Advances in Experimental Medicine and Biology (1989), 247B (Kinins 5, Pt. B), 271-6, which is incorporated herein by reference in its entirety, also describes a heteroarylcarboxylic acid ester having a protease inhibitory activity, which is represented by the following formula. However, only compounds wherein the heteroaryl moiety is unsubstituted are disclosed, and no description is given as to the enteropeptidase inhibitory activity and blood glucose elevation suppressing action of these compounds.

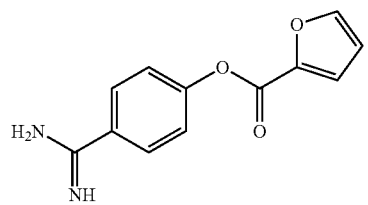 [SMILES: N=C(N)c1ccc(OC(=O)c2ccco2)cc1]

Furthermore, WO99/41231, which is incorporated herein by reference in its entirety, describes a compound represented by the following formula. However, it has a structure wherein an aryl group substituted by a carboxyl group is directly bonded to the heteroaryl moiety, which is completely different from the compound of the present invention. The document discloses an inhibitory activity against blood coagulation factor VIIa; however, no description is given as to the enteropeptidase inhibitory activity and blood glucose elevation suppressing action.

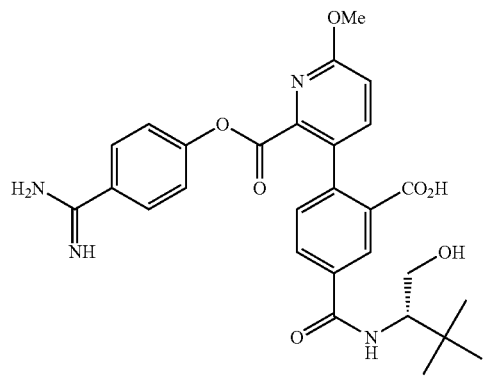 [SMILES: COc1ccc(-c2ccc(C(=O)N[C@H](CO)C(C)(C)C)cc2C(=O)O)c(C(=O)Oc2ccc(C(=N)N)cc2)n1]

On the other hand, trypsin is one of the intestinal serine proteases and is produced by degradation of inactive trypsinogen by enteropeptidase. Trypsin is known to activate various digestive enzymes by acting on chymotrypsinogen, proelastase, procarboxylesterase, procolipase and pro-sucrase-isomaltase, and the like. Therefore, it is considered that an inhibitor of enteropeptidase and trypsin lowers the digestive capacity for protein, lipid, and carbohydrates, and is effective as a drug for the treatment or prophylaxis of obesity and hyperlipidemia.

WO2006/050999, which is incorporated herein by reference in its entirety describes that a medicament that inhibits both enteropeptidase and trypsin is interesting as a body fat-reducing agent. In addition, WO2009/071601, which is incorporated herein by reference in its entirety reports a compound having an inhibitory activity against enteropeptidase, trypsin, plasmin, kallikrein, and the like as an antiobesity drug. However, neither of these publications describe suppression of blood glucose elevation and hypoglycemic effect afforded by simultaneous inhibition of enteropeptidase and trypsin, and the protease inhibitor described therein has a structure completely different from that of the compound of the present invention.

Accordingly, there remains a need for compounds which are useful for the treatment or prophylaxis of diabetes. Therefore, to further satisfy the clinical needs from the aspects of effect, safety and the like, a hyperglycemic inhibitor having a serine protease inhibitory action, which is a new drug for the treatment or prophylaxis of diabetes, is desired.

SUMMARY OF THE INVENTION

Accordingly, it is one object of the present invention to provide novel compounds which are useful for the treatment or prophylaxis of diabetes.

It is another object of the present invention to provide novel compounds having a serine protease inhibitory action.

It is another object of the present invention to provide novel serine protease (particularly trypsin and enteropeptidase) inhibitors.

It is another object of the present invention to provide novel hyperglycemic inhibitors or hypoglycemic agents, and further, drug for the treatment and/or prophylaxis of any of diabetes, obesity, hyperlipidemia, diabetic complication, and metabolic syndrome.

It is another object of the present invention to provide novel methods for the treatment and/or prophylaxis of any of diabetes, obesity, hyperlipidemia, diabetic complication, and metabolic syndrome.

These and other objects, which will become apparent during the following detailed description, have been achieved by the inventors' discovery that the heteroarylcarboxylic acid ester derivatives described below have serine protease inhibitory activity and are useful for the treatment and/or prophylaxis of any of diabetes, obesity, hyperlipidemia, diabetic complication, and metabolic syndrome.

Thus, in view of the above-mentioned current situation, the present inventors have conducted intensive studies and considered that simultaneous inhibition of trypsin and enteropeptidase is particularly effective for the suppression of blood glucose elevation. They have synthesized various heteroarylcarboxylic acid ester derivatives, which are novel compounds, evaluated trypsin and enteropeptidase inhibitory activity, and found that certain heteroarylcarboxylic acid ester derivatives are protease inhibitors that simultaneously inhibit them, which resulted in the completion of the present invention. Furthermore, they have also found that such representative compounds show a blood glucose elevation suppressing effect in diabetes animal model.

Accordingly, the present invention provides a heteroarylcarboxylic acid ester derivative represented by the following formula (I):

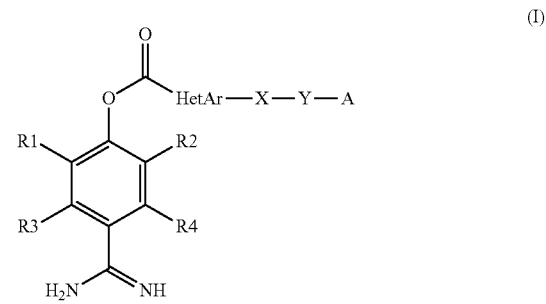

wherein

R1, R2, R3, and R4 may be the same or different and are each independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group, HetAr is a heteroaromatic ring optionally having substituent(s), X is a lower alkylene group optionally having substituent(s), a lower alkenylene group optionally having substituent(s), a lower alkynylene group optionally having substituent(s), a phenylene group, or a thiophenylene group, Y is a carbonyl group, a thiocarbonyl group, or a sulfonyl group, and A is —OR5 (R5 is a hydrogen atom or a lower alkyl group);
a group of the following formula (II):

wherein R6 and R7 may be the same or different and are each independently a hydrogen atom, a hydroxyl group, a lower alkyl group optionally having substituent(s), a lower alkenyl group optionally having substituent(s), a lower alkynyl group optionally having substituent(s) or a lower alkoxyl group optionally having substituent(s), or R6 and R7 may be bonded to form a cyclic amino group optionally having substituent(s);

a group of the following formula (II-2):

wherein U is O or S, and R6' and R7' may be the same or different and are each independently a hydrogen atom, a hydroxyl group, a carboxyl group, a lower alkyl group optionally having substituent(s), a lower alkenyl group optionally having substituent(s), a lower alkynyl group optionally having substituent(s) or a lower alkoxyl group optionally having substituent(s), or R6' and R7' may be bonded to form a cyclic amino group optionally having substituent(s); or a group of the following formula (II-3):

wherein R6" and R7" may be the same or different and are each independently a hydrogen atom, a hydroxyl group, a lower alkyl group optionally having substituent(s), a lower alkenyl group optionally having substituent(s), a lower alkynyl group optionally having substituent(s) or a lower alkoxyl group optionally having substituent(s), or R6" and R7" may be bonded to form a cyclic amino group optionally having substituent(s), or a pharmaceutically acceptable salt thereof (hereinafter sometimes to be simply referred to as "the compound of the present invention"), a pharmaceutical composition containing the same, or a serine protease inhibitor containing the same as an active ingredient.

The present invention also provides a compound represented by the aforementioned formula (I) wherein R1, R2, R3, and R4 may be the same or different and are each independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group, HetAr is a heteroaromatic ring optionally having substituent(s).

X is a lower alkylene group optionally having substituent(s), a lower alkenylene group optionally having substituent(s), or a lower alkynylene group optionally having substituent(s), Y is a carbonyl group, a thiocarbonyl group, or a sulfonyl group, and A is —OR5 (R5 is a hydrogen atom or a lower alkyl group), or a group of the following formula (II):

wherein R6 and R7 may be the same or different and are each independently a hydrogen atom, a hydroxyl group, a lower alkyl group optionally having substituent(s), a lower alkenyl group optionally having substituent(s), a lower alkynyl group optionally having substituent(s) or a lower alkoxyl group optionally having substituent(s), or R6 and R7 may be bonded to form a cyclic amino group optionally having substituent(s), or a pharmaceutically acceptable salt thereof.

The present invention also provides a compound represented by the aforementioned formula (I) wherein R1, R2, R3, and R4 are each independently a hydrogen atom, a nitro group or a halogeno group, or a pharmaceutically acceptable salt thereof.

The present invention also provides a compound represented by the aforementioned formula (I) wherein HetAr is a 5- to 10-membered aromatic ring containing 1 to 3 hetero atoms, which optionally has substituent(s), or a pharmaceutically acceptable salt thereof.

The present invention also provides a compound represented by the aforementioned formula (I) wherein -HetAr— is a heteroaromatic ring group represented by the following formula (III-1) or (III-2):

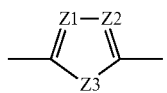

(III-1)

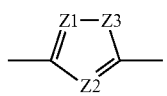

(III-2)

wherein Z1 and Z2 are each independently CRa or a nitrogen atom, and Z3 is an oxygen atom, a sulfur atom, or NRb, wherein Ra and Rb may be the same or different and are each independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group, or a pharmaceutically acceptable salt thereof.

The present invention also provides a compound represented by the aforementioned formula (I) wherein -HetAr— is a group containing a heteroaromatic ring group represented by the formula (III-1) or (III-2), and in the formulas (III-1) and (III-2), Z1 and Z2 are each independently CRa or a nitrogen atom, and Z3 is an oxygen atom or a sulfur atom, or a pharmaceutically acceptable salt thereof.

The present invention also provides a compound represented by the aforementioned formula (I) wherein X is a lower alkylene group optionally having substituent(s) or a lower alkenylene group optionally having substituent(s), and the substituent is selected from the group consisting of a halogeno group, a hydroxyl group, an amino group, a lower alkyl group, a lower alkoxyl group, and a lower acyl group, or a pharmaceutically acceptable salt thereof.

The present invention also provides a compound represented by the aforementioned formula (I) wherein Y is a carbonyl group or a sulfonyl group, or a pharmaceutically acceptable salt thereof.

The present invention also provides a compound represented by the aforementioned formula (I) wherein A is —OR5 (R5 is a hydrogen atom or a lower alkyl group), or a pharmaceutically acceptable salt thereof.

The present invention also provides a compound represented by the aforementioned formula (I) wherein A is a group of the following formula (IV):

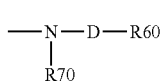

(IV)

wherein R60 is a carboxyl group, a sulfo group, a phosphono group, a lower alkoxycarbonyl group, or a hydroxyl group, D is a lower alkylene group optionally having substituent(s), a lower alkenylene group optionally having substituent(s), or a lower alkynylene group optionally having substituent(s), wherein the substituent is selected from the group consisting of a nitro group, a halogeno group, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), and an oxo group, and R70 is a hydrogen atom, a hydroxyl group, a lower alkyl group optionally having substituent(s) or a lower alkoxyl group optionally having substituent(s), or R70 and D may be bonded to form a cyclic amino group optionally having substituent(s), or a pharmaceutically acceptable salt thereof.

The present invention also provides a compound represented by the aforementioned formula (I) wherein A is a group of the aforementioned formula (IV), in the group of the formula (IV), R60 is a carboxyl group, a sulfo group, a lower alkoxycarbonyl group, or a hydroxyl group, D is a lower alkylene group optionally having substituent(s), wherein the substituent is selected from the group consisting of a halogeno group, a hydroxyl group, a thiol group, an amino group, a guanidino group, a carboxyl group, a sulfo group, a lower alkoxyl group, a lower alkylthio group, a lower alkylamino group, a lower acylamino group, a lower alkoxycarbonyl group, a carbamoyl group, a lower alkylcarbamoyl group, a lower alkylsulfonylamino group, an arylsulfonylamino group optionally having substituent(s), an aryl group optionally having substituent(s), a heterocyclic group optionally having substituent(s), and an oxo group, and R70 is a hydrogen atom, a hydroxyl group, a lower alkyl group optionally having substituent(s), or a lower alkoxyl group optionally having substituent(s), or R70 and D may be bonded to form a cyclic amino group optionally having substituent(s), or a pharmaceutically acceptable salt thereof.

The present invention also provides a compound represented by the aforementioned formula (I) wherein R1, R2, R3, and R4 are each independently a hydrogen atom, a nitro group, or a fluorine atom, and HetAr is furan, thiophene, or thiazole each optionally having substituent(s), or a pharmaceutically acceptable salt thereof.

The present invention also provides an intestinal serine protease inhibitor, comprising the above-mentioned heteroarylcarboxylic acid ester derivative, or a pharmaceutically acceptable salt thereof as an active ingredient.

The present invention also provides a dual inhibitor of trypsin and enteropeptidase, comprising the above-mentioned heteroarylcarboxylic acid ester derivative, or a pharmaceutically acceptable salt thereof as an active ingredient.

The present invention also provides a hyperglycemic inhibitor or hypoglycemic agent, comprising the above-mentioned heteroarylcarboxylic acid ester derivative, or a pharmaceutically acceptable salt thereof as an active ingredient.

The present invention also provides a prophylactic or therapeutic drug for diabetes, comprising the above-mentioned heteroarylcarboxylic acid ester derivative, or a pharmaceutically acceptable salt thereof as an active ingredient.

The present invention also provides an insulin sensitizer comprising the above-mentioned heteroarylcarboxylic acid ester derivative, or a pharmaceutically acceptable salt thereof as an active ingredient.

The present invention also provides a prophylactic or therapeutic drug for obesity, hyperlipidemia, diabetic complication or metabolic syndrome, comprising the above-mentioned heteroarylcarboxylic acid ester derivative, or a pharmaceutically acceptable salt thereof as an active ingredient.

The present invention also provides a method for preventing or treating diabetes, comprising administering an effective amount of the above-mentioned heteroarylcarboxylic acid ester derivative, or a pharmaceutically acceptable salt thereof.

The present invention also provides a method for improving insulin resistance, comprising administering an effective amount of the above-mentioned heteroarylcarboxylic acid ester derivative, or a pharmaceutically acceptable salt thereof.

The present invention also provides a method for preventing or treating obesity, hyperlipidemia, diabetic complication or metabolic syndrome, comprising administering an effective amount of the above-mentioned heteroarylcarboxylic acid ester derivative, or a pharmaceutically acceptable salt thereof.

The present invention also provides use of the above-mentioned heteroarylcarboxylic acid ester derivative, or a pharmaceutically acceptable salt thereof for the prophylaxis or treatment of diabetes.

The present invention also provides use of the above-mentioned heteroarylcarboxylic acid ester derivative, or a pharmaceutically acceptable salt thereof for the improvement of insulin resistance.

The present invention also provides use of the above-mentioned heteroarylcarboxylic acid ester derivative, or a pharmaceutically acceptable salt thereof for the prophylaxis or treatment of obesity, hyperlipidemia, diabetic complication or metabolic syndrome.

The compound of the present invention has a blood glucose elevation suppressing action and can be preferably used as a drug for the treatment or prophylaxis of diabetes.

DETAILED DESCRIPTION OF THE PREFERRED EMBODIMENTS

The present invention is explained in detail in the following.

In the present specification, the phrase "optionally having substituent(s)" means "being substituted or unsubstituted". Unless otherwise specified, the position and number of the substituents may be any, and are not particularly limited. When substituted by two or more substituents, the substituents may be the same or different. Examples of the substituent include a nitro group, a halogeno group, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and the like.

In the present specification, examples of the substituent of the "arylsulfonylamino group optionally having substituent(s)", "cycloalkyl group optionally having substituent(s)", "aryl group optionally having substituent(s)", "aryloxy group optionally having substituent(s)", "arylthio group optionally having substituent(s)", "aralkyl group optionally having substituent(s)", "aralkyloxy group optionally having substituent(s)", "aralkylthio group optionally having substituent(s)", "heterocyclic group optionally having substituent(s)", "heterocyclic oxy group optionally having substituent(s)" and "heterocyclic thio group optionally having substituent(s)" include a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and the like.

The "heteroaromatic ring" in the present specification is a 5- to 10-membered aromatic ring optionally containing 1 to 3 hetero atoms such as a nitrogen atom, an oxygen atom, a sulfur atom, and the like, and examples thereof include a monocycle, and a fused aromatic ring wherein two aromatic rings are fused. Examples of the monocycle include furan, thiophene, pyrrole, oxazole, isoxazole, thiazole, isothiazole, imidazole, pyrazole, oxadiazole, thiadiazole, pyridine, pyridazine, pyrimidine, pyrazine, and the like. Examples of the fused aromatic ring include indole, isoindole, benzofuran, benzothiophene, indolizine, quinoline, isoquinoline, purine, 1H-indazole, quinazoline, cinnoline, quinoxaline, phthalazine, pteridine, benzoxazole, benzothiazole, benzimidazole, and the like.

The "cyclic amino group" in the present specification is a saturated or unsaturated cyclic amino group having a carbon number of 2 to 7, which may contain one or more hetero atoms in the ring, such as a nitrogen atom, an oxygen atom, a sulfur atom, and the like. For example, a pyrrolidinyl group, a pyrrolinyl group, a piperidinyl group, a morpholinyl group, a piperazinyl group, a thiomorpholinyl group, a piperidinonyl group, a piperazinonyl group and the like can be mentioned.

The "lower alkyl group" is a straight chain or branched chain or cyclic alkyl group having a carbon number of 1 to 6. For example, a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 2-hexyl group, a cyclopropyl group, a cyclopentyl group, and the like can be mentioned.

The "lower alkenyl group" is a straight chain or branched chain alkenyl group having a carbon number of 2 to 6, which includes each isomer. For example, a vinyl group, an allyl group, a propenyl group, a butenyl group, a pentenyl group, a hexenyl group, and the like can be mentioned.

The "lower alkynyl group" is a straight chain or branched chain alkynyl group having a carbon number of 2 to 6, which includes each isomer. For example, an ethynyl group, a 1-propynyl group, a 2-propynyl group, a 2-butynyl group, a 3-butynyl group, a pentynyl group, and the like can be mentioned.

The "lower alkylene group" is a straight chain or branched chain or cyclic alkylene group having a carbon number of 1 to 6, with preference given to a straight chain or a branched chain. For example, a methylene group, an ethylene group, an n-propylene group (—$(CH_2)_3$—), an n-butylene group (—$(CH_2)_4$—) an n-pentylene group (—$(CH_2)_5$—), an n-hexylene group (—$(CH_2)_6$—), an isopropylene group, an isobutylene group, an isopentylene group, —$CH_2$—CH($CH_3$)—, —$CH_2$—CH($CH_2CH_3$)—, —$CH_2$—CH($CH_2CH_2CH_3$)—, —$CH_2$—CH($CH_3$)—, —$CH_2CH_2$—, —$CH_2$—CH(CH($CH_3$)_2)—, —CH($CH_2CH_3$)—, —CH($CH_3$)—, —$CH_2$—C($CH_3$)_2—, and the like can be mentioned.

The "lower alkenylene group" is a straight chain or branched chain alkenylene group having a carbon number of 2 to 6, which includes each isomer. For example, a vinylene group, a 1-propenylene group, a 2-propenylene group, a 2-butenylene group, a 3-butenylene group, a pentenylene group, a hexenylene group, —CH=C($CH_3$)—, and the like can be mentioned.

The "lower alkynylene group" is a straight chain or branched chain alkynylene group having a carbon number of 2 to 6, which includes each isomer. For example, an ethynylene group, a 1-propynylene group, a 2-propynylene group, a 2-butynylene group, a 3-butynylene group, a pentynylene group, and the like can be mentioned.

Examples of the "halogeno group" include a fluorine atom, a chlorine atom, a bromine atom, an iodine atom, and the like.

The "lower acyl group" is an acyl group having a straight chain or branched chain or cyclic alkyl group or alkenyl group having a carbon number of 1 to 6. For example, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a cyclopropanoyl group, a cyclobutanoyl group, a cyclopentanoyl group, a cyclohexanoyl group, and the like can be mentioned.

The "lower alkoxyl group" is an alkoxyl group having a straight chain or branched chain or cyclic alkyl group having a carbon number of 1 to 6. For example, a methoxy group, an ethoxy group, an n-propoxy group, an n-butoxy group, an n-pentyloxy group, an n-hexyloxy group, an isopropoxy group, an isobutoxy group, a sec-butoxy group, a tert-butoxy group, a cyclopropyloxy group, a cyclobutyloxy group, a cyclopentyloxy group, and a cyclohexyloxy group can be mentioned.

The "lower alkylthio group" is an alkylthio group having a straight chain or branched chain or cyclic alkyl group having a carbon number of 1 to 6. For example, a methylthio group, an ethylthio group, an n-propylthio group, an isopropylthio group, an n-butylthio group, an isobutylthio group, a sec-butylthio group, a tert-butylthio group, a cyclopropylthio group, a cyclobutylthio group, a cyclopentylthio group, a cyclobutylthio group, and the like can be mentioned.

The "lower alkylamino group" is an amino group mono- or di-substituted by the aforementioned "lower alkyl group". For example, a methylamino group, an ethylamino group, a propylamino group, an isopropylamino group, a dimethylamino group, a diethylamino group, a dipropylamino group, a diisopropylamino group, an ethylmethylamino group, and the like can be mentioned.

The "lower acyloxy group" is a group wherein an oxygen atom is bonded to the carbon of the carbonyl moiety of the aforementioned "lower acyl group". For example, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a methacryloyloxy group, a crotonoyloxy group, an isocrotonoyloxy group, and the like can be mentioned.

The "lower acylamino group" is a group wherein a nitrogen atom is bonded to the carbon of the carbonyl moiety of the aforementioned "lower acyl group". For example, an acetylamino group, a propionylamino group, a butyrylamino group, an isobutyrylamino group, a valerylamino group, an isovalerylamino group, a pivaloylamino group, a hexanoylamino group, an acryloylamino group, a methacryloylamino group, a crotonoylamino group, an isocrotonoylamino group, and the like can be mentioned.

The "lower alkoxycarbonyl group" is a carbonyl group having the aforementioned "lower alkoxyl group". For example, a methoxycarbonyl group, an ethoxycarbonyl group, a propoxycarbonyl group, an isopropoxycarbonyl group, an n-butoxycarbonyl group, an isobutoxycarbonyl group, a sec-butoxycarbonyl group, a tert-butoxycarbonyl group, and the like can be mentioned.

The "lower alkylcarbamoyl group" is a group wherein a nitrogen atom of the aforementioned "lower alkylamino group" or "cyclic amino group", and a carbon atom of the carbonyl group are bonded. For example, an N-methylcarbamoyl group, an N-ethylcarbamoyl group, an N,N-dimethylcarbamoyl group, a 1-pyrrolidinylcarbonyl group, a 1-piperidinylcarbonyl group, a 4-morpholinylcarbonyl group, and the like can be mentioned.

The "lower alkylsulfonylamino group" is a group wherein a nitrogen atom is bonded to a sulfonyl group wherein the aforementioned "lower alkyl group" is bonded to a sulfur atom. For example, a methylsulfonylamino group, an ethylsulfonylamino group, a propylsulfonylamino group, an isopropylsulfonylamino group, a butylsulfonylamino group, an isobutylsulfonylamino group, and the like can be mentioned.

The "arylsulfonylamino group" is a group wherein a nitrogen atom is bonded to a sulfur atom of a sulfonyl group substituted by an aryl group. For example, a phenylsulfonylamino group, a naphthylsulfonylamino group, and the like can be mentioned.

Examples of the "aryl group" include an aryl group having a carbon number of 6 to 14 such as a phenyl group, a naphthyl group, and the like.

The "heterocyclic group" is a 5- to 14-membered monocyclic to tricyclic heterocyclic group containing, as a ring atom, 1 to 4 hetero atoms selected from an oxygen atom, a sulfur atom, and a nitrogen atom. Any carbon atom as a ring atom may be substituted by an oxo group, and a sulfur atom or a nitrogen atom may be oxidized to form an oxide. In addition, it may be condensed with a benzene ring. For example, a pyridyl group, a pyridazinyl group, a pyrimidinyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, an oxadiazolyl group, a thiadiazolyl group, a triazolyl group, a tetrazolyl group, a benzofuranyl group, a benzothienyl group, an indolyl group, an isoindolyl group, a benzoxazolyl group (=a benzooxazolyl group), a benzothiazolyl group, a benzimidazolyl group (=a benzoimidazolyl group), an indazolyl group, a benzisoxazolyl group, a benzisothiazolyl group, a benzofurazanyl group, a benzothiadiazolyl group, a purinyl group, a quinolinyl group, an isoquinolyl group, a cinnolinyl group, a phthalazinyl group, a quinazolinyl group, a quinoxalinyl group, a pteridinyl group, an imidazooxazolyl group, an imidazothiazolyl group, an imidazoimidazolyl group, a dibenzofuranyl group, a dibenzothienyl group, a carbazolyl group, an acridinyl group, a pyrrolidinyl group, a pyrazolidinyl group, an imidazolidinyl group, a pyrrolinyl group, a pyrazolinyl group, an imidazolinyl group, a tetrahydrofuranyl group, a tetrahydrothiophenyl group, a thiazolidinyl group, a piperidinyl group, a piperazinyl group, a quinuclidinyl group, a tetrahydropyranyl group, a tetrahydrothiopyranyl group, a morpholinyl group, a thiomorpholinyl group, a dioxolanyl group, a homopiperidinyl group, a homopiperazinyl group, an indolinyl group, an isoindolinyl group, a chromanyl group, an isochromanyl group, a tetrahydronaphthyridinyl group, an azaindolyl group, and the like can be mentioned. Preferably, a thiadiazolyl group, an imidazolyl group, a tetrazolyl group, a piperidinyl group, a piperazinyl group, a thiazolidinyl group, and the like can be mentioned.

As the "phenylene group", a 1,4-phenylene group, a 1,3-phenylene group, and the like can be mentioned.

The "thiophenylene group" is divalent thiophene. For example, a thiophene-2,5-diyl group and the like can be mentioned.

The "serine protease" in the present specification is a protease having, as a catalytic residue, a serine residue having nucleophilicity. For example, trypsin, chymotrypsin, elastase, enteropeptidase, kallikrein, thrombin, factor Xa, and tryptase, and the like can be mentioned. In addition, the "serine protease inhibition" in the present specification means decrease or disappearance of the aforementioned serine protease activity. Preferably, it is an inhibition of the activity of intestinal serine proteases such as trypsin, enteropeptidase, chymotrypsin, elastase and the like, particularly preferably inhibition of trypsin and enteropeptidase activities.

The serine protease inhibitor of the present invention is a dual inhibitor that simultaneously inhibits at least trypsin and enteropeptidase.

The diabetes in the present specification means type I diabetes mellitus and type II diabetes mellitus, with preference given to type II diabetes mellitus.

In the present invention, the heteroarylcarboxylic acid ester derivative represented by formula (I) or a pharmaceutically acceptable salt thereof is preferably as follows.

In formula (I), preferably, R1, R2, R3, and R4 are each independently a hydrogen atom, a nitro group, a halogeno group, and the like, more preferably a hydrogen atom, a nitro group, a fluorine atom, a chlorine atom, a bromine atom, and the like, particularly extremely preferably a hydrogen atom, a fluorine atom, and the like.

In formula (I), the group represented by HetAr is preferably a 5- to 10-membered aromatic ring containing 1 to 3 hetero atoms, which optionally has substituent(s), and furan, thiophene, oxazole, isoxazole, thiazole, isothiazole, benzofuran, benzothiophene, benzoxazole, benzothiazole, and the like can be mentioned. A 5-membered heteroaryl ring is more preferable, and furan, thiophene, oxazole, isoxazole, thiazole, isothiazole, and the like can be mentioned, and particularly preferably, furan, thiophene, thiazole, and the like can be mentioned.

Here, as the hetero atom, an oxygen atom, a sulfur atom, a nitrogen atom, and the like can be mentioned.

In addition, when a group represented by HetAr has a substituent, examples of the substituent include a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, and the like.

Preferably, a halogeno group, a hydroxyl group, an amino group, a lower alkyl group, a lower alkenyl group, a lower alkynyl group, a lower acyl group, a carboxyl group, a sulfo group, a phosphono group, a lower alkoxyl group, a lower alkylamino group, a lower alkoxycarbonyl group, a carbamoyl group, a lower alkylcarbamoyl group, a lower alkylsulfonylamino group, a sulfamoyl group, and the like can be mentioned. More preferably, a halogeno group, a hydroxyl group, an amino group, a lower alkyl group, a lower alkoxyl group, a lower alkylamino group, and the like can be mentioned. The number of the substituents is preferably 1 to 3, more preferably 1 or 2, further preferably 1. In addition, the group represented by HetAr is preferably unsubstituted.

A group represented by HetAr is preferably a group of the following formula (III-1) or (III-2).

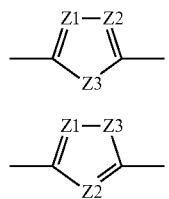

wherein Z1 and Z2 are each independently CRa or a nitrogen atom, and Z3 is an oxygen atom, a sulfur atom or NRb, wherein Ra and Rb may be the same or different, and are each independently selected from a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, and a sulfamoyl group.

In groups of the formulas (III-1) and (III-2), Z1 is preferably CH or a nitrogen atom, and CH is particularly preferable.

In groups of the formulas (III-1) and (III-2), Z2 is preferably CH.

In groups of the formulas (III-1) and (III-2), Z3 is preferably an oxygen atom or a sulfur atom.

In groups of the formulas (III-1) and (III-2), preferably, Ra and Rb are each independently a hydrogen atom, a halogeno group, a hydroxyl group, an amino group, a lower alkyl group, a lower alkenyl group, a lower alkynyl group, a lower acyl group, a carboxyl group, a sulfo group, a phosphono group, a lower alkoxyl group, a lower alkylamino group, a lower alkoxycarbonyl group, a carbamoyl group, a lower alkylcarbamoyl group, a lower alkylsulfonylamino group, a sulfamoyl group, and the like, and a hydrogen atom, a halogeno group, a hydroxyl group, an amino group, a lower alkyl group, a lower alkoxyl group, a lower alkylamino group, and the like are more preferable.

In the formula (I), X is preferably a straight chain or branched chain lower alkylene group having a carbon number of 1 to 6 or a straight chain or branched chain lower alkenylene group having a carbon number of 2 to 4, and a straight chain or branched chain lower alkylene group having a carbon number of 1 to 5 is more preferable.

When X is a phenylene group or a thiophenylene group, it is an unsubstituted phenylene group or an unsubstituted thiophenylene group.

In the formula (I), when a group represented by X has a substituent, examples of the substituent include a nitro group, a halogeno group, a cyano group, a hydroxyl group, a thiol group, an amino group, a lower alkyl group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, and the like, and a halogeno group, a hydroxyl group, an amino group, a lower alkyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, and the like are preferable. The number of the substituents is preferably 1 to 3, more preferably 1 or 2, further preferably 1. In addition, the group represented by X is preferably unsubstituted.

In the formula (I), Y is preferably a carbonyl group.

In the formula (I), A is preferably a group represented by —OR5, a group of the following formula (II), a group of the following formula (IV), —U—CH(R6')R7' or —NH—N(R6")R7".

In addition, in the formula (I), A is preferably a group represented by —OR5, a group of the following formula (II) or a group of the following formula (IV). Among these, a group represented by the following formula (IV) is particularly preferable.

When the group represented by A is —OR5, preferred as R5 is a hydrogen atom.

In a group of formula (II), preferably, R6 and R7 are each independently a hydrogen atom, a hydroxyl group, a lower alkyl group, a lower alkoxyl group, and the like, and a hydrogen atom, a lower alkyl group having a carbon number of 1 to 3, or the like is particularly preferable.

Here, when a group represented by R6 or R7 has a substituent, examples of the substituent include a nitro group, a halogeno group, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), an oxo group, and the like. A halogeno group, a hydroxyl group, a carboxyl group, a sulfo group, a phosphono group, a lower alkoxycarbonyl group, an aryl group optionally having substituent(s), a heterocyclic group optionally having substituent(s), an oxo group, and the like are preferable, and a hydroxyl group, a carboxyl group, a sulfo group, a lower alkoxycarbonyl group, and the like are particularly preferable. The number of the substituents is preferably 1 to 3, more preferably 1 or 2.

As a cyclic amino group formed by R6 and R7 bonded to each other, a pyrrolidinyl group, a piperidinyl group, and the like are preferable.

When the cyclic amino group formed by R6 and R7 bonded to each other has a substituent, examples of the substituent include a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like. A hydroxyl group, a carboxyl group, a sulfo group, a phosphono group, a lower alkoxycarbonyl group, and the like are preferable. The number of the substituents is preferably 1 to 3, more preferably 1 or 2.

In a group of formula (IV), R60 is preferably a carboxyl group or a sulfo group, and a carboxyl group is particularly preferable.

In a group of formula (IV), D is preferably a lower alkylene group optionally having substituent(s), and a lower alkylene group having a carbon number of 1 to 3 is particularly preferable.

In a group of formula (IV), when a group represented by D has a substituent, preferable examples of the substituent include a halogeno group, a hydroxyl group, a carboxyl group, a sulfo group, a phosphono group, a lower alkoxycarbonyl group, an aryl group optionally having substituent(s), a heterocyclic group optionally having substituent(s), an oxo group, and the like, and a hydroxyl group, a carboxyl group, a sulfo group, a lower alkoxycarbonyl group, and the like are particularly preferable. The number of the substituents is preferably 1 to 3, more preferably 1 or 2, further preferably 1. In addition, the group represented by D is preferably unsubstituted.

In a group of the formula (IV), R70 is preferably a hydrogen atom, a lower alkyl group having a carbon number of 1 to 3, a lower alkoxyl group having a carbon number of 1 to 2, or the like, and a hydrogen atom, a lower alkyl group having a carbon number of 1 to 3, and the like are particularly preferable.

In a group of formula (IV), when the group represented by R70 has a substituent, examples of the substituent include a nitro group, a halogeno group, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), an oxo group. and the like. A halogeno group, a hydroxyl group, a carboxyl group, a sulfo group, a phosphono group, a lower alkoxycarbonyl group, an aryl group optionally having substituent(s), a heterocyclic group optionally having substituent(s), an oxo group, and the like are preferable, and a hydroxyl group, a carboxyl group, a sulfo group, and a lower alkoxycarbonyl group are particularly preferable. The number of the substituents is preferably 1 to 3, more preferably 1 or 2, further preferably 1.

As the cyclic amino group formed by R70 and D bonded to each other, a pyrrolidinyl group, a piperidinyl group, and the like are preferable.

When the cyclic amino group formed by R70 and D bonded to each other has a substituent, examples of the substituent include a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like, and a hydroxyl group, a carboxyl group, a sulfo group, a phosphono group, a lower alkoxycarbonyl group, and the like are preferable. The number of the substituents is preferably 1 to 3, more preferably 1 or 2, further preferably 1.

A heteroarylcarboxylic acid ester derivative wherein, in a group of the formula (IV), R60 is a carboxyl group, D is a lower alkylene group optionally having a carboxyl group, and R70 is a lower alkyl group optionally having a carboxyl group or a hydrogen atom, or a pharmaceutically acceptable salt thereof is particularly preferable.

A heteroarylcarboxylic acid ester derivative represented by any of the following formulas or a pharmaceutically acceptable salt thereof is preferable.

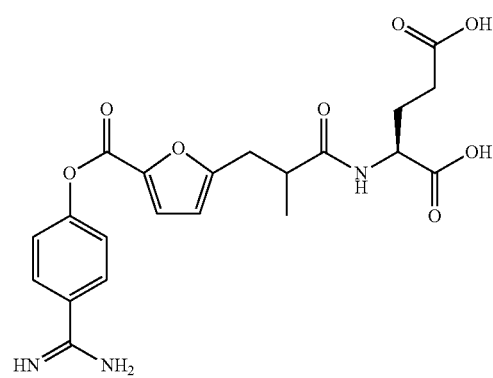

A-15

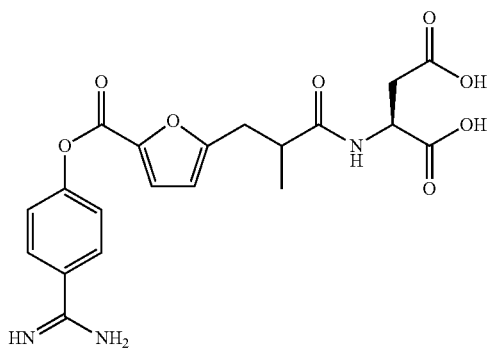
A-18
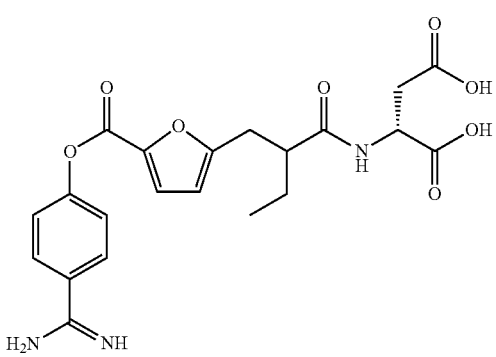
A-31
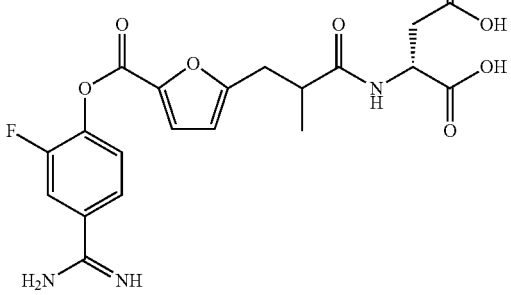
A-26
A-35
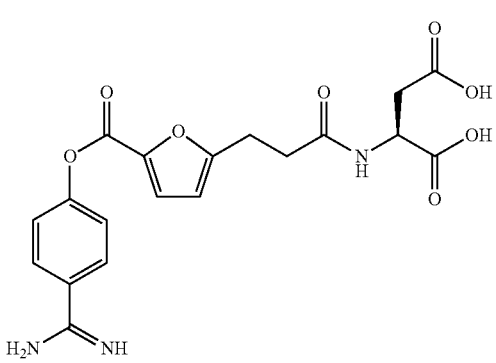
A-28
A-38
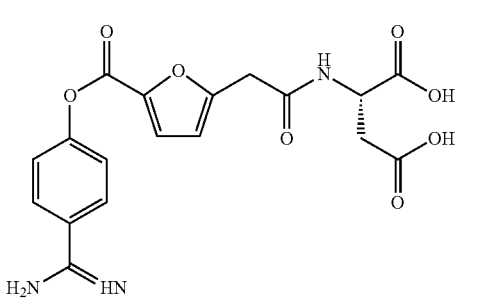
A-30
A-39

A-40
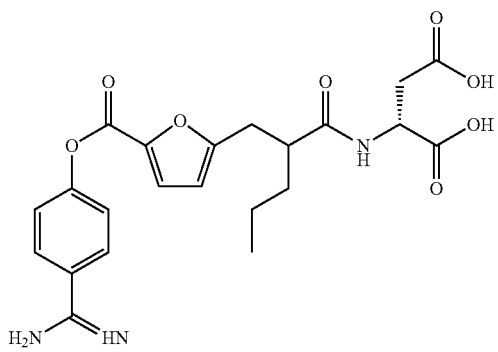
B-22
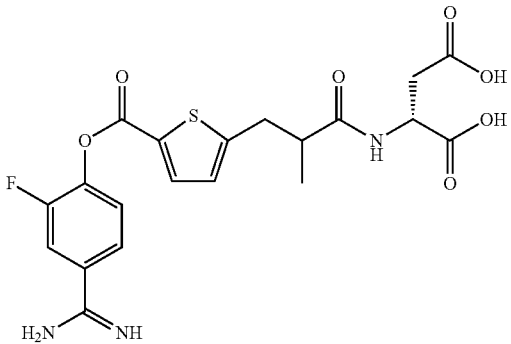
B-18
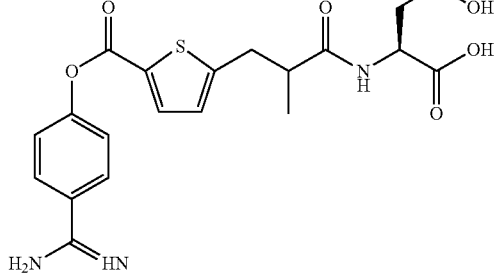
B-23
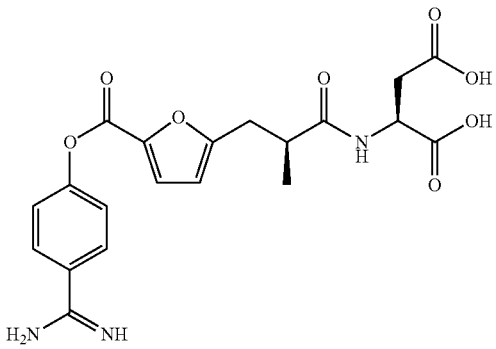
A heteroarylcarboxylic acid ester derivative represented by any of the following formulas or a pharmaceutically acceptable salt thereof is also preferable.
B-20
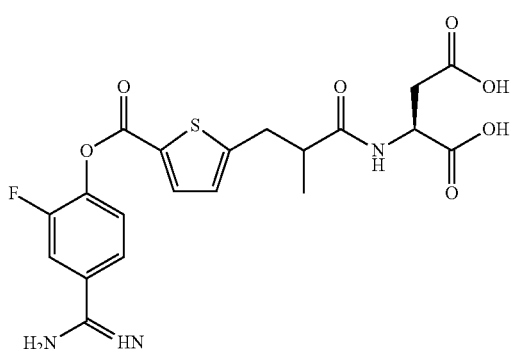
A-43
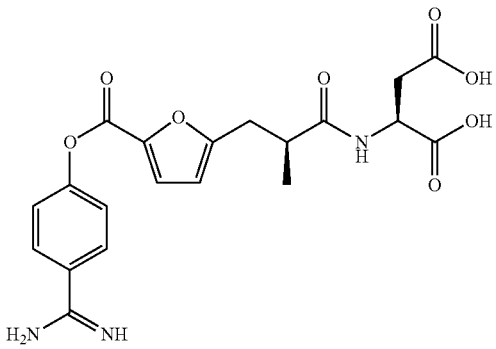
B-21
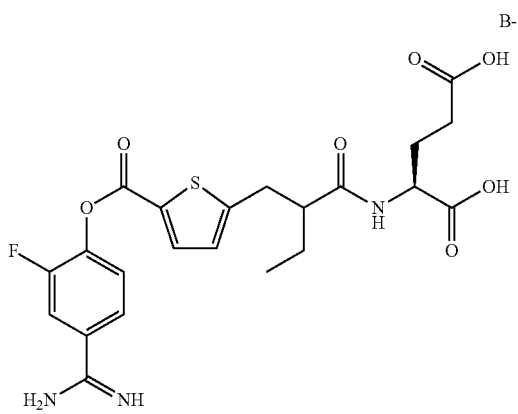
A-44
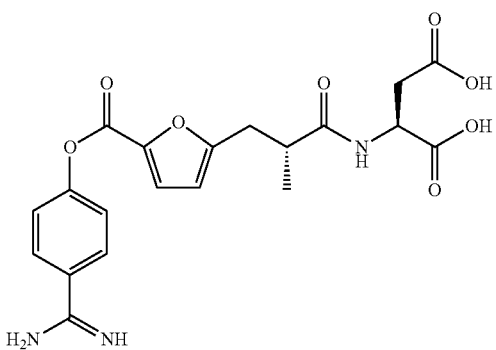

A-45
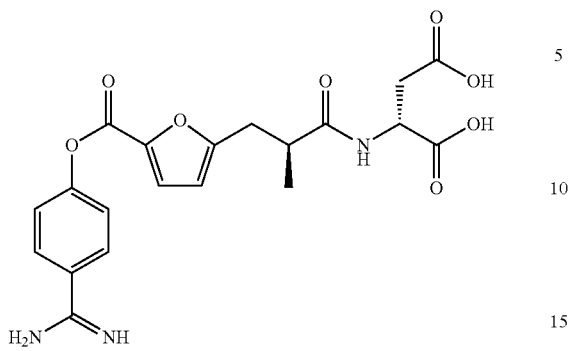
A-55
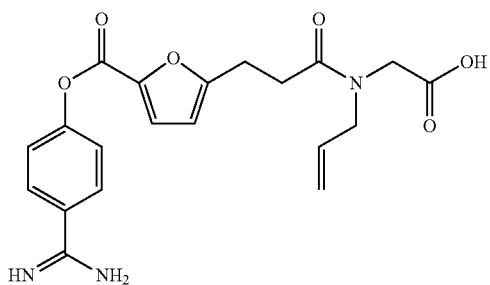
A-46
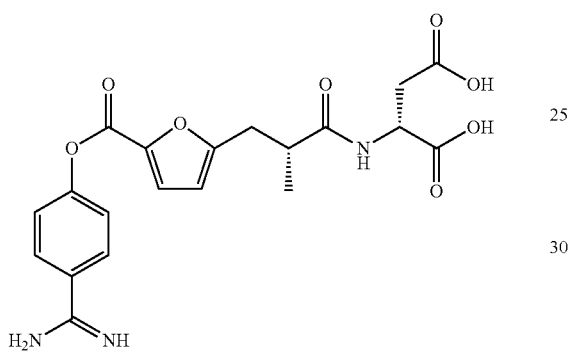
A-57
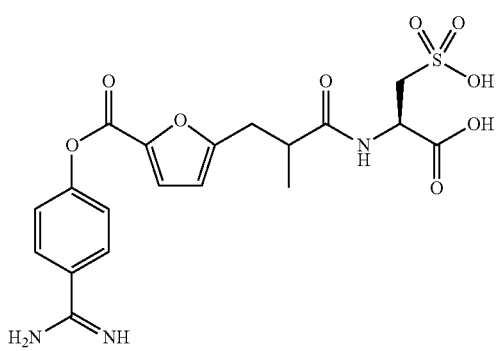
A-53
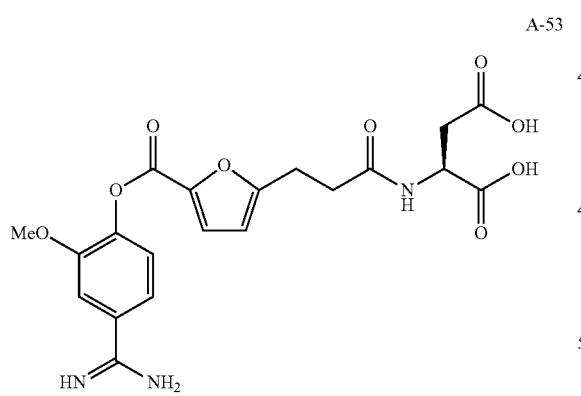
B-25
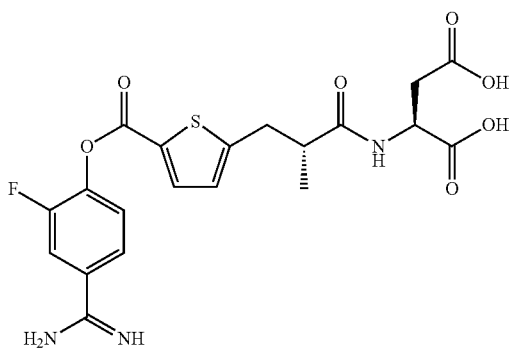
A-54
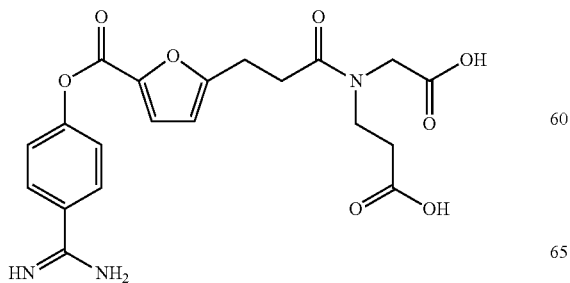
B-26
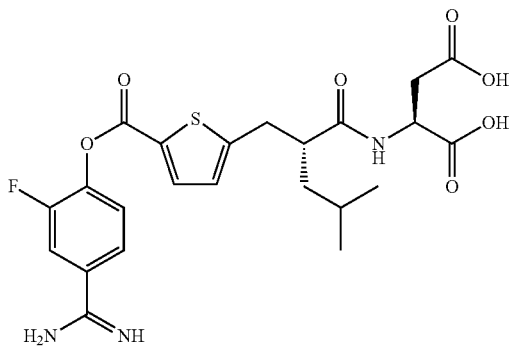

B-27
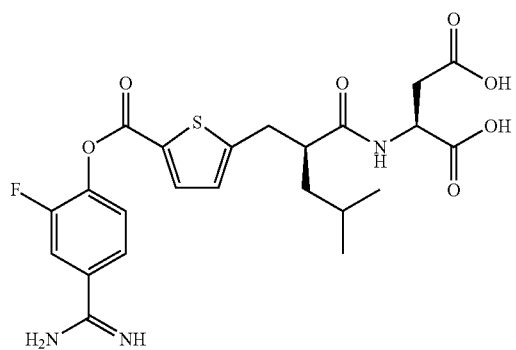
B-31
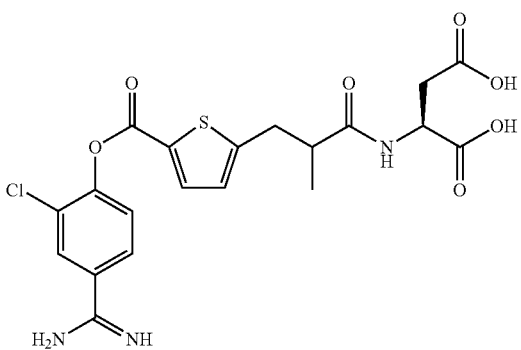
B-28
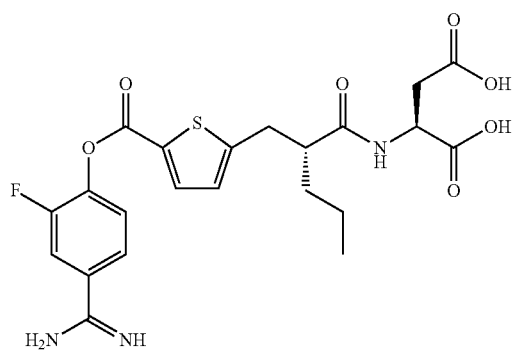
B-32
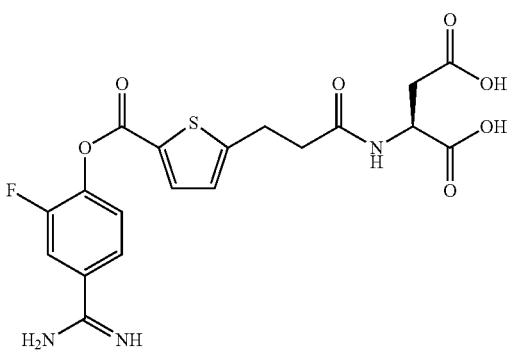
B-29
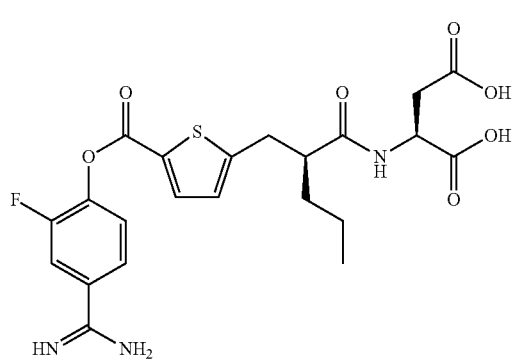
B-33
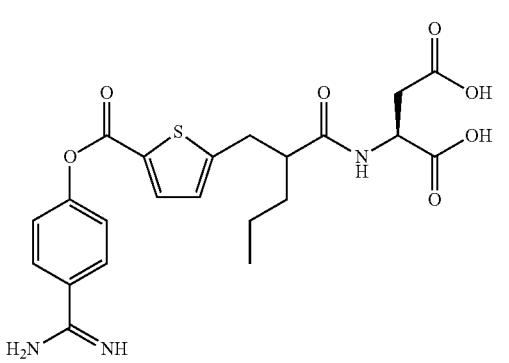
B-30
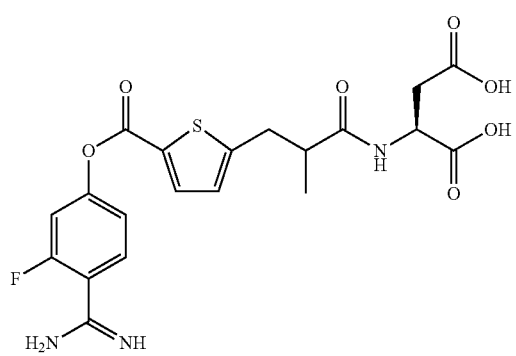
B-36
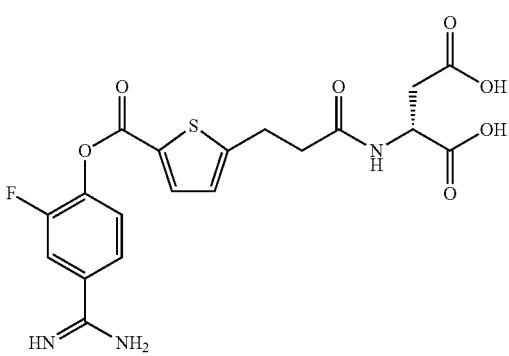

B-37
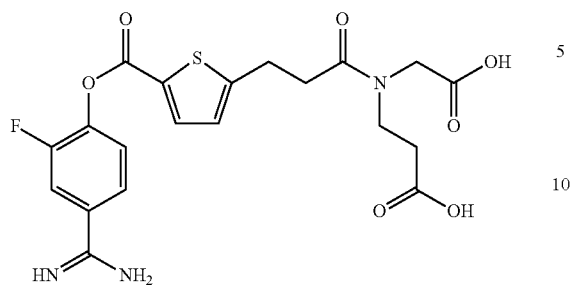
B-44
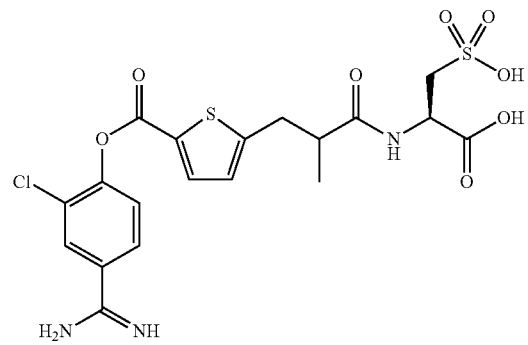
B-38
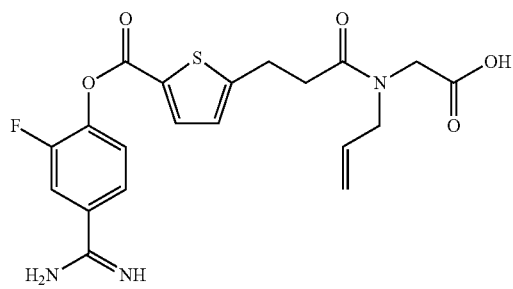
B-45
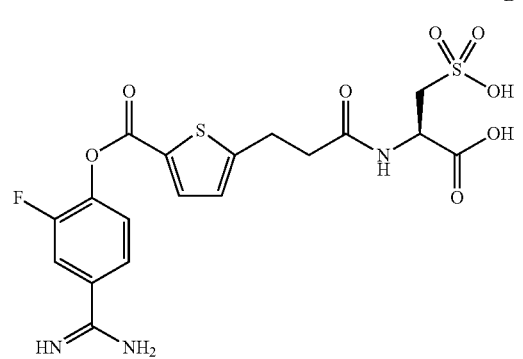
B-39
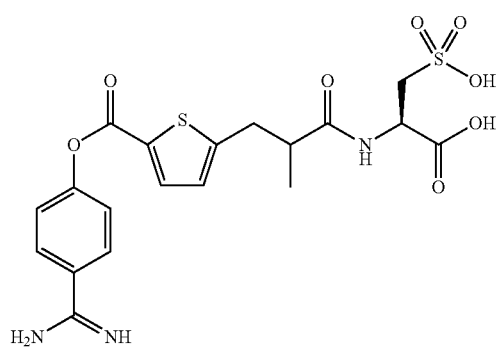
B-61
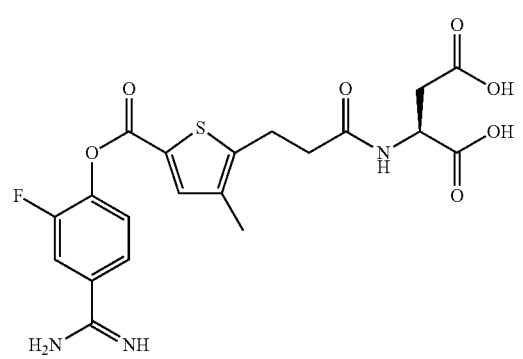
B-41
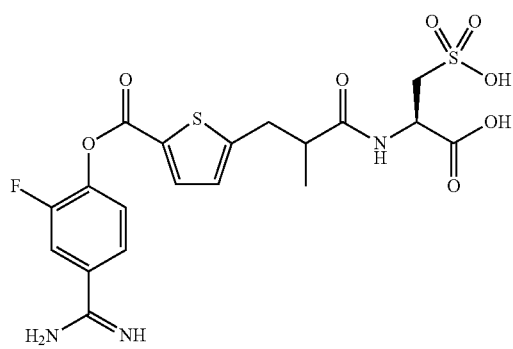
B-62
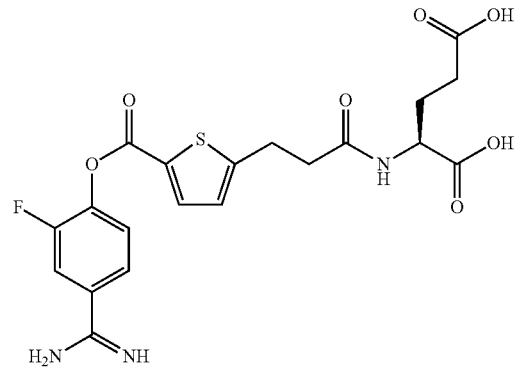

-continued

B-63

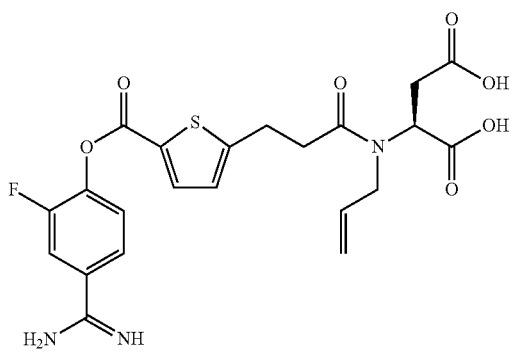

B-64

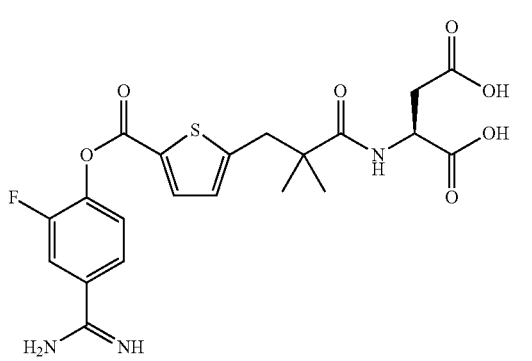

As preferable embodiments of the heteroarylcarboxylic acid ester derivative represented by the formula (I) or a pharmaceutically acceptable salt thereof, the following can also be mentioned.

Compound a

A compound represented by the formula (I) wherein R1 is a hydrogen atom, a nitro group, a halogeno group, or a straight chain or branched chain alkoxyl group having a carbon number of 1 to 6;
R3 is a hydrogen atom or a halogeno group;
R2 and R4 are hydrogen atoms;
HetAr is furan, thiophene, or thiazole each optionally having 1 or 2 substituents selected from a straight chain or branched chain alkyl group having a carbon number of 1 to 6;
X is
(1) a straight chain or branched chain alkylene group having a carbon number of 1 to 6, which optionally has a carboxyl group,
(2) a straight chain or branched chain alkenylene group having a carbon number of 2 to 6,
(3) a phenylene group, or
(4) a thiophenylene group;
Y is a carbonyl group or a sulfonyl group; and
A is —OR5 (R5 is a hydrogen atom);
a group of the following formula (II):

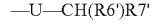 (II)

wherein R6 is a straight chain or branched chain alkyl group having a carbon number of 1 to 6, which optionally has 1 or 2 substituents selected from the group consisting of an aryl group having a carbon number of 6 to 14 and optionally having a hydroxyl group, a hydroxyl group, a carboxyl group, sulfo group, a phosphono group, an amino group mono- or di-substituted by a straight chain or branched chain alkyl group having a carbon number of 1 to 6 and a carbamoyl group and
R7 is
(1) a hydrogen atom,
(2) a straight chain or branched chain alkyl group having a carbon number of 1 to 6 and optionally having 1 or 2 substituents selected from the group consisting of an aryl group having a carbon number of 6 to 14, a hydroxyl group, and a carboxyl group, or
(3) a straight chain or branched chain alkenyl group having a carbon number of 2 to 6, or
R6 and R7 are optionally bonded to form a pyrrolidinyl group or a piperidinyl group, each of which optionally has 1 or 2 substituents selected from the group consisting of a hydroxyl group and a carboxyl group;
a group of the following formula (II-2):

—U—CH(R6')R7' (II-2)

wherein U is O or S, and R6' and R7' may be the same or different and are each independently a straight chain or branched chain alkyl group having a carbon number of 1 to 6 and optionally having a carboxyl group, or a carboxyl group; or
a group of the following formula (II-3):

—NH—N(R6'')R7'' (II-3)

wherein R6'' and R7'' may be the same or different and are each independently a straight chain or branched chain alkyl group having a carbon number of 1 to 6 and optionally having a carboxyl group,
or a pharmaceutically acceptable salt thereof.

Compound b.

A compound represented by the formula (I) wherein R1 is a hydrogen atom, a nitro group, a halogeno group or a straight chain or branched chain alkoxyl group having a carbon number of 1 to 6;
R3 is a hydrogen atom or a halogeno group;
R2 and R4 are hydrogen atoms;
HetAr is furan, thiophene, or thiazole each optionally having 1 or 2 substituents selected from a straight chain or branched chain alkyl group having a carbon number of 1 to 6;
X is
(1) a straight chain or branched chain alkylene group having a carbon number of 1 to 6 and optionally having a carboxyl group,
(2) a straight chain or branched chain alkenylene group having a carbon number of 2 to 6,
(3) a phenylene group, or
(4) a thiophenylene group;
Y is a carbonyl group or a sulfonyl group, and
A is —OR5 (R5 is a hydrogen atom),
a group of the following formula (II):

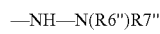 (II)

wherein R6 is a straight chain or branched chain alkyl group having a carbon number of 1 to 6 and having 1 or 2 substituents selected from the group consisting of an aryl group having a carbon number of 6 to 14 and optionally having a hydroxyl group, a hydroxyl group, a carboxyl group, a sulfo group, a phosphono group, an amino group mono- or di-substituted by a straight chain or branched chain alkyl group having a carbon number of 1 to 6, and a carbamoyl group, and R7 is
(1) a hydrogen atom,
(2) a straight chain or branched chain alkyl group having a carbon number of 1 to 6 and optionally having 1 or 2 substituents selected from the group consisting of an aryl group having a carbon number of 6 to 14, a hydroxyl group and a carboxyl group, or
(3) a straight chain or branched chain alkenyl group having a carbon number of 2 to 6, or
R6 and R7 are optionally bonded to form a pyrrolidinyl group or a piperidinyl group each having 1 or 2 substituents selected from the group consisting of a hydroxyl group and a carboxyl group,
a group of the following formula (II-2):

—U—CH(R6')R7'     (II-2)

wherein U is O or S, and R6' and R7' may be the same or different and are each independently a straight chain or branched chain alkyl group having a carbon number of 1 to 6 and having a carboxyl group or a carboxyl group, or
a group of the following formula (II-3):

—NH—N(R6")R7"     (II-3)

wherein R6" and R7" may be the same or different and are each independently a straight chain or branched chain alkyl group having a carbon number of 1 to 6 and having a carboxyl group,
or a pharmaceutically acceptable salt thereof.
Compound c.

A compound represented by the formula (I) wherein R1 is a hydrogen atom, a nitro group, a halogeno group, or a straight chain or branched chain alkoxyl group having a carbon number of 1-6;
R3 is a hydrogen atom or a halogeno group;
R2 and R4 are hydrogen atoms;
HetAr is furan, thiophene or thiazole each optionally having 1 or 2 substituents selected from a straight chain or branched chain alkyl group having a carbon number of 1 to 6,
X is
(1) a straight chain or branched chain alkylene group having a carbon number of 1 to 6 and optionally having a carboxyl group,
(2) a straight chain or branched chain alkenylene group having a carbon number of 2 to 6,
(3) a phenylene group, or
(4) a thiophenylene group;
Y is a carbonyl group or a sulfonyl group; and
A is —OR5 (R5 is a hydrogen atom) or
a group of the following formula (IV):

(IV)

wherein R60 is a carboxyl group, a sulfo group, a phosphono group, or a hydroxyl group,
D is a straight chain or branched chain alkylene group having a carbon number of 1 to 6 and optionally having substituent(s), and the substituent is selected from the group consisting of an aryl group having a carbon number of 6 to 14 and optionally having a hydroxyl group, a hydroxyl group, a carboxyl group, a sulfo group, and a carbamoyl group, and R70 is
(1) a hydrogen atom,
(2) a straight chain or branched chain alkyl group having a carbon number of 1 to 6 and optionally having 1 or 2 substituents selected from the group consisting of an aryl group having a carbon number of 6 to 14, a hydroxyl group, and a carboxyl group, or
(3) a straight chain or branched chain alkenyl group having a carbon number of 2 to 6, or
R70 and D are optionally bonded to form a pyrrolidinyl group or a piperidinyl group each optionally having 1 or 2 substituents selected from the group consisting of a hydroxyl group and a carboxyl group,
or a pharmaceutically acceptable salt thereof.

As the serine protease inhibitory activity, an activity of simultaneously inhibiting trypsin and enteropeptidase is preferable.

When the compound of the present invention can form a salt, a pharmaceutically acceptable salt is preferable. Examples of such pharmaceutically acceptable salts for a compound having an acidic group such as a carboxyl group and the like include an ammonium salt, salts with alkali metals such as sodium, potassium, and the like, salts with alkaline earth metals such as calcium, magnesium, and the like, an aluminum salt, a zinc salt, salts with an organic amines such as triethylamine, ethanolamine, morpholine, pyrrolidine, piperidine, piperazine, dicyclohexylamine, and the like, and salts with a basic amino acid such as arginine, lysine, and the like. Examples of such pharmaceutically acceptable salts for a compound having a basic group include salts with an inorganic acid such as hydrochloric acid, sulfuric acid, phosphoric acid, nitric acid, hydrobromic acid, and the like, salts with an organic carboxylic acid such as acetic acid, citric acid, benzoic acid, maleic acid, fumaric acid, tartaric acid, succinic acid, tannic acid, butyric acid, hibenzic acid (2-(4-hydroxybenzoyl)benzoic acid), pamoic acid, enanthic acid, decanoic acid, teoclic acid, salicylic acid, lactic acid, oxalic acid, mandelic acid, malic acid, and the like, and salts with an organic sulfonic acid such as methanesulfonic acid, benzenesulfonic acid, p-toluenesulfonic acid, and the like.

The compound of the present invention also encompasses all optical isomers, stereoisomers, tautomers, rotamers, and mixtures thereof at optional ratios. These can be obtained each as a single product according to a synthesis method and separation method known per se. For example, an optical isomer can be obtained by using an optically active synthesis intermediate or by optically resolving a racemate of a synthesis intermediate or final product by a conventional method.

The compound of the present invention also includes solvates of the compound such as hydrates, alcohol adducts, and the like.

The compound of the present invention may be converted to a prodrug. The prodrug of the present invention means a compound that is converted in the body to produce the compound of the present invention. For example, when an active form contains a carboxyl group or a phosphoric acid group, an ester thereof, amide thereof, and the like can be mentioned. When an active form contains a carboxyl group, a group to be converted to a carboxyl group by oxidative metabolism, such as a hydroxymethyl group and the like can be mentioned. In addition, when the active form contains an amino group, examples thereof include amide thereof, a carbamate thereof and the like. When the active form contains a hydroxyl group, examples thereof include esters thereof, carbonates thereof, carbamates thereof, and the like. When the compound of the present invention is converted to a prodrug, it may be bonded to amino acid or saccharide.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose, or an amino acid is bonded to the carboxylic acid moiety of the compound of the present invention or a hydroxyl group is added by the metabolism, and the like can be mentioned.

The compound of the present invention and a pharmaceutically acceptable salt thereof have a superior blood glucose elevation suppressing action for mammals such as humans, bovines, horses, dogs, mice, rats, and the like, and can be used as a medicament, which is administered as it is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations, and the like). While the dose used for the above-mentioned objects is determined according to the desired treatment effect, administration method, duration of treatment, age, body weight, and the like, a daily dose of 1 µg to 10 g for oral administration and 0.01 µg to 1 g, preferably 0.1 µg to 1 g, for parenteral administration is used, which is generally administered to an adult by an oral or parenteral route in one to several portions per day. In addition, the content of the compound of the present invention in the above-mentioned pharmaceutical composition is about 0.01 wt % to 100 wt % of the whole composition.

Examples of the pharmaceutically acceptable carrier for the pharmaceutical composition of the present invention include various organic or inorganic carrier substances conventionally used as preparation materials. For example, an excipient, lubricant, binder, disintegrant, water-soluble polymer, and basic inorganic salt in a solid preparation; a solvent, solubilizing agents, suspending agent, isotonicity agent, buffering agent, and soothing agent in a liquid preparation, and the like can be mentioned. Where necessary, general additives such as a preservative, antioxidant, colorant, sweetening agent, souring agent, effervescing agent, flavor, and the like can also be used.

The dosage form of such pharmaceutical composition may be a tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape, or eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, a excipient and, where necessary, a binder, disintegrant, lubricant, colorant, flavoring agent, and the like are further added, and the mixture is processed to give, for example, a tablet, powder, pill, granule, capsule, suppository, solution, sugar-coated agent, depot, syrup, and the like according to a conventional method. Examples of the excipient include lactose, cornstarch, sucrose, glucose, sorbitol, crystalline cellulose, and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, and the like. Examples of the disintegrant include starch, agar, gelatin powder, crystalline cellulose, calcium carbonate, sodium hydrogen carbonate, calcium citrate, dextran, pectin, and the like. Examples of the lubricant include magnesium stearate, talc, polyethylene glycol, silica, hydrogenated vegetable oil, and the like. As the colorant, one acceptable to add to a pharmaceutical product is used, and as the flavoring agent, cocoa powder, menthol, aromatic acid, peppermint oil, borneol, powdered cinnamon bark, and the like are used. Where necessary, these tablets and granules are applied with a coating as appropriate such as sugar coating, gelatin coating, and the like.

When an injection is to be prepared, a pH adjuster, buffering agent, stabilizer, preservative, and the like are added where necessary, and the mixture is processed to give subcutaneous, intramuscular, or intravenous injection according to a conventional method.

While the compound of the present invention can be used as an agent for the treatment or prophylaxis of diabetes as mentioned above, it can also be used in combination with other therapeutic agents for diabetes and agents for the treatment or prophylaxis of diabetic complications, which are used generally. Examples of the therapeutic agents for diabetes and agents for the treatment or prophylaxis of diabetic complications, which are used generally, include combinations and mixtures of one or more kinds of insulin preparation, insulin derivative, insulin-like agent, insulin secretagogue, insulin sensitizer, biguanide, gluconeogenesis inhibitor, glucose absorption inhibitor, renal glucose reabsorption inhibitor, β3 adrenoceptor agonist, glucagon-like peptide-1 (7-37), glucagon-like peptide-1 (7-37) analogs, glucagon-like peptide-1 receptor agonist, dipeptidyl peptidase IV inhibitor, aldose reductase inhibitor, inhibitor of advanced glycation end product formation, glycogen synthase kinase-3 inhibitor, glycogen phosphorylase inhibitor, antihyperlipidemic drug, anorectic agent, lipase inhibitor, antihypertensive agent, peripheral circulation improving agent, antioxidant, a therapeutic drug for diabetic neuropathy, and the like.

A medicament to be used in combination with the compound of the present invention may be mixed to give a single agent or each may be formulated into separate preparations, or prepared into a combination preparation (set, kit, pack) obtained by packaging each of the separately formulated preparations in one container.

The administration form of combined use is not particularly limited and, for example, (1) administration as a single preparation, (2) simultaneous administration of separate preparations by the same administration route, (3) administration of separate preparations in a staggered manner by the same administration route, (4) simultaneous administration of separate preparations by different administration routes, (5) administration of separate preparations in a staggered manner by different administration routes, and the like can be mentioned.

In addition, the compound of the present invention is also useful even when contained in food.

A food composition containing the compound of the present invention is useful as a food for the treatment or prophylaxis of diabetes.

The "food" of the present invention means general foods, which include food for specified health uses and food with nutrient function claims defined by Food with Health Claims of Consumer Affairs Agency, Government of Japan, in addition to general foods including so-called health food, and further encompasses dietary supplements.

The form of the food composition of the present invention is not particularly limited, and the composition may take any form as long as it can be orally ingested.

Examples thereof include powder, granule, tablet, hard capsules, soft capsule, liquid (drinks, jelly drinks, and the like), candy, chocolate, and the like, all of which can be produced according to a method known per se in the technical field.

The content of the compound of the present invention in the food composition is appropriately determined to afford an appropriate dose within the indicated range.

The food composition of the present invention can use other food additives as necessary. Examples of such food additives include those generally used as components of health foods such as a fruit juice, dextrin, cyclic oligosaccharide, saccharides (monosaccharides such as fructose, glucose, and the like, and polysaccharides), acidulant, flavor, powdered green tea, and the like, which are used for controlling and improving taste, emulsifier, collagen, whole milk powder, polysaccharide thickener, agar, and the like, which are used for improving texture, and further, vitamins, eggshell calcium, calcium pantothenate, the other minerals, royal jelly, propolis, honey, dietary fiber, Agaricus, chitin, chitosan, flavonoids, carotenoids, lutein, traditional Japanese herbal medicine, chondroitin, various amino acids, and the like.

A production method of a representative compound from the heteroarylcarboxylic acid ester derivatives represented by the formula (I), which is the compound of the present invention, is shown below.

Heteroarylcarboxylic acid ester derivative (F) represented by the formula (I) wherein X is a lower alkylene group or a lower alkenylene group, A is —OR5, and R5 is a lower alkyl group can be produced as follows.

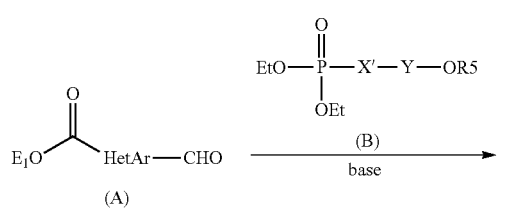

(A)

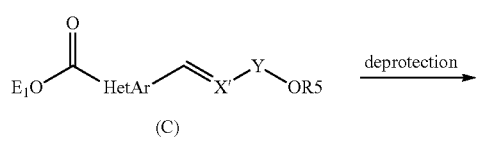

(C)

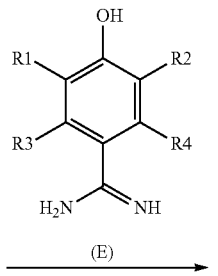

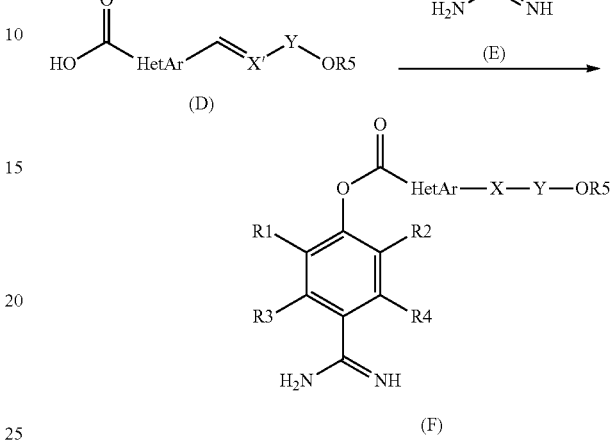

Alkenylene derivative (C) can be synthesized by reacting aldehyde (A) (wherein $E_1$ is a protecting group such as a methyl group, an ethyl group, a tert-butyl group, a benzyl group, and the like) with Wittig reagent (B) (wherein X' is X or a group capable of chemically converting to X together with methyne between HetAr and X' in (C)) in, for example, a solvent that does not adversely influence the reaction, such as tetrahydrofuran and the like, in the presence of, for example, a base such as sodium hydride and the like. Alkenylene derivative (C) can be converted to carboxylic acid derivative (D) by deprotection such as hydrolysis and the like in, for example, a solvent that does not adversely influence the reaction, such as tetrahydrofuran, methanol, and the like, by using, for example, a base such as sodium hydroxide and the like. Objective heteroarylcarboxylic acid ester derivative (F) wherein X is a lower alkenylene group can be produced by esterifying carboxylic acid derivative (D) with amidinophenol derivative (E). In addition, heteroarylcarboxylic acid ester derivative (F) wherein X is a lower alkylene group can be produced by, during any stage in the production steps, conducting a step of treating with a catalyst such as 10% palladium/carbon under a hydrogen atmosphere in, for example, a solvent that does not adversely influence the reaction such as methanol, ethanol, ethyl acetate, and the like.

The esterification reaction can be performed by a known method which is, for example, (1) a method using acid halide, (2) a method using a condensation agent, and the like.

(1) The method using acid halide is performed, for example, by reacting an acid chloride obtained by reaction with thionyl chloride, oxalyl chloride, and the like in a solvent that does not adversely influence the reaction, such as dichloromethane and the like, or without solvent in the presence or absence of, for example, a catalyst such as N,N-dimethylformamide and the like, with alcohol in a solvent that does not adversely influence the reaction such as dichloromethane, tetrahydrofuran, and the like in the presence of a base such as pyridine and triethylamine.

(2) The method using a condensation agent is performed, for example, by reacting carboxylic acid with alcohol in, for example, a solvent that does not adversely influence the reaction such as tetrahydrofuran, N,N-dimethylformamide, dichloromethane, and the like in, for example, the presence or absence of a base such as pyridine, triethylamine, and the like, by using a condensation agent such as 1-ethyl-3-(3'-dimethylaminopropyl)carbodiimide (WSC), 1,3-dicyclohexylcarbodiimide, and the like.

Heteroarylcarboxylic acid ester derivative (i) of the formula (I) wherein A is —OR5 and R5 is a hydrogen atom can be produced by subjecting ester derivative (H) obtained by using Wittig reagent (G) (wherein $E_2$ is a protecting group such as a methyl group, an ethyl group, an isopropyl group, a tert-butyl group, a benzyl-group, and the like) instead of Wittig reagent (B) to, for example, deprotection by hydrolysis with a base such as sodium hydroxide and the like, hydrolysis with an acid such as hydrochloric acid, trifluoroacetic acid and the like, or treating with, for example, 10% palladium/carbon and the like under a hydrogen atmosphere, and the like.

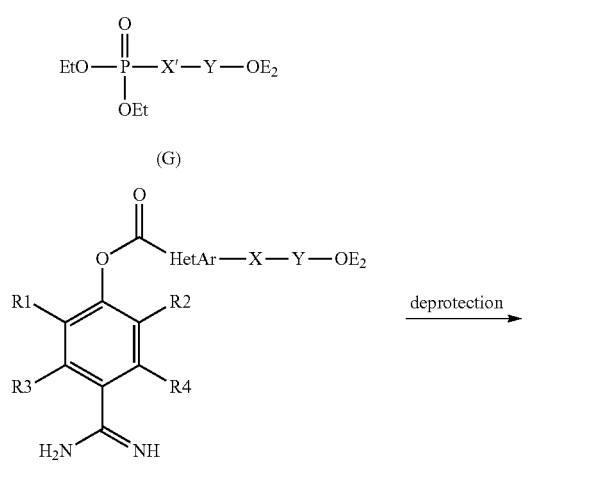

In addition, heteroarylcarboxylic acid ester derivative (K) of the formula (I) wherein A is a group of the formula (II) can be produced by amidating carboxylic acid, thiocarboxylic acid, or sulfonic acid derivative (i) with amine (J). The amidation reaction of carboxylic acid and thiocarboxylic acid derivative is performed using the corresponding amine instead of alcohol and in the same manner as in the aforementioned esterification reaction. The amidation reaction of the sulfonic acid derivative is performed using the corresponding amine instead of alcohol in the same manner as in (1) the method using acid halide for the aforementioned esterification reaction.

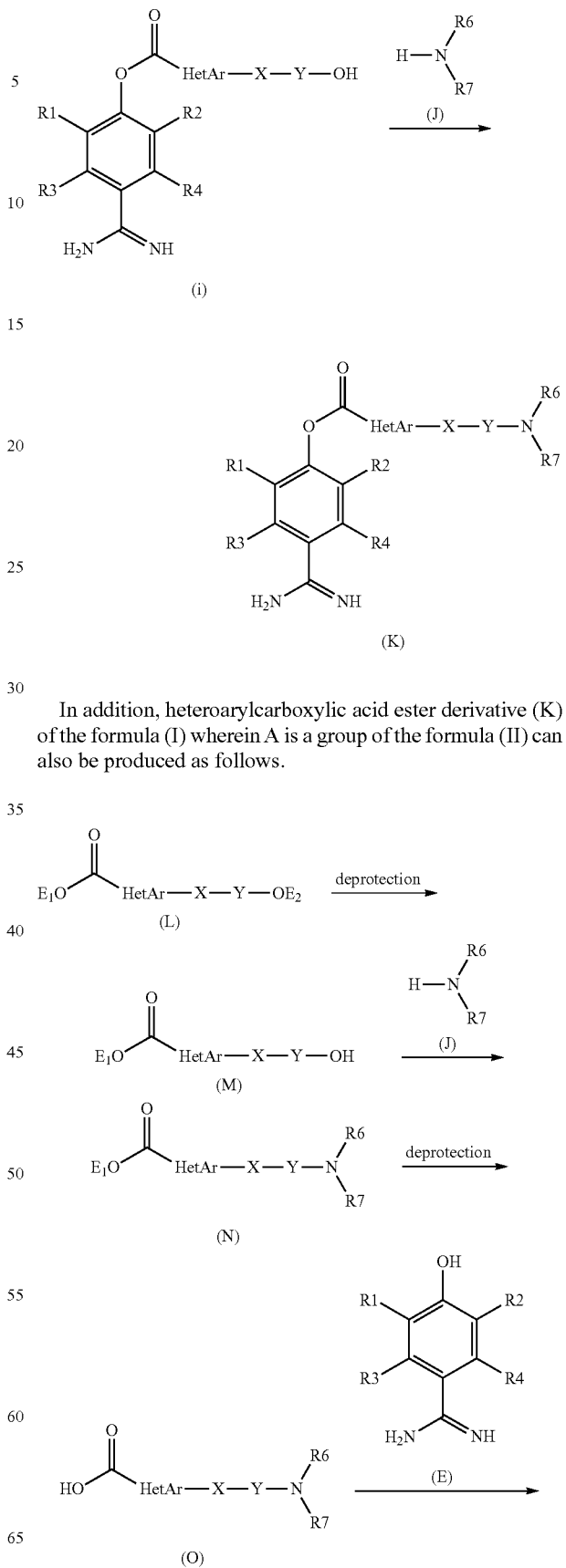

In addition, heteroarylcarboxylic acid ester derivative (K) of the formula (I) wherein A is a group of the formula (II) can also be produced as follows.

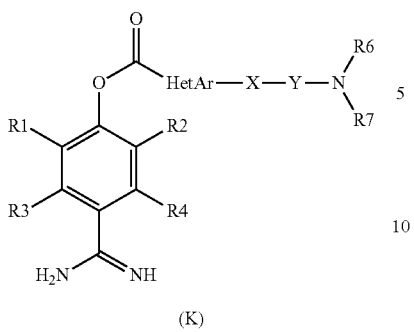

(K)

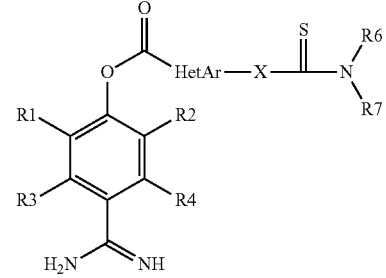

(S)

Carboxylic acid, thiocarboxylic acid, or sulfonic acid derivative (M) can be obtained by deprotecting ester, thioester, or sulfonic acid ester derivative (L) by, for example, hydrolysis with a base such as sodium hydroxide and the like, hydrolysis with an acid such as hydrochloric acid, trifluoroacetic acid, and the like or treatment with, for example, 10% palladium/carbon and the like under a hydrogen atmosphere. Amide derivative (N) can be synthesized by amidating carboxylic acid, thiocarboxylic acid, or sulfonic acid derivative (M) with amine (J). Amide derivative (N) can be converted to carboxylic acid derivative (O) by hydrolysis in, for example, a solvent that does not adversely influence the reaction, such as tetrahydrofuran, methanol, and the like, by using, for example, a base such as sodium hydroxide and the like. The objective heteroarylcarboxylic acid ester derivative (K) can be produced by esterifying carboxylic acid derivative (O) with amidinophenol derivative (E).

In addition, heteroarylcarboxylic acid ester derivative (S) of the formula (I) wherein Y is a thiocarbonyl group and A is a group of the formula (II) can also be produced as follows.

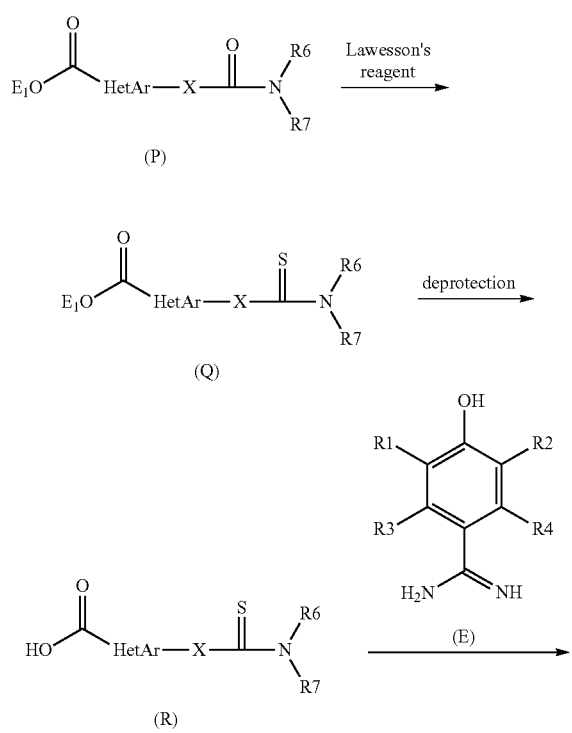

Thioamide derivative (Q) can be synthesized by reacting amide derivative (P) with Lawesson's reagent and the like in, for example, a solvent that does not adversely influence the reaction such as toluene and the like. Thioamide derivative (Q) can be converted to carboxylic acid derivative (R) by hydrolysis in, for example, a solvent that does not adversely influence the reaction, such as tetrahydrofuran, methanol, and the like, by using, for example, a base such as sodium hydroxide and the like. The objective heteroarylcarboxylic acid ester derivative (S) can be produced by esterifying carboxylic acid derivative (R) with amidinophenol derivative (E).

Other features of the invention will become apparent in the course of the following descriptions of exemplary embodiments which are given for illustration of the invention and are not intended to be limiting thereof.

EXAMPLES

Example 1

Synthesis of 4-amidino-2-nitrophenol hydrochloride (M-8)

4-Amidinophenol hydrochloride (1.0 g, 5.8 mmol) was dissolved in concentrated sulfuric acid (2.5 mL), and concentrated nitric acid (0.38 mL) was added at −15° C. The reaction mixture was stirred for 1 hour while maintaining the temperature of the reaction mixture at −15° C. to −2° C., and slowly added to ice water. The mixture was neutralized by slowly adding sodium hydrogen carbonate, and the precipitated orange solid was collected by filtration. The solid was washed with water and acetone, and suspended in methanol. 4N Hydrochloric acid/dioxane was added to dissolve the solid. Diisopropyl ether was added to the solution, and the precipitated solid was collected by filtration. The solid was washed with diisopropyl ether and dried to give the title compound (0.98 g) as a pale-yellow powder.

$^1$H-NMR (300 MHz, DMSO-d6) δ 12.40 (1H, br), 9.36 (2H, br), 9.05 (2H, br), 8.42 (1H, d, J=2.3 Hz), 7.98 (1H, dd, J=8.9, 2, 3 Hz), 7.34 (1H, d, J=8.9 Hz).

MS (ESI) m/z 182 (M+H)+

Example 2

Synthesis of 4-amidino-2-bromophenol trifluoroacetic acid salt (M-9)

4-Amidinophenol hydrochloride (1.0 g, 5.8 mmol) was dissolved in methanol (20 mL), the mixture was cooled to −78° C., and a solution of bromine (0.30 mL, 5.8 mmol) in methanol (10 mL) was added slowly. The reaction mixture was gradually warmed to room temperature and stirred overnight. The mixture was concentrated under reduced pressure and the obtained residue was purified by high performance liquid chromatography (water-acetonitrile, each containing 0.1% trifluoroacetic acid) to give the title compound (0.24 g, 0.73 mmol, 13%).

$^1$H-NMR (300 MHz, DMSO-d6) δ 11.58 (1H, br), 9.12 (2H, br), 8.83 (2H, br), 8.04 (1H, d, J=2.4 Hz), 7.69 (1H, dd, J=8.7, 2.4 Hz), 7.10 (1H, d, J=8.7 Hz).

MS (ESI) m/z 215[M($^{79}$Br)+H]$^+$, 217[M($^{81}$Br)+H]$^+$

Example 3

Synthesis of 4-amidino-2-chlorophenol trifluoroacetic acid salt (M-10)

4-Amidinophenol hydrochloride (0.50 g, 2.9 mmol) was dissolved in N,N-dimethylformamide (25 mL), N-chlorosuccinimide (0.39 g, 2.9 mmol) was added, and the mixture was stirred overnight. The reaction mixture was concentrated under reduced pressure, and the obtained residue was purified by high performance liquid chromatography (water-acetonitrile, each containing 0.1% trifluoroacetic acid) to give the title compound (0.25 g, 0.88 mmol, 30%).

$^1$H-NMR (300 MHz, DMSO-d6) δ 11.50 (1H, br), 9.12 (2H, br), 8.81 (2H, br), 7.91 (1H, d, J=2.3 Hz), 7.66 (1H, dd, J=8.7, 2.3 Hz), 7.13 (1H, d, J=8.7 Hz).

MS (ESI) m/z 171 [M($^{35}$Cl)+H]$^+$, 173 [M($^{37}$Cl)+H]$^+$

Example 4

Synthesis of 4-amidino-2-fluorophenol trifluoroacetic acid salt (M-11)

To 3-fluoro-4-hydroxybenzonitrile (3.0 g) were added ethanol (3 mL) and 4N hydrochloric acid-dioxane (27 mL), and the mixture was stirred at room temperature. After 18 hours, the mixture was concentrated and dried with a vacuum pump. Then, the mixture was dissolved in ethanol (60 mL), ammonium carbonate (10.5 g) was added, and the mixture was stirred at room temperature. After 20 hours, ethanol (150 mL) was added, the solid was filtered off, and the obtained solution was concentrated. The residue was purified by high performance liquid chromatography to give the title compound (786 mg, 2.9 mmol, 13%).

$^1$H-NMR (300 MHz, DMSO-d6) δ 11.28 (1H, br s), 9.19 (2H, br 5), 9.02 (2H, br s), 7.75 (1H, dd, J=2.4, 12.0 Hz), 7.59 (1H, m), 7.18 (1H, dd, J=8.4, 8.7 Hz).

MS (ESI) m/z 155 (M+H)+

Example 5

Synthesis of 4-amidino-3-fluorophenol trifluoroacetic acid salt (M-12)

In the same manner as in the synthesis of M-11 except that 2-fluoro-4-hydroxybenzonitrile was used instead of 3-fluoro-4-hydroxybenzonitrile, the title compound was obtained (yield 12%).

$^1$H-NMR (300 MHz, DMSO-d6) δ 9.38-8.61 (4H, br), 7.50 (1H, dd, J=9.6, 8.4 Hz), 6.78-6.73 (2H, m).

MS (ESI) m/z 155 (M+H)+

Example 6

Synthesis of 2-(diethylphosphono)propanoic acid tert-butyl ester (M-13)

2-Bromo-propanoic acid tert-butyl ester (17.4 g, 83 mmol) and triethyl phosphite (14.5 g, 87 mmol) were mixed, and the mixture was stirred at 110° C. overnight. The reaction mixture was dried under reduced pressure to give the title compound (23.9 g).

$^1$H-NMR (300 MHz, CDC$_3$) δ 4.20-4.08 (4H, m), 2.92 (1H, dq, J=30.6, 7.2 Hz), 1.48 (9H, s), 1.45 (3H, d, J=7.2 Hz), 1.40-1.30 (6H, m).

Example 7

Synthesis of 2-(diethylphosphono)butanoic acid tert-butyl ester (M-14)

Diethylphosphonoacetic acid tert-butyl ester (1.0 g, 4.0 mmol) was dissolved in N,N-dimethylformamide (1.4 and 60% sodium hydride (0.17 g, 4.4 mmol) was added at 0° C. After stirring at room temperature for 30 minutes, the reaction mixture was cooled again to 0° C., ethyl iodide (0.33 mL, 4.1 mmol) was added, and the mixture was stirred at room temperature overnight. The reaction mixture was diluted with ethyl acetate, washed successively with 0.5N hydrochloric acid, water and saturated brine, and concentrated under reduced pressure. The obtained residue was purified by silica gel column chromatography (ethyl acetate/hexane=57/43) to give the title compound (0.92 g, 3.3 mmol, 83%).

$^1$H-NMR (300 MHz, CDC$_3$) δ 4.20-4.09 (4H, m), 2.76 (1H, ddd, J=22.1, 10.4, 4.3 Hz), 2.00-1.83 (2H, m), 1.48 (9H, s), 1.35 (3H, t, J=7.2 Hz), 1.34 (3H, t, J=7.1 Hz), 0.99 (3H, td, J=7.5, 1.1 Hz).

Example 8

Synthesis of 2-(diethylphosphono)pentanoic acid tert-butyl ester (M-15)

In the same manner as in the synthesis of M-14 except that propyl bromide was used instead of ethyl iodide, the title compound was obtained (yield 77%).

$^1$H-NMR (300 MHz, CDC$_3$) δ 4.20-4.09 (4H, m), 2.85 (1H, ddd, J=22.3, 11.2, 3.8 Hz), 2.05-1.73 (4H, m), 1.47 (9H, s), 1.45-1.29 (6H, m), 0.93 (3H, t, J=7.2 Hz).

Example 9

Synthesis of 1-(diethylphosphono)ethanesulfonic acid isopropyl ester (M-16)

Step 1. Synthesis of Ethanesulfonic Acid Isopropyl Ester

To a solution of 2-propanol (2.4 mL, 32 mmol) in dichloromethane (50 were added triethylamine (3.5 ml, 25 mmol) and ethanesulfonyl chloride (2.0 mL, 21 mmol), and the mixture was stirred at room temperature for 3 hours. The reaction mixture was washed successively with 1N hydrochloric acid, saturated aqueous sodium hydrogen carbonate and saturated brine, and dried over sodium sulfate. The drying agent was filtered off, and the filtrate was concentrated under reduced pressure to give the title compound (2.4 g, 16 mmol, 75%).

$^1$H-NMR (300 MHz, CDC$_3$) δ 4.81 (1H, sep, J=6.4 Hz), 3.25 (2H, q, J=7.3 Hz), 1.30 (6H, d, J=6.4 Hz), 1.21 (3H, t, J=7.3 Hz).

Step 2. Synthesis of 1-(diethylphosphono)ethanesulfonic acid isopropyl ester (M-16)

A solution of ethanesulfonic acid isopropyl ester (1.0 g, 6.6 mmol) in tetrahydrofuran (15 mL) was cooled to −78° C., and n-butyllithium (1.57 M, 4.6 mL, 7.2 mmol) was added. After stirring at −78° C. for 20 minutes, diethyl chlorophosphate (0.52 mL, 3.6 mmol) was added to the reaction mixture, and the mixture was further stirred for 30 minutes. 1N Hydrochloric acid was added to the reaction mixture, and the mixture was extracted with ethyl acetate. The organic layer was washed with saturated brine and dried over sodium sulfate. The solvent was evaporated under reduced pressure and the obtained residue was purified by silica gel column chromatography (hexane/ethyl acetate=40/60) to give the title compound (0.61 g, 2.1 mmol, 58%).

$^1$H-NMR (300 MHz, CDC$_3$) δ 5.08 (1H, sep, J=6.3 Hz), 4.29-4.18 (4H, m), 3.57 (1H, dq, J=19.2, 7.3 Hz), 1.69 (3H, dd, J=15.6, 7.3 Hz), 1.45 (6H, d, J=6.3 Hz), 1.37 (6H, t, J=6.9 Hz).

Example 10

Synthesis of 5-[(1E)-2-(tert-butoxycarbonyl)-prop-1-en-1-yl]furan-2-carboxylic acid (M-1)

Step 1. Synthesis of 5-[(1E)-2-(tert-butoxycarbonyl)-prop-1-en-1-yl]furan-2-carboxylic acid methyl ester 5-Formyl-2-furancarboxylic acid (5 g, 35.7 mmol) was dissolved in acetone (100 mL), and trimethylsilyl-diazomethane/2M hexane solution (23.2 mL, 46.4 mmol) was slowly added dropwise at room temperature. After stirring at room temperature for 10 minutes, the solvent was evaporated under reduced pressure to give 5-formyl-2-furancarboxylic acid methyl ester as a crude product.

A tetrahydrofuran solution (30 mL) of M-13 (14.3 g, 53.6 mmol) was added dropwise to a stirring suspension of 60% sodium hydride (1.86 g, 46.4 mmol) in tetrahydrofuran (120 mL) at 0° C. The mixture was stirred at room temperature for 30 minutes, and a tetrahydrofuran solution (30 mL) of the crude product obtained earlier was added dropwise at 0° C. After stirring at room temperature overnight, the mixture was worked up according to a conventional method, and the object product was extracted by column chromatography (5-10% ethyl acetate/hexane mixed solvent) to give the title compound (5.55 g, 20.8 mmol, 2 steps 58%).

$^1$H-NMR (300 MHz, CDC$_3$) δ 7.39 (1H, d, J=0.9 Hz), 7.22 (1H, d, J=3.6 Hz), 6.64 (1H, d, J=3.6 Hz), 3.92 (3H, s), 2.21 (3H, d, J=0.9 Hz), 1.53 (9H, s).

MS (ESI) m/z 267 (M+H)+

Step 2. Synthesis of 5-[(1E)-2-(tert-butoxycarbonyl)-prop-1-en-1-yl]furan-2-carboxylic acid (M-1)

5-[(1E)-2-(tert-butoxycarbonyl)-prop-1-en-1-yl]furan-2-carboxylic acid methyl ester (1.11 g, 4.17 mmol) obtained in step 1 was dissolved in methanol (7.65 mL), 1N aqueous lithium hydroxide solution (6.25 mL, 6.25 mmol) was added, and the mixture was stirred at room temperature for 100 minutes. 1N aqueous hydrochloric acid solution (6.25 mL) was added, the mixture was stirred for 10 minutes, and the solvent was evaporated under reduced pressure. To the residue were added ethyl acetate and 0.5N aqueous hydrochloric acid solution, the organic layer was extracted, and the aqueous layer was extracted three times with ethyl acetate. The organic layers were collected, washed with saturated brine and dried by dehydration with sodium sulfate. The solvent of the filtrate after filtration was evaporated under reduced pressure to give the title compound.

$^1$H-NMR (300 MHz, DMSO-d6) δ 7.33-7.25 (2H, m), 6.98 (1H, d, J=3.6 Hz), 2.15 (3H, s), 1.48 (9H, s).

MS (ESI) m/z 253 (M+H)+

Example 11

Synthesis of 5-(2-tert-butoxycarbonylpropyl)furan-2-carboxylic acid (M-2)

Step 1. Synthesis of 5-(2-tert-butoxycarbonylpropyl)-furan-2-carboxylic acid methyl ester (2E)-(5-Methoxycarbonylfuran-2-yl)-2-methylpropenoic acid tert-butyl ester (2.96 g, 11.1 mmol) was dissolved in methanol (100 mL), 10% palladium/carbon (0.3 g) was added, and the mixture was stirred at room temperature for 2 hours under a hydrogen atmosphere. After completion of the reaction, palladium/carbon was removed by celite filtration, and the solvent was evaporated under reduced pressure to give the title compound (2.72 g).

$^1$H-NMR (300 MHz, DMSO-d6) δ 7.20 (1H, d, J=3.3 Hz), 6.35 (1H, d, J=3.3 Hz), 3.76 (3H, s), 2.90-2.60 (3H, m), 1.34 (9H, s), 1.07 (3H, d, J=6.9 Hz).

Step 2. Synthesis of 5-(2-tert-butoxycarbonylpropyl)-furan-2-carboxylic acid (M-2)

5-(2-tert-Butoxycarbonylpropyl)furan-2-carboxylic acid methyl ester (1.0 g, 3.76 mmol) obtained in step 1 was dissolved in tetrahydrofuran (4.5 mL) and methanol (3 mL), 1N aqueous sodium hydroxide solution (4.5 mL) was added, and the mixture was stirred overnight. The mixture was neutralized with 1N hydrochloric acid, extracted with ethyl acetate, and washed successively with water and saturated brine. After drying over anhydrous magnesium sulfate, the drying agent was filtered off, and the solvent was evaporated to give the title compound (0.98 g).

$^1$H-NMR (300 MHz, DMSO-d6) δ 7.11 (1H, s), 6.32 (1H, s), 2.95-2.65 (3H, m), 2.50 (3H, s), 1.35 (9H, s).

MS (ESI) m/z 253 (M+H)+

Example 12

Synthesis of 5-[(1E)-2-(tert-butoxycarbonyl)-prop-1-en-1-yl]thiophene-2-carboxylic acid (M-3)

Step 1. Synthesis of 5-[(1E)-2-(tert-butoxycarbonyl)-prop-1-en-1-yl]thiophene-2-carboxylic acid methyl ester M-13 (2.08 g, 7.8 mmol) was dissolved in tetrahydrofuran (30 mL), 60% sodium hydride (0.37 g, 9.25 mmol) was added at 0° C., and the mixture was stirred for 30 minutes. To the reaction mixture was added a solution of 5-formyl-2-thiophenecarboxylic acid methyl ester (1.02 g, 6.0 mmol) in tetrahydrofuran (5 mL), and the mixture was stirred at room temperature overnight. The solvent was evaporated, and the residue was partitioned between ethyl acetate and 1N hydrochloric acid, and washed successively with water and saturated brine. After drying over anhydrous magnesium sulfate, the residue was purified by silica gel column chromatography to give the title compound (1.18 g).

$^1$H-NMR (300 MHz, CDC$_3$) δ 7.75 (1H, d, J=4.2 Hz), 7.69 (1H, s), 7.19 (1H, d, J=4.2 Hz), 3.90 (3H, s), 2.19 (3H, s), 1.54 (9H, s).

Step 2. Synthesis of 5-[(1E)-2-(tert-butoxycarbonyl)-prop-1-en-1-yl]thiophene-2-carboxylic acid (M-3)

5-[(1E)-2-(tert-Butoxycarbonyl)-prop-1-en-1-yl]thiophene-2-carboxylic acid methyl ester (1.18 g, 4.19 mmol) obtained in step 1 was dissolved in tetrahydrofuran (5 mL), 1N aqueous lithium hydroxide solution (4.6 mL) was added, and the mixture was stirred overnight. The mixture was neutralized with 1N hydrochloric acid, and extracted with ethyl acetate. The organic layer was dried over anhydrous magnesium sulfate, and the solvent was evaporated to give the title compound (1.06 g).

$^1$H-NMR (300 MHz, CDC$_3$) δ 7.70 (1H, d, J=3.9 Hz), 7.66 (1H, s), 7.63 (1H, d, J=3.9 Hz), 7.16 (1H, d, J=3.9 Hz), 2.16 (3H, s), 1.51 (9H, s).

MS (ESI) m/z 269 (M+H)+

Example 13

Synthesis of 5-(2-tert-butoxycarbonylpropyl)-thiophene-2-carboxylic acid (M-4)

Using 5-[(1E)-2-(tert-butoxycarbonyl)-prop-1-en-1-yl]thiophene-2-carboxylic acid methyl ester obtained in Example 12, step 1 and in the same manner as in Example 11, the title compound was obtained.

$^1$H-NMR (300 MHz, CDC$_3$) δ 7.72 (1H, d, J=3.6 Hz), 6.85 (1H, d, J=3.6 Hz), 3.24-2.65 (3H, m), 1.42 (9H, s), 1.19 (3H, d, J=6.9 Hz).

MS (ESI) m/z 271 (M+H)+

Example 14

Synthesis of 2-[{3-triisopropylsilyloxypropyl}-amino]acetic acid tert-butyl ester (M-5)

To a solution of 3-amino-1-propanol (2.0 mL, 26 mmol) in dichloromethane (20 mL) was added triisopropylsilyl trifluoromethanesulfonate (7.2 mL, 27 mmol), and the mixture was stirred at room temperature for 1 hour. Triethylamine (3.7 mL, 26 mmol) and bromoacetic acid tert-butyl ester (3.1 mL, 21 mmol) were added to the reaction mixture, and the mixture was further stirred at room temperature for 1 hour. The reaction mixture was diluted with dichloromethane and washed with saturated aqueous sodium hydrogen carbonate. The organic layer was dried over sodium sulfate and concentrated under reduced pressure, and the obtained residue was purified by silica gel column chromatography (dichloromethane/methanol=97/3) to give the title compound (1.85 g, 5.4 mmol, 25%).

$^1$H-NMR (300 MHz, CDC$_3$) δ 3.96 (2H, t, J=5.4 Hz), 3.80 (2H, s), 3.34 (2H, t, J=5.9 Hz), 2.03 (2H, m), 1.50 (9H, s), 1.17-1.07 (21H, m).

Example 15

Synthesis of N-(3-triisopropylsilyloxypropyl)-taurine isopropyl ester (M-7)

Step 1. Synthesis of Vinylsulfonic Acid Isopropyl Ester

2-Chloroethylsulfonyl chloride (2 g, 12.3 mmol), isopropanol (1 mL), and pyridine (2.7 mL) were dissolved in dichloromethane (20 mL), and the mixture was stirred at room temperature for 3 hours. The reaction mixture was washed successively with 1N hydrochloric acid and water, and the organic layer was dried over anhydrous magnesium sulfate. The drying agent was filtered, and the solvent was evaporated to give the title compound (1.06 g).

$^1$H-NMR (300 MHz, CDC$_3$) δ 6.56 (1H, dd, J=9.9, 16.8 Hz), 6.39 (1H, d, J=16.8 Hz), 6.07 (1H, d, J=9.9 Hz), 4.81 (1H, sep, J=6.3 Hz), 1.40 (6H, d, J=6.3 Hz).

Step 2. Synthesis of N-(3-triisopropylsilyloxypropyl)-taurine isopropyl ester (M-7)

Vinylsulfonic acid isopropyl ester (0.3 g, 2.00 mmol) obtained in step 1 and 3-triisopropylsilyloxypropylamine (0.9 g, 3.89 mmol) were dissolved in methanol (10 mL), and the mixture was stirred at room temperature overnight. The solvent was evaporated and the residue was purified by silica gel column chromatography to give the title compound (0.65 g).

$^1$H-NMR (300 MHz, CDC$_3$) δ 4.97 (1H, sep, J=6.0 Hz), 3.78 (2H, t, J=6.9 Hz), 3.29 (2H, t, J=6.9 Hz), 3.13 (2H, t, J=6.9 Hz), 2.78 (2H, t, J=6.9 Hz), 1.74 (2H, m), 1.42 (6H, d, J=6.0 Hz), 1.05 (21H, m).

Example 16

Synthesis of (2E)-3-[5-(4-amidinophenoxycarbonyl)-furan-2-yl]-2-methylpropenoic acid trifluoroacetic acid salt (A-3)

M-1, 4-hydroxybenzamidine hydrochloride (712 mg, 4.17 mmol) and WSC hydrochloride (869 mg, 4.53 mmol) were dissolved in pyridine (10 mL), and the mixture was stirred at room temperature overnight. The solvent was evaporated under reduced pressure, trifluoroacetic acid (10 mL) was added, and the mixture was stirred at room temperature for 15 minutes. The solvent was evaporated under reduced pressure, and the resultant solid was washed with diethyl ether, collected by filtration with Kiriyama funnel, and dried in a desiccator to give the title compound (1.46 g, 3.41 mmol, 3 steps 82%).

$^1$H-NMR (300 MHz, DMSO-d6) δ 9.35 (2H, br s), 8.95 (2H, br s), 7.91 (2H, d, J=8.7 Hz), 7.72 (1H, d, J=3.9 Hz), 7.59 (2H, d, J=8.7 Hz), 7.43 (1H, s), 7.14 (1H, d, J=3.9 Hz), 2.73 (1H, s), 2.24 (3H, s).

MS (ESI) m/z 315 (M+H)+

Example 17

Synthesis of 3-[5-(4-amidinophenoxycarbonyl)furan-2-yl]-2-methylpropionic acid trifluoroacetic acid salt (A-6)

10% Palladium/carbon (49.5 mg) and A-3 (495 mg, 1.16 mmol) were suspended in methanol (3.0 mL), and the suspension was stirred at room temperature overnight under a hydrogen atmosphere (1 atm). After completion of the reaction, palladium/carbon was removed by celite filtration. The solvent was evaporated under reduced pressure, and the object product was extracted by high performance liquid chromatography (10-40% water (containing 0.1% trifluoroacetic acid)/acetonitrile (containing 0.1% trifluoroacetic acid) mixed solvent) to give the title compound (246 mg, 0.57 mmol, 49.3%).

$^1$H-NMR (300 MHz, DMSO-d6) δ 9.35 (2H, br s), 9.10 (2H, br s), 7.90 (2H, d, J=6.9 Hz), 7.61-7.52 (3H, m), 6.52

(1H, d, J=3.6 Hz), 3.13-2.98 (1H, m), 2.91-2.70 (2H, m), 1.14 (3H, d, J=6.9 Hz).
MS (ESI) m/z 317 (M+H)+

Example 18

Synthesis of N-{(2E)-3-[5-(4-amidino-2-phenoxycarbonyl)furan-2-yl]-2-methylpropenoyl}-N-(3-hydroxypropyl)-β-alanine trifluoroacetic acid salt (A-12)

Step 1. Synthesis of 3-triisopropylsilyloxypropylamine

3-Hydroxylpropylamine (100 µL, 1.31 mmol) was dissolved in dichloromethane (4.4 mL), and triisopropylsilyl triflate (371 µL, 1.38 mmol) was added dropwise at room temperature. After stirring at room temperature for 15 minutes, the mixture was worked up according to a conventional method to give the title compound as a crude product.

Step 2. Synthesis of N-(3-triisopropylsilyloxypropyl)-β-alanine tert-butyl ester (M-6)

The crude product obtained in step 1 was dissolved in toluene (3.0 mL), acrylic acid tert-butyl ester (173 µL, 1.19 mmol) was added, and the mixture was stirred under reflux for 6 hours. The solvent was evaporated under reduced pressure, and crudely purified by silica gel column chromatography (0-4% methanol/dichloromethane mixed solvent) to give the title compound as a crude product.

Step 3. Synthesis of N-{(2E)-3-[5-(4-amidino-2-phenoxycarbonyl)furan-2-yl]-2-methylpropenoyl}-N-(3-hydroxypropyl)-β-alanine trifluoroacetic acid salt (A-12)

A-3 (87 mg, 0.20 mmol) was dissolved in thionyl chloride (500 µL), and the mixture was stirred at 70° C. for 10 minutes. Thionyl chloride was evaporated under reduced pressure to give acid chloride. The obtained acid chloride was dissolved in dichloromethane (500 µL), the amine obtained in step 2 and pyridine (250 µL) were added thereto, and the mixture was stirred at room temperature for 30 minutes. After evaporation of the solvent, trifluoroacetic acid (500 µL: containing 5% water) was added, and the mixture was stirred at room temperature overnight. Trifluoroacetic acid was evaporated under reduced pressure, saturated aqueous sodium hydrogen carbonate solution (1 mL) was added, and the mixture was stirred for 1 hour. The object product was extracted by high performance liquid chromatography (5-35% water (containing 0.1% trifluoroacetic acid)/acetonitrile (containing 0.1% trifluoroacetic acid) mixed solution) to give the title compound (4.0 mg, 0.007 mmol, 3.5%).
MS (ESI) m/z 444 (M+H)+

Example 19

Synthesis of N-{(2E)-3-[5-(4-amidinophenoxycarbonyl)furan-2-yl]-2-methylpropenyl}-L-glutamic acid trifluoroacetic acid salt (A-13)

A-3 (49 mg, 0.11 mmol) was dissolved in thionyl chloride (0.5 mL), and the mixture was heated at 70° C. for 5 minutes. Thionyl chloride was evaporated under reduced pressure, and the obtained residue was dissolved in dichloromethane (0.35 mL). Glutamic acid di-tert-butyl ester hydrochloride (50.8 mg, 0.17 mmol) and pyridine (0.15 mL) were added, and the mixture was stirred at room temperature for 40 minutes. The solvent was evaporated under reduced pressure, trifluoroacetic acid (0.5 mL: containing 5% water) was added, and the mixture was stirred at room temperature for 2 hours. The solvent was evaporated again, water (0.5 mL) was added, and the mixture was stirred at room temperature overnight. The solvent was evaporated under reduced pressure, and the object product was extracted by high performance liquid chromatography (5-35% water (containing 0.1% trifluoroacetic acid)/acetonitrile (containing 0.1% trifluoroacetic acid) mixed solution) to give the title compound (32 mg, 0.06 mmol, 50%).
$^1$H-NMR (300 MHz, DMSO-d6) δ 9.35 (2H, br s), 9.02 (2H, br s), 8.35 (1H, d, J=7.5 Hz), 7.91 (2H, d, J=8.7 Hz), 7.72 (1H, d, J=3.3 Hz), 7.59 (2H, d, J=7.5 Hz), 7.18 (1H, s), 7.04 (1H, d, J=3.3 Hz), 4.35-4.22 (2H, m), 2.42-2.30 (2H, m), 2.22 (3H, s), 2.15-1.81 (2H, m).
MS (ESI) m/z 444 (M+H)+

Example 20

Synthesis of 3-[5-(4-amidinophenoxycarbonyl)furan-2-yl]-2-ethylpropionic acid trifluoroacetic acid salt (A-29)

Step 1. Synthesis of [5-(benzyloxycarbonyl)furan-2-yl]-2-ethylpropenoic acid tert-butyl ester 5-Formyl-2-furancarboxylic acid benzyl ester (200 mg, 0.87 mmol) and M-14 (364.4 mg, 1.30 mmol) were dissolved in tetrahydrofuran (3.0 mL), and 60% sodium hydride (45.3 mg, 1.13 mmol) was added at 0° C. After removing from the ice bath, the mixture was stirred at room temperature for 30 minutes. The mixture was worked up according to a conventional method to give the title compound as a crude product.

Step 2. Synthesis of 3-(5-hydroxycarbonylfuran-2-yl)-2-ethylpropionic acid tert-butyl ester The crude product obtained in step 1 and 10% palladium/carbon (30 mg) were suspended in ethanol (3.0 mL), and the suspension was stirred overnight at ambient temperature and normal pressure under a hydrogen atmosphere. Palladium/carbon was removed by celite filtration, and the solvent was evaporated under reduced pressure to give the title compound as a crude product.

Step 3. Synthesis of 3-[5-(4-amidinophenoxycarbonyl)-furan-2-yl]-2-ethylpropionic acid trifluoroacetic acid salt (A-29)

The crude product obtained in step 2 and 4-hydroxybenzamidine hydrochloride (180 mg, 1.04 mmol) were dissolved in pyridine (3.0 mL), and WSC hydrochloride (217 mg, 1.13 mmol) was added with stirring at room temperature. After stirring at room temperature for 100 minutes, the solvent was evaporated under reduced pressure. Trifluoroacetic acid (3.0 mL) was added to the obtained residue, and the mixture was stirred at room temperature for 15 minutes. The solvent was evaporated, and the object product was extracted by column chromatography (5-35% water (containing 0.1% trifluoroacetic acid/acetonitrile (containing 0.1% trifluoroacetic acid) mixed solvent) to give the title compound (225 mg, 0.57 mmol, 3 steps 66%).

$^1$H-NMR (300 MHz, DMSO-d6) δ 9.34 (2H, br s), 9.13 (2H, br s), 7.90 (2H, d, J=8.7 Hz), 7.63-7.49 (3H, m), 6.51 (1H, d, J=3.6 Hz), 3.10-2.82 (2H, m), 2.69-2.55 (1H, m), 1.64-1.49 (2H, m), 0.90 (3H, t, J=7.5 Hz).

MS (ESI) m/z 331 (M+H)+

Example 21

Synthesis of N-(5-(4-amidinophenoxycarbonyl)furan-2-ylacetic acid trifluoroacetic acid salt (A-32)

Step 1. Synthesis of 5-ethoxycarbonylfuran-2-ylacetic acid

5-Chloromethyl-2-furancarboxylic acid ethyl ester (1.0 g, 5.3 mmol), potassium iodide (0.044 g, 0.27 mmol), and chloro(1,5-cyclooctadiene)rhodium(I) dimer (0.26 g, 0.53 mmol) were dissolved in formic acid (25 mL), and the mixture was stirred at 75° C. for 6 hours under a carbon monoxide atmosphere. The solvent was evaporated, and the residue was partitioned between ethyl acetate and aqueous sodium hydrogen carbonate solution. The organic layer was washed with saturated brine and dried over anhydrous magnesium sulfate. The drying agent was filtered off, the solvent was evaporated, and the residue was purified by silica gel column chromatography to give the title compound (0.61 g).

$^1$H-NMR (300 MHz, CDC$_3$) δ 7.13 (1H, d, J=3.6 Hz), 6.42 (1H, d, J=3.6 Hz), 4.35 (2H, q, J=7.5 Hz), 3.83 (2H, s), 1.37 (3H, t, J=7.5 Hz).

MS (ESI) m/z 199 (M+H)+

Step 2. Synthesis of 5-ethoxycarbonylfuran-2-ylacetic acid tert-butyl ester

5-Ethoxycarbonylfuran-2-ylacetic acid (0.61 g, 3.08 mmol) obtained in step 1 was dissolved in thionyl chloride (10 mL), and the mixture was stirred at 70° C. for 1 hour. The solvent was evaporated under reduced pressure, tert-butanol (5 mL) and triethylamine (2 mL) were added, and the mixture was stirred for 30 minutes. The solvent was evaporated, and the residue was purified by silica gel column chromatography to give the title compound (0.37 g).

$^1$H-NMR (300 MHz, CDC$_3$) δ 7.13 (1H, d, J=3.3 Hz), 6.36 (1H, d, J=3.3 Hz), 4.35 (2H, q, J=6.9 Hz), 3.68 (2H, s), 1.25 (9H, s), 1.25 (3H, t, J=6.9 Hz).

Step 3. Synthesis of 5-tert-butoxycarbonylmethyl-2-furancarboxylic acid

5-Ethoxycarbonylfuran-2-ylacetic acid tert-butyl ester (0.37 g, 1.46 mmol) obtained in step 2 was dissolved in tetrahydrofuran (2 mL), dissolved in 1N aqueous sodium hydroxide solution (1.5 mL), and the mixture was stirred overnight. 1N Hydrochloric acid (1.5 mL) was added to the reaction mixture, and the mixture was neutralized, purified by high performance liquid chromatography and freeze-dried to give the title compound (80 mg).

$^1$H-NMR (300 MHz, CDC$_3$) δ 7.26 (1H, d, J=3.6 Hz), 6.42 (1H, d, J=3.6 Hz), 3.70 (2H, s), 1.47 (9H, s).

Step 4. Synthesis of 5-(4-amidinophenoxycarbonyl)furan-2-ylacetic acid trifluoroacetic acid salt (A-32)

5-tert-Butoxycarbonylmethyl-2-furancarboxylic acid (80 mg, 0.24 mmol) obtained in step 3 and 4-hydroxybenzamidine hydrochloride (80 mg, 0.46 mmol) were dissolved in pyridine (5 mL), WSC hydrochloride (0.10 g, 0.52 mmol) was added, and the mixture was stirred overnight. After evaporation of the solvent, trifluoroacetic acid (5 mL) was added, and the mixture was stirred for 30 minutes. The mixture was purified by high performance liquid chromatography and freeze-dried to give the title compound.

$^1$H-NMR (300 MHz, DMSO-d6) δ 9.34 (2H, s), 9.01 (2H, s), 7.89 (2H, J=8.7 Hz), 6.64 (1H, d, J=3.6 Hz), 7.57 (3H, m), 3.89 (2H, s).

MS (ESI) m/z 289 (M+H)+

Example 22

Synthesis of N-{3-[5-(4-amidino-2-fluorophenoxycarbonyl)furan-2-yl]-2-methylpropanoyl}-N-(D)-aspartic acid trifluoroacetic acid salt (A-35)

A-33 (68 mg, 0.15 mmol) and (D)-aspartic acid dibenzyl ester 4-toluenesulfonate (96 mg, 0.20 mmol) were dissolved in pyridine (0.5 mL), WSC hydrochloride (44 mg, 0.23 mmol) was added, and the mixture was stirred at room temperature overnight. After evaporation of the solvent, ethanol (2 mL) and 10% palladium/carbon (10 mg) were added, and the mixture was stirred at room temperature overnight under a hydrogen atmosphere. The reaction mixture was filtered through celite, and the filtrate was concentrated under reduced pressure to give a residue. The obtained residue was purified by high performance liquid chromatography (water-acetonitrile, each containing 0.1% trifluoroacetic acid) to give the title compound (12.7 mg).

$^1$H-NMR (DMSO-d6) δ 9.42 (br s, 2H), 9.19 (br s, 2H), 8.42-8.31 (m, 1H), 7.93 (d, J=11.4 Hz, 1H), 7.81-7.69 (m, 2H), 7.61-7.56 (m, 1H), 6.56-6.45 (m, 1H), 4.61-4.42 (m, 1H), 3.11-2.88 (m, 2H), 2.87-2.47 (m, 3H), 1.06 (t, J=6.6 Hz, 1H).

MS (ESI) m/z 450 (M+H)+

Example 23

Synthesis of 1-[5-(4-amidinophenoxycarbonyl)furan-2-yl]propane-2-sulfonic acid trifluoroacetic acid salt (A-36)

Step 1. Synthesis of isopropyl 1-[5-(benzyloxycarbonyl)-furan-2-yl]propane-2-sulfonate Using M-16 and 4-hydroxybenzamidine hydrochloride and by an operation in the same manner as in Example 20, the title compound was obtained.

$^1$H-NMR (300 MHz, CDCl3) δ 7.46-7.33 (6H, m), 7.25 (1H, d, J=3.7 Hz), 6.71 (1H, d, J=3.7 Hz), 5.36 (2H, s), 4.77 (1H, sep, J=6.2 Hz), 2.45 (1H, d, J=1.2 Hz), 1.39 (3H, d, J=6.2 Hz).

Step 2. Synthesis of 1-[5-(4-amidinophenoxycarbonyl)-furan-2-yl]propane-2-sulfonic acid trifluoroacetic acid salt (A-36)

Isopropyl 1-[5-(benzyloxycarbonyl)furan-2-yl]propane-2-sulfonate obtained in step 1 was stirred in 4N hydrochloric acid overnight, and the mixture was purified by high performance liquid chromatography and freeze-dried to give the title compound.

$^1$H-NMR (300 MHz, DMSO-d6) δ 9.32 (2H, br), 8.90 (2H, br), 7.87 (2H, 0.30 d, J=8.7 Hz), 7.55 (2H, d, J=8.7 Hz), 7.51

(1H, d, J=3.6 Hz), 6.54 (1H, d, J=3.6 Hz), 2.73-2.57 (3H, m), 1.05 (3H, d, J=6.9 Hz).

MS (ESI) m/z 353 (M+H)+

Example 24

Synthesis of N-[5-(4-amidinophenoxycarbonyl)furan-2-ylacetyl]-(L)-aspartic acid trifluoroacetic acid salt (A-39)

5-Carboxymethyl-2-furancarboxylic acid (117 mg, 0.69 mmol) obtained as a byproduct in Example 21, step 3 and L-aspartic acid di-tert-butyl ester hydrochloride (193 mg, 0.68 mmol) were dissolved in dichloromethane (5 mL), WSC hydrochloride (158 mg, 0.82 mmol) and triethylamine (0.5 mL) were added, and the mixture was stirred overnight. After evaporation of the solvent, the residue was purified by high performance liquid chromatography and freeze-dried. The obtained solid (31 mg) and 4-hydroxybenzamidine hydrochloride (15 mg, 0.087 mmol) were dissolved in pyridine (5 mL), WSC hydrochloride (30 mg, 0.16 mmol) was added, and the mixture was stirred overnight. After evaporation of the solvent, trifluoroacetic acid (5 mL) was added, and the mixture was stirred for 30 min. The mixture was purified by high performance liquid chromatography and freeze-dried to give the title compound (23 mg).

$^1$H-NMR (300 MHz, DMSO-d6) δ 9.34 (2H, s), 9.09 (2H, s), 8.55 (1H, d, J=7.8 Hz), 7.89 (2H, d, J=8.7 Hz), 7.56 (3H, m), 6.58 (1H, d, J=3.6 Hz), 4.53 (1H, m), 2.89 (2H, s), 2.64 (2H, m).

MS (ESI) m/z 404 (M+H)+

Example 25

Synthesis of (2E)-3-[5-(4-amidinophenoxycarbonyl)-thiophen-2-yl]-2-methylpropenoic acid trifluoroacetic acid salt (B-1)

Step 1. Synthesis of 3-[5-(4-amidinophenoxycarbonyl)-thiophen-2-yl]-2-methylpropenoic acid tert-butyl ester 5-(2-(tert-Butoxycarbonyl)-1-propenyl)-2-thiophenecarboxylic acid (0.51 g, 1.89 mmol) and 4-hydroxybenzamidine hydrochloride (0.33 g, 1.89 mmol) were dissolved in pyridine (10 mL), WSC hydrochloride (0.54 g, 2.8 mmol) was added, and the mixture was stirred overnight. The mixture was purified by high performance liquid chromatography and freeze-dried to give the title compound (0.63 g).

$^1$H-NMR (300 MHz, DMSO-d6) δ 9.33 (2H, s), 8.98 (2H, s), 8.07 (1H, d, J=3.9 Hz), 7.89 (2H, d, J=8.7 Hz), 7.78 (1H, s), 7.63 (1H, d, J=3.9 Hz), 7.58 (1H, d, J=8.7 Hz), 2.15 (3H, s), 1.49 (9H, s).

Step 2. Synthesis of (2E)-3-[5-(4-amidinophenoxycarbonyl)thiophen-2-yl]-2-methylpropenoic acid trifluoroacetic acid salt (B-1)

To 3-[5-(4-amidinophenoxycarbonyl)thiophen-2-yl]-2-methylpropenoic acid tert-butyl ester (0.63 g) was added trifluoroacetic acid (5 mL), and the mixture was stirred for 30 minutes. The solvent was evaporated to give the title compound (0.62 g).

$^1$H-NMR (300 MHz, DMSO-d6) δ 9.35 (2H, s), 9.00 (2H, s), 8.09 (1H, d, J=3.9 Hz), 7.88 (3H, m), 7.60 (3H, m), 2.18 (3H, s).

MS (ESI) m/z 331 (M+H)+

Example 26

Synthesis of 3-[5-(4-amidinophenoxycarbonyl)-thiophen-2-yl]-2-methylpropanoic acid trifluoroacetic acid salt (B-6)

B-1 (50 mg, 0.11 mmol) was dissolved in a mixed solution of ethanol/water (1/1, 5 mL), a catalytic amount of 10% palladium/carbon was added, and the mixture was stirred at room temperature for 5 hours under a hydrogen atmosphere. The reaction mixture was filtered, and the solvent was evaporated to give the title compound.

$^1$H-NMR (300 MHz, DMSO-d6) δ 9.34 (2H, s), 9.01 (2H, s), 7.91 (2H, m), 7.56 (1H, d, J=9.0 Hz), 7.10 (1H, d, J=3.6 Hz), 3.37 (1H, m), 3.01 (1H, m), 2.73 (1H, m), 1.13 (3H, d, J=4.2 Hz).

MS (ESI) m/z 333 (M+H)+

Example 27

Synthesis of N-{(2E)-3-[5-(4-amidinophenoxycarbonyl)thiophen-2-yl]-2-methylpropenoyl}-N-hydroxypropyltaurine trifluoroacetic acid salt (B-7)

B-1 (30 mg, 0.068 mmol) was suspended in thionyl chloride (4 mL), and the suspension was stirred at 70° C. for 30 minutes. After evaporation of the solvent, dichloromethane (2 mL), M-7 (25 mg, 0.072 mmol) and pyridine (50 µL) were added, and the mixture was stirred for 30 minutes. After evaporation of the solvent, trifluoroacetic acid (3 mL) was added, and the mixture was stirred for 30 minutes. After evaporation of the solvent, 4M hydrochloric acid (2 mL) and acetonitrile (0.5 mL) were added, and the mixture was stirred at room temperature for 2 days. The mixture was purified by high performance liquid chromatography and freeze-dried to give the title compound (4.9 mg).

$^1$H-NMR (300 MHz, DMSO-d6) δ 9.35 (2H, s), 8.91 (2H, s), 8.03 (1H, d, J=4.2 Hz), 7.90 (2H, d, J=8.7 Hz), 7.60 (2H, d, J=8.7 Hz), 7.40 (1H, d, J=4.2 Hz), 6.84 (1H, s), 4.48 (1H, br s), 3.55 (2H, m), 3.20-3.45 (4H, m), 2.70 (2H, m), 2.15 (3H, s), 1.67 (2H, m).

MS (ESI) m/z 496 (M+H)+

Example 28

Synthesis of N-{3-[5-(4-amidino-2-nitrophenoxycarbonyl)thiophen-2-yl]-2-methylpropanoyl}-N-(3-hydroxypropyl)glycine hydrochloride (B-11)

Step 1. Synthesis of N-{(1E)-3-[5-(methoxycarbonyl)-thiophen-2-yl]-2-methylpropenoyl}-N-[3-(triisopropylsilyloxy)-propyl]glycine tert-butyl ester To 5-[(1E)-2-(tert-butoxycarbonyl)-2-methyl-prop-1-en-1-yl]thiophene-2-carboxylic acid methyl ester (600 mg, 2.13 mmol) obtained in Example 12, step 1 was added trifluoroacetic acid (5 mL), and the mixture was stirred at room temperature for 10 minutes. The reaction mixture was concentrated under reduced pressure. The obtained residue was dissolved in dichloromethane (15 mL), oxalyl chloride (0.37 mL, 4.26 mmol) and N,N-dimethylformamide (50 µL) were added, and the mixture was stirred at room temperature for 15 minutes. The reaction mixture was concentrated under reduced pressure, the obtained residue was dissolved in dichloromethane (10 mL), and M-5 (0.81 g, 2.34 mmol) obtained in step 1 and pyridine (5 mL) were added. After stirring at room temperature for 15 minutes, the reaction mixture was concentrated under reduced pressure, and the obtained residue was purified by silica gel column chromatography (hexane/ethyl acetate=80/20) to give the title compound (477 mg, 0.86 mmol, 40%).

MS (ESI) m/z 554 (M+H)+

Step 2. Synthesis of N-{3-[5-(4-amidino-2-nitrophenoxycarbonyl)thiophen-2-yl]-2-methylpropanoyl}-N-(3-hydroxypropyl)glycine hydrochloride (B-11)

The compound (477 mg, 0.86 mmol) obtained in step 1 was dissolved in tetrahydrofuran (15 mL) and methanol (3 mL), and water (1 mL), and 1N aqueous sodium hydroxide solution (1.0 mL, 1.0 mmol) were added thereto. After stirring at room temperature for 22 hours, 1N aqueous sodium hydroxide solution (0.43 mL, 0.43 mmol) was added to the reaction mixture, and the mixture was further stirred for 4 hours. 1N Aqueous sodium hydroxide solution (1.2 mL, 1.2 mmol) was added to the reaction mixture, and the mixture was stirred for 3 hours and acidified with 1N hydrochloric acid. To the reaction mixture was added saturated brine, and the mixture was extracted three times with dichloromethane. The extract was dried over sodium sulfate, and the solvent was evaporated under reduced pressure to give a residue (430 mg).

The obtained residue (400 mg) was dissolved in ethanol (12 mL) and chloroform (50 μL), 10% palladium/carbon (40 mg) was added, and the mixture was stirred at room temperature overnight under a hydrogen atmosphere. The reaction mixture was filtered through celite, and the filtrate was concentrated under reduced pressure to give a residue (335 mg).

To the obtained residue (335 mg) were added M-8 (209 mg, 0.96 mmol), WSC hydrochloride (169 mg, 0.88 mmol), and pyridine (33 mL), and the mixture was stirred at room temperature for 15 hours. The reaction mixture was concentrated under reduced pressure, trifluoroacetic acid (10 mL) was added to the obtained residue, and the mixture was stirred at room temperature for 1 hour. Trifluoroacetic acid was evaporated under reduced pressure to give a residue. Water (5 mL) and acetonitrile (2 mL) were added to the obtained residue, and the mixture was stirred overnight and purified by high performance liquid chromatography (water-acetonitrile, each containing 0.1% trifluoroacetic acid) to give trifluoroacetic acid salt of the title compound.

To the obtained trifluoroacetic acid salt were added 0.1N hydrochloric acid (3.6 mL) and water (10 mL), and the mixture was freeze-dried to give the title compound (162 mg, 0.30 mmol, 38%).

$^1$H-NMR (300 MHz, DMSO-d6) δ 9.62 (2H, br), 9.30 (2H, br), 8.64 (1H, d, J=2.1 Hz), 8.26 (1H, dd, J=8.4, 2.1 Hz), 7.94-7.91 (2H, m), 7.14-7.11 (1H, m), 4.57-3.77 (3H, m), 3.51-2.92 (6H, m), 1.62-1.51 (2H, m), 1.12-1.04 (3H, m).

MS (ESI) m/z 493 (M+H)+

Example 29

Synthesis of 3-[5-(4-amidino-2-bromophenoxycarbonyl)thiophen-2-yl]-2-methylpropionic acid trifluoroacetic acid salt (B-16)

M-9 (33 mg, 0.10 mmol), M-4 (27 mg, 0.10 mmol), and WSC hydrochloride (21 mg, 0.11 mmol) were dissolved in pyridine (1.0 mL), and the mixture was stirred overnight and concentrated under reduced pressure. Trifluoroacetic acid (1.5 mL) was added to the residue, and the mixture was stirred for 30 minutes and concentrated under reduced pressure. The obtained residue was purified by high performance liquid chromatography (water-acetonitrile, each containing 0.1% trifluoroacetic acid) to give the title compound (9.0 mg, 0.017 mmol, 17%).

MS (ESI) m/z 411[M($^{79}$Br)+H]$^+$, 413[M ($^{81}$Br)+1.1]$^+$

Example 30

Synthesis of (2E)-3-[4-(4-amidinophenoxycarbonyl)-thiazol-2-yl]-2-methylpropenoic acid trifluoroacetic acid salt (C-1)

Step 1. Synthesis of 2-formyl-4-thiazolecarboxylic acid ethyl ester 2-(Diethoxymethyl)-4-thiazolecarboxylic acid ethyl ester (2.90 g, 11.8 mmol) synthesized according to Bull. Chem. Soc. Jpn., 58, 352 (1985), which is incorporated herein by reference in its entirety, was dissolved in acetone (37.3 mL), 1N aqueous hydrochloric acid solution (3.73 mL) was added, and the mixture was stirred with heating at 60° C. for 4 hours. After evaporation of the solvent, the mixture was worked up according to a conventional method to give the title compound as a crude product (2.13 g).

Step 2. Synthesis of 3-[4-(ethoxycarboxyl)thiazol-2-yl]-2-methylpropenoic acid tert-butyl ester To tetrahydrofuran (38.0 mL) was added 60% sodium hydride (669 mg, 15.3 mmol) at 0° C. to give a suspension, a tetrahydrofuran solution (8 mL) of M-13 (4.17 g, 15.7 mmol) was added dropwise thereto, and the mixture was heated to room temperature. After stirring for 30 minutes, the mixture was cooled again to 0° C., and a tetrahydrofuran solution (10 mL) of the crude product (2.07 g) obtained in step 1 was added dropwise. Thereafter, the mixture was heated to room temperature and stirred at room temperature overnight. The mixture was worked up according to a conventional method, and the object product was extracted by column chromatography (10-15% ethyl acetate/hexane mixed solvent) to give the title compound (1.84 g, 6.19 mmol, 2 steps 55%).

$^1$H-NMR (300 MHz, CDC$_3$) δ 8.29 (1H, s), 7.88 (1H, t, J=1.2 Hz), 4.46 (2H, q, J=7.2 Hz), 2.30 (3H, d, J=1.2 Hz), 1.54 (9H, s), 1.43 (3H, t, J=7.2 Hz).

MS (ESI) m/z 278 (M+H)+

Step 3. Synthesis of (2E)-3-[4-(4-amidinophenoxycarbonyl)thiazol-2-yl]-2-methylpropenoic acid trifluoroacetic acid salt (C-1)

Using 3-[4-(ethoxycarboxyl)thiazol-2-yl]-2-methylpropenoic acid tert-butyl ester obtained in step 2 and 4-hydroxybenzamidine hydrochloride and by an operation in the same manner as in Example 16, the title compound was obtained.

$^1$H-NMR (DMSO-d6) δ 9.36 (2H, br s), 9.09 (2H, br s), 7.93 (2H, d, J=8.6 Hz), 7.75 (1H, s), 7.63 (2H, d, J=8.6 Hz), 2.33 (3H, s), 2.30 (1H, s).

MS (ESI) m/z 332 (M+H)+

The compounds A-1, A-2, A-4, A-5, A-7, A-9 to A-11, A-14 to A-21, A-26 to A-28, A-30, A-31, A-38, A-40, B-2 to B-5, B-10, B-12, B-18, B-20 to B-24, C-2, and C-3 shown in the following Table 2 were each synthesized using M-1 to M-16 and commercially available reagents and by an operation in the same manner as in the above-mentioned Example 19.

Furthermore, B-18 was converted to a salt according to Example 28, step 2, and hydrochloride thereof was also obtained (B-18 hydrochloride).

The compounds A-8, A-33, A-34, A-37, B-1, B-8, B-9, B-17, and B-24 shown in the following Table 2 were each synthesized using M-1 to M-16 and commercially available reagents and by an operation in the same manner as in the above-mentioned Example 17.

The compounds B-13 to B-15 shown in the following Table 2 were each synthesized using M-1 to M-16 and commercially available reagents and by an operation in the same manner as in the above-mentioned Example 28.

Example 31

Synthesis of 3-[5-(4-amidinophenoxycarbonyl)furan-2-yl]-2S-methylpropionic acid trifluoroacetic acid salt (A-41)

Step 1. Optical resolution of 5-(2-tert-butoxycarbonylpropyl)furan-2-carboxylic acid methyl ester 5-(2-tert-Butoxycarbonylpropyl)furan-2-carboxylic acid methyl ester (303 mg, 1.13 mmol) synthesized in Example 11, step 1 was optically resolved by high performance liquid chromatography using a chiral column (CHIRALCEL (registered trademark) OD, 20 mm×250 mm, 2-propanol:n-hexane=1:99, 1 mL/minute) to give respective optically active forms (S form: 105 mg, R form: 131 mg).

Step 2. Synthesis of 3-[5-(4-amidinophenoxycarbonyl)-furan-2-yl]-2S-methylpropionic acid trifluoroacetic acid salt (A-41)

The optically active S form (105 mg, 0.39 mmol) obtained in step 1 was dissolved in ethanol (1.3 mL), 1N aqueous lithium hydroxide solution (1 mol/L, 0.47 mL, 0.47 mmol) was added, and the mixture was stirred at room temperature for 4 hours. 1N Hydrochloric acid (0.47 mL) was added to the reaction mixture, and the mixture was concentrated under reduced pressure. 0.5N Hydrochloric acid and ethyl acetate were added to the obtained residue, the organic layer was extracted, and the aqueous layer was extracted three times with ethyl acetate. The organic layers were collected, washed with saturated brine, and dried by dehydration with sodium sulfate. After filtration, the solvent of the filtrate was evaporated under reduced pressure.

To the obtained residue were added 4-amidinophenol hydrochloride (88 mg, 0.51 mmol) and WSC hydrochloride (112 mg, 0.59 mmol), and the mixture was dissolved in pyridine (1.5 mL). After stirring at room temperature overnight, the reaction mixture was concentrated under reduced pressure, the obtained residue was dissolved in trifluoroacetic acid (containing 5% water, 1.5 mL), and the mixture was stirred at room temperature for 2 hours. The reaction mixture was concentrated under reduced pressure, and the obtained residue was purified by high performance liquid chromatography (acetonitrile-water, each containing 0.1% trifluoroacetic acid, 5-35%) to give the title compound (90.0 mg, 0.209 mmol, 53%).

$^1$H-NMR (300 MHz, DMSO-d6) δ 9.35 (2H, br s), 9.08 (2H, br s), 7.90 (2H, dd, J=6.9, 1.8 Hz), 7.61-7.49 (3H, m), 6.52 (1H, d, J=3.6 Hz), 3.15-2.98 (1H, m), 2.90-2.70 (2H, m), 1.14 (3H, d, J=6.9 Hz).

MS (ESI) m/z 317 (M+H)+

Example 32

Synthesis of 3-[5-(4-amidinophenoxycarbonyl)furan-2-yl]-2R-methylpropionic acid trifluoroacetic acid salt (A-42)

The optically active R form (130 mg, 0.48 mmol) obtained in Example 31, step 1 was dissolved in ethanol (1.0 mL), 1N aqueous lithium hydroxide solution (1 mol/L, 0.73 mL, 0.73 mmol) was added, and the mixture was stirred at room temperature for 2 hours. 1N Hydrochloric acid (0.73 mL) was added to the reaction mixture, and the mixture was concentrated under reduced pressure. 0.5N Hydrochloric acid and ethyl acetate were added to the obtained residue, the organic layer was extracted, and the aqueous layer was extracted three times with ethyl acetate. The organic layers were collected, washed with saturated brine, and dried by dehydration with sodium sulfate. After filtration, the solvent of the filtrate was evaporated under reduced pressure.

To the obtained residue were added 4-amidinophenol hydrochloride (108 mg, 0.62 mmol) and WSC hydrochloride (138 mg, 0.72 mmol), and the mixture was dissolved in pyridine (1.6 mL). After stirring at room temperature overnight, the reaction mixture was concentrated under reduced pressure, the obtained residue was dissolved in trifluoroacetic acid (containing 5% water, 1.6 mL), and the mixture was stirred at room temperature for 2 hours. The reaction mixture was concentrated under reduced pressure and the obtained residue was purified by high performance liquid chromatography (acetonitrile-water, each containing 0.1% trifluoroacetic acid, 5-35%) to give the title compound (112 mg, 0.260 mmol, 54%).

$^1$H-NMR (300 MHz, DMSO-d6) δ 9.35 (2H, br s), 9.08 (2H, br s), 7.90 (2H, dd, J=6.9, 1.8 Hz), 7.61-7.49 (3H, m), 6.52 (1H, d, J=3.6 Hz), 3.15-2.98 (1H, m), 2.90-2.70 (2H, m), 1.14 (3H, d, J=6.9 Hz).

MS (ESI) m/z 317 (M+H)+

Example 33

Synthesis of N-{3-[5-(4-amidinophenoxycarbonyl)-furan-2-yl]-2S-methylpropionyl}-L-aspartic acid trifluoroacetic acid salt (A-43)

A-41 (31 mg, 0.072 mmol) was dissolved in thionyl chloride (500 μL), and the mixture was stirred at 70° C. for 20 minutes. Thionyl chloride was evaporated under reduced pressure, and the obtained residue and L-aspartic acid di-tert-butyl ester hydrochloride (30.4 mg, 0.11 mmol) were dissolved in dichloromethane (350 μL). Pyridine (150 μL) was added, and the mixture was stirred at room temperature overnight. The reaction mixture was concentrated under reduced pressure, trifluoroacetic acid (500 μL) was added to the obtained residue, and the mixture was stirred at room temperature for 30 minutes. The reaction mixture was concentrated under reduced pressure and the obtained residue was purified by high performance liquid chromatography (acetonitrile-water, each containing 0.1% trifluoroacetic acid, 5-35%) to give the title compound (32 mg, 0.059 mmol, 81%).

$^1$H-NMR (300 MHz, DMSO-d6) δ 9.34 (2H, br s), 9.10 (2H, br s), 8.32 (1H, d, J=8.7 Hz), 7.90 (2H, d, J=8.7 Hz), 7.54 (2H, d, J=8.7 Hz), 7.50 (1H, d, J=3.3 Hz), 6.46 (1H, d, J=3.3 Hz), 4.59-4.49 (1H, m), 3.08-2.47 (5H, m), 1.07 (3H, d, J=5.4 Hz).

MS (ESI) m/z 432 (M+H)+

Example 34

Synthesis of N-{3-[5-(4-amidinophenoxycarbonyl)-furan-2-yl]-2R-methylpropionyl}-L-aspartic acid trifluoroacetic acid salt (A-44)

A-42 (30.8 mg, 0.072 mmol) was dissolved in thionyl chloride (500 µL), and the mixture was stirred at 70° C. for 20 minutes. Thionyl chloride was evaporated under reduced pressure, and the obtained residue and L-aspartic acid di-tert-butyl ester hydrochloride (30.3 mg, 0.11 mmol) were dissolved in dichloromethane (350 µL). Pyridine (150 µL) was added, and the mixture was stirred at room temperature overnight. The reaction mixture was concentrated under reduced pressure, trifluoroacetic acid (500 µL) was added to the obtained residue, and the mixture was stirred at room temperature for 30 minutes. The reaction mixture was concentrated under reduced pressure, and the obtained residue was purified by high performance liquid chromatography (acetonitrile-water, each containing 0.1% trifluoroacetic acid, 5-35%) to give the title compound (33 mg, 0.061 mmol, 85%).

$^1$H-NMR (300 MHz, DMSO-d6) δ 9.34 (2H, br s), 9.09 (2H, br s), 8.36 (1H, d, J=8.4 Hz), 7.90 (2H, d, J=8.7 Hz), 7.55 (2H, J=8.7 Hz), 7.51 (1H, d, J=3.6 Hz), 6.50 (1H, d, J=3.6 Hz), 4.57-4.45 (1H, m), 3.05-2.42 (5H, m), 1.05 (3H, d, J=6.6 Hz).

MS (ESI) m/z 432 (M+H)+

Example 35

Synthesis of N-{3-[5-(4-amidinophenoxycarbonyl)-furan-2-yl]-2S-methylpropionyl}-D-aspartic acid trifluoroacetic acid salt (A-45)

A-41 (31 mg, 0.072 mmol) was dissolved in thionyl chloride (500 µL), and the mixture was stirred at 70° C. for 20 minutes. Thionyl chloride was evaporated under reduced pressure, and the obtained residue and D-aspartic acid dibenzyl ester tosylate (56.7 mg, 0.12 mmol) were dissolved in dichloromethane (350 µL). Pyridine (150 µL) was added, and the mixture was stirred at room temperature for 2 hours. The reaction mixture was concentrated under reduced pressure, and the obtained residue was dissolved in ethanol (1 mL). 10% Palladium/carbon (5 mg) was added, and the mixture was stirred at room temperature overnight under a hydrogen atmosphere. After completion of the reaction, palladium/carbon was removed by celite filtration. The solvent was evaporated under reduced pressure, and the obtained residue was purified by high performance liquid chromatography (acetonitrile-water, each containing 0.1% trifluoroacetic acid, 5-45%) to give the title compound (8.0 mg, 0.015 mmol, 19%).

$^1$H-NMR (300 MHz, DMSO-d6) δ 9.34 (2H, br s), 9.09 (2H, br s), 8.36 (1H, d, J=8.4 Hz), 7.90 (2H, d, J=8.7 Hz), 7.55 (2H, d, J=8.7 Hz), 7.51 (1H, d, J=3.6 Hz), 6.50 (1H, d, J=3.6 Hz), 4.57-4.45 (1H, m), 3.05-2.42 (5H, m), 1.05 (3H, d, J=6.6 Hz).

MS (ESI) m/z 432 (M+H)+

Example 36

Synthesis of N-{3-[5-(4-amidinophenoxycarbonyl)-furan-2-yl]-2R-methylpropionyl}-D-aspartic acid trifluoroacetic acid salt (A-46)

A-42 (34.4 mg, 0.080 mmol) was dissolved in thionyl chloride (500 µL), and the mixture was stirred at 70° C. for 20 minutes. Thionyl chloride was evaporated under reduced pressure, and the obtained residue and D-aspartic acid dibenzyl ester tosylate (58.2 mg, 0.12 mmol) were dissolved in dichloromethane (350 µL). Pyridine (150 µL) was added, and the mixture was stirred at room temperature for 2 hours. The reaction mixture was concentrated under reduced pressure, and the obtained residue was dissolved in ethanol (1 mL). 10% Palladium/carbon (5 mg) was added, and the mixture was stirred at room temperature overnight under a hydrogen atmosphere. After completion of the reaction, palladium/carbon was removed by celite filtration. The solvent was evaporated under reduced pressure, and the obtained residue was purified by high performance liquid chromatography (acetonitrile-water, each containing 0.1% trifluoroacetic acid, 5-35%) to give the title compound (33.0 mg, 0.061 mmol, 76%).

$^1$H-NMR (300 MHz, DMSO-d6) δ 9.34 (2H, br s), 9.10 (2H, br s), 8.32 (1H, d, J=8.7 Hz), 7.90 (2H, d, J=8.7 Hz), 7.54 (2H, d, J=8.7 Hz), 7.50 (1H, d, J=3.3 Hz), 6.46 (1H, d, J=3.3 Hz), 4.59-4.49 (1H, m), 3.08-2.47 (5H, m), 1.07 (3H, d, J=5.4 Hz).

MS (ESI) m/z 432 (M+H)+

Example 37

Synthesis of N-{3-[5-(4-amidino-2-fluorophenoxycarbonyl)thiophen-2-yl]-2R-methylpropionyl}-L-aspartic acid trifluoroacetic acid salt (B-25)

Step 1. Synthesis of (2R)-5-(2-tert-butoxycarbonylpropyl)thiophene-2-carboxylic acid Using 5-(2-tert-butoxycarbonylpropyl)thiophene-2-carboxylic acid methyl ester obtained as an intermediate of Example 13, and in the same manner as in Example 31, optical resolution was performed. The obtained (2R)-5-(2-tert-butoxycarbonylpropyl)thiophene-2-carboxylic acid methyl ester (0.18 g, 0.63 mmol) was suspended in methanol (1.6 mL) and tetrahydrofuran (1.6 mL), 1N aqueous lithium hydroxide solution (1.6 mL) was added, and the mixture was stirred overnight. 1N Hydrochloric acid (2 mL) was added to the reaction mixture, and the mixture was extracted with ethyl acetate. The extract was washed with saturated brine, dried over anhydrous sodium sulfate, and concentrated under reduced pressure to give the title compound (0.17 g).

MS (ESI) m/z 271 (M+H)+

Step 2. Synthesis of N-{3-[5-(4-amidino-2-fluorophenoxycarbonyl)thiophen-2-yl]-2R-methylpropionyl}-L-aspartic acid trifluoroacetic acid salt (B-25)

The obtained (2R)-5-(2-tert-butoxycarbonylpropyl)-thiophene-2-carboxylic acid (0.17 g, 0.66 mmol), 4-amidino-2-fluorophenol hydrochloride (0.27 g, 0.99 mmol), and WSC hydrochloride (0.82 g, 1.31 mmol) were dissolved in pyridine, and the mixture was stirred for 2 hours. Trifluoroacetic acid (5 mL) was added, and the mixture was stirred for 20 minutes. The solvent was evaporated under reduced pressure, purified by high performance liquid chromatography and freeze-dried to give a white solid (75 mg). The obtained white solid (30 mg, 0.06 mmol), L-aspartic acid di-tert-butyl ester hydrochloride (20 mg, 0.07 mmol), and WSC hydrochloride (35 mg, 0.18 mmol) were dissolved in pyridine (3 mL), and the mixture was stirred for 3 hours. The solvent was evaporated under reduced pressure, trifluoroacetic acid (3 mL) was added, and the mixture was stirred for 20 minutes. The solvent was evaporated under reduced pressure, and purified by high performance liquid chromatography and freeze-dried to give the title compound (28 mg).

$^1$H-NMR (400 MHz, DMSO-d6) δ 9.41 (2H, s), 9.12 (2H, s), 8.32 (1H, d, J=8.0 Hz), 7.93 (2H, m), 7.74 (2H, m), 7.09 (1H, d, J=3.6 Hz), 4.50 (1H, m), 3.16 (1H, dd, J=14.8, 7.6 Hz), 2.90 (1H, dd, J=14.8, 6.4 Hz), 2.75-2.65 (2H, m), 2.55 (1H, dd, J=8.4, 1.2 Hz), 1.05 (3H, d, J=6.8 Hz).

MS (ESI) m/z 466 (M+H)+

Example 38

Synthesis of N-{3-[5-(4-amidino-2-fluorophenoxycarbonyl)thiophen-2-yl]-2R-isobutylpropionyl}-L-aspartic acid trifluoroacetic acid salt (B-26)

Step 1. Synthesis of 2-(diethylphosphono)-4-methylpentanoic acid tert-butyl ester (M-17)

Using isobutyl bromide instead of ethyl iodide and in the same manner as in Example 7, the compound was synthesized.

$^1$H-NMR (300 MHz, DMSO-d6) δ 4.08-3.98 (4H, m), 2.85 (1H, ddd, J=22.8, 11.4, 3.3 Hz), 1.85-1.75 (1H, m), 1.60-1.45 (2H, m), 1.50 (9H, s), 1.22 (6H, m), 0.88 (6H, d, J=7.5 Hz).

MS (ESI) m/z 309 (M+H)+

Step 2. Synthesis of N-{3-[5-(4-amidino-2-fluorophenoxycarbonyl)thiophen-2-yl]-2R-isobutylpropionyl}-L-aspartic acid trifluoroacetic acid salt (B-26)

Using M-17 obtained in step 1 and in the same manner as in Examples 12, 13 and 37, the title compound was synthesized.

$^1$H-NMR (400 MHz, DMSO-d6) δ 9.41 (2H, s), 9.15 (2H, s), 8.39 (1H, d, J=8.0 Hz), 7.93 (2H, m), 7.75 (2H, m), 7.10 (1H, d, J=4.0 Hz), 4.51 (1H, m), 3.07 (1H, dd, J=14.8, 8.0 Hz), 2.92 (1H, dd, J=14.8, 6.4 Hz), 2.80-2.65 (2H, m), 2.55 (1H, m), 1.50 (2H, m), 1.13 (1H, m), 0.80 (6H, m).

MS (ESI) m/z 508 (M+H)+

Example 39

Synthesis of 5-{2-methyl-2-[(2-phenylethyl)-carbamoyl]ethyl}furan-2-carboxylic acid 4-amidinophenyl ester trifluoroacetic acid salt (A-47)

A-6 (50 mg, 0.12 mmol), phenethylamine (17 mg, 0.14 mmol), and WSC hydrochloride (46 mg, 0.24 mmol) were dissolved in pyridine (2 mL), and the mixture was stirred at room temperature for 2 hours. The solvent was evaporated under reduced pressure and the residue was purified by high performance liquid chromatography to give the title compound (31 mg).

$^1$H-NMR (300 MHz, DMSO-d6) δ 9.32 (2H, s), 9.00 (2H, s), 8.00 (1H, t, J=5.4 Hz), 7.87 (2H, d, J=8.7 Hz), 7.52 (2H, m), 7.30-7.10 (6H, m), 6.40 (1H, d, J=3.3 Hz), 3.30-3.20 (2H, m), 3.00-2.90 (1H, m), 2.70-2.60 (4H, m), 1.01 (3H, d, J=6.6 Hz).

MS (ESI) m/z 420 (M+H)+

Example 40

Synthesis of N-{3-[5-(4-amidinophenoxycarbonyl)-furan-2-yl]-2-methylpropanoyl}nipecotic acid trifluoroacetic acid salt (A-52)

A-6 (30 mg, 0.07 mmol), nipecotic acid tert-butyl ester (13 mg, 0.07 mmol), and WSC hydrochloride (63 mg, 0.33 mmol) were dissolved in pyridine (3 mL), and the mixture was stirred at room temperature overnight. The solvent was evaporated under reduced pressure, trifluoroacetic acid (3 mL) was added, and the mixture was stirred at room temperature for 30 minutes. The solvent was evaporated under reduced pressure and the residue was purified by high performance liquid chromatography to give the title compound (20 mg).

$^1$H-NMR (400 MHz, DMSO-d6) δ 9.34 (2H, s), 8.98 (2H, s), 7.89 (2H, m), 7.55 (3H, m), 6.48 (1H, d, J=3.2 Hz), 3.90-3.80 (2H, m), 3.55-3.25 (2H, m), 3.08-2.98 (2H, m), 2.80-2.70 (2H, m), 2.10-1.20 (4H, m), 1.07 (3H, d, J=6.4 Hz).

MS (ESI) m/z 428 (M+H)+

Example 41

Synthesis of N-{3-[5-(4-amidino-2-methoxyphenoxycarbonyl)furan-2-yl]-propanoyl}-L-aspartic acid trifluoroacetic acid salt (A-53)

Step 1. Synthesis of 4-amidino-2-methoxyphenol hydrochloride

To 3-methoxy-4-hydroxybenzonitrile (2.0 g, 13.4 mmol) were added ethanol (3 mL) and 4N hydrochloric acid/1,4-dioxane (27 mL), and the mixture was stirred at room temperature overnight. The solvent was evaporated under reduced pressure and the residue was dissolved in ethanol (50 mL). Ammonium carbonate (6.4 g, 67 mmol) was added, and the mixture was stirred at room temperature overnight. The solvent was evaporated under reduced pressure, water was added and the mixture was freeze-dried to give the title compound (1.82 g).

$^1$H-NMR (400 MHz, DMSO-d6) δ 9.40-8.70 (5H, br s), 7.46 (1H, d, J=2.4 Hz), 7.40 (1H, dd, J=8.4, 2.4 Hz), 6.97 (1H, d, J=8.4 Hz), 3.86 (3H, s).

MS (ESI) m/z 167 (M+H)+

Step 2. Synthesis of 5-(2-tert-butoxycarbonylethenyl)-furan-2-carboxylic acid benzyl ester A solution of diethylphosphonoacetic acid tert-butyl ester (1.54 g, 6.09 mmol) in tetrahydrofuran (3 mL) was added dropwise to a suspension of 60% sodium hydride (0.19 g, 4.87 mmol) in tetrahydrofuran (50 mL) with stirring at 0° C. After stirring at room temperature for 20 minutes, a solution of 5-formyl-2-furancarboxylic acid benzyl ester (1.0 g, 4.06 mmol) in tetrahydrofuran (3 mL) was added, and the mixture was stirred at room temperature for 1 hour. The mixture was worked up according to a conventional method, and the object product was extracted by column chromatography (10-30% ethyl acetate/hexane mixed solvent) to give the title compound (1.17 g)

$^1$H-NMR (400 MHz, CDC$_3$) δ 7.45-7.35 (5H, m), 7.32 (1H, d, J=16.0 Hz), 7.20 (1H, d, J=3.6 Hz), 6.62 (1H, d, J=3.6 Hz), 6.49 (1H, d, J=16.0 Hz), 5.35 (2H, s), 1.50 (9H, s).

Step 3. Synthesis of 5-(2-tert-butoxycarbonylethyl)-furan-2-carboxylic acid (M-22)

5-(2-tert-Butoxycarbonylethenyl)furan-2-carboxylic acid benzyl ester (0.97 g, 2.80 mmol) was dissolved in methanol (50 mL), 10% palladium/carbon (0.1 g) was added, and the mixture was stirred at room temperature for 2 hours under a hydrogen atmosphere. After completion of the reaction, palladium/carbon was removed by celite filtration, and the solvent was evaporated under reduced pressure to give the title compound (0.66 g).
$^1$H-NMR (400 MHz, CDC$_3$) δ 7.23 (1H, d, J=3.6 Hz), 6.22 (1H, d, J=3.6 Hz), 3.01 (2H, t, J=7.6 Hz), 2.63 (2H, t, J=7.6 Hz), 1.44 (9H, s).
MS (ESI) m/z 241 (M+H)+

Step 4. Synthesis of N-{3-[5-(4-amidino-2-methoxyphenoxycarbonyl)furan-2-yl]-propanoyl}-L-aspartic acid trifluoroacetic acid salt (A-53)

4-Amidino-2-methoxyphenol hydrochloride (63 mg, 0.31 mmol) obtained in step 1, M-22 (50 mg, 0.21 mmol) and WSC hydrochloride (80 mg, 0.42 mmol) were dissolved in pyridine, and the mixture was stirred for 1 hour. The solvent was evaporated, and the residue was purified by high performance liquid chromatography to give a white solid (39 mg). The obtained white solid (20 mg), L-aspartic acid di-tert-butyl ester hydrochloride (20 mg, 0.07 mmol), and WSC hydrochloride (20 mg, 0.10 mmol) were dissolved in pyridine (3 mL), and the mixture was stirred overnight. The solvent was evaporated under reduced pressure, trifluoroacetic acid (3 mL) was added, and the mixture was stirred for 30 minutes. The solvent was evaporated under reduced pressure, and the residue was purified by high performance liquid chromatography and freeze-dried to give the title compound (19 mg).
$^1$H-NMR (400 MHz, DMSO-d6) δ 9.35 (2H, s), 9.01 (2H, s), 8.37 (1H, d, J=8.0 Hz), 7.57 (1H, d, J=2.0 Hz), 7.52-7.44 (3H, m), 6.47 (1H, d, J=2.0 Hz), 4.55 (1H, m), 3.88 (3H, s), 2.97 (2H, t, J=7.6 Hz), 2.68-2.55 (4H, m).
MS (ESI) m/z 448 (M+H)+

Example 42

Synthesis of N-{3-[5-(4-amidinophenoxycarbonyl)-furan-2-yl]-propanoyl}-N-(2-carboxyethyl)-glycine trifluoroacetic acid salt (A-54)

Step 1. Synthesis of N-(2-carboxyethyl)glycine di-tert-butyl ester hydrochloride (M-20)

β-Alanine tert-butyl ester hydrochloride (1.0 g, 5.5 mmol) was dissolved in dichloromethane (10 mL), triethylamine (1.52 mL, 11.1 mmol) and bromoacetic acid tert-butyl ester (0.57 g, 2.9 mmol) were added, and the mixture was stirred for 2 hours. The solvent was evaporated, and the residue was purified by high performance liquid chromatography. To the fraction containing the object product was added 0.1N hydrochloric acid (30 mL), and the mixture was freeze-dried to give the title compound (0.52 g).
$^1$H-NMR (400 MHz, CDC$_3$) δ 3.75 (2H, s), 3.29 (2H, t, J=6.4 Hz), 2.94 (2H, d, J=6.4 Hz), 1.51 (9H, s), 1.47 (9H, s).
MS (ESI) m/z 246 (M+H)+

Step 2. Synthesis of (2E)-3-[5-(benzyloxycarbonyl)furan-2-yl]-2-propenoic acid To 5-(2-tert-butoxycarbonylethenyl)furan-2-carboxylic acid benzyl ester (0.15 g, 0.46 mmol) obtained in Example 41, step 2 was added trifluoroacetic acid (3 mL), and the mixture was stirred for 30 minutes. The solvent was evaporated under reduced pressure to give the title compound.
$^1$H-NMR (400 MHz, CDC$_3$) δ 7.80 (1H, d, J=15.6 Hz), 7.75 (1H, d, J=3.6 Hz), 7.45-7.35 (5H, m), 7.25 (1H, d, J=3.6 Hz), 6.35 (1H, d, J=15.6 Hz), 5.34 (2H, s).

Step 3. Synthesis of N-{3-[5-(4-amidinophenoxycarbonyl)-furan-2-yl]-propanoyl}-N-(2-carboxyethyl) glycine trifluoroacetic acid salt (A-54)

(2E)-3-[5-(benzyloxycarbonyl)furan-2-yl]-2-propenoic acid (40 mg, 0.15 mmol) was suspended in thionyl chloride (4 mL), and the suspension was stirred at 70° C. for 30 minutes. After evaporation of the solvent, dichloromethane (2 mL), M-20 (42 mg, 0.16 mmol) and triethylamine (42 μL, 0.3 mmol) were added, and the mixture was stirred for 30 minutes. After evaporation of the solvent, the residue was purified by silica gel column chromatography. The obtained solid was dissolved in ethanol (5 mL), a catalytic amount of 10% palladium/carbon was added, and the mixture was stirred at room temperature for 1 hour under a hydrogen atmosphere. The reaction mixture was filtered through celite, and the filtrate was concentrated under reduced pressure to give a residue (30 mg). The obtained residue, 4-hydroxybenzamidine hydrochloride (15 mg, 0.09 mmol) and WSC hydrochloride (20 mg, 0.10 mmol) were dissolved in pyridine (3 mL), and the mixture was stirred at room temperature overnight. After evaporation of the solvent, trifluoroacetic acid (3 mL) was added, and the mixture was stirred for 30 minutes. After evaporation of the solvent, the residue was purified by high performance liquid chromatography and freeze-dried to give the title compound (14 mg).
$^1$H-NMR (400 MHz, DMSO-d6) δ 9.34 (2H, s), 8.96 (2H, s), 7.89 (2H, dd, J=6.8, 2.0 Hz), 7.54 (3H, m), 6.52 (0.5H, d, J=3.6 Hz), 6.48 (0.5H, d, J=3.6 Hz), 4.23 (1H, s), 3.96 (1H, s), 3.60 (1H, t, J=6.8 Hz), 3.46 (1H, t, J=6.8 Hz), 2.98-2.85 (2H, m), 2.70-2.40 (2H, m).
MS (ESI) m/z 418 (M+H)+

Example 43

Synthesis of N-{3-[5-(4-amidinophenoxycarbonyl)-furan-2-yl]-propionyl}-N-allylglycine trifluoroacetic acid salt (A-55)

Step 1. Synthesis of N-allylglycine tert-butyl ester (M-21)

Allylamine (10 mL, 0.13 mol) was cooled to 0° C., and a solution of bromoacetic acid tert-butyl ester (1.0 mL, 6.7 mmol) in dichloromethane (10 mL) was slowly added. After stirring at 0° C. for 3 hours, the reaction mixture was concentrated under reduced pressure. The obtained residue was dissolved in diethyl ether, washed successively with saturated aqueous sodium hydrogen carbonate and saturated brine, and dried over anhydrous sodium sulfate. The obtained solution was concentrated under reduced pressure to give the title compound as a yellow liquid (1.15 g, 6.7 mmol, 99%).
$^1$H-NMR (400 MHz, DMSO-d6) δ 5.87 (1H, ddt, J=17.1, 10.2, 6.1 Hz), 5.19 (1H, ddt, J=17.1, 3.2, 1.7 Hz), 5.11 (1H, ddt, J=10.2, 3.2, 1.2 Hz), 3.29 (2H, s), 3.25 (2H, ddd, J=6.1, 1.7, 1.2 Hz), 1.47 (9H, s).
MS (ESI) m/z 172 (M+H)+

Step 2. Synthesis of N-{3-[5-(4-amidinophenoxycarbonyl)-furan-2-yl]-propionyl}-N-allylglycine trifluoroacetic acid salt (A-55)

A-37 (31.5 mg, 0.076 mmol) was dissolved in thionyl chloride (500 μL), and the mixture was stirred at room temperature for 30 minutes. The reaction mixture was concentrated under reduced pressure, M-21 (38.9 mg, 0.23 mmol), dichloromethane (300 μL), and pyridine (200 μL) were added to the obtained residue, and the mixture was stirred at room temperature for 25 minutes. The reaction mixture was concentrated under reduced pressure, trifluoroacetic acid (containing 5% water, 500 μL) was added to the obtained residue, and the mixture was stirred at room temperature for 35 minutes. The reaction mixture was concentrated under reduced pressure, and the obtained residue was purified by high performance liquid chromatography (acetonitrile-water, each containing 0.1% trifluoroacetic acid, 5-35%) to give the title compound (28.3 mg, 0.056 mmol, 74%).

$^1$H-NMR (400 MHz, DMSO-d6) δ 9.35 (1H, br s), 9.26-9.02 (2H, m), 7.95-7.86 (2H, m), 7.58-7.51 (2H, m), 6.52-6.47 (3H, m), 5.94-5.62 (1H, m), 5.23-5.03 (2H, m), 4.13-3.88 (4H, m), 3.04-2.91 (2H, m), 2.83-2.65 (2H, m).

MS (ESI) m/z 400 (M+H)+

Example 44

Synthesis of N-{3-[5-(4-amidino-2-fluorophenoxycarbonyl)thiophen-2-yl]propanoyl}-L-aspartic acid trifluoroacetic acid salt (B-32)

Step 1. Synthesis of 5-(2-tert-butoxycarbonylethyl)-thiophene-2-carboxylic acid benzyl ester Using 5-formyl-2-thiophenecarboxylic acid benzyl ester and in the same manner as in Example 12, the title compound was synthesized.

$^1$H-NMR (400 MHz, CDC$_3$) δ 7.72 (1H, d, J=4.0 Hz), 7.61 (1H, d, J=16.0 Hz), 7.43-7.30 (5H, m), 7.18 (1H, d, J=4.0 Hz), 6.28 (1H, d, J=16.0 Hz), 5.38 (2H, s), 1.52 (9H, s).

Step 2. Synthesis of 5-(2-tert-butoxycarbonylethyl)-thiophene-2-carboxylic acid (M-23)

The compound (0.5 g, 1.45 mmol) obtained in step 1 was dissolved in methanol (5 mL) and chloroform (0.5 mL), palladium hydroxide (0.1 g) was added, and the mixture was stirred at room temperature overnight under a hydrogen atmosphere. The reaction mixture was filtered through celite, and the solvent was evaporated under reduced pressure to give the title compound.

$^1$H-NMR (300 MHz, DMSO-d6) δ 7.54 (1H, d, J=3.3 Hz), 6.94 (1H, d, J=3.3 Hz), 3.04 (2H, t, J=7.5 Hz), 2.59 (2H, t, J=7.5 Hz), 1.38 (9H, s).

MS (ESI) m/z 257 (M+H)+

Step 3. Synthesis of N-{3-[5-(4-amidino-2-fluorophenoxycarbonyl)thiophen-2-yl]propanoyl}-L-aspartic acid trifluoroacetic acid salt (B-32)

The title compound was synthesized in the same manner as in Example 38.

$^1$H-NMR (400 MHz, DMSO-d6) δ 9.41 (2H, s), 9.11 (2H, s), 8.33 (1H, d, J=8.0 Hz), 7.93 (2H, m), 7.73 (2H, m), 7.12 (1H, d, J=3.6 Hz), 4.55 (1H, m), 3.13 (2H, t, J=7.2 Hz), 2.68 (1H, dd, J=12.4, 6.0 Hz), 2.62-2.55 (3H, m).

MS (ESI) m/z 452 (M+H)+

Example 45

Synthesis of N-{3-[5-(4-amidino-2-fluorophenoxycarbonyl)thiophen-2-yl]propionyl}-N-allylglycine trifluoroacetic acid salt (B-38)

3-[5-(4-Amidino-2-fluorophenoxycarbonyl)thiophen-2-yl]propanoic acid trifluoroacetic acid salt (38 mg, 0.084 mmol) was dissolved in thionyl chloride (500 μL), and the mixture was stirred at room temperature for 20 minutes. The reaction mixture was concentrated under reduced pressure, M-21 (18.8 mg, 0.11 mmol), dichloromethane (200 μL) and pyridine (300 μL) were added to the obtained residue, and the mixture was stirred for 90 minutes. The reaction mixture was concentrated under reduced pressure, trifluoroacetic acid (500 μL) was added to the obtained residue, and the mixture was stirred at room temperature for 30 minutes. The reaction mixture was concentrated under reduced pressure, and the obtained residue was purified by high performance liquid chromatography (acetonitrile-water, each containing 0.1% trifluoroacetic acid, 5-35%) to give the title compound (25.5 mg, 0.047 mmol, 55%).

$^1$H-NMR (400 MHz, DMSO-d6) δ 9.41 (2H, br s), 9.07 (2H, br), 7.96-7.89 (2H, m), 7.79-7.70 (2H, m), 7.14 (1H, d, J=3.6 Hz), 5.92-5.62 (1H, m), 5.23-5.06 (2H, m), 4.11-3.90 (4H, m), 3.21-3.09 (2H, m), 2.84-2.62 (2H, m).

MS (ESI) m/z 434 (M+H)+

Example 46

Synthesis of N-{3-[5-(4-amidinophenoxycarbonyl)-thiophen-2-yl]-2-methylpropanoyl}-L-cysteic acid trifluoroacetic acid salt (B-39)

Step 1. Synthesis of L-cysteic acid methyl ester hydrochloride (M-18)

L-cysteic acid (300 mg, 1.77 mmol) was dissolved in methanol (12 mL), and thionyl chloride (2.5 mL, 34 mmol) was slowly added at 0° C. After stirring at room temperature overnight, the reaction mixture was concentrated under reduced pressure, and the obtained residue was suspended in diisopropyl ether. The suspension was filtered to give the title compound as white crystals (291 mg, 1.33 mmol, 75%).

$^1$H-NMR (300 MHz, DMSO-d6) δ 8.26 (3H, br s), 4.23 (1H, m), 3.72 (3H, s), 3.00 (1H, dd, J=14.3, 3.5 Hz), 2.92 (1H, dd, J=14.3, 8.0 Hz).

MS (ESI) m/z 184 (M+H)+

Step 2. Synthesis of N-{3-[5-(4-amidinophenoxycarbonyl)-thiophen-2-yl]-2-methylpropanoyl}-L-cysteic acid trifluoroacetic acid salt (B-39)

B-6 (10 mg, 0.022 mmol), M-18 (5.9 mg, 0.027 mmol), and WSC hydrochloride (6.4 mg, 0.034 mmol) were dissolved in pyridine (1 mL), and the mixture was stirred at room temperature overnight. The reaction mixture was concentrated under reduced pressure, 4N hydrochloric acid (0.5 mL) and dioxane (0.5 mL) were added to the obtained residue, and the mixture was stirred at 60° C. for 3 hours. The reaction mixture was concentrated under reduced pressure, and the obtained residue was purified by high performance liquid chromatography (water-acetonitrile, each containing 0.1% trifluoroacetic acid) to give the title compound (7.4 mg, 0.012 mmol, 56%).

$^1$H-NMR (400 MHz, DMSO-d6) δ 9.34 (2H, br), 8.89 (2H, br), 8.22-8.18 (1H, m), 7.90-7.86 (3H, m), 7.60-7.56 (2H, m), 7.12-7.11 (1H, m), 4.39-4.33 (1H, m), 3.22-2.60 (5H, m), 1.09-1.06 (3H, m).

MS (ESI) m/z 484 (M+H)+

Example 47

Synthesis of N-{3-[5-(4-amidinophenoxycarbonyl)-thiophen-2-yl]-2-methylpropanoyl}aminomethylphosphonic acid trifluoroacetic acid salt (B-40)

Step 1. Synthesis of aminomethylphosphonic acid diethyl ester hydrochloride (M-19)

To a solution of phthalimidomethylphosphonic acid diethyl ester (4.56 g, 15.3 mmol) in ethanol (55 mL) was added hydrazine monohydrate (0.89 mL, 18.4 mmol), and the mixture was heated under reflux for 5 hours. The insoluble material was filtered off, and the filtrate was concentrated under reduced pressure. The obtained residue was purified by silica gel column chromatography (dichloromethane/methanol=95/5), and to the obtained oil (1.21 g) were added water (15 mL) and 1N hydrochloric acid (8.0 mL). The mixture was concentrated under reduced pressure and lyophilized to give the title compound (1.48 g, 7.27 mmol, 48%).

$^1$H-NMR (300 MHz, DMSO-d6) δ 8.50 (3H, br s), 4.12 (4H, m), 3.30 (2H, d, J=13.5 Hz), 1.28 (6H, t, J=7.1 Hz).

MS (ESI) m/z 168 (M+H)+

Step 2. Synthesis of N-{3-[5-(4-amidinophenoxycarbonyl)-thiophen-2-yl]-2-methylpropanoyl}aminomethylphosphonic acid trifluoroacetic acid salt (B-40)

Using B-6 (10 mg, 0.022 mmol) and M-19 (5.5 mg, 0.027 mmol), and by an operation in the same manner as in Example 46, the title compound (6.6 mg, 0.012 mmol, 55%) was obtained.

$^1$H-NMR (400 MHz, DMSO-d6) δ 9.45 (2H, br s), 9.20 (2H, br s), 7.98 (1H, br s), 7.85-7.87 (3H, m), 7.50 (1H, br s), 7.08 (1H, d, J=3.0 Hz), 3.17-2.75 (5H, m), 1.05 (3H, d, J=6.6 Hz).

MS (ESI) m/z 426 (M+H)+

Example 48

Synthesis of 5-[5-(4-amidinophenoxycarbonyl)furan-2-yl]-4-methylpentanoic acid trifluoroacetic acid salt (A-58)

Step 1. Synthesis of 5-(1-hydroxy-2-methylprop-2-enyl)furan-2-carboxylic acid benzyl ester 5-Formyl-2-furancarboxylic acid benzyl ester (300 mg, 1.30 mmol) was dissolved in tetrahydrofuran (12 mL), 2-propenylmagnesium bromide (0.5 mol/L tetrahydrofuran solution, 2.6 mL, 1.3 mmol) was added at −78° C., and the mixture was stirred for 15 minutes. 1N Hydrochloric acid was added to the reaction mixture, the mixture was heated to room temperature and extracted with ethyl acetate. The extract was washed with saturated brine, dried over anhydrous sodium sulfate, and concentrated under reduced pressure. The obtained residue was purified by silica gel column chromatography (hexane/ethyl acetate=70/30) to give the title compound (332 mg, 1.23 mmol, 94%).

$^1$H-NMR (300 MHz, CDC$_3$) δ 7.45-7.33 (5H, m), 7.16 (1H, d, J=3.3 Hz), 6.38 (1H, d, J=3.3 Hz), 5.33 (2H, s), 5.21 (1H, s), 5.19 (1H, s), 5.05 (1H, s), 1.75 (3H, s).

Step 2. Synthesis of (E)-5-(4-ethoxycarbonyl-2-methylbut-1-enyl)furan-2-carboxylic acid benzyl ester To the compound (332 mg, 1.23 mmol) obtained in step 1 were added triethyl orthoformate (5.0 mL, 27 mmol) and propionic acid (0.020 mL, 0.27 mmol), and the mixture was stirred at 138° C. overnight. The reaction mixture was purified by silica gel column chromatography (hexane/ethyl acetate=90/10) to give the title compound (149 mg, 0.435 mmol, 35%).

$^1$H-NMR (300 MHz, CDC$_3$) δ 7.45-7.35 (5H, m), 7.19 (1H, d, J=3.5 Hz), 6.29 (1H, d, J=3.5 Hz), 6.16 (1H, br s), 5.33 (2H, s), 4.14 (2H, q, J=7.2 Hz), 2.51 (4H, br s), 2.05 (3H, d, J=0.9 Hz), 1.25 (3H, t, J=7.2 Hz).

MS (ESI) m/z 343 (M+H)+

Step 3. Synthesis of 5-(4-ethoxycarbonyl-2-methylbutyl)furan-2-carboxylic acid

To a solution of the compound (149 mg, 0.435 mmol) obtained in step 2 in ethanol (3 mL) was added 5% palladium/carbon (15 mg), and the mixture was stirred under a hydrogen atmosphere for 9 hours. The catalyst was filtered off, and the solvent was evaporated under reduced pressure. The obtained residue was purified by high performance liquid chromatography (water-acetonitrile, each containing 0.1% trifluoroacetic acid) to give the title compound (75 mg, 0.30 mmol, 68%).

$^1$H-NMR (300 MHz, CDC$_3$) δ 7.25 (1H, d, J=3.4 Hz), 6.21 (1H, d, J=3.4 Hz), 4.13 (2H, q, J=7.2 Hz), 2.72 (1H, dd, J=15.0, 6.5 Hz), 2.56 (1H, dd, J=15.0, 7.6 Hz), 2.41-2.25 (2H, m), 1.99-1.92 (1H, m), 1.80-1.68 (1H, m), 1.57-1.45 (1H, m), 1.25 (3H, t, J=7.2 Hz), 0.93 (3H, d, J=6.7 Hz).

MS (ESI) m/z 255 (M+H)+

Step 4. Synthesis of 5-[5-(4-amidinophenoxycarbonyl)-furan-2-yl]-4-methylpentanoic acid ethyl ester trifluoroacetic acid salt To the compound (75 mg, 0.30 mmol) obtained in step 3, 4-amidinophenol hydrochloride (56 mg, 0.32 mmol), and WSC hydrochloride (68 mg, 0.35 mmol) was added pyridine (1.5 mL), and the mixture was stirred at room temperature overnight. The reaction mixture was concentrated under reduced pressure, and the obtained residue was purified by high performance liquid chromatography (water-acetonitrile, each containing 0.1% trifluoroacetic acid) to give the title compound (80 mg, 0.16 mmol, 55%).

$^1$H-NMR (300 MHz, DMSO-d6) δ 9.14 (4H, br s), 7.88 (2H, d, J=8.7 Hz), 7.54 (1H, d, J=3.5 Hz), 7.54 (2H, d, J=8.7 Hz), 6.52 (1H, d, J=3.5 Hz), 4.03 (2H, q, J=7.1 Hz), 2.75 (1H, dd, J=15.0, 6.2 Hz), 2.60 (1H, dd, J=15.0, 7.6 Hz), 2.40-2.26 (2H, m), 1.92-1.83 (1H, m), 1.68-1.56 (1H, m), 1.48-1.38 (1H, m), 1.16 (3H, t, J=7.1 Hz), 0.88 (3H, d, J=6.7 Hz).

MS (ESI) m/z 373 (M+H)+

Step 5. Synthesis of 5-[5-(4-amidinophenoxycarbonyl)-furan-2-yl]-4-methylpentanoic acid trifluoroacetic acid salt (A-58)

To the compound (77 mg, 0.16 mmol) obtained in step 4 were added 4N hydrochloric acid (1 mL) and 1,4-dioxane (1 mL), and the mixture was stirred at 60° C. for 5 hours. The reaction mixture was concentrated under reduced pressure, and the obtained residue was purified by high performance liquid chromatography (water-acetonitrile, each containing 0.1% trifluoroacetic acid) to give the title compound (33 mg, 0.072 mmol, 46%).

$^1$H-NMR (300 MHz, DMSO-d6) δ 9.23 (4H, br s), 7.88 (2H, d, J=8.7 Hz), 7.55 (1H, d, J=3.4 Hz), 7.54 (2H, d, J=8.7 Hz), 6.52 (1H, d, J=3.4 Hz), 1.73-2.37 (7H, m), 0.89 (3H, d, J=6.7 Hz).

MS (ESI) m/z 345 (M+H)+

Example 49

Synthesis of N-{5-[5-(4-amidinophenoxycarbonyl)furan-2-yl]-4-methylpentanoyl}-L-aspartic acid trifluoroacetic acid salt (A-59)

To A-58 (30 mg, 0.065 mmol), L-aspartic acid di-tert-butyl ester hydrochloride (17 mg, 0.059 mmol), and WSC hydrochloride (13 mg, 0.065 mmol) was added pyridine (1 mL), and the mixture was stirred at room temperature overnight. The reaction mixture was concentrated under reduced pressure, trifluoroacetic acid (1 mL) was added to the obtained residue, and the mixture was stirred at room temperature for 2 hours. The reaction mixture was concentrated under reduced pressure, and the obtained residue was purified by high performance liquid chromatography (water-acetonitrile, each containing 0.1% trifluoroacetic acid) to give the title compound (23 mg, 0.040 mmol, 62%).

$^1$H-NMR (300 MHz, DMSO-d6) δ 9.33 (2H, br s), 9.10 (2H, br s), 8.10 (1H, d, J=7.6 Hz), 7.89 (2H, d, J=8.8 Hz), 7.56 (2H, d, J=8.8 Hz), 7.55 (1H, d, J=3.5 Hz), 6.53-6.51 (1H, m), 4.50-4.43 (1H, m), 2.75 (1H, dd, J=15.0, 6.2 Hz), 2.69-2.47 (3H, m), 2.25-2.11 (2H, m), 1.88-1.81 (1H, m), 1.63-1.57 (1H, m), 1.41-1.34 (1H, m), 0.89 (3H, d, J=6.6 Hz).

MS (ESI) m/z 460 (M+H)+

Example 50

Synthesis of 5-[5-(4-amidinophenoxycarbonyl)furan-2-yl]-4-carboxypentanoic acid trifluoroacetic acid salt (A-60)

Step 1. Synthesis of 2-{[5-(benzyloxycarbonyl)furan-2-yl](hydroxy)methyl}prop-2-enoic acid tert-butyl ester 5-Formyl-2-furancarboxylic acid benzyl ester (0.2 g, 0.87 mmol), acrylic acid tert-butyl ester (0.52 mL), and 1,4-diazabicyclo[2.2.2]octane (20 mg, 0.18 mmol) were mixed, and the mixture was stirred for 4 days. Excess acrylic acid tert-butyl ester was evaporated under reduced pressure and the residue was purified by silica gel column chromatography to give the title compound (0.26 g).

$^1$H-NMR (300 MHz, CDC$_3$) δ 7.43-7.32 (5H, m), 7.16 (1H, d, J=3.6 Hz), 6.39 (1H, d, J=3.6 Hz), 6.31 (1H, s), 5.85 (1H, s), 5.55 (1H, br s), 5.32 (2H, s), 3.40 (1H, m), 1.45 (9H, s).

MS (ESI) m/z 359 (M+H)+

Step 2. Synthesis of 5-[5-(benzyloxycarbonyl)furan-2-yl]-4-tert-butoxycarbonyl-4-pentenoic acid ethyl ester 2-{[5-(Benzyloxycarbonyl)furan-2-yl](hydroxy)methyl}prop-2-enoic acid tert-butyl ester (90 mg, 0.25 mmol) was dissolved in ethyl orthoformate (2.0 mL, 10.9 mmol), propanoic acid (8 mg, 0.10 mmol) was added, and the mixture was stirred at 138° C. for 5 hours. The mixture was purified by silica gel column chromatography to give the title compound.

MS (ESI) m/z 429 (M+H)+

Step 3. Synthesis of 5-[2-(tert-butoxycarbonyl)-5-ethoxy-5-oxopentyl]furan-2-carboxylic acid 5-[5-(Benzyloxycarbonyl)furan-2-yl]-4-tert-butoxycarbonyl-4-pentenoic acid ethyl ester obtained in step 2 was dissolved in ethanol (5 mL), a catalytic amount of 10% palladium/carbon was added, and the mixture was stirred at room temperature for 1 hour under a hydrogen atmosphere. The reaction mixture was filtered through celite, and the filtrate was concentrated under reduced pressure to give the title compound (82 mg).

MS (ESI) m/z 341 (M+H)+

Step 4. Synthesis of 5-[5-(4-amidinophenoxycarbonyl)-furan-2-yl]-4-carboxypentanoic acid trifluoroacetic acid salt (A-60)

Using 5-{2-(tert-butoxycarbonyl)-5-ethoxy-5-oxopentyl}furan-2-carboxylic acid and 4-hydroxybenzamidine hydrochloride, and in the same manner as in Example 46, the title compound was synthesized.

$^1$H-NMR (300 MHz, DMSO-d6) δ 9.31 (2H, br s), 9.26 (2H, br s), 7.90 (2H, d, J=8.7 Hz), 7.55 (3H, m), 6.51 (1H, d, J=3.6 Hz), 3.00 (1H, m), 2.90 (1H, m), 2.73 (1H, m), 2.28 (2H, m), 1.77 (2H, m).

MS (ESI) m/z 375 (M+H)+

Example 51

Synthesis of N-{3-[5-(4-amidinophenoxycarbonyl)-furan-2-yl]-2-(carboxyethyl)propanoyl}-L-aspartic acid trifluoroacetic acid salt (A-61)

Step 1. Synthesis of 5-[5-(4-amidinophenoxycarbonyl)-furan-2-yl]-2-(2-ethoxycarbonyl)ethylpropanoic acid trifluoroacetic acid salt 5-[2-(tert-Butoxycarbonyl)-5-ethoxy-5-oxopentyl]furan-2-carboxylic acid (82 mg, 0.19 mmol) obtained in Example 50, step 3, 4-hydroxybenzamidine hydrochloride (65 mg, 0.33 mmol), and WSC hydrochloride (92 mg, 0.50 mmol) were dissolved in pyridine (3 mL), and the mixture was stirred at room temperature overnight. The reaction mixture was concentrated under reduced pressure, trifluoroacetic acid (2 mL) was added to the obtained residue, and the mixture was stirred at room temperature for 30 minutes. The reaction mixture was concentrated under reduced pressure, and the obtained residue was purified by high performance liquid chromatography to give the title compound (11 mg).

MS (ESI) m/z 403 (M+H)+

Step 2. Synthesis N-{3-[5-(4-amidinophenoxycarbonyl)-furan-2-yl]-2-(carboxyethyl)propanoyl}-L-aspartic acid trifluoroacetic acid salt (A-61)

Using 5-[5-(4-amidinophenoxycarbonyl)furan-2-yl]-2-(2-ethoxycarbonyl)ethylpropanoic acid trifluoroacetic acid salt and 4-hydroxybenzamidine hydrochloride and in the same manner as in Example 46, the title compound was synthesized.

¹H-NMR (300 MHz, DMSO-d6) δ 9.34 (2H, s), 9.06 (2H, s), 8.40 (1H, m), 8.89 (2H, d, J=8.7 Hz), 7.55 (2H, d, J=8.7 Hz), 7.50 (1H, d, J=3.3 Hz), 6.48 (1H, m), 4.50 (1H, m), 2.95-2.40 (5H, m), 2.22 (2H, m), 1.80-1.60 (2H, m).
MS (ESI) m/z 490 (M+H)+

Example 52

Synthesis of N-{3-[4-(4-amidinophenoxycarbonyl)-furan-2-yl]-2-methylpropanoyl}-L-aspartic acid trifluoroacetic acid salt (A-62)

Step 1. Synthesis of 4-ethoxycarbonylfuran-2-carboxylic acid

3-Furancarboxylic acid ethyl ester (1.4 g, 10.0 mmol) was dissolved in acetic acid (10 mL), bromine (1.6 g, 10.0 mmol) was added, and the mixture was stirred overnight. The solvent was evaporated under reduced pressure, and the obtained residue was purified by silica gel column chromatography (hexane/ethyl acetate=80/20). The obtained crude fraction was dissolved in N,N-dimethylformamide (15 mL), palladium acetate (0.18 g, 0.78 mmol), triphenylphosphine (0.41 g, 1.55 mmol), triethylamine (2.2 mL, 15.5 mmol), and water (0.7 mL, 38.8 mmol) were added, and the mixture was stirred at 80° C. overnight under a carbon monoxide atmosphere. 1N Hydrochloric acid was added to the reaction mixture, and the mixture was extracted with ethyl acetate. The extract was washed with saturated brine, dried over anhydrous sodium sulfate and concentrated under reduced pressure. The obtained residue was purified by high performance liquid chromatography to give the title compound (0.47 g).
¹H-NMR (300 MHz, DMSO-d6) δ 8.59 (1H, s), 7.37 (1H, s), 4.26 (2H, q, J=6.9 Hz), 1.28 (3H, t, J=6.9 Hz).

Step 2. Synthesis of 5-hydroxymethyl-3-furancarboxylic acid ethyl ester

4-Ethoxycarbonylfuran-2-carboxylic acid (0.47 g, 2.53 mmol) was dissolved in tetrahydrofuran (10 mL), triethylamine (0.53 mL, 3.80 mmol) and ethyl chloroformate (0.29 mL, 3.04 mmol) were added at 0° C., and the mixture was stirred at room temperature for 1 hour. The reaction mixture was filtered through celite, water (0.23 mL, 12.7 mmol) and sodium borohydride (0.19 g, 5.06 mmol) were added to the filtrate, and the mixture was stirred overnight. 1N Hydrochloric acid was added to the reaction mixture, and the mixture was extracted with ethyl acetate. The extract was washed with saturated brine, dried over anhydrous sodium sulfate and concentrated under reduced pressure. The obtained residue was purified by silica gel column chromatography (hexane/ethyl acetate=50/50) to give the title compound (0.34 g).
¹H-NMR (300 MHz, CDC₃) δ 7.97 (1H, s), 6.64 (1H, s), 4.62 (2H, s), 4.32 (2H, q, J=6.9 Hz), 1.34 (3H, t, J=6.9 Hz).

Step 3. Synthesis 5-formyl-3-furancarboxylic acid ethyl ester

5-Hydroxymethyl-3-furancarboxylic acid ethyl ester (0.34 g, 2.0 mmol) was dissolved in dichloromethane (20 mL), manganese dioxide (1.4 g, 15.9 mmol) was added, and the mixture was stirred overnight. The reaction mixture was filtered through celite, and the solvent was evaporated under reduced pressure to give the title compound (0.26 g).
¹H-NMR (300 MHz, CDC₃) δ 9.65 (1H, s), 8.75 (1H, s), 7.80 (1H, s), 4.62 (2H, s), 4.27 (2H, q, J=6.9 Hz), 1.30 (3H, t, J=6.9 Hz).

Step 4. Synthesis of 5-(2-tert-butoxycarbonylpropyl)-furan-3-carboxylic acid

M-13 (0.62 g, 2.33 mmol) was added dropwise to a suspension of 60% sodium hydride (0.74 g, 1.86 mmol) in tetrahydrofuran (10 mL) with stirring at 0° C. After stirring at room temperature for 20 minutes, a solution of 5-formyl-3-furancarboxylic acid ethyl ester (0.26 g, 1.55 mmol) in tetrahydrofuran (3 mL) was added dropwise at 0° C. After stirring at room temperature overnight, the mixture was worked up according to a conventional method and purified by column chromatography to give an oil (0.37 g). The obtained oil was dissolved in ethanol (10 mL), 10% palladium/carbon (0.04 g) was added, and the mixture was stirred at room temperature for hours under a hydrogen atmosphere. After completion of the reaction, palladium/carbon was removed by celite filtration, and the solvent was evaporated under reduced pressure. The obtained residue was dissolved in tetrahydrofuran (1.9 mL) and methanol (0.95 mL), 1N aqueous sodium hydroxide solution (1.9 mL) was added, and the mixture was stirred overnight. 1N Hydrochloric acid (2.5 mL) was added to the reaction mixture, and the mixture was extracted with ethyl acetate. The extract was washed with saturated brine, dried over anhydrous sodium sulfate and concentrated under reduced pressure to give the title compound (0.33 g).
¹H-NMR (300 MHz, CDC₃) δ 8.11 (1H, s), 6.34 (1H, s), 2.85 (1H, dd, J=14.7, 7.5 Hz), 2.70-2.55 (2H, m), 1.33 (9H, s), 1.03 (3H, J=6.6 Hz).

Step 5. Synthesis of N-{3-[4-(4-amidinophenoxycarbonyl)-furan-2-yl]-2-methylpropanoyl}-L-aspartic acid trifluoroacetic acid salt (A-62)

Using 5-(2-tert-butoxycarbonylpropyl)furan-3-carboxylic acid, 4-hydroxybenzamidine, and L-aspartic acid di-tert-butyl ester hydrochloride, and in the same manner as in Example 40, the title compound was obtained.
¹H-NMR (300 MHz, DMSO-d6) δ 9.33 (2H, s), 9.05 (2H, s), 8.51 (1H, s), 8.24 (0.5H, d, J=7.8 Hz), 8.26 (0.5H, d, J=7.8 Hz), 7.89 (2H, d, J=8.7 Hz), 7.52 (2H, d, J=8.7 Hz), 6.61 (0.5H, s), 6.58 (0.5H, s), 4.54 (1H, m), 3.10-2.80 (5H, m), 1.02 (3H, m). MS (ESI) m/z 432 (M+H)+

Example 53

Synthesis of 3-[4-(4-amidino-2-fluorophenoxycarbonyl)furan-2-yl]-2-methylpropanoic acid trifluoroacetic acid salt (A-63)

Using 5-(2-tert-butoxycarbonylpropyl)furan-3-carboxylic acid obtained in Example 52, step 4, and M-11 instead of M-1 and 4-hydroxybenzamidine hydrochloride, and by an operation in the same manner as in Example 16, the title compound was obtained (yield 52%).
¹H-NMR (400 MHz, DMSO-d6) δ 12.35 (1H, br s), 9.41 (2H, br s), 9.18 (2H, br s), 8.62 (1H, d, J=0.8 Hz), 7.92 (1H, dd, J=11.6, 1.6 Hz), 7.76-7.70 (2H, m), 6.63 (1H, d, J=0.8 Hz), 2.99 (1H, dd, J=15.0, 6.6 Hz), 2.83-2.72 (2H, m), 1.11 (3H, d, J=6.8 Hz).
MS (ESI) m/z 335 (M+H)+

Example 54

Synthesis of N-{3-[2-(4-amidinophenoxycarbonyl)-furan-4-yl]-2-methylpropanoyl}-L-aspartic acid trifluoroacetic acid salt (A-67)

Step 1. Synthesis of 4-formyl-2-furancarboxylic acid benzyl ester

3-Furfural (0.96 g, 10 mmol) was dissolved in toluene (10 mL), N,N'-dimethylethylenediamine (1.08 mL, 10.0 mmol) and p-toluenesulfonic acid monohydrate (10 mg, 0.11 mmol) were added, and the mixture was stirred at 105° C. overnight. The solvent was evaporated under reduced pressure and the residue was partitioned between ethyl acetate and 5% aqueous sodium hydrogen carbonate solution. The organic layer was washed with saturated brine, and dried over anhydrous sodium sulfate, and the solvent was evaporated under reduced pressure. The obtained residue was dissolved in tetrahydrofuran (20 mL), 1.54N n-butyllithium/hexane solution (3 mL) was added dropwise at −78° C., and the mixture was stirred for 1 hour. Dry ice was added to the reaction mixture, and the mixture was stirred at room temperature for 2 hour. The solvent was evaporated under reduced pressure, N,N-dimethylformamide (10 mL), potassium carbonate (0.55 g, 4.0 mmol), and benzyl bromide (2.04 g, 11.9 mmol) were added to the obtained residue, and the mixture was stirred at 60° C. overnight. 1N Hydrochloric acid was added to the reaction mixture, and the mixture was extracted with ethyl acetate. The extract was washed with saturated brine, dried over anhydrous sodium sulfate and concentrated under reduced pressure. The obtained residue was purified by silica gel column chromatography to give the title compound (0.33 g).

$^1$H-NMR (400 MHz, CDC$_3$) δ 9.96 (1H, s), 8.17 (1H, s), 7.52 (1H, s), 7.45-7.35 (5H, m), 5.37 (2H, s).

Step 2. Synthesis of 4-(2-tert-butoxycarbonylpropyl)-furan-2-carboxylic acid The title compound was obtained in the same manner as in Example 52, step 4.

$^1$H-NMR (400 MHz, DMSO-d6) δ 7.68 (1H, s), 7.10 (1H, s), 2.65-2.55 (3H, m), 1.35 (9H, s), 1.04 (3H, d, J=6.8 Hz).

Step 3. Synthesis of N-{3-[2-(4-amidinophenoxycarbonyl)-furan-4-yl]-2-methylpropanoyl}-L-aspartic acid trifluoroacetic acid salt (A-67)

The title compound was obtained in the same manner as in Example 52, step 5.

$^1$H-NMR (300 MHz, DMSO-d6) δ 9.33 (2H, s), 8.97 (2H, s), 8.23 (1H, m), 7.90-7.80 (3H, m), 7.55 (2H, d, J=8.4 Hz), 7.47 (1H, s), 4.48 (1H, m), 3.10-2.90 (3H, m), 2.70-2.50 (2H, m), 1.02 (3H, m).

MS (ESI) m/z 432 (M+H)+

Example 55

Synthesis of 3-[4-(4-amidino-2-fluorophenoxycarbonyl)thiophen-2-yl]-2-methylpropanoic acid trifluoroacetic acid salt (B-51)

Step 1. Synthesis of 5-(2-tert-butoxycarbonylpropyl)-thiophene-3-carboxylic acid Using 3-thiophenecarboxylic acid methyl ester instead of 3-furancarboxylic acid ethyl ester, palladium hydroxide instead of palladium/carbon, and lithium hydroxide instead of sodium hydroxide, and in the same manner as in Example 52, step 1 to step 4, the title compound was synthesized.

$^1$H-NMR (300 MHz, CDC$_3$) δ 8.03 (1H, d, J=1.2 Hz), 7.25 (1H, d, J=1.2 Hz), 3.13 (1H, dd, J=14.8, 8.0 Hz), 2.86 (1H, dd, J=14.8, 6.4 Hz), 2.66 (1H, m), 1.45 (9H, s), 1.16 (3H, d, J=7.2 Hz).

MS (ESI) m/z 271 (M+H)+

Step 2. Synthesis of 3-[4-(4-amidino-2-fluorophenoxycarbonyl)thiophen-2-yl]-2-methylpropanoic acid trifluoroacetic acid salt (B-51)

Using the compound obtained in step 1 and M-11 instead of M-1 and 4-amidinophenol hydrochloride, and by an operation in the same manner as in Example 16, the title compound was obtained (yield 58%).

$^1$H-NMR (400 MHz, DMSO-d6) δ 12.37 (1H, br s), 9.41 (2H, br s), 9.18 (2H, br s), 8.53 (1H, d, J=1.2 Hz), 7.93 (1H, dd, J=10.6, 1.0 Hz), 7.74-7.75 (2H, m), 7.38 (1H, d, J=1.2 Hz), 3.12 (1H, dd, J=15.3, 7.8 Hz), 2.98 (1H, dd, J=15.3, 6.0 Hz), 2.71 (1H, m), 1.13 (3H, d, J=7.2 Hz).

MS (ESI) m/z 351 (M+H)+

Example 56

Synthesis of N-{3-[4-(4-amidino-2-fluorophenoxycarbonyl)thiophen-2-yl]propanoyl}-L-aspartic acid trifluoroacetic acid salt (B-54)

Step 1. Synthesis of 5-(2-tert-butoxycarbonylethyl)-thiophene-3-carboxylic acid Using diethylphosphonoacetic acid tert-butyl ester instead of M-13 and in the same manner as in Example 55, step 1, the title compound was synthesized.

$^1$H-NMR (300 MHz, DMSO-d6) δ 8.03 (1H, d, J=1.2 Hz), 7.17 (1H, d, J=1.2 Hz), 3.00 (2H, t, J=6.4 Hz), 2.58 (2H, t, J=6.4 Hz), 1.38 (9H, s).

MS (ESI) m/z 257 (M+H)+

Step 2. Synthesis of N-{3-[4-(4-amidino-2-fluorophenoxycarbonyl)thiophen-2-yl]propanoyl}-L-aspartic acid trifluoroacetic acid salt (B-54)

Using the compound obtained in step 1 and in the same manner as in Example 55 and Example 38, the title compound was synthesized.

$^1$H-NMR (400 MHz, DMSO-d6) δ 9.40 (2H, br s), 9.09 (2H, br s), 8.49 (1H, s), 8.30 (1H, d, J=8.0 Hz), 7.92 (1H, d, J=8.0 Hz), 7.73 (2H, m), 7.38 (1H, s), 4.55 (1H, m), 3.07 (2H, t, J=7.6 Hz), 2.70-2.55 (4H, m).

MS (ESI) m/z 452 (M+H)+

Example 57

Synthesis of N-{4-[5-(4-amidinophenoxycarbonyl)-furan-2-yl]benzoyl}-L-aspartic acid trifluoroacetic acid salt (A-68)

4-Amidinophenol hydrochloride (50 mg, 0.29 mmol) was dissolved in pyridine (1.5 mL), 4-(5-chlorocarbonylfuran-2-yl)benzoic acid ethyl ester (81 mg, 0.29 mmol) was added, and the mixture was stirred at room temperature overnight. The reaction mixture was concentrated under reduced pressure, and 4N hydrochloric acid/dioxane (2 mL) and water (1 mL) were added to the obtained residue. After stirring at 60°

C. overnight, the mixture was concentrated under reduced pressure. L-Aspartic acid di-tert-butyl ester hydrochloride (22 mg, 0.078 mmol), WSC hydrochloride (15 mg, 0.078 mmol), and pyridine (1 mL) were added to the obtained residue, and the mixture was stirred at room temperature overnight. The reaction mixture was concentrated under reduced pressure, and trifluoroacetic acid (2 mL) was added to the obtained residue. After stirring at room temperature for 2 hours, the reaction mixture was concentrated under reduced pressure, and the obtained residue was purified by high performance liquid chromatography (water-acetonitrile, each containing 0.1% trifluoroacetic acid) to give the title compound (17 mg, 0.029 mmol, 10%).

$^1$H-NMR (400 MHz, DMSO-d6) δ 9.36 (2H, br s), 8.98 (2H, br s), 8.88 (1H, d, J=8.0 Hz), 8.01 (4H, s), 7.93 (2H, d, J=8.8 Hz), 7.79 (1H, d, J=3.6 Hz), 7.62 (2H, d, J=8.8 Hz), 7.48 (1H, d, J=3.6 Hz), 4.80-4.75 (1H, m), 2.87 (1H, dd, J=16.0, 5.6 Hz), 2.73 (1H, dd, J=16.0, 8.0 Hz).

MS (ESI) m/z 466 (M+H)+

Example 58

Synthesis of N-{3-[5-(4-amidinophenoxycarbonyl)-furan-2-yl]benzoyl}-L-aspartic acid trifluoroacetic acid salt (A-71)

Step 1. Synthesis of 5-(3-methoxycarbonylphenyl)furan-2-carboxylic acid

To 5-bromofuran-2-carboxylic acid (0.50 g, 2.6 mmol), 3-methoxycarbonylphenylboronic acid (0.52 g, 2.9 mmol), tetrakis(triphenylphosphine)palladium (45 mg, 0.039 mmol), and sodium hydrogen carbonate (0.49 g, 5.9 mmol) were added toluene (3.5 mL), tetrahydrofuran (3.0 mL) and water (3.5 mL), and the mixture was stirred at 90° C. for 2 hours. Water was added to the reaction mixture, and the mixture was washed with ethyl acetate. The aqueous layer was acidified with 1N hydrochloric acid, and the mixture was extracted with ethyl acetate. The ethyl acetate layer was washed with saturated brine, dried over anhydrous sodium sulfate and concentrated under reduced pressure to give the title compound as a pale-yellow powder (0.58 g, 2.3 mmol, 91%).

$^1$H-NMR (400 MHz, CDC$_3$) δ 8.44 (1H, d, J=1.6 Hz), 8.06-8.01 (2H, m), 7.54 (1H, dd, J=8.0, 7.6 Hz), 7.42 (1H, d, J=3.6 Hz), 6.89 (1H, d, J=3.6 Hz), 3.97 (3H, s).

MS (ESI) m/z 247 (M+H)+

Step 2. Synthesis of N-{3-[5-(4-amidinophenoxycarbonyl)-furan-2-yl]benzoyl}-L-aspartic acid trifluoroacetic acid salt (A-71)

To the carboxylic acid obtained by using the compound (100 mg, 0.41 mmol) obtained in step 1 and 4-amidinophenol hydrochloride (70 mg, 0.41 mmol) instead of B-6 and M-18, and by an operation in the same manner as in Example 46, step 2 were added L-aspartic acid di-tert-butyl ester hydrochloride (114 mg, 0.41 mmol), WSC hydrochloride (93 mg, 0.48 mmol), and pyridine (5 mL), and the mixture was stirred at room temperature overnight. The reaction mixture was concentrated under reduced pressure, and trifluoroacetic acid (5 mL) was added to the obtained residue. After stirring at room temperature for 2 hours, the reaction mixture was concentrated under reduced pressure, and the obtained residue was purified by high performance liquid chromatography (water-acetonitrile, each containing 0.1% trifluoroacetic acid) to give the title compound (15 mg, 0.026 mmol, 6%).

MS (ESI) m/z 466 (M+H)+

Example 59

Synthesis of O-{3-[5-(4-amidinophenoxycarbonyl)-furan-2-yl]-2-methylpropionyl}-D-malic acid trifluoroacetic acid salt (A-72)

A-6 (34.5 mg, 0.08 mmol) was dissolved in thionyl chloride (500 μL), and the mixture was stirred at 70° C. for 15 minutes. The reaction mixture was concentrated under reduced pressure, D-malic acid dibenzyl ester (37.8 mg, 0.12 mmol), dichloromethane (350 μL), and pyridine (150 μL) were added to the obtained residue, and the mixture was stirred at room temperature for 25 minutes. The reaction mixture was concentrated under reduced pressure, water was added, and the mixture was freeze-dried overnight. After freeze-drying, palladium/carbon (10 mg) and ethanol (1 mL) were added, and the mixture was stirred at room temperature for 3 hours. The reaction mixture was filtered through celite to remove palladium/carbon. The filtrate was concentrated under reduced pressure, and the obtained residue was purified by high performance liquid chromatography (acetonitrile-water, each containing 0.1% trifluoroacetic acid, 15-55%) to give the title compound (14.4 mg, 0.026 mmol, 33%).

$^1$H-NMR (300 MHz, DMSO-d6) δ 9.34 (2H, br s), 9.01 (2H, br s), 7.89 (2H, d, J=8.7 Hz), 7.56 (2H, d, J=8.7 Hz), 7.54 (1H, s), 6.61-6.49 (1H, m), 5.28-2.19 (1H, m), 3.39-2.60 (5H, m), 1.24-1.04 (3H, m).

MS (ESI) m/z 433 (M+H)+

Example 60

Synthesis of S-{3-[5-(4-amidinophenoxycarbonyl)-furan-2-yl]-2-methylpropionyl}thiomalic acid trifluoroacetic acid salt (A-73)

Step 1. Synthesis of S-{3-[5-(4-amidinophenoxycarbonyl)-furan-2-yl]-2-methylpropionyl}thiomalic acid diethyl ester trifluoroacetic acid salt A-6 (30 mg, 0.070 mmol) was dissolved in thionyl chloride (500 μL), and the mixture was stirred at 60° C. for 10 minutes. The reaction mixture was concentrated under reduced pressure, and thiomalic acid diethyl ester (21.6 mg, 0.105 mmol), dichloromethane (350 μL), and pyridine (150 μL) were added to the obtained residue, and the mixture was stirred at room temperature for 45 minutes. The reaction mixture was concentrated under reduced pressure, and the obtained residue was purified by high performance liquid chromatography (acetonitrile-water, each containing 0.1% trifluoroacetic acid, 5-45%) to give the title compound (40 mg, 0.065 mmol, 93%).

Step 2. Synthesis of S-{3-[5-(4-amidinophenoxycarbonyl)-furan-2-yl]-2-methylpropionyl}thiomalic acid trifluoroacetic acid salt (A-73)

To S-{3-[5-(4-amidinophenoxycarbonyl)furan-2-yl]-2-methylpropionyl}thiomalic acid diethyl ester trifluoroacetic acid salt (40 mg, 0.065 mmol) obtained in step 1 was added 4N hydrochloric acid/dioxane solution:water=3:1 (500 μL), and the mixture was stirred at 60° C. overnight. The reaction mixture was concentrated under reduced pressure, and the obtained residue was purified by high performance liquid chromatography (acetonitrile-water, each containing 0.1% trifluoroacetic acid, 10-45%) to give the title compound (5.0 mg, 0.0089 mmol, 14%).

$^1$H-NMR (400 MHz, DMSO-d6) δ 9.34 (2H, s), 9.15 (2H, s), 7.93-7.87 (2H, m), 7.59-7.51 (3H, m), 6.54 (1H, d, J=3.6 Hz), 4.37-4.28 (1H, m), 3.21-3.03 (2H, m), 3.01-2.62 (3H, m), 1.25-1.13 (3H, m)

MS (ESI) m/z 449 (M+H)+

Example 61

Synthesis of (N'-carboxymethyl-{3-[5-(4-amidinophenoxycarbonyl)furan-2-yl]-2-methylpropane}hydrazido)-acetic acid trifluoroacetic acid salt (A-74)

Step 1. Synthesis of N,N-bis(tert-butoxycarbonylmethyl)-N'-benzyloxycarbonylhydrazine Benzyloxycarbonylhydrazine (3.0 g, 18 mmol), bromoacetic acid tert-butyl ester (7.9 mL, 54 mmol), and diisopropylethylamine (6.3 mL, 36 mmol) were dissolved in toluene (30 mL), and the mixture was stirred at 75° C. overnight. After allowing to cool to room temperature, saturated brine was added, and the mixture was extracted three times with dichloromethane. The extract was dried over anhydrous sodium sulfate and concentrated under reduced pressure, and the obtained residue was purified by silica gel column chromatography (hexane/ethyl acetate=2/1) to give the title compound (5.8 g, 15 mmol, 81%).

$^1$H-NMR (400 Mz, CDC$_3$) δ 7.40-7.20 (5H, m), 7.00 (1H, br s), 5.20 (2H, s), 3.60 (4H, s), 1.45 (18H, s).

MS (ESI) m/z 397 (M+H)+

Step 2. Synthesis of N,N-bis(tert-butoxycarbonylmethyl)-hydrazine

The compound (5.8 g, 15 mmol) obtained in step 1 was dissolved in methanol (60 mL), 10% palladium/carbon (M) (3.0 g) was added, and the mixture was stirred overnight under a hydrogen atmosphere. The reaction mixture was filtered through a filter cell, and the filtrate was concentrated. The obtained residue was purified by silica gel column chromatography (dichloromethane/methanol=9/1) to give the title compound (2.9 g, 11 mmol, 76%).

$^1$H-NMR (400 Mz, CDC$_3$) δ 3.60 (4H, s), 1.45 (18H, s).

MS (ESI) m/z 261 (M+H)+

Step 3. Synthesis of (N'-carboxymethyl-{3-[5-(4-amidinophenoxycarbonyl)furan-2-yl]-2-methylpropane}hydrazido)-acetic acid trifluoroacetic acid salt (A-74)

To the compound (15 mg, 0.056 mmol) obtained in step 2 were added A-6 (20 mg, 0.046 mmol), WSC hydrochloride (13 mg, 0.070 mmol), and pyridine (1 mL), and the mixture was stirred at room temperature overnight. The reaction mixture was concentrated under reduced pressure, and trifluoroacetic acid (1 mL) was added to the obtained residue. After stirring at room temperature for 2 hours, the reaction mixture was concentrated under reduced pressure, and the obtained residue was purified by high performance liquid chromatography (water-acetonitrile, each containing 0.1% trifluoroacetic acid) to give the title compound (13 mg, 0.023 mmol, 50%).

$^1$H-NMR (400 MHz, DMSO-d6) δ 12.50 (2H, br s), 9.59 (1H, s), 9.34 (2H, br s), 9.04 (2H, br s), 7.89 (2H, d, J=8.7 Hz), 7.54 (2H, d, J=8.7 Hz), 7.49 (1H, d, J=3.5 Hz), 6.45 (1H, d, J=3.5 Hz), 3.70 (4H, s), 2.93 (1H, dd, J=14.6, 7.8 Hz), 2.78-2.70 (2H, m), 1.03 (3H, d, J=6.6 Hz).

MS (ESI) m/z 447 (M+H)+

Example 62

Synthesis of N-{5-[5-(4-amidinophenoxycarbonyl)-thiophen-2-yl]thiophen-2-ylcarbonyl}-L-aspartic acid trifluoroacetic acid salt (B-59)

Step 1. Synthesis of 2,2'-bithiophene-5,5'-dicarboxylic acid 2,2'-Bithiophene (0.50 g, 3.0 mmol) was dissolved in tetrahydrofuran (10 mL), n-butyllithium (2.76 M hexane solution, 2.4 mL, 6.6 mmol) was added at room temperature under an argon atmosphere, and the mixture was stirred at 50° C. for 30 minutes. After cooling to room temperature, carbon dioxide was blown into the reaction mixture. The reaction mixture was concentrated under reduced pressure and the obtained residue was washed with hexane to give a yellow powder (0.97 g) containing a lithium salt of the title compound as a main component. The obtained powder was dissolved in water and acidified with 1N hydrochloric acid, and the precipitate was collected by filtration to give the title compound as a green powder (0.55 g, 2.2 mmol, 72%).

MS (ESI) m/z 255 (M+H)+

Step 2. Synthesis of N-{5-[5-(4-amidinophenoxycarbonyl)-thiophen-2-yl]thiophen-2-ylcarbonyl}-L-aspartic acid trifluoroacetic acid salt (B-59)

To the compound (0.20 g, 0.79 mmol) obtained in step 1, 4-amidinophenol hydrochloride (0.14 g, 0.79 mmol), and WSC hydrochloride (0.18 g, 0.94 mmol) was added pyridine (10 mL), and the mixture was stirred at room temperature overnight. L-aspartic acid di-tert-butyl ester hydrochloride (0.22 g, 0.79 mmol) and WSC hydrochloride (0.18 g, 0.79 mmol) were added to the reaction mixture, and the mixture was further stirred at room temperature overnight. The reaction mixture was concentrated under reduced pressure, and trifluoroacetic acid (2 mL) was added to the obtained residue. After stirring at room temperature for 2 hours, the reaction mixture was concentrated under reduced pressure, and the obtained residue was purified by high performance liquid chromatography (water-acetonitrile, each containing 0.1% trifluoroacetic acid) to give the title compound (1.4 mg, 0.0023 mmol, 0.3%).

MS (ESI) m/z 488 (M+H)+

Example 63

Synthesis of N-[5-(4-amidino-2-fluorophenoxycarbonyl)thiophen-2-ylacetyl]-L-aspartic acid trifluoroacetic acid salt (B-60)

Step 1. Synthesis of 5-tert-butoxycarbonylmethyl-2-thiophenecarboxylic acid

5-Bromomethyl-2-thiophenecarboxylic acid methyl ester (2.6 g, 10.4 mmol) and chloro(1,5-cyclooctadiene)rhodium (I) dimer (0.5 g, 1.02 mmol) were dissolved in formic acid (30 mL), and the mixture was stirred at 75° C. overnight under a carbon monoxide atmosphere. After evaporation of the solvent, thionyl chloride (10 mL) was added, and the mixture was stirred at 70° C. for 1 hour. The solvent was evaporated under reduced pressure, tert-butanol (10 mL) and triethylamine (2 mL) were added, and the mixture was stirred for 30 minutes. After evaporation of the solvent, water was added, and the mixture was extracted with ethyl acetate. The extract was concentrated and purified by silica gel column chromatography to give an oil (0.62 g). The oil (0.42 g) was dissolved in methanol (4.1 mL), aqueous lithium hydroxide solution (4.1 mL) was added, and the mixture was stirred for 2 hours. The reaction mixture was neutralized with 1N hydrochloric acid (5 mL), purified by high performance liquid chromatography and freeze-dried to give the title compound (29 mg).

$^1$H-NMR (400 MHz, CDC$_3$) δ 7.74 (1H, d, J=4.0 Hz), 6.96 (1H, d, J=4.0 Hz), 3.78 (2H, s), 1.48 (9H, s).

Step 2. Synthesis of 5-(4-amidino-2-fluorophenoxycarbonyl)thiophen-2-ylacetic acid trifluoroacetic acid salt The compound (29 mg, 0.12 mmol) obtained in step 1 and M-11 (34 mg, 0.18 mmol) were suspended in pyridine (3 mL), WSC hydrochloride (70 mg, 0.36 mmol) was added, and the mixture was stirred for 2 hours. The solvent was evaporated, trifluoroacetic acid (3 mL) was added, and the mixture was stirred for 15 minutes. The reaction mixture was concentrated under reduced pressure, and the obtained residue was purified by high performance liquid chromatography (acetonitrile-water, each containing 0.1% trifluoroacetic acid, 5-35%) to give the title compound (19 mg).

$^1$H-NMR (400 MHz, DMSO-d6) δ 9.41 (2H, br s), 9.14 (2H, br s), 7.97 (1H, d, J=3.6 Hz), 7.94 (1H, m), 7.80 (2H, m), 7.20 (1H, d, J=3.6 Hz), 4.05 (2H, s).

MS (ESI) m/z 323 (M+H)+

Step 3. Synthesis of N-[5-(4-amidino-2-fluorophenoxycarbonyl)thiophen-2-ylacetyl]-L-aspartic acid trifluoroacetic acid salt (B-60)

Using the compound obtained in step 2 and in the same manner as in Example 37, the title compound was obtained.

$^1$H-NMR (400 MHz, DMSO-d6) δ 9.41 (2H, br s), 9.10 (2H, br s), 8.64 (1H, d, J=4.0 Hz), 7.98 (2H, m), 7.75 (2H, m), 7.14 (1H, J=3.6 Hz), 4.55 (1H, m), 3.90 (2H, s), 3.08-2.98 (1H, m), 2.70-2.60 (1H, m).

MS (ESI) m/z 438 (M+H)+

Example 64

Synthesis of N-{3-[5-(4-amidino-2-fluorophenoxycarbonyl)thiazol-2-yl]-methylpropionyl}-L-aspartic acid trifluoroacetic acid salt (C-4)

Step 1. Synthesis of 5-(tert-butyldimethylsilyloxy)-methylthiazole

5-Hydroxymethylthiazole (5.0 g, 43 mmol), imidazole (7.4 g, 109 mmol), and diisopropylethylamine (14 g, 109 mmol) were dissolved in N,N-dimethylformamide (50 mL), tert-butyldimethylsilyl chloride (13.1 g, 87 mmol) was added, and the mixture was stirred at room temperature for 20 hours. Ethyl acetate (200 mL) and water (100 mL) were added to the reaction mixture, the mixture was partitioned, and the organic layer was washed with saturated brine. The organic layer was dried over anhydrous sodium sulfate and purified by silica gel column chromatography to give the title compound.

$^1$H-NMR (300 MHz, DMSO-d6) δ 8.71 (1H, s), 7.70 (1H, s), 4.90 (2H, s), 0.90 (9H, s), 0.08 (6H, s).

Step 2. Synthesis of 5-(tert-butyldimethylsilyloxy)-methyl-2-formylthiazole

The compound (4.5 g, 20 mmol) obtained in step 1 was dissolved in tetrahydrofuran (30 mL), and 2.5M n-butyllithium/hexane solution (16 mL, 40 mmol) was added dropwise at –78° C. The reaction mixture was stirred at –78° C. for 35 minutes, N,N-dimethylformamide (4 mL) was added dropwise, and the mixture was stirred at –30° C. for 1 hour. The reaction mixture was neutralized with water and 2N hydrochloric acid, and the solvent was evaporated under reduced pressure. The residue was purified by silica gel chromatography to give the title compound (1.6 g).

$^1$H-NMR (300 MHz, DMSO-d6) δ 9.91 (1H, s), 7.89 (1H, s), 4.95 (2H, s), 0.90 (9H, s), 0.10 (6H, s).

Step 3. Synthesis of 5-[2-(tert-butoxycarbonyl)-1-propenyl]-2-(tert-butyldimethylsilyloxy)methylthiazole To a suspension of 60% sodium hydride (0.12 g, 3.0 mmol) in tetrahydrofuran (5 mL) was added M-13 (0.92 g, 2.57 mmol) at 0° C., and the mixture was stirred for 35 minutes. A solution of the compound (0.5 g, 2.0 mmol) obtained in step 2 in tetrahydrofuran (20 mL) was added, and the mixture was stirred at room temperature for 2 hours. Ethyl acetate (30 mL) and water (5 mL) were added to the reaction mixture, the mixture was partitioned, and the organic layer was washed with saturated brine. The organic layer was dried over anhydrous sodium sulfate and purified by silica gel column chromatography to give the title compound (0.68 g).

$^1$H-NMR (300 MHz, CDC$_3$) δ 7.74 (1H, s), 7.70 (1H, s), 4.93 (2H, s), 2.29 (3H, s), 1.53 (9H, s), 0.92 (9H, s), 0.11 (6H, s).

Step 4. Synthesis of 5-[2-(tert-butoxycarbonyl)propyl]-2-(tert-butyldimethylsilyloxy)methylthiazole The compound (0.5 g, 1.4 mmol) obtained in step 3 was dissolved in ethanol (20 mL), palladium/carbon (0.1 g) was added, and the mixture was stirred at 50° C. for 20 hours under a hydrogen atmosphere (55 psi). The reaction mixture was filtered, and the solvent was evaporated under reduced pressure to give the title compound (0.3 g).

$^1$H-NMR (300 MHz, CDC$_3$) δ 7.42 (1H, s), 4.82 (2H, s), 3.32-3.23 (1H, m), 3.01-2.91 (1H, m), 2.89-2.80 (1H, m), 1.38 (9H, s), 1.17 (3H, d, J=6.8 Hz), 0.87 (9H, s), 0.05 (6H, s).

Step 5. Synthesis of 5-[2-(tert-butoxycarbonyl)propyl]-2-formylmethylthiazole

To a solution of n-tetrabutylammonium fluoride (0.39 g, 1.5 mmol) in tetrahydrofuran (5 mL) was added a solution of the compound (0.30 g, 0.76 mmol) obtained in step 4 in tetrahydrofuran (2 mL), and the mixture was stirred at room temperature overnight. The solvent was evaporated under reduced pressure, and the residue was partitioned between ethyl acetate and water. The organic layer was washed with saturated brine. The organic layer was dried over anhydrous sodium sulfate and the solvent was evaporated under reduced pressure. The residue was purified by silica gel chromatography to give an oil (0.16 g). The obtained oil was dissolved in dichloromethane (15 mL), manganese dioxide (0.27 g, 3.0 mmol) was added, and the mixture was refluxed overnight.

The solvent was evaporated under reduced pressure, and the residue was purified by silica gel chromatography to give an oil (0.10 g).

$^1$H-NMR (300 MHz, CDC$_3$) δ 9.97 (1H, s), 8.27 (1H, s), 3.42-3.34 (1H, m), 3.11-3.03 (1H, m), 2.96-2.89 (1H, m), 1.39 (9H, s), 1.20 (3H, d, J=6.9 Hz).

Step 6. Synthesis of 5-[2-(tert-butoxycarbonyl)propyl]-thiazole-2-carboxylic acid To a solution of the compound (1.8 g, 7.0 mmol) obtained in step 5 in tert-butanol (27.1 mL) were added water (6.0 mL), 2-methyl-2-butene (3.7 g, 52.9 mmol), sodium dihydrogen phosphate (3.1 g, 17.6 mmol), and sodium chlorite (3.2 g, 35.2 mmol), and the mixture was stirred at room temperature for 20 minutes. The solvent was evaporated, and the pH was adjusted to 8-9 with water and sodium hydrogen carbonate solution. The reaction mixture was washed with ethyl acetate, and the aqueous layer was adjusted to pH 5-6 with 2N hydrochloric acid. The aqueous layer was extracted with ethyl acetate, and the organic layer was washed with saturated brine and dried over anhydrous sodium sulfate. The solvent was evaporated to give the title compound (1.1 g).

$^1$H-NMR (300 MHz, CDC$_3$) δ 13.44 (1H, br s), 8.21 (1H, s), 3.30-3.20 (1H, m), 3.18-3.03 (1H, m), 2.91-2.84 (1H, m), 1.35 (9H, s), 1.14 (3H, d, J=7.2 Hz).

Step 7. Synthesis of N-{3-[5-(4-amidino-2-fluorophenoxycarbonyl)thiazol-2-yl]-methylpropionyl}-L-aspartic acid trifluoroacetic acid salt (C-4)

Using the compound obtained in step 6 and in the same manner as in Example 37, the title compound was obtained.

$^1$H-NMR (400 MHz, DMSO-d6) δ 9.42 (2H, s), 9.16 (2H, s), 8.62 (1H, s), 8.36 (1H, m), 7.95 (1H, dd, J=11.0, 2.0 Hz), 7.76 (2H, m), 4.50 (1H, m), 3.30 (1H, m), 3.10-2.85 (1H, m), 2.75-2.55 (3H, m), 1.10 (3H, m).

MS (ESI) m/z 467 (M+H)+

Example 65

Synthesis of 3-{3-[4-(4-amidinophenoxycarbonyl)-1,3-thiazol-2-yl]-Narboxymethyl)propanamido}propanoic acid trifluoroacetic acid salt (C-5)

Step 1. Synthesis of 3-[4-(ethoxycarboxyl)thiazol-2-yl]propenoic acid tert-butyl ester Using 2-formyl-4-thiazolecarboxylic acid ethyl ester obtained in Example 30, step 1 and diethylphosphonoacetic acid tert-butyl ester, and in the same manner as in Example 30, the title compound was obtained.

$^1$H-NMR (400 MHz, CDC$_3$) δ 8.19 (1H, s), 7.75 (1H, d, J=16.0 Hz), 6.64 (1H, d, J=16.0 Hz), 4.45 (2H, q, J=6.8 Hz), 1.53 (9H, s), 1.42 (3H, t, J=6.8 Hz).

Step 2. Synthesis of 2-[(1E)-2-{[2-(tert-butoxy)-2-oxoethyl][3-(tert-butoxy)-3-oxopropyl]carbamoyl}eth-1-en-1-yl]-1,3-thiazole-4-carboxylic acid ethyl ester The compound (0.45 g, 1.51 mmol) obtained in step 1 was dissolved in trifluoroacetic acid (10 mL), and the mixture was stirred for 1 hour. The solvent was evaporated to give a white solid (0.36 g). The white solid (0.26 g, 1.06 mmol) was dissolved in dichloromethane (15 mL), oxalyl chloride (0.15 mL, 1.75 mmol) and N,N-dimethylformamide (1 drop) were added, and the mixture was stirred for 10 minutes. The solvent was evaporated under reduced pressure, a solution of M-20 (0.32 g, 1.08 mmol) in dichloromethane (10 mL) and pyridine (0.25 mL) were added, and the mixture was stirred for 2 hours. The solvent was evaporated under reduced pressure, and the residue was purified by silica gel column chromatography to give the title compound.

$^1$H-NMR (400 MHz, CDC$_3$) δ 8.21 (0.5H, s), 8.19 (0.5H, s), 7.80 (0.5H, d, J=15.2 Hz), 7.74 (0.5H, d, J=14.8 Hz), 7.39 (0.5H, d, J=15.2 Hz), 7.08 (0.5H, d, J=14.8 Hz), 4.43 (2H, m), 4.23 (1H, s), 4.13 (1H s), 3.81 (1H, t, J=6.8 Hz), 3.71 (1H, t, J=6.8 Hz), 2.62 (2H, m), 1.43 (21H, m).

Step 3. Synthesis of 2-(2-{[2-(tert-butoxy)-2-oxoethyl][3-(tert-butoxy)-3-oxopropyl]carbamoyl}ethyl)-1,3-thiazole-4-carboxylic acid The compound (0.4 g, 0.85 mmol) obtained in step 2 was dissolved in methanol (9 mL) and chloroform (1 mL), palladium hydroxide (0.08 g) was added, and the mixture was stirred at room temperature overnight under a hydrogen atmosphere. The reaction mixture was filtered through celite, and the solvent was evaporated. The residue was dissolved in methanol (1 mL), 1N aqueous lithium hydroxide solution (1.55 mL) was added, and the mixture was stirred for 3 hours. The mixture was neutralized with 1N hydrochloric acid, and extracted with ethyl acetate. The reaction mixture was concentrated under reduced pressure, and the obtained residue was purified by high performance liquid chromatography (acetonitrile-water, each containing 0.1% trifluoroacetic acid) to give the title compound (0.26 g).

$^1$H-NMR (400 MHz, CDC$_3$) δ 8.16 (1H, s), 4.12 (1H, s), 4.02 (1H, s), 3.69 (1H, t, J=6.8 Hz), 3.60 (1H, t, J=6.8 Hz), 3.43-3.35 (2H m), 3.01 (1H, t, J=6.8 Hz), 2.77 (1H, t, J=6.8 Hz), 2.58-2.48 (2H, m), 1.45 (18H, m).

Step 4. Synthesis of 3-{3-[4-(4-amidinophenoxycarbonyl)-1,3-thiazol-2-yl]-Narboxymethyl)propanamido}propanoic acid trifluoroacetic acid salt (C-5)

Using the compound obtained in step 3 and in the same manner as in Example 37, the title compound was obtained.

$^1$H-NMR (400 MHz, DMSO-d6) δ 9.35 (2H, s), 9.02 (2H, s), 8.72 (1H, s), 7.91 (2H, d, J=8.4 Hz), 7.57 (2H, d, J=8.4 Hz), 4.22 (1H, s), 3.97 (1H, s), 3.65-3.30 (4H, m), 2.95 (1H, t, J=6.8 Hz), 2.75 (1H, t, J=6.8 Hz), 2.55 (1H, t, J=6.8 Hz), 2.45 (1H, t, J=6.8 Hz).

MS (ESI) m/z 449 (M+H)+

Example 66

Synthesis of N-{3-[5-(4-amidino-2-fluorophenoxycarbonyl)-3-methylthiophen-2-yl]propanoyl}-L-aspartic acid trifluoroacetic acid salt (B-61)

Step 1. Synthesis of 1,3-dimethyl-2-(3-methylthiophen-2-yl)imidazolidine

2-Formyl-3-methylthiophene (3.0 g, 23.8 mmol) and N,N'-dimethylethylenediamine (2.3 g, 26.2 mmol) were dissolved in toluene (80 mL), and the mixture was stirred at 120° C. overnight. The solvent was evaporated under reduced pressure, and the obtained residue was purified by silica gel column chromatography to give the title compound (3.1 g, 15.8 mmol).

$^1$H-NMR (400 MHz, CDC$_3$) δ 7.23 (1H, d, J=5.2 Hz), 6.77 (1H, d, J=5.2 Hz), 3.79 (1H, s), 3.40-3.33 (2H, m), 2.60-2.55 (2H, m), 2.25 (9H, s).

Step 2. Synthesis of 5-formyl-4-methylthiophene-2-carboxylic acid benzyl ester 1,3-Dimethyl-2-(3-methylthiophen-2-yl)imidazolidine (3.1 g, 15.8 mmol) obtained in step 1 was dissolved in tetrahydrofuran (80 mL), 2.76N n-butyllithium/hexane solution (6.9 mL) was added dropwise at −78° C., and the mixture was stirred for 30 minutes. Dry ice was added to the reaction mixture, and the mixture was stirred at room temperature for 1 hour. The solvent was evaporated under reduced pressure, N,N-dimethylformamide (80 mL), potassium carbonate (6.54 g, 47.4 mmol), and benzyl bromide (8.0 g, 46.8 mmol) were added to the obtained residue, and the mixture was stirred at 60° C. for 3 hour. Water was added to the reaction mixture, and the mixture was extracted with ethyl acetate. The extract was washed with saturated brine, dried over anhydrous sodium sulfate and concentrated under reduced pressure. The obtained residue was purified by silica gel column chromatography to give the title compound (1.84 g).

$^1$H-NMR (400 MHz, CDC$_3$) δ 10.07 (1H, s), 7.63 (1H, s), 7.45-7.35 (5H, m), 5.35 (2H, s), 2.57 (3H, s).

Step 3. Synthesis of (E)-3-(5-benzyloxycarbonyl-3-methylthiophen-2-yl)-2-propenoic acid tert-butyl ester A solution of diethylphosphonoacetic acid tert-butyl ester (0.44 g, 1.74 mmol) in tetrahydrofuran (3 mL) was added dropwise to a suspension of 60% sodium hydride (0.055 g, 1.38 mmol) in tetrahydrofuran (15 mL) with stirring at 0° C. After stirring at room temperature for 30 minutes, a solution of 5-formyl-4-methylthiophene-2-carboxylic acid benzyl ester (0.3 g, 1.15 mmol) obtained in step 2 in tetrahydrofuran (3 mL) was added dropwise at 0° C. After stirring at room temperature for 2 hours, the mixture was worked up according to a conventional method, and purified by silica gel column chromatography to give the title compound (0.35 g).

$^1$H-NMR (400 MHz, CDC$_3$) δ 7.70 (1H, d, J=15.6 Hz), 7.55 (1H, s), 7.45-7.35 (5H, m), 6.23 (1H, d, J=15.6 Hz), 5.32 (2H, s), 2.31 (3H, s), 1.52 (9H, s).

Step 4. Synthesis of 3-(5-hydroxycarbonyl-3-methylthiophen-2-yl)propanoic acid tert-butyl ester (E)-3-(5-Benzyloxycarbonyl-3-methylthiophen-2-yl)-2-propenoic acid tert-butyl ester (1.42 g, 4.12 mmol) obtained in step 3 was dissolved in ethanol (12 mL), 10% palladium/carbon (142 mg) was added, and the mixture was stirred at room temperature overnight under a hydrogen atmosphere. After completion of the reaction, palladium/carbon was removed by celite filtration, and the solvent was evaporated under reduced pressure to give the title compound (1.02 g, 3.77 mmol, 92%).

$^1$H-NMR (400 MHz, CDC$_3$) δ 7.48 (1H, s), 2.98 (2H, t, J=7.6 Hz), 2.51 (2H, t, J=7.6 Hz), 2.11 (3H, s), 1.43 (9H, s).

Step 5. Synthesis of 3-[5-(4-amidino-2-fluorophenoxycarbonyl)-3-methylthiophen-2-yl]propanoic acid trifluoroacetic acid salt The compound (1.02 g, 3.77 mmol) obtained in step 4, M-11 (1.08 g, 5.66 mmol), and WSC hydrochloride (1.45 g, 7.55 mmol) were dissolved in pyridine (10 ml), and the mixture was stirred at room temperature overnight. The reaction mixture was concentrated, and the solvent was evaporated under reduced pressure. Trifluoroacetic acid (10 mL) was added, and the mixture was stirred at room temperature for 1 hour. The solvent was evaporated under reduced pressure, and the obtained residue was purified by high performance liquid chromatography (water-acetonitrile, each containing 0.1% trifluoroacetic acid) to give the title compound (535 mg, 1.15 mmol, 31%).

$^1$H-NMR (400 MHz, DMSO-d$_6$) δ 9.41 (2H, br s), 9.14 (2H, br s), 7.96-7.89 (1H, m), 7.86 (1H, s), 7.77-7.71 (2H, m), 3.05 (2H, t, J=7.2 Hz), 2.61 (2H, t, J=7.2 Hz), 2.22 (3H, s).

MS (ESI) m/z 351 (M+H)+

Step 6. Synthesis of N-{3-[5-(4-amidino-2-fluorophenoxycarbonyl)-3-methylthiophen-2-yl]propanoyl}-L-aspartic acid trifluoroacetic acid salt (B-61)

The compound (432 mg, 0.93 mmol) obtained in step 5, aspartic acid di-tert-butyl ester (393 mg, 1.40 mmol), and WSC hydrochloride (357 mg, 1.86 mmol) were dissolved in pyridine (3.0 mL), and the mixture was stirred at room temperature. The solvent was evaporated under reduced pressure, trifluoroacetic acid (3.0 mL) was added to the residue, and the mixture was stirred at room temperature for 3 hours. The reaction mixture was concentrated under reduced pressure, and the obtained residue was purified by high performance liquid chromatography (water-acetonitrile, each containing 0.1% trifluoroacetic acid) to give the title compound (474 mg, 0.82 mmol, 88%).

$^1$H-NMR (400 MHz, DMSO-d$_6$) δ 9.40 (2H, br s), 9.11 (2H, br s), 8.29 (1H, d, J=7.2 Hz), 7.92 (1H, d, J=11.2 Hz), 7.84 (1H, s), 7.77-7.71 (2H, m), 4.57-4.46 (1H, m), 3.03 (2H, t, J=7.6 Hz), 2.71-2.49 (4H, m), 2.21 (3H, s).

MS (ESI) m/z 466 (M+H)+

Example 67

Synthesis of N-{3-[5-(4-amidino-2-fluorophenoxycarbonyl)thiophen-2-yl]propanoyl}-N-allyl-L-aspartic acid trifluoroacetic acid salt (B-63)

Step 1. Synthesis of N-allyl-L-aspartic acid di-tert-butyl ester hydrochloride

L-aspartic acid di-tert-butyl ester hydrochloride (1.0 g, 3.5 mmol) was dissolved in acetonitrile (7 ml), potassium carbonate (0.98 g, 7.1 mmol) and allyl bromide (0.29 mL, 3.4 mmol) were added, and the mixture was stirred at room temperature overnight. The insoluble material was removed by filtration, the filtrate was concentrated under reduced pressure, and the obtained residue was purified by silica gel column chromatography (hexane/ethyl acetate=95/5) to give N-allyl-L-aspartic acid di-tert-butyl ester (0.50 g, 1.8 mmol).

$^1$H-NMR (400 MHz, CDC$_3$) δ 5.86 (1H, dddd, J=17.2, 10.2, 6.1, 5.9 Hz), 5.16-5.21 (1H, m), 5.06-5.10 (1H, m), 3.47 (1H, dd, J=6.8, 5.9 Hz), 3.30-3.36 (1H, m), 3.15-3.20 (1H, m), 2.60 (1H, dd, J=15.7, 5.9 Hz), 2.51 (1H, dd, J=15.7, 6.8 Hz), 1.47 (9H, s), 1.45 (9H, s).

MS (ESI) m/z 286 (M+H)+

The obtained N-allyl-L-aspartic acid di-tert-butyl ester was dissolved in acetonitrile (10 mL), and water (17 mL) and 1N hydrochloric acid (1.8 mL, 1.8 mmol) were added. The solution was concentrated under reduced pressure and freeze-dried to give the title compound (0.54 g, 1.7 mmol, 47%).

$^1$H-NMR (400 MHz, DMSO-d6) δ 9.25 (2H, br s), 5.84-5.94 (1H, m), 5.48 (1H, d, J=17.2 Hz), 5.41 (1H, d, J=9.6 Hz), 4.11 (1H, br s), 3.65 (2H, br s), 2.96 (1H, br d, J=17.8 Hz), 2.86 (1H, dd, J=17.8, 5.8 Hz), 1.45 (9H, s), 1.44 (9H, s).
MS (ESI) m/z 286 (M+H)+

Step 2. Synthesis of N-{3-[5-(4-amidino-2-fluorophenoxycarbonyl)thiophen-2-yl]propanoyl}-N-allyl-L-aspartic acid trifluoroacetic acid salt (B-63)

Using N-allyl-L-aspartic acid di-tert-butyl ester hydrochloride obtained in step 1, M-11, and M-23, and by an operation in the same manner as in Example 33, the title compound (yield 24%) was obtained.
$^1$H-NMR (400 MHz, DMSO-d$_6$) δ 9.56-9.10 (4H, m), 7.98-7.89 (2H, m), 7.79-7.70 (2H, m), 718-7.09 (1H, m), 5.95-5.65 (1H, m), 5.46-4.95 (2H, m), 4.61-4.48 (1H, m), 4.18-3.84 (2H, m), 3.71-2.41 (6H, m).
MS (ESI) m/z 492 (M+H)+

Example 68

Synthesis of N-{3-[5-(4-amidino-2-fluorophenoxycarbonyl)thiophen-2-yl]-2,2-dimethylpropanoyl}-L-aspartic acid trifluoroacetic acid salt (B-64)

Step 1. Synthesis of 5-chloromethylthiophene-2-carboxylic acid tert-butyl ester

5-Formylthiophene-2-carboxylic acid (5.27 g, 33.7 mmol), di-tert-butyl dicarbonate (8.1 g, 37.1 mmol), and N,N-dimethylaminopyridine (0.41 g, 3.39 mmol) were dissolved in tert-butanol (120 mL) and dichloromethane (40 mL), and the mixture was stirred overnight. The solvent was evaporated under reduced pressure, and 0.5N aqueous hydrochloric acid solution was added to the residue, and the mixture was extracted with ethyl acetate. The extract was washed with saturated brine, dried over anhydrous magnesium sulfate, and concentrated under reduced pressure. The obtained residue was dissolved in tetrahydrofuran (100 mL) and methanol (10 mL), sodium borohydride (1.28 g, 33.7 mmol) was added at 0° C., and the mixture was stirred for 3 hours. The solvent was evaporated under reduced pressure, 0.5N aqueous hydrochloric acid solution was added to the residue, and the mixture was extracted with ethyl acetate. The extract was washed with saturated brine, dried over anhydrous magnesium sulfate, and concentrated under reduced pressure. The obtained residue was dissolved in dichloromethane (100 mL), methanesulfonyl chloride (2.87 mL, 37.1 mmol) and diisopropylethylamine (8.9 mL, 51.1 mmol) were added at 0° C., and the mixture was stirred for 2 days. The solvent was evaporated under reduced pressure, 0.5N aqueous hydrochloric acid solution was added to the residue, and the mixture was extracted with ethyl acetate. The extract was washed with saturated brine, dried over anhydrous magnesium sulfate, and concentrated under reduced pressure. The obtained residue was purified by silica gel column chromatography to give the title compound (7.5 g).
$^1$H-NMR (400 MHz, DMSO-d6) δ 7.56 (1H, d, J=4.0 Hz), 7.04 (1H, d, J=4.0 Hz), 4.75 (2H, s), 1.57 (9H, s).

Step 2. Synthesis of 3-(5-carboxythiophen-2-yl)-2,2-dimethylpropanoic acid

Diisopropylamine (478 μL, 3.40 mmol) was dissolved in tetrahydrofuran (2.0 mL), the mixture was stirred at −78° C. for 15 minutes, and 2.6N n-butyllithium/hexane solution (1.31 mL, 3.40 mmol) was added dropwise. After dropwise addition, the mixture was stirred at 0° C. for 30 minutes, and isobutyric acid (158 μL, 1.70 mmol) was added dropwise at −78° C. After the completion of the dropwise addition, the mixture was stirred at 0° C. for 20 minutes, 5-chloromethylthiophene-2-carboxylic acid tert-butyl ester (360 mg, 1.55 mmol) dissolved in tetrahydrofuran (1.5 mL) was added at 0° C., and the mixture was stirred at room temperature overnight. Ethyl acetate and 1N aqueous hydrochloric acid solution were added to the reaction mixture, the mixture was partitioned, and the organic layer was separated. The aqueous layer was extracted three times with ethyl acetate, and the organic layers was combined and washed with saturated brine. The organic layer was dried over magnesium sulfate, and the solvent was evaporated to give the title compound as a crude product.

Step 3. Synthesis of N-[3-(5-carboxythiophen-2-yl)-2,2-dimethylpropanoyl]-L-aspartic acid dimethyl ester The crude product obtained in step 2 was dissolved in thionyl chloride (3.0 mL), and the mixture was stirred at 60° C. for 30 minutes. The reaction mixture was concentrated under reduced pressure, L-aspartic acid dimethyl ester hydrochloride (460 mg, 2.33 mmol), dichloromethane (1.0 mL), and pyridine (2.0 mL) were added to the obtained residue, and the mixture was stirred at room temperature for 1 hour. The reaction mixture was concentrated under reduced pressure, trifluoroacetic acid (3.0 mL) was added to the obtained residue, and the mixture was stirred at room temperature for 5 hours. The reaction mixture was concentrated under reduced pressure, and the obtained residue was purified by high performance liquid chromatography (water-acetonitrile, each containing 0.1% trifluoroacetic acid) to give the title compound (59.7 mg, 0.16 mmol, yield in 4 steps 10%).
MS (ESI) m/z 372 (M+H)+

Step 4. Synthesis of N-{3-[5-(4-amidino-2-fluorophenoxycarbonyl)thiophen-2-yl]-2,2-dimethylpropanoyl}-L-aspartic acid trifluoroacetic acid salt (B-64)

The compound (56 mg, 0.15 mmol) obtained in step 3, M-11 (43.1 mg, 0.23 mmol), and WSC hydrochloride (57.8 mg, 0.30 mmol) were dissolved in pyridine (500 μL), and the mixture was stirred at room temperature for 1 hour. The solvent was evaporated, and the residue was azeotropically distilled with benzene. 4N Hydrochloric acid/1,4-dioxane solution (750 μL) and water (250 μL) were added, and the mixture was stirred at 60° C. overnight. The reaction mixture was concentrated under reduced pressure, and the obtained residue was purified by high performance liquid chromatography (acetonitrile-water, each containing 0.1% trifluoroacetic acid, 10-40%) to give the title compound (11 mg, 0.019 mmol, 12%).
$^1$H-NMR (400 MHz, DMSO-d$_6$) δ 9.41 (2H, br s), 9.10 (2H, br s), 7.96-7.89 (3H, m), 7.79-7.71 (2H, m), 7.07 (1H, d, J=4.0 Hz), 4.57 (1H, dt, J=7.2, 6.8 Hz), 3.13 (2H, s), 2.76 (1H, dd, J=16.4, 6.8 Hz), 2.58 (1H, dd, J=16.4, 6.8 Hz), 1.14 (3H, s), 1.13 (3H, s).
MS (ESI) m/z 480 (M+H)+

Compound B-37 shown in the following Table 2 was synthesized using M-20 and by an operation in the same manner as in the above-mentioned Example 18.

The compounds A-22, A-23, A-24, A-25, A-66, B-33, B-35, B-52, and B-53 shown in the following Table 2 were each synthesized using M-1 to M-23 and commercially available reagents and by an operation in the same manner as in the above-mentioned Examples 33 and 34.

Compound B-36 shown in the following Table 2 was synthesized using M-1 to M-23 and commercially available reagents and by an operation in the same manner as in the above-mentioned Example 35.

The compounds B-27, B-28, and B-29 shown in the following Table 2 were each synthesized using M-1 to M-23 and commercially available reagents and by an operation in the same manner as in the above-mentioned Example 38.

The compounds A-48, A-49, A-50, and A-51 shown in the following Table 2 were each synthesized using M-1 to M-23 and commercially available reagents and by an operation in the same manner as in the above-mentioned Example 39.

The compounds B-30, B-31, and B-34 shown in the following Table 2 were each synthesized using M-1 to M-23 and commercially available reagents and by an operation in the same manner as in the above-mentioned Example 40.

Compound B-45 shown in the following Table 2 was synthesized using M-1 to M-23 and commercially available reagents and by an operation in the same manner as in the above-mentioned Examples 44 and 46.

Compound B-46 shown in the following Table 2 was synthesized using M-1 to M-23 and commercially available reagents and by an operation in the same manner as in the above-mentioned Examples 44 and 47.

The compounds A-57, B-41, and B-44 shown in the following Table 2 were each synthesized using M-1 to M-23 and commercially available reagents and by an operation in the same manner as in the above-mentioned Example 46.

The compounds A-56, B-42, and B-43 shown in the following Table 2 were each synthesized using M-1 to M-23 and commercially available reagents and by an operation in the same manner as in the above-mentioned Example 47.

The compounds A-64 and A-65 shown in the following Table 2 were each synthesized using M-1 to M-23 and commercially available reagents and by an operation in the same manner as in the above-mentioned Examples 47 and 52.

Compound A-70 shown in the following Table 2 was synthesized using M-1 to M-23 and commercially available reagents and by an operation in the same manner as in the above-mentioned Examples 47 and 57.

The compounds B-47 and B-48 shown in the following Table 2 were each synthesized using M-1 to M-23 and commercially available reagents and by an operation in the same manner as in the above-mentioned Example 48.

The compounds B-49 and B-50 shown in the following Table 2 were each synthesized using M-1 to M-23 and commercially available reagents and by an operation in the same manner as in the above-mentioned Example 49.

Compound B-55 shown in the following Table 2 was synthesized using M-1 to M-23 and commercially available reagents and by an operation in the same manner as in the above-mentioned Examples 55 and 56.

The compounds A-69, B-56, and B-57 shown in the following Table 2 were each synthesized using M-1 to M-23 and commercially available reagents and by an operation in the same manner as in the above-mentioned Example 57.

Compound B-58 shown in the following Table 2 was synthesized using M-1 to M-23 and commercially available reagents and by an operation in the same manner as in the above-mentioned Example 58.

The compounds B-62, B-65, and B-66 shown in the following Table 2 were each synthesized using M-11, M-23, and commercially available reagents and by an operation in the same manner as in the above-mentioned Example 33.

The structural formulas and physical properties of the synthesis intermediate compounds M-1 to M-16 are shown in Table 1-1 and Table 1-2, and the structural formulas and physical properties of M-17 to M-23 are shown in Table 1-3.

TABLE 1-1

| Compound No. | Structure | Analysis data |
| --- | --- | --- |
| M-1 | 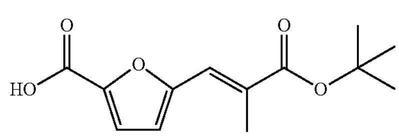 [SMILES: C/C(=C\c1ccc(C(=O)O)o1)C(=O)OC(C)(C)C] | 1H-NMR (300 MHz, DMSO-d6) δ 7.33-7.25 (2H, m), 6.98 (1H, d, J = 3.6 Hz), 2.15 (3H, s), 1.48 (9H, s). MS (ESI) m/z 253 (M + H)+ |
| M-2 | 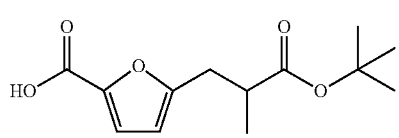 [SMILES: CC(Cc1ccc(C(=O)O)o1)C(=O)OC(C)(C)C] | 1H-NMR (300 MHz, DMSO-d6) δ 7.11 (1H, s), 6.32 (1H, s), 2.95-2.65 (3H, m), 2.50 (3H, s), 1.35 (9H, s). MS (ESI) m/z 253 (M + H)+ |
| M-3 | 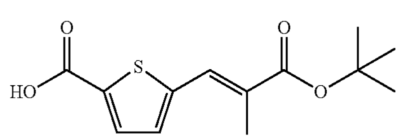 | 1H-NMR (300 MHz, CDCl3) δ 7.70 (1H, d, J = 3.9 Hz), 7.66 (1H, s), 7.63 (1H, d, J = 3.9 Hz), 7.16 (1H, d, J = 3.9 Hz), 2.16 (3H, s), 1.51 (9H, s). MS (ESI) m/z 269 (M + H)+ |
| M-4 | 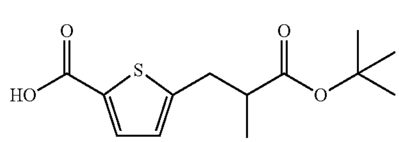 [SMILES: CC(Cc1ccc(C(=O)O)s1)C(=O)OC(C)(C)C] | 1H-NMR (300 MHz, CDCl3) δ 7.72 (1H, d, J = 3.6 Hz), 6.85 (1H, d, J = 3.6 Hz), 3.24-2.65 (3H, m), 1.42 (9H, s), 1.19 (3H, d, J = 6.9 Hz). MS (ESI) m/z 271 (M + H)+ |

TABLE 1-1-continued

| Compound No. | Structure | Analysis data |
|---|---|---|
| M-5 | 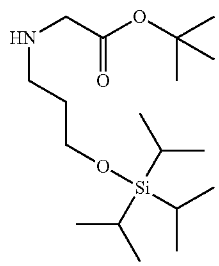 [SMILES: CC(C)[Si](OCCCNCC(=O)OC(C)(C)C)(C(C)C)C(C)C] | 1H-NMR (300 MHz, CDCl3) δ 3.96 (2H, t, J = 5.4 Hz), 3.80 (2H, s), 3.34 (2H, t, J = 5.9 Hz), 2.03 (2H, m), 1.50 (9H, s), 1.17-1.07 (21H, m). |
| M-6 | 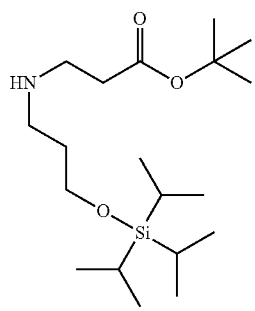 [SMILES: CC(C)[Si](OCCCNCCC(=O)OC(C)(C)C)(C(C)C)C(C)C] | MS (ESI) m/z 360 (M + H)+ |
| M-7 | 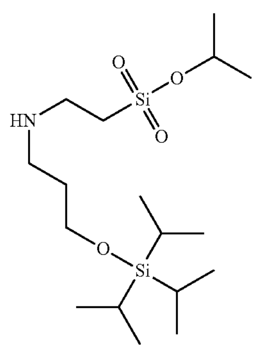 | 1H-NMR (300 MHz, CDCl3) δ 4.97 (1H, sep, J = 6.0 Hz), 3.78 (2H, t, J = 6.9 Hz), 3.29 (2H, t, J = 6.9 Hz), 3.13 (2H, t, J = 6.9 Hz), 2.78 (2H, t. J = 6.9 Hz), 1.74 (2H, m), 1.42 (6H, d, J = 6.0 Hz), 1.05 (21H, m). |
| M-8 | 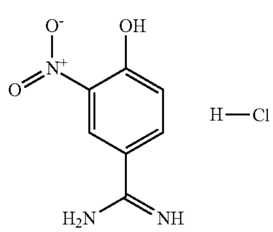 | 1H-NMR (300 MHz, DMSO-d6) δ 12.40 (1H, br), 9.36 (2H, br), 9.05 (2H, br), 8.42 (1H, d, J = 2.3 Hz), 7.98 (1H, dd, J = 8.9, 2.3 Hz), 7.34 (1H, d, J = 8.9 Hz).<br>MS (ESI) m/z 182 (M + H)+ |

TABLE 1-2

| Compound No. | Structure | Analysis data |
|---|---|---|
| M-9 | 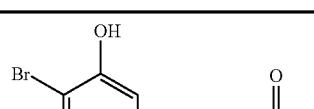 | 1H-NMR (300 MHz, DMSO-d6) δ 11.58 (1H, br), 9.12 (2H, br), 8.83 (2H, br), 8.04 (1H, d, J = 2.4 Hz), 7.69 (1H, dd, J = 8.7, 2.4 Hz), 7.10 (1H, d, J = 8.7 Hz).<br>MS (ESI) m/z 215 [M(79Br) + H]+, 217 [M(81Br) + H]+ |

TABLE 1-2-continued

| Compound No. | Structure | Analysis data |
|---|---|---|
| M-10 | 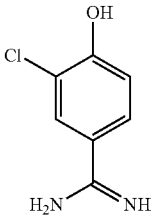 | 1H-NMR (300 MHz, DMSO-d6) δ 11.50 (1H, br), 9.12 (2H, br), 8.81 (2H, br), 7.91 (1H, d, J = 2.3 Hz), 7.66 (1H, dd, J = 8.7, 2.3 Hz), 7.13 (1H, d, J = 8.7 Hz).<br>MS (ESI) m/z 171 [M(35Cl) + H]+, 173 [M(37Cl) + H]+ |
| M-11 | 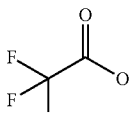 | 1H-NMR (300 MHz, DMSO-d6) δ 11.28 (1H, brs), 9.19 (2H, brs), 9.02 (2H, brs), 7.75 (1H, dd, J = 2.4, 12.0 Hz), 7.59 (1H, m), 7.18 (1H, dd, J = 8.4, 8.7 Hz).<br>MS (ESI) m/z 155 (M + H)+ |
| M-12 | 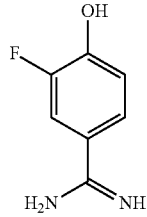 | 1H-NMR (300 MHz, DMSO-d6) δ 9.38-8.61 (4H, br), 7.50 (1H, dd, J = 9.6, 8.4 Hz), 6.78-6.73 (2H, m).<br>MS (ESI) m/z 155 (M + H)+ |
| M-13 | 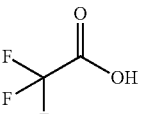 | 1H-NMR (300 MHz, CDCl3) δ 4.20-4.08 (4H, m), 2.92 (1H, dq, J = 30.6, 7.2 Hz), 1.48 (9H, s), 1.45 (3H, d, J = 7.2 Hz), 1.40-1.30 (6H, m). |
| M-14 | 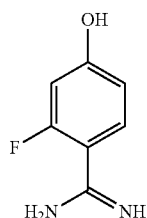 | 1H-NMR (300 MHz, CDCl3) δ 4.20-4.09 (4H, m), 2.76 (1H, ddd, J = 22.1, 10.4, 4.3 Hz), 2.00-1.83 (2H, m), 1.48 (9H, s), 1.35(3H, t, J = 7.2 Hz), 1.34 (1H, t, J = 7.1 Hz), 0.99 (3H, td, J = 7.5, 1.1 Hz). |
| M-15 | 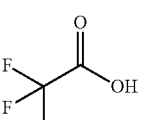 | 1H-NMR (300 MHz, CDCl3) δ 4.20-4.09 (4H, m), 2.85 (1H, ddd, J = 22.3, 11.2, 3.8 Hz), 2.05-1.73 (4H, m), 1.47 (9H, s), 1.45-1.29 (6H, m), 0.93 (3H, t, J = 7.2 Hz). |
| M-16 | 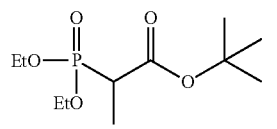 [SMILES: CCOP(=O)(OCC)C(C)C(=O)OC(C)(C)C] | 1H-NMR (300 MHz, CDCl3) δ 5.08 (1H, sep, J = 6.3 Hz), 4.29-4.18 (4H, m), 3.57 (1H, dq, J = 19.2, 7.3 Hz), 1.69 (3H, dd, J = 15.6, 7.3 Hz), 1.45 (6H, d, J = 6.3 Hz), 1.37 (6H, t, J = 6.9 Hz). |

TABLE 1-3

| Compound No. | Structure | Analysis data |
| --- | --- | --- |
| M-17 | 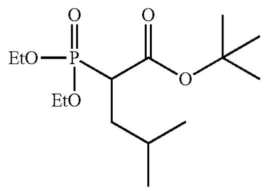 [SMILES: CCOP(=O)(OCC)C(CC(C)C)C(=O)OC(C)(C)C] | 1H-NMR (300 MHz, DMSO-d6) δ 4.08-3.98 (4H, m), 2.85 (1H, ddd, J = 22.8, 11.4, 3.3 Hz), 1.85-1.75 (1H, m), 1.60-1.45 (2H, m), 1.50 (9H, s), 1.22 (6H, m), 0.88 (6H, d, J = 7.5 Hz).<br>MS (ESI) m/z 309 (M + H)+ |
| M-18 | 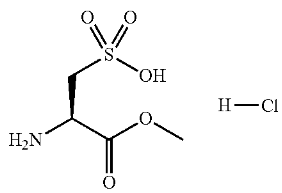 | 1H-NMR (300 MHz, DMSO-d6) δ 8.26 (3H, br s), 4.23 (1H, m), 3.72 (3H, s), 3.00 (1H, dd, J = 14.3, 3.5 Hz), 2.92 (1H, dd, J = 14.3, 8.0 Hz).<br>MS (ESI) m/z 184 (M + H)+ |
| M-19 | 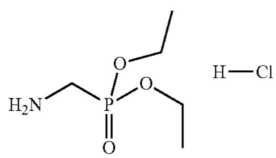 | 1H-NMR (300 MHz, DMSO-d6) δ 8.50 (3H, br s), 4.12 (4H, m), 3.30 (2H, d, J = 13.5 Hz), 1.28 (6H, t, J = 7.1 Hz).<br>MS (ESI) m/z 168 (M + H)+ |
| M-20 | 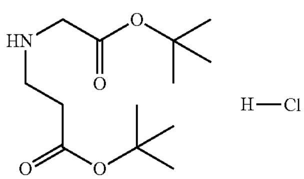 | 1H-NMR (400 MHz, CDCl3) δ 3.75 (2H, s), 3.29 (2H, t, J = 6.4 Hz), 2.94 (2H, d, J = 6.4 Hz), 1.51 (9H, s), 1.47 (9H, s).<br>MS (ESI) m/z 246 (M + H)+ |
| M-21 | 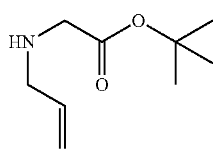 | 1H-NMR (400 MHz, DMSO-d6) δ 5.87 (1H, ddt, J = 17.1, 10.2, 6.1 Hz), 5.19 (1H, ddt, J = 17.1, 3.2, 1.7 Hz), 5.11 (1H, ddt, J = 10.2, 3.2, 1.2 Hz), 3.29 (2H, s), 3.25 (2H, ddd, J = 6.1, 1.7, 1.2 Hz), 1.47 (9H, s).<br>MS (ESI) m/z 172 (M + H)+ |
| M-22 | 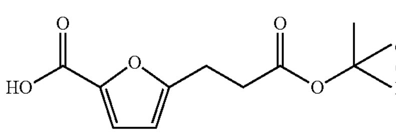 | 1H-NMR (400 MHz, CDCl3) δ 7.23 (1H, d, J = 3.6 Hz), 6.22 (1H, d, J = 3.6 Hz), 3.01 (2H, t, J = 7.6 Hz), 2.63 (2H, t, J = 7.6 Hz), 1.44 (9H, s).<br>MS (ESI) m/z 241 (M + H)+ |
| M-23 | 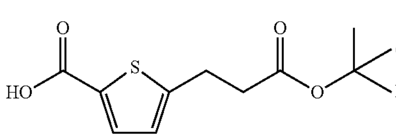 | 1H-NMR (300 MHz, DMSO-d6) δ 7.54 (1H, d, J = 3.3 Hz), 6.94 (1H, d, J = 3.3 Hz), 3.04 (2H, t, J = 7.5 Hz), 2.59 (2H, t, J = 7.5 Hz), 1.38 (9H, s).<br>MS (ESI) m/z 257 (M + H)+ |

The structural formulas and physical properties of compounds A-1 to A-40, B-1 to B-24, and C-1 to C-3 are shown in Table 2-1 to Table 2-10, and the structural formulas and physical properties of A-41 to A-74, B-25 to B-66, C-4, and C-5 are shown in Table 2-11 to Table 2-22.

TABLE 2-1

| Compound No. | Structure | Analysis data |
| --- | --- | --- |
| A-1 | 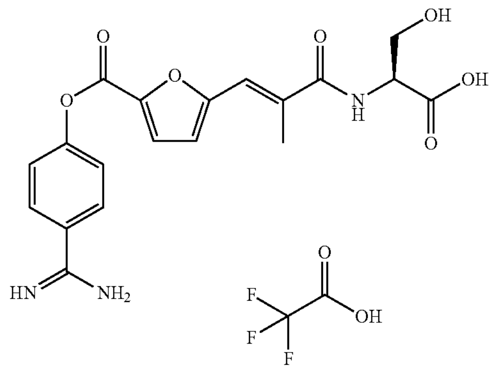 [SMILES: C/C(=C\c1ccc(C(=O)Oc2ccc(C(=N)N)cc2)o1)C(=O)N[C@@H](CO)C(=O)O ; O=C(O)C(F)(F)F] | 1H-NMR (DMSO-d6) δ 9.34 (br s, 2H), 8.95 (br s, 2H), 8.12 (d, J = 7.8 Hz, 1H), 7.91 (d, J = 8.7 Hz, 2H), 7.72 (d, J = 3.9 Hz, 1H), 7.60 (d, J = 8.7 Hz, 2H), 7.21 (s, 1H), 7.05 (d, J = 3.9 Hz, 1H), 4.37 (m, 1H), 3.76 (m, 2H), 2.73 (s, 1H), 2.24 (s, 3H).<br>MS (ESI) m/z 402 (M + H)+ |
| A-2 | 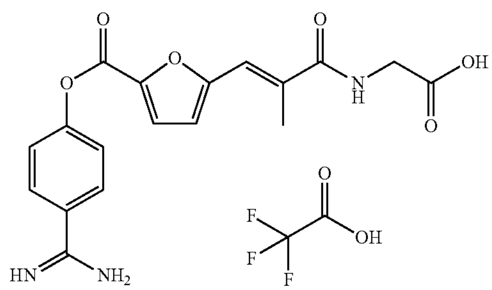 [SMILES: C/C(=C\c1ccc(C(=O)Oc2ccc(C(=N)N)cc2)o1)C(=O)NCC(=O)O ; O=C(O)C(F)(F)F] | 1H-NMR (DMSO-d6) δ 9.34 (br s, 2H), 8.95 (br s, 2H), 8.48 (m, 1H), 7.91 (d, J = 8.7 Hz, 2H), 7.72 (d, J = 3.9 Hz, 1H), 7.60 (d, J = 8.7 Hz, 2H), 7.21 (s, 1H), 7.05 (d, J = 3.9 Hz, 1H), 3.84 (m, 2H), 2.73 (s, 1H), 2.24 (s, 3H).<br>MS (ESI) m/z 372 (M + H)+ |
| A-3 | 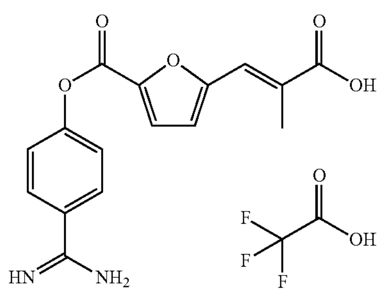 [SMILES: C/C(=C\c1ccc(C(=O)Oc2ccc(C(=N)N)cc2)o1)C(=O)O ; O=C(O)C(F)(F)F] | 1H-NMR (300 MHz, DMSO-d6) δ 9.35 (2H, br s), 8.95 (2H, br s), 7.91 (2H, d, J = 8.7 Hz), 7.72 (1H, d, J = 3.9 Hz), 7.59 (2H, d, J = 8.7 Hz), 7.43 (1H, s), 7.14 (1H, d, J = 3.9 Hz), 2.73 (1H, s), 2.24 (3H, s).<br>MS (ESI) m/z 315 (M + H)+ |
| A-4 | 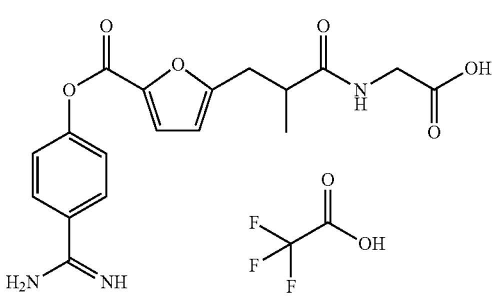 [SMILES: CC(Cc1ccc(C(=O)Oc2ccc(C(=N)N)cc2)o1)C(=O)NCC(=O)O ; O=C(O)C(F)(F)F] | MS (ESI) m/z 374 (M + H)+ |

TABLE 2-1-continued
| Compound No. | Structure | Analysis data |
|---|---|---|
| A-5 | 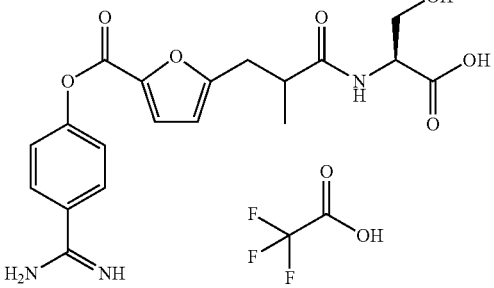 | MS (ESI) m/z 404 (M + H)+ |
| A-6 | 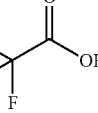 | 1H-NMR (300 MHz, DMSO-d6) δ 9.35 (2H, br s), 9.10 (2H, br s), 7.90 (2H, d, J = 6.9 Hz), 7.61-7.52 (3H, m), 6.52 (1H, d, J = 3.6 Hz), 3.13-2.98 (1H, m), 2.91-2.70 (2H, m), 1.14 (3H, d, J = 6.9 Hz).<br>MS (ESI) m/z 317 (M + H)+ |
| A-7 | 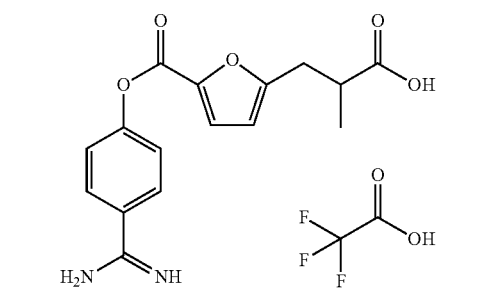 | MS (ESI) m/z 430 (M + H)+ |
| A-8 | 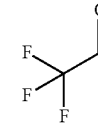 | 1H-NMR (300 MHz, DMSO-d6) δ 9.65-9.28 (4H, m), 8.63 (1H, d, J = 2.3 Hz), 8.24 (1H, dd, J = 8.6, 2.3 Hz), 7.97 (1H, d, J = 8.6 Hz), 7.91 (1H, d, J = 3.5 Hz), 7.43 (1H, s), 7.18 (1H, d, J = 3.5 Hz), 2.22 (3H, s).<br>MS (ESI) m/z 360 (M + H)+ |
TABLE 2-2
| Compound No. | Structure | Analysis data |
|---|---|---|
| A-9 | 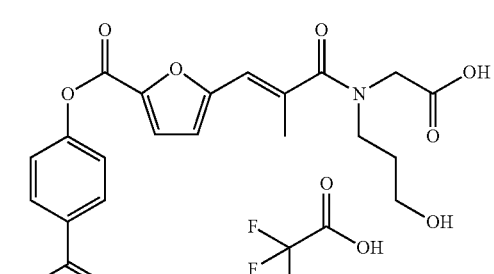 | MS (ESI) m/z 432 (M + H)+ |

TABLE 2-2-continued

| Compound No. | Structure | Analysis data |
| --- | --- | --- |
| A-10 | 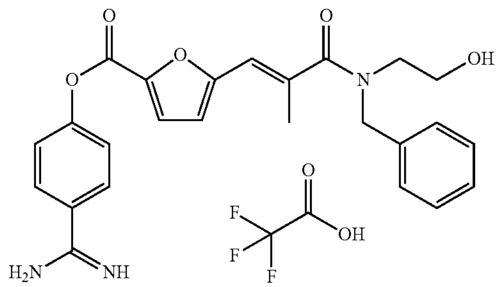 | MS (ESI) m/z 448 (M + H)+ |
| A-11 | 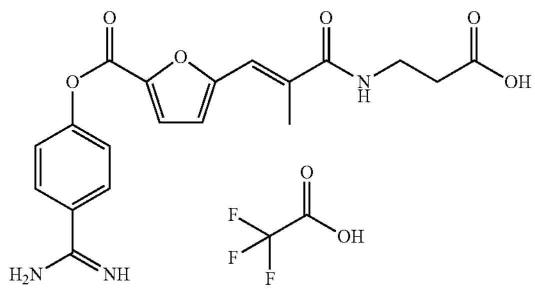 | MS (ESI) m/z 386 (M + H)+ |
| A-12 | 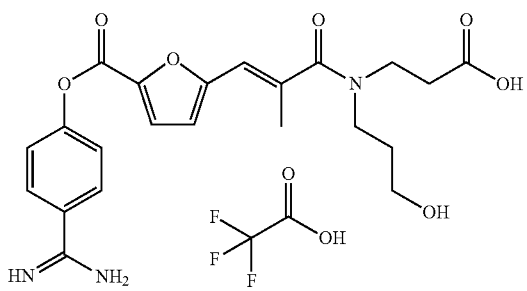 | MS (ESI) m/z 444 (M + H)+ |
| A-13 | 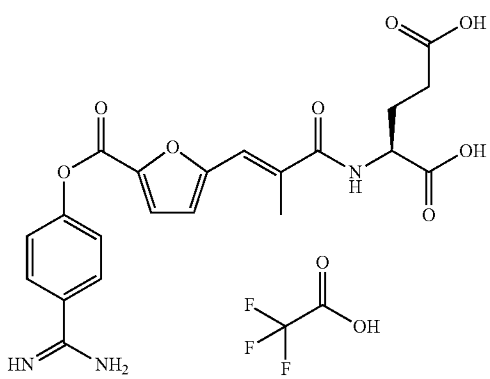 [SMILES: C/C(=C\c1ccc(C(=O)Oc2ccc(C(=N)N)cc2)o1)C(=O)N[C@@H](CCC(=O)O)C(=O)O ; O=C(O)C(F)(F)F] | 1H-NMR (300 MHz, DMSO-d6) δ 9.35 (2H, br s), 9.02 (2H, br s), 8.35 (1H, d, J = 7.5 Hz), 7.91 (2H, d, J = 8.7 Hz), 7.72 (1H, d, J = 3.3 Hz), 7.59 (2H, d, J = 7.5 Hz), 7.18 (1H, s), 7.04 (1H, d, J = 3.3 Hz), 4.35-4.22 (2H, m), 2.42-2.30 (2H, m), 2.22 (3H, s), 2.15-1.81 (2H, m).<br>MS (ESI) m/z 444 (M + H)+ |
| A-14 | 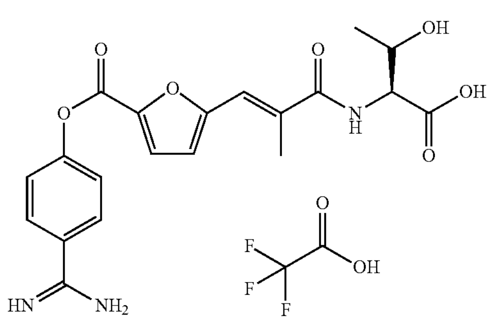 [SMILES: C/C(=C\c1ccc(C(=O)Oc2ccc(C(=N)N)cc2)o1)C(=O)N[C@H](C(=O)O)C(C)O ; O=C(O)C(F)(F)F] | MS (ESI) m/z 416 (M + H)+ |

TABLE 2-2-continued
| Compound No. | Structure | Analysis data |
|---|---|---|
| A-15 | 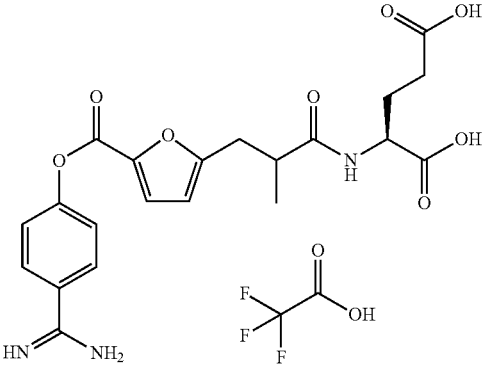 [SMILES: CC(Cc1ccc(C(=O)Oc2ccc(C(=N)N)cc2)o1)C(=O)N[C@@H](CCC(=O)O)C(=O)O ; O=C(O)C(F)(F)F] | MS (ESI) m/z 446 (M + H)+ |
| A-16 | 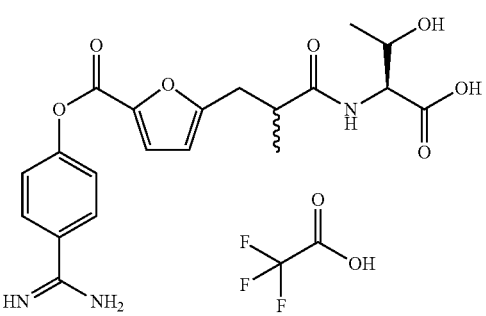 [SMILES: CC(Cc1ccc(C(=O)Oc2ccc(C(=N)N)cc2)o1)C(=O)N[C@H](C(=O)O)C(C)O ; O=C(O)C(F)(F)F] | MS (ESI) m/z 418 (M + H)+ |
TABLE 2-3
| Compound No. | Structure | Analysis data |
|---|---|---|
| A-17 | 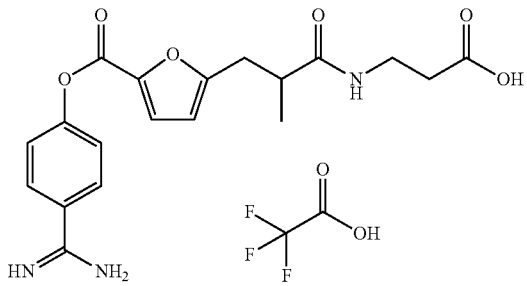 [SMILES: CC(Cc1ccc(C(=O)Oc2ccc(C(=N)N)cc2)o1)C(=O)NCCC(=O)O ; O=C(O)C(F)(F)F] | MS (ESI) m/z 388 (M + H)+ |
| A-18 | 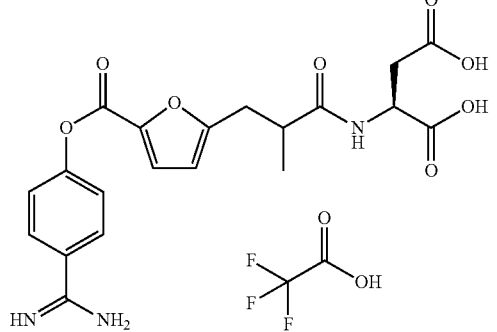 | 1H-NMR (DMSO-d6) δ 9.35 (br s, 2H), 9.12 (br s, 2H), 8.41-8.27 (m, 1H), 7.90 (d, J = 8.7 Hz, 2H), 7.55 (d, J = 8.7 Hz, 2H), 7.54-7.49 (m, 1H), 6.57-6.42 (m, 1H), 4.62-4.40 (m, 1H), 3.13-2.42 (m, 5H), 1.17-0.99 (m, 3H). MS (ESI) m/z 432 (M + H)+ |

TABLE 2-3-continued

| Compound No. | Structure | Analysis data |
| --- | --- | --- |
| A-19 | 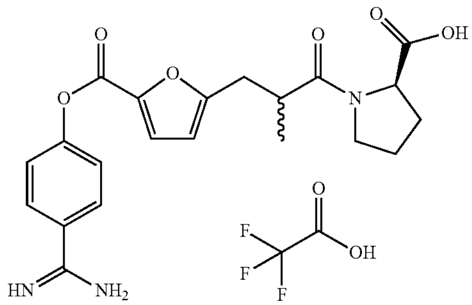 | MS (ESI) m/z 414 (M + H)+ |
| A-20 | 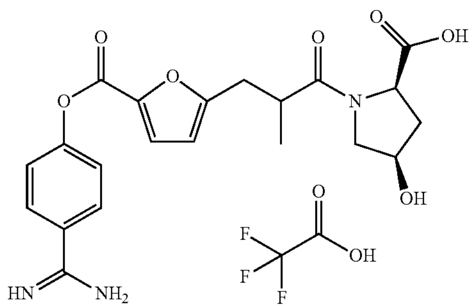 | MS (ESI) m/z 430 (M + H)+ |
| A-21 | 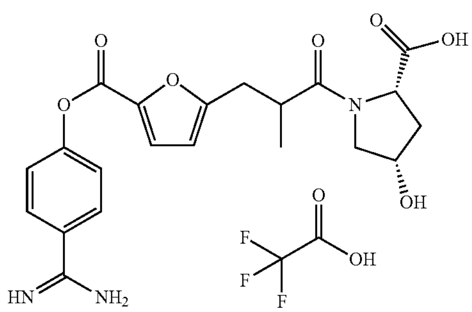 | MS (ESI) m/z 430 (M + H)+ |
| A-22 | 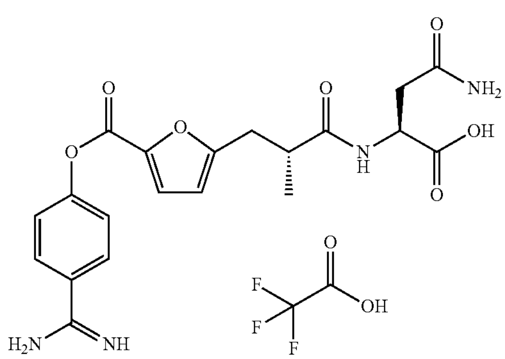 [SMILES: C[C@H](Cc1ccc(C(=O)Oc2ccc(C(=N)N)cc2)o1)C(=O)N[C@@H](CC(N)=O)C(=O)O ; O=C(O)C(F)(F)F] | 1H-NMR (300 MHz, DMSO-d6) δ 12.53 (1H, br s), 9.34 (2H, s), 8.98 (2H, br s), 8.25 (1H, d, J = 7.9 Hz), 7.89 (2H, d, J = 8.7 Hz), 7.55 (2H, d, J = 8.7 Hz), 7.51 (1H, d, J = 3.5 Hz), 7.34 (1H, s), 6.90 (1H, s), 6.51 (1H, d, J = 3.5 Hz), 4.49 (1H, m), 2.99 (1H, dd, J = 14.4, 6.4 Hz), 2.81-2.41 (4H, m), 1.05 (3H, d, J = 6.6 Hz).<br>MS (ESI) m/z 431 (M + H)+ |

TABLE 2-3-continued

| Compound No. | Structure | Analysis data |
|---|---|---|
| A-23 | 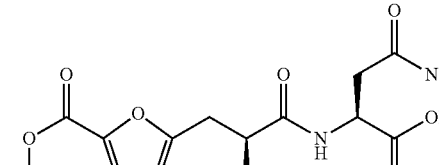 | 1H-NMR (300 MHz, DMSO-d6) δ 9.33 (2H, br s), 9.05 (2H, br s), 8.20 (1H, d, J = 7.6 Hz), 7.89 (2H, d, J = 8.8 Hz), 7.55 (2H, d, J = 8.8 Hz), 7.51 (1H, d, J = 3.5 Hz), 7.35 (1H, s), 6.88 (1H, s), 6.48 (1H, d, J = 3.5 Hz), 4.49 (1H, m), 2.97 (1H, dd, J = 13.7, 6.0 Hz), 2.83-2.38 (4H, m), 1.07 (3H, d, J = 6.2 Hz).<br>MS (ESI) m/z 431 (M + H)+ |
| A-24 | 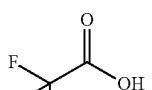 | 1H-NMR (300 MHz, DMSO-d6) δ 12.56 (1H, br s), 9.34 (2H, br s), 8.98 (2H, br s), 8.28 (1H, d, J = 7.6 Hz), 7.89 (2H, d, J = 8.7 Hz), 7.55 (2H, d, J = 8.7 Hz), 7.52 (1H, d, J = 3.5 Hz), 7.29 (1H, s), 6.78 (1H, s), 6.51 (1H, d, J = 3.5 Hz), 4.15 (1H, m), 2.99 (1H, dd, J = 14.1, 6.5 Hz), 2.82-2.70 (2H, m), 2.15-2.10 (2H, m), 1.98-1.76 (2H, m), 1.08 (3H, d, J = 6.5 Hz).<br>MS (ESI) m/z 445 (M + H)+ |

TABLE 2-4

| Compound No. | Structure | Analysis data |
|---|---|---|
| A-25 | 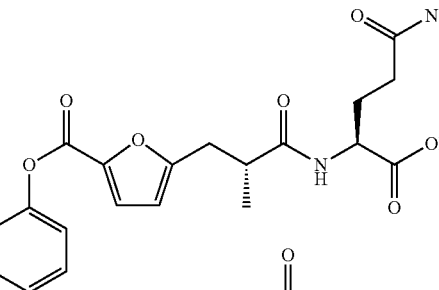 | 1H-NMR (300 MHz, DMSO-d6) δ 12.56 (1H, br s), 9.34 (2H, br s), 9.00 (2H, br s), 8.26 (1H, d, J = 7.9 Hz), 7.89 (2H, d, J = 8.7 Hz), 7.55 (2H, d, J = 8.7 Hz), 7.52 (1H, d, J = 3.5 Hz), 7.25 (1H, s), 6.77 (1H, s), 6.48 (1H, d, J = 3.5 Hz), 4.15 (1H, m), 2.99 (1H, dd, J = 13.2, 6.2 Hz), 2.82-2.72 (2H, m), 2.10-2.04 (2H, m), 1.93-1.74 (2H, m), 1.07 (3H, d, J = 6.4 Hz).<br>MS (ESI) m/z 445 (M + H)+ |
| A-26 | 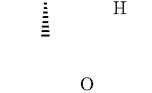 | 1H-NMR (300 MHz, DMSO-d6) δ 9.34 (2H, br), 9.02 (2H, br), 7.89 (2H, d, J = 8.9 Hz), 7.55 (2H, d, J = 8.9 Hz), 7.51 (1H, d, J = 3.5 Hz), 6.50 (1H, d, J = 3.5 Hz), 4.17 (2H, s), 3.94 (2H, s), 3.10-2.95 (2H, m), 2.76 (1H, dd, J = 14.9, 5.9 Hz), 1.06 (3H, d, J = 8.5 Hz).<br>MS (ESI) m/z 432 (M + H)+ |

TABLE 2-4-continued
| Compound No. | Structure | Analysis data |
|---|---|---|
| A-27 | 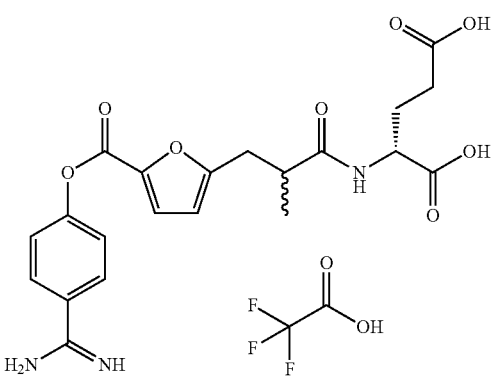 [SMILES: CC(Cc1ccc(C(=O)Oc2ccc(C(=N)N)cc2)o1)C(=O)N[C@H](CCC(=O)O)C(=O)O ; O=C(O)C(F)(F)F] | 1H-NMR (DMSO-d6) δ 9.34 (br s, 2H), 9.05 (br s, 2H), 8.33-8.18 (m, 1H), 7.90 (d, J = 8.7 Hz, 2H), 7.61-7.42 (m, 3H), 6.57-6.42 (m, 1H), 427-4.16 (m, 1H), 3.09-2.90 (m, 1H), 2.90-2.63 (m, 2H), 2.37-2.08 (m, 2H), 2.05-1.87 (m, 1H), 1.86-1.63 (m, 1H), 1.08 (d, J = 5.7 Hz, 3H). MS (ESI) m/z 446 (M + H)+ |
| A-28 | 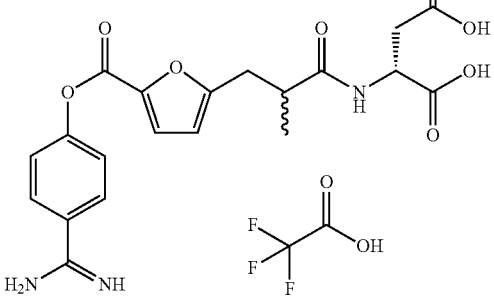 | 1H-NMR (DMSO-d6) δ 9.35 (br s, 2H), 9.12 (br s, 2H), 8.41-8.27 (m, 1H), 7.90 (d, J = 8.7 Hz, 2H), 7.55 (d, J = 8.7 Hz, 2H), 7.54-7.49 (m, 1H), 6.57-6.42 (m, 1H), 4.62-4.40 (m, 1H), 3.13-2.42 (m, 5H), 1.17-0.99 (m, 3H), MS (ESI) m/z 432 (M + H)+ |
| A-29 | 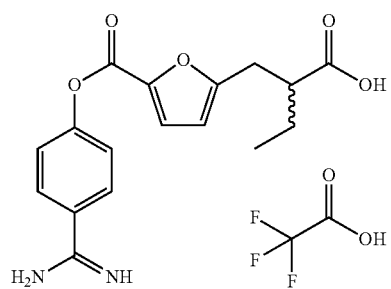 [SMILES: CCC(Cc1ccc(C(=O)Oc2ccc(C(=N)N)cc2)o1)C(=O)O ; O=C(O)C(F)(F)F] | 1H-NMR (300 MHz, DMSO-d6) δ 9.34 (2H, br s), 9.13 (2H, br s), 7.90 (2H, d, J = 8.7 Hz), 7.63-7.49 (3H, m), 6.51 (1H, d, J = 3.6 Hz), 3.10-2.82 (2H, m), 2.69-2.55 (1H, m), 1.64-1.49 (2H, m), 0.90 (3H, t, J = 7.5 Hz). MS (ESI) m/z 331 (M + H)+ |
| A-30 | 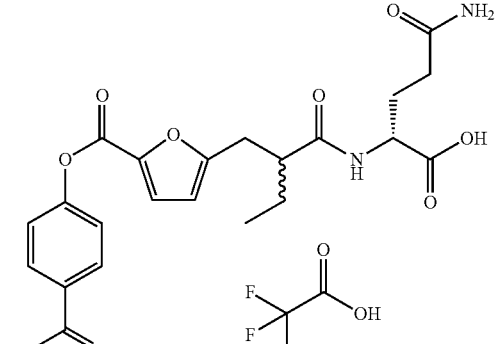 | MS (ESI) m/z 460 (M + H)+ |

TABLE 2-4-continued
| Compound No. | Structure | Analysis data |
|---|---|---|
| A-31 | 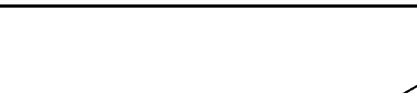 | 1H-NMR (DMSO-d6) δ 9.34 (br s, 2H), 9.05 (br s, 2H), 8.43-8.29 (m, 1H), 7.89 (d, J = 8.4 Hz, 1H), 7.54 (d, J = 8.4 Hz, 1H), 7.52-7.46 (m, 1H), 6.53-6.42 (m, 1H), 4.60-4.44 (m, 1H), 3.07-2.51 (m, 5H), 1.61-1.38 (m, 2H), 0.97-0.77 (m, 3H).<br>MS (ESI) m/z 446 (M + H)+ |
TABLE 2-5
| Compound No. | Structure | Analysis data |
|---|---|---|
| A-32 | 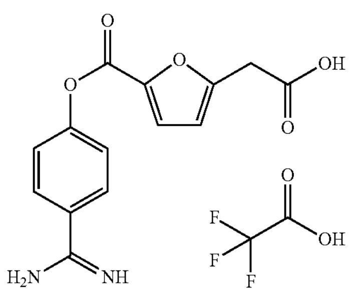 | 1H-NMR (300 MHz, DMSO-d6) δ 9.34 (2H, s), 9.01 (2H, s), 7.89 (2H, d, J = 8.7 Hz), 6.64 (1H, d, J = 3.6 Hz), 7.57 (3H, m), 3.89 (2H, s).<br>MS (ESI) m/z 289 (M + H)+ |
| A-33 | 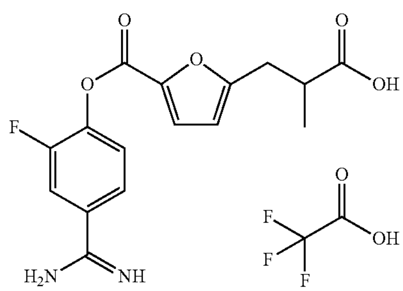 [SMILES: CC(Cc1ccc(C(=O)Oc2ccc(C(=N)N)cc2F)o1)C(=O)O ; O=C(O)C(F)(F)F] | 1H-NMR (DMSO-d6) δ 9.42 (br s, 2H), 9.16 (br s, 2H), 7.93 (d, J = 9.9 Hz, 1H), 7.78-7.70 (m, 2H), 7.62 (d, J = 3.3 Hz, 1H), 6.55 (d, J = 3.3 Hz, 1H), 3.13-2.99 (m, 1H), 2.92-2.73 (m, 2H), 1.14 (d, J = 6.9 Hz, 3H).<br>MS (ESI) m/z 335 (M + H)+ |
| A-34 | 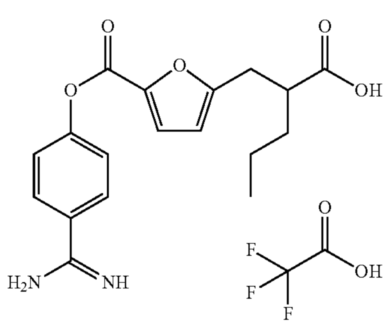 | MS (ESI) m/z 345 (M + H)+ |

TABLE 2-5-continued
| Compound No. | Structure | Analysis data |
|---|---|---|
| A-35 | 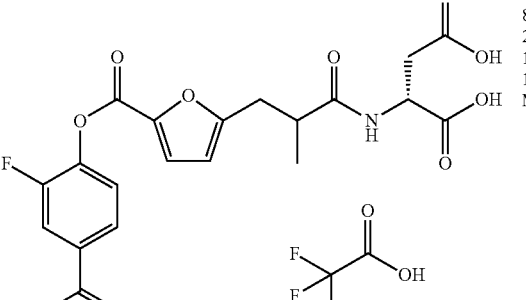 | 1H-NMR (DMSO-d6) δ 9.42 (br s, 2H), 9.19 (br s, 2H), 8.42-8.31 (m, 1H), 7.93 (d, J = 11.4 Hz, 1H), 7.81-7.69 (m, 2H), 7.61-7.56 (m, 1H), 6.56-6.45 (m, 1H), 4.61-4.42 (m, 1H), 3.11-2.88 (m, 2H), 2.87-2.47 (m, 3H), 1.06 (t, J = 6.6 Hz, 1H).<br>MS (ESI) m/z 450 (M + H)+ |
| A-36 | 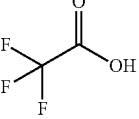 | 1H-NMR (300 MHz, DMSO-d6) δ 9.32 (2H, br), 8.90 (2H, br), 7.87 (2H, d, J = 8.7 Hz), 7.55 (2H, d, J = 8.7 Hz), 7.51 (1H, d, J = 3.6 Hz), 6.54 (1H, d, J = 3.6 Hz), 2.73-2.57 (3H, m), 1.05 (3H, d, J = 6.9 Hz).<br>MS (ESI) m/z 353 (M + H)+ |
| A-37 | 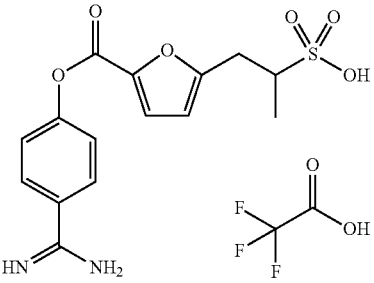 [SMILES: CC(Cc1ccc(C(=O)Oc2ccc(C(=N)N)cc2)o1)S(=O)(=O)O ; O=C(O)C(F)(F)F] | 1H-NMR (300 MHz, DMSO-d6) δ 9.33 (2H, s), 9.02 (2H, s), 7.89 (2H, d, J = 8.4 Hz), 7.54 (3H, m), 6.52 (1H, d, J = 3.6 Hz), 2.98 (2H, t, J = 7.2 Hz), 2.66 (2H, t, J = 7.2 Hz).<br>MS (ESI) m/z 303 (M + H)+ |
| A-38 | 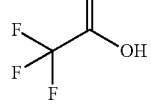 | 1H-NMR (300 MHz, DMSO-d6) δ 9.34 (2H, s), 9.02 (2H, s), 8.36 (1H, d, J = 8.1 Hz), 7.89 (2H, d, J = 8.7 Hz), 7.53 (3H, m), 6.48 (1H, d, J = 3.3 Hz), 4.54 (1H, m), 2.97 (2H, t, J = 7.2 Hz), 2.50-2.73 (4H, m).<br>MS (ESI) m/z 418 (M + H)+ |

TABLE 2-6
| Compound No. | Structure | Analysis data |
|---|---|---|
| A-39 | 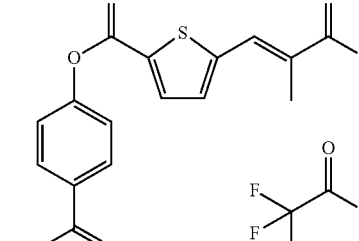 | 1H-NMR (300 MHz, DMSO-d6) δ 9.34 (2H, s), 9.09 (2H, s), 8.55 (1H, d, J = 7.8 Hz), 7.89 (2H, d, J = 8.7 Hz), 7.56 (3H, m), 6.58 (1H, d, J = 3.6 Hz), 4.53 (1H, m), 2.89 (2H, s), 2.64 (2H, m).<br>MS (ESI) m/z 404 (M + H)+ |
| A-40 | 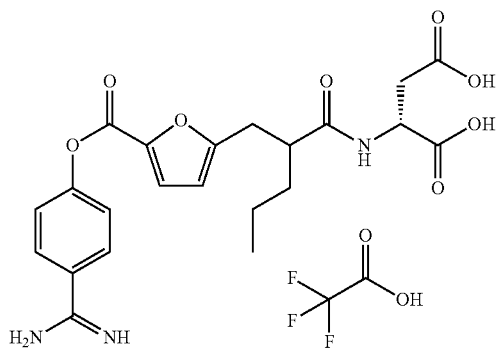 | MS (ESI) m/z 360 (M + H)+ |
TABLE 2-7
| Compound No. | Structure | Analysis data |
|---|---|---|
| B-1 | 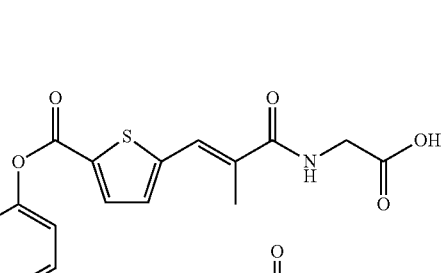 | 1H-NMR (300 MHz, DMSO-d6) δ 9.35 (2H, s), 9.00 (2H, s), 8.09 (1H, d, J = 3.9 Hz), 7.88 (3H, m), 7.60 (3H, m), 2.18 (3H, s).<br>MS (ESI) m/z 331 (M + H)+ |
| B-2 | 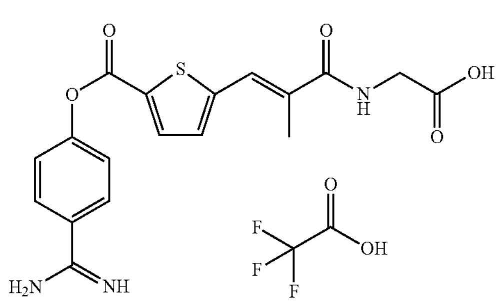 [SMILES: C/C(=C\c1ccc(C(=O)Oc2ccc(C(=N)N)cc2)s1)C(=O)NCC(=O)O ; O=C(O)C(F)(F)F] | 1H-NMR (300 MHz, DMSO-d6) δ 9.30 (2H, brs), 9.10 (2H, brs), 8.50 (1H, t, J = 5.7 Hz), 8.06 (1H, d, J = 3.0 Hz), 7.89 (2H, d, J = 8.1 Hz), 7.58 (2H, d, J = 8.1 Hz), 7.54 (1H, s), 7.50 (1H, d, J = 3.0 Hz), 3.82 (2H, d, J = 5.7 Hz), 2.18 (3H, s).<br>MS (ESI) m/z 388 (M + H)+ |

TABLE 2-7-continued

| Compound No. | Structure | Analysis data |
|---|---|---|
| B-3 | 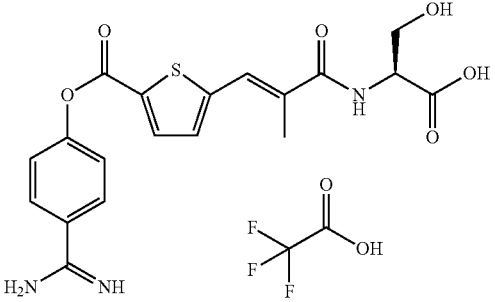 [SMILES: C/C(=C\c1ccc(C(=O)Oc2ccc(C(=N)N)cc2)s1)C(=O)N[C@@H](CO)C(=O)O ; O=C(O)C(F)(F)F] | 1H-NMR (300 MHz, DMSO-d6) δ 9.35 (2H, s), 8.99 (2H, s), 8.61 (1H, m), 8.06 (1H, d, J = 3.6 Hz), 7.89 (2H, d, J = 8.4 Hz), 7.59 (2H, d, J = 8.4 Hz), 7.54 (1H, s), 7.50 (1H, d, J = 3.9 Hz), 4.36 (1H, m), 3.74 (2H, d, J = 4.8 Hz), 2.19 (3H, s).<br>MS (ESI) m/z 418 (M + H)+ |
| B-4 | 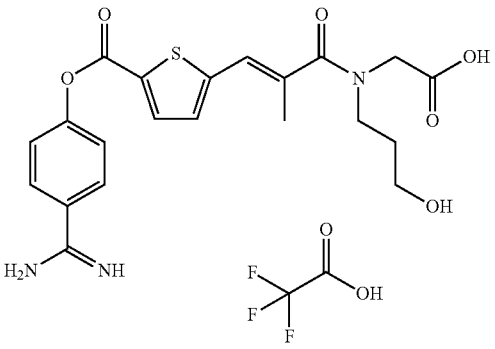 [SMILES: C/C(=C\c1ccc(C(=O)Oc2ccc(C(=N)N)cc2)s1)C(=O)N(CCCO)CC(=O)O ; O=C(O)C(F)(F)F] | 1H-NMR (300 MHz, DMSO-d6) δ 9.35 (2H, s), 8.99 (2H, s), 8.04 (1H, m), 7.90 (2H, d, J = 8.7 Hz), 7.59 (2H, d, J = 8.7 Hz), 7.43 (1H, m), 6.84 (1H, m), 4.01 (2H, s). 3.20-3.50 (4H, m), 2.17 (3H, s), 1.70 (2H, m).<br>MS (ESI) m/z 446 (M + H)+ |
| B-5 | 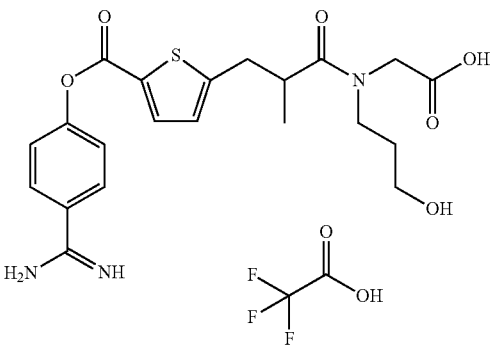 [SMILES: CC(Cc1ccc(C(=O)Oc2ccc(C(=N)N)cc2)s1)C(=O)N(CCCO)CC(=O)O ; O=C(O)C(F)(F)F] | 1H-NMR (300 MHz, DMSO-d6) δ 9.34 (2H, s), 8.99 (2H, s), 7.90 (3H, m), 7.56 (2H, d, J = 9.0 Hz), 7.07 (1H, m), 4.01 (1H, d, J = 11.7 Hz), 3.80 (1H, d, J = 17.1 Hz), 3.42 (2H, m), 3.15 (3H, m), 2.90 (2H, m), 1.55 (2H, m), 1.10 (3H, d, J = 4.8 Hz).<br>MS (ESI) m/z 448 (M + H)+ |
| B-6 | 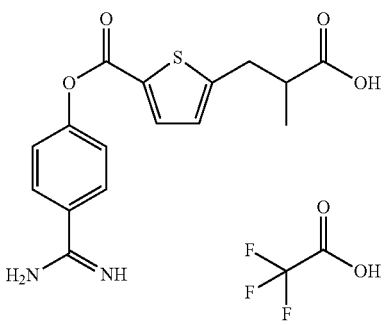 [SMILES: CC(Cc1ccc(C(=O)Oc2ccc(C(=N)N)cc2)s1)C(=O)O ; O=C(O)C(F)(F)F] | 1H-NMR (300 MHz, DMSO-d6) δ 9.34 (2H, s), 9.01 (2H, s), 7.91 (2H, m), 7.56 (1H, d, J = 9.0 Hz), 7.10 (1H, d, J = 3.6 Hz), 3.37 (1H, m), 3.01 (1H, m), 2.73 (1H, m), 1.13 (3H, d, J = 4.2 Hz).<br>MS (ESI) m/z 333 (M + H)+ |

TABLE 2-7-continued
| Compound No. | Structure | Analysis data |
|---|---|---|
| B-7 | 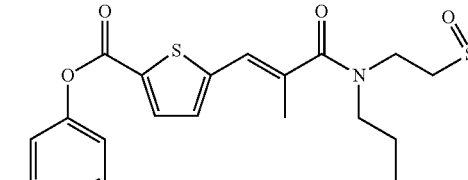 | 1H-NMR (300 MHz, DMSO-d6) δ 9.35 (2H, s), 8.91 (2H, s), 8.03 (1H, d, J = 4.2 Hz), 7.90 (2H, d, J = 8.7 Hz), 7.60 (2H, d, J = 8.7 Hz), 7.40 (1H, d, J = 4.2 Hz), 6.84 (1H, s), 4.48 (1H, brs), 3.55 (2H, m), 320-3.45 (4H, m), 2.70 (2H, m), 2.15 (3H, s), 1.67 (2H, m).<br>MS (ESI) m/z 496 (M + H)+ |
| B-8 | 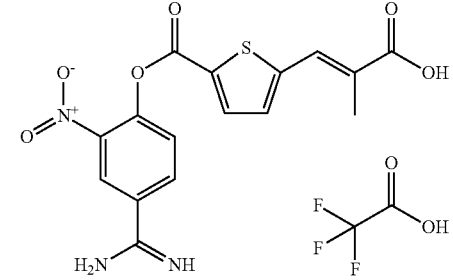 | 1H-NMR (300 MHz, DMSO-d6) δ 9.56 (2H, br), 9.26 (2H, br), 8.65 (1H, d, J = 2.4 Hz), 8.27 (1H, dd, J = 8.6, 2.4 Hz), 8.15 (1H, d, J = 5.2 Hz), 7.98 (1 H, d, J = 8.6 Hz), 7.90 (1H, s), 7.69 (1H, d, J = 5.2 Hz), 2.19 (3H, s).<br>MS (ESI) m/z 376 (M + H)+ |
TABLE 2-8
| Compound No. | Structure | Analysis data |
|---|---|---|
| B-9 | 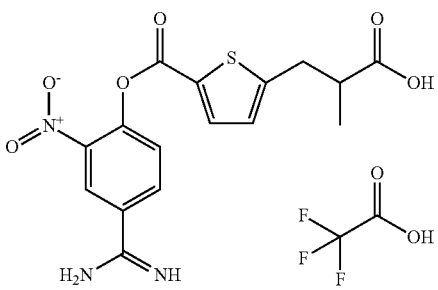 [SMILES: CC(Cc1ccc(C(=O)Oc2ccc(C(=N)N)cc2[N+](=O)[O-])s1)C(=O)O ; O=C(O)C(F)(F)F] | MS (ESI) m/z 378 (M + H)+ |
| B-10 | 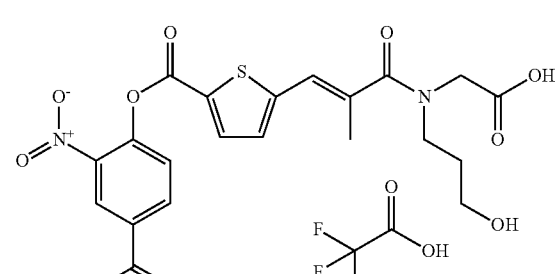 | MS (ESI) m/z 491 (M + H)+ |

TABLE 2-8-continued

| Compound No. | Structure | Analysis data |
|---|---|---|
| B-11 | 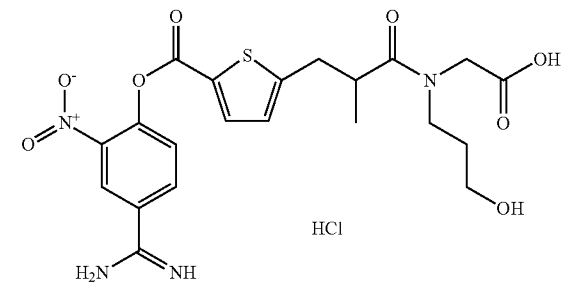 [SMILES: CC(Cc1ccc(C(=O)Oc2ccc(C(=N)N)cc2[N+](=O)[O-])s1)C(=O)N(CCCO)CC(=O)O ; Cl] | 1H-NMR (300 MHz, DMSO-d6) δ 9.62 (2H, br), 9.30 (2H, br), 8.64 (1H, d, J = 2.1 Hz), 8.26 (1H, dd, J = 8.4, 2.1 Hz), 7.94-7.91 (2H, m), 7.14-7.11 (1H, m), 4.57-3.77 (3H, m), 3.51-2.92 (6H, m), 1.62-1.51 (2H, m), 1.12-1.04 (3H, m). MS (ESI) m/z 493 (M + H)+ |
| B-12 | 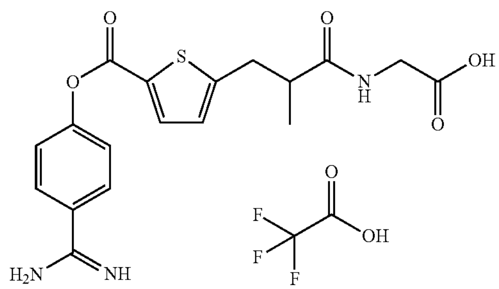 [SMILES: CC(Cc1ccc(C(=O)Oc2ccc(C(=N)N)cc2)s1)C(=O)NCC(=O)O ; O=C(O)C(F)(F)F] | MS (ESI) m/z 390 (M + H)+ |
| B-13 | 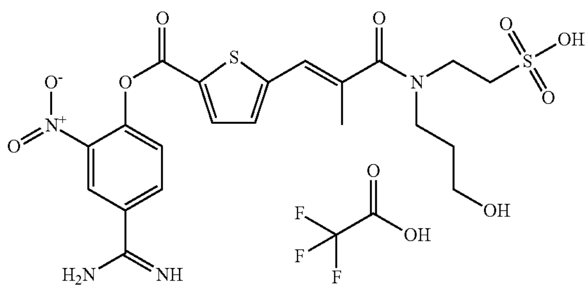 | 1H-NMR (300 MHz, DMSO-d6) δ 9.57 (2H, s), 9.17 (2H, s), 8.64 (1H, s), 8.25 (1H, dd, J = 2.4, 8.7 Hz), 8.09 (1H, d, J = 4.2 Hz), 7.98 (1H, d, J = 8.7 Hz), 7.43 (1H, d, J = 4.2 Hz), 6.86 (1H, s), 3.60-3.25 (6H, m), 2.71 (2H, m), 2.15 (3H, s), 1.68 (2H, m). MS (ESI) m/z 540 (M + H)+ |
| B-14 | 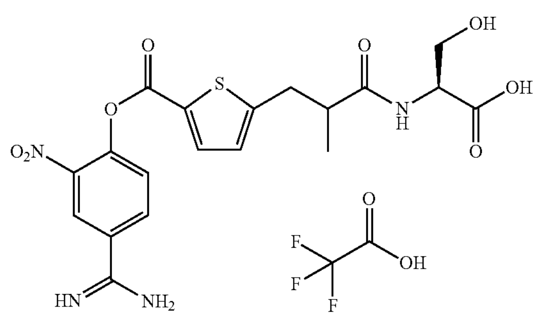 [SMILES: CC(Cc1ccc(C(=O)Oc2ccc(C(=N)N)cc2[N+](=O)[O-])s1)C(=O)N[C@@H](CO)C(=O)O ; O=C(O)C(F)(F)F] | MS (ESI) m/z 465 (M + H)+ |
| B-15 | 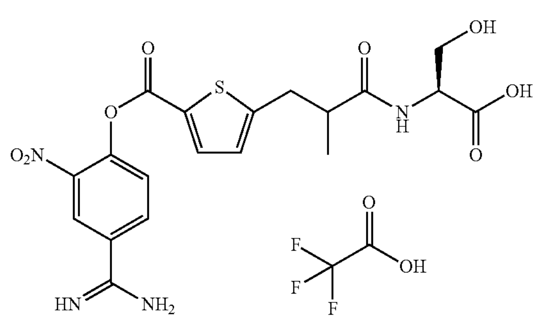 [SMILES: CC(Cc1ccc(C(=O)Oc2ccc(C(=N)N)cc2[N+](=O)[O-])s1)C(=O)N[C@@H](CO)C(=O)O ; O=C(O)C(F)(F)F] | MS (ESI) m/z 465 (M + H)+ |

TABLE 2-8-continued

| Compound No. | Structure | Analysis data |
|---|---|---|
| B-16 | 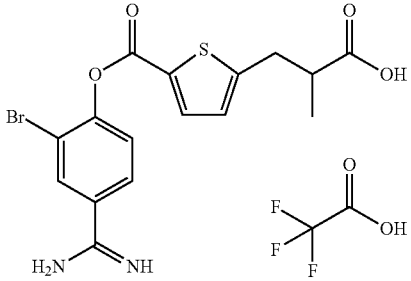 [SMILES: CC(Cc1ccc(C(=O)Oc2ccc(C(=N)N)cc2Cl)s1)C(=O)O ; O=C(O)C(F)(F)F] | MS (ESI) m/z 411 [M(79Br) + H]+, 413 [M(81Br) + H]+ |

TABLE 2-9

| Compound No. | Structure | Analysis data |
|---|---|---|
| B-17 | 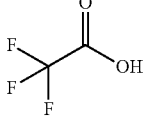 | 1H-NMR (300 MHz, DMSO-d6) δ 12.42 (1H, br), 9.43 (2H, s), 9.24 (2H, brs), 8.11 (1H, d, J = 2.2 Hz), 7.96 (1H, d, J = 3.7 Hz), 7.86 (1H, dd, J = 8.7, 2.2 Hz), 7.78 (1H, d, J = 8.7 Hz), 7.13 (1H, d, J = 3.7 Hz), 3.19 (1H, dd, J = 14.8, 8.0 Hz), 3.04 (1H, dd, J = 14.8, 6.0 Hz), 2.75 (1H, m), 1.14 (3H, d, J = 7.2 Hz).<br>MS (ESI) m/z 367 [M(35Cl) + H]+, 368 [M(37Cl) + H]+ |
| B-18 | 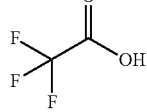 | 1H-NMR (300 MHz, DMSO-d6) δ 9.34 (2H, s), 8.99 (2H, s), 8.29 (1H, m), 7.90 (2H, d, J = 8.4 Hz), 7.56 (2H, d, J = 8.4 Hz), 7.05 (1H, m), 4.50 (1H, m), 3.20-2.50 (5H, s), 1.06 (3H, m), MS (ESI) m/z 448 (M + H)+ |
| B-19 | 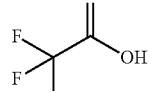 | 1H-NMR (300 MHz, DMSO-d6) δ 12.41 (1H, brs), 9.41 (2H, s), 9.15 (2H, brs), 7.97-7.75 (4H, m), 7.13 (1H, d, J = 3.9 Hz), 3.19 (1H, dd, J = 15.0, 8.4 Hz), 3.04 (1H, dd, J = 15.0, 6.0 Hz), 2.75 (1H, m), 1.14 (3H, d, J = 7.2 Hz).<br>MS (ESI) m/z 351 (M + H)+ |

TABLE 2-9-continued

| Compound No. | Structure | Analysis data |
| --- | --- | --- |
| B-20 | 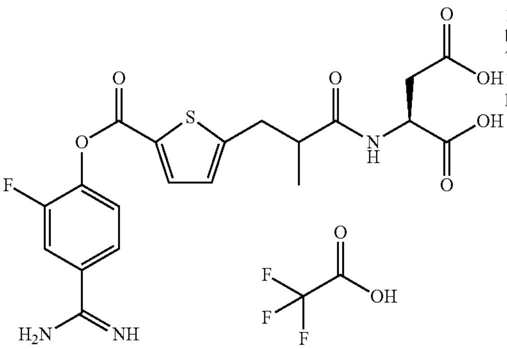 [SMILES: CC(Cc1ccc(C(=O)Oc2ccc(C(=N)N)cc2F)s1)C(=O)N[C@@H](CC(=O)O)C(=O)O ; O=C(O)C(F)(F)F] | 1H-NMR (300 MHz, DMSO-d6) δ 9.41 (2H, br), 9.12 (2H, br), 8.33-8.27 (1H, m), 7.95-7.92 (2H, m), 7.76-7.74 (2H, m), 7.10-7.07 (1H, m), 4.54-4.48 (1H, m), 3.46-2.50 (5H, m), 1.10-1.04 (3H, m).<br>MS (ESI) m/z 466 (M + H)+ |
| B-21 | 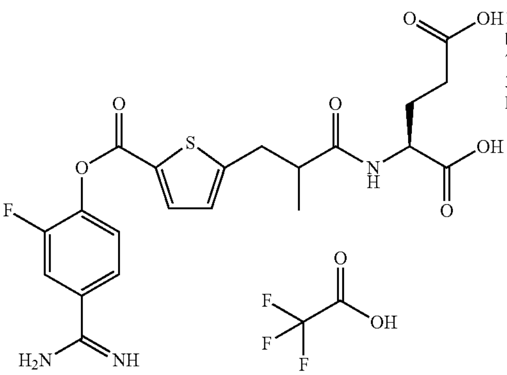 [SMILES: CC(Cc1ccc(C(=O)Oc2ccc(C(=N)N)cc2F)s1)C(=O)N[C@@H](CCC(=O)O)C(=O)O ; O=C(O)C(F)(F)F] | 1H-NMR (300 MHz, DMSO-d6) δ 12.24 (1H, br), 9.41 (2H, br), 9.13 (2H, br), 8.23-8.17 (1H, m), 7.94-7.91 (2H, m), 7.76-7.74 (2H, m), 7.10-7.07 (1H, m), 4.24-4.17 (1H, m), 3.47-1.71 (7H, m), 1.10-1.07 (3H, m).<br>MS (ESI) m/z 480 (M + H)+ |
| B-22 | 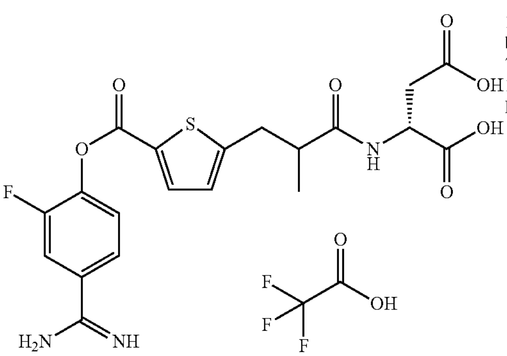 [SMILES: CC(Cc1ccc(C(=O)Oc2ccc(C(=N)N)cc2F)s1)C(=O)N[C@H](CC(=O)O)C(=O)O ; O=C(O)C(F)(F)F] | 1H-NMR (300 MHz, DMSO-d6) δ 9.41 (2H, br), 9.12 (2H, br), 8.33-8.27 (1H, m), 7.95-7.92 (2H, m), 7.76-7.74 (2H, m), 7.10-7.07 (1H, m), 4.54-4.48 (1H, m), 3.46-2.50 (5H, m), 1.10-1.04 (3H, m).<br>MS (ESI) m/z 466 (M + H)+ |
| B-23 | 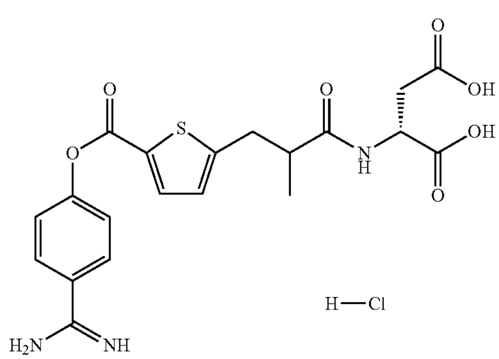 [SMILES: CC(Cc1ccc(C(=O)Oc2ccc(C(=N)N)cc2)s1)C(=O)N[C@H](CC(=O)O)C(=O)O ; Cl] | 1H-NMR (300 MHz, DMSO-d6) δ 9.36 (2H, br), 9.02 (2H, br), 8.31-8.19 (1H, m), 7.91-7.87 (3H, m), 7.55 (2H, d, J = 8.5 Hz), 7.08-7.04 (1H, m), 4.52-4.42 (1H, m), 3.51-2.54 (5H, m), 1.09-1.04 (3H, m).<br>MS (ESI) m/z 448 (M + H)+ |

TABLE 2-9-continued

| Compound No. | Structure | Analysis data |
|---|---|---|
| B-24 | 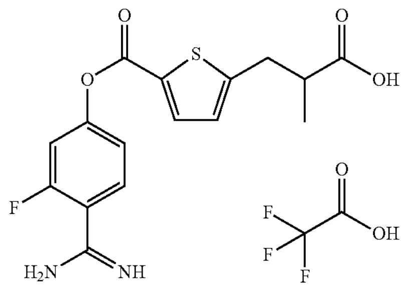 [SMILES: CC(Cc1ccc(C(=O)Oc2ccc(C(=N)N)c(F)c2)s1)C(=O)O ; O=C(O)C(F)(F)F] | 1H-NMR (300 MHz, DMSO-d6) δ 12.40 (1H, br), 9.49 (2H, br), 9.24 (2H, br), 7.91 (1H, d, J = 3.8 Hz), 7.80 (1H, dd, J = 8.5, 8.2 Hz), 7.63 (1H, dd, J = 10.9, 2.0 Hz), 7.41 (1H, dd, J = 8.5, 2.0 Hz), 7.11 (1H, dd, J = 3.8 Hz), 3.18 (1H, dd, J = 15.0, 7.6 Hz), 3.03 (1H, dd, J = 15.0, 6.2 Hz), 2.77-2.70 (1H, m), 1.13 (3H, d, J = 7.0 Hz).<br>MS (ESI) m/z 351 (M + H)+ |

TABLE 2-10

| Compound No. | Structure | Analysis data |
|---|---|---|
| C-1 | 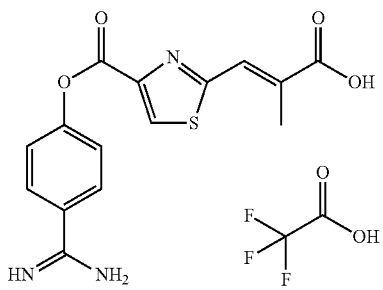 [SMILES: C/C(=C\c1nc(C(=O)Oc2ccc(C(=N)N)cc2)cs1)C(=O)O ; O=C(O)C(F)(F)F] | 1H-NMR (DMSO-d6) δ 9.36 (2H, br s), 9.09 (2H, br s), 7.93 (2H, d, J = 8.6 Hz), 7.75 (1H, s), 7.63 (2H, d, J = 8.6 Hz), 2.33 (3H, s), 2.30 (1H, s).<br>MS (ESI) m/z 332 (M + H)+ |
| C-2 | 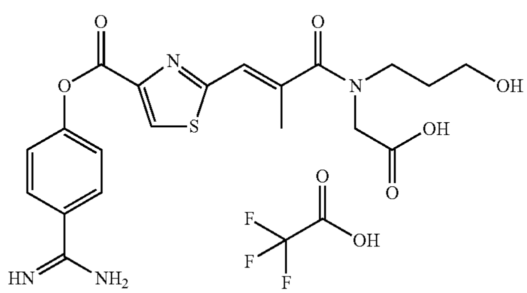 | MS (ESI) m/z 447 (M + H)+ |
| C-3 | 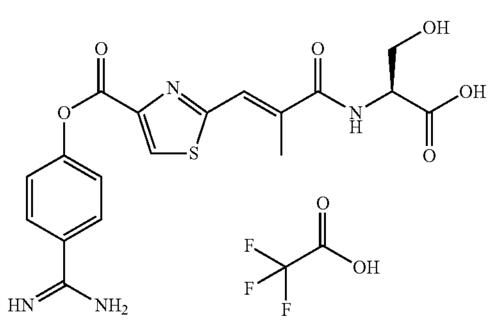 [SMILES: C/C(=C\c1nc(C(=O)Oc2ccc(C(=N)N)cc2)cs1)C(=O)N[C@@H](CO)C(=O)O ; O=C(O)C(F)(F)F] | MS (ESI) m/z 419 (M + H)+ |

TABLE 2-11

| Compound No. | Structure | Analysis data |
|---|---|---|
| A-41 | 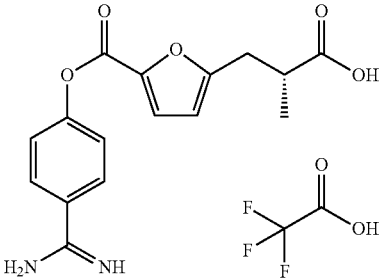 [SMILES: C[C@H](Cc1ccc(C(=O)Oc2ccc(C(=N)N)cc2)o1)C(=O)O ; O=C(O)C(F)(F)F] | 1H-NMR (300 MHz, DMSO-d6) δ 9.35 (2H, br s), 9.08 (2H, br s), 7.90 (2H, dd, J = 6.9, 1.8 Hz), 7.61-7.49 (3H, m), 6.52 (1H, d, J = 3.6 Hz), 3.15-2.98 (1H, m), 2.90-2.70 (2H, m), 1.14 (3H, d, J = 6.9 Hz).<br>MS (ESI) m/z 317 (M + H)+ |
| A-42 | 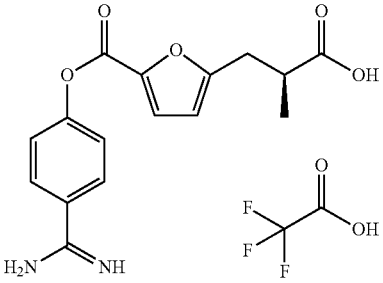 [SMILES: C[C@@H](Cc1ccc(C(=O)Oc2ccc(C(=N)N)cc2)o1)C(=O)O ; O=C(O)C(F)(F)F] | 1H-NMR (300 MHz, DMSO-d6) δ 9.35 (2H, br s), 9.08 (2H, br s), 7.90 (2H, dd, J = 6.9, 1.8 Hz), 7.61-7.49 (3H, m), 6.52 (1H, d, J = 3.6 Hz,), 3.15-2.98 (1H, m), 2.90-2.70 (2H, m), 1.14 (3H, d, J = 6.9 Hz).<br>MS (ESI) m/z 317 (M + H)+ |
| A-43 | 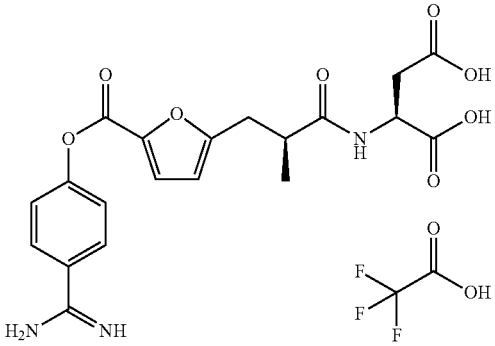 | 1H-NMR (300 MHz, DMSO-d6) δ 9.34 (2H, br s), 9.10 (2H, br s), 8.32 (1H, d, J = 8.7 Hz), 7.90 (2H, d, J = 8.7 Hz), 7.54 (2H, d, J = 8.7 Hz), 7.50 (1H, d, J = 3.3 Hz), 6.46 (1H, d, J = 3.3 Hz), 4.59-4.49 (1H, m), 3.08-2.47 (5H, m), 1.07 (3H, d, J = 5.4 Hz).<br>MS (ESI) m/z 432 (M + H)+ |
| A-44 | 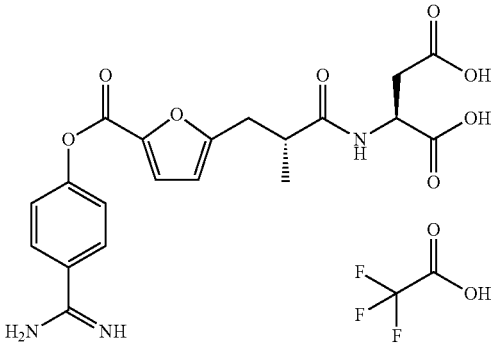 | 1H-NMR (300 MHz, DMSO-d6) δ 9.34 (2H, br s), 9.09 (2H, br s), 8.36 (1H, d, J = 8.4 Hz), 7.90 (2H, d, J = 8.7 Hz), 7.55 (2H, d, J = 8.7 Hz), 7.51 (1H, d, J = 3.6 Hz), 6.50 (1H, d, J = 3.6 Hz), 4.57-4.45 (1H, m), 3.05-2.42 (5H, m), 1.05 (3H, d, J = 6.6 Hz).<br>MS (ESI) m/z 432 (M + H)+ |

TABLE 2-11-continued

| Compound No. | Structure | Analysis data |
|---|---|---|
| A-45 | 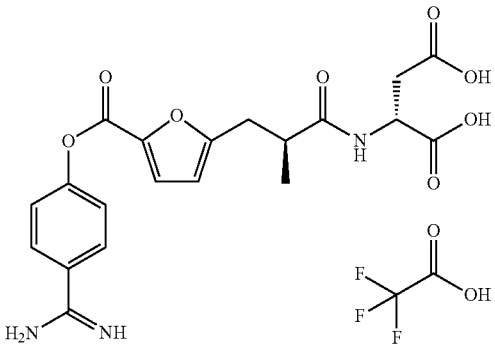 | 1H-NMR (300 MHz, DMSO-d6) δ 9.34 (2H, br s), 9.09 (2H, br s), 8.36 (1H, d, J = 8.4 Hz), 7.90 (2H, d, J = 8.7 Hz), 7.55 (2H, d, J = 8.7 Hz), 7.51 (1H, d, J = 3.6 Hz), 6.50 (1H, d, J = 3.6 Hz), 4.57-4.45 (1H, m), 3.05-2.42 (5H, m), 1.05 (3H, d, J = 6.6 Hz).<br>MS (ESI) m/z 432 (M + H)+ |
| A-46 | 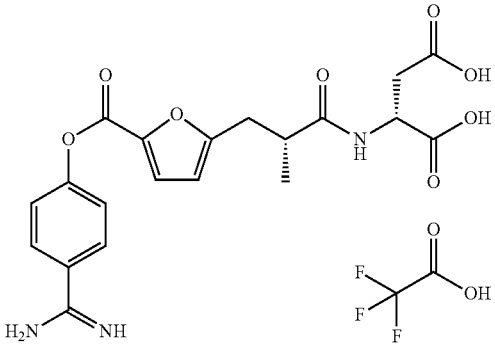 | 1H-NMR (300 MHz, DMSO-d6) δ 9.34 (2H, br s), 9.10 (2H, br s), 8.32 (1H, d, J = 8.7 Hz), 7.90 (2H, d, J = 8.7 Hz), 7.54 (2H, d, J = 8.7 Hz), 7.50 (1H, d, J = 3.3 Hz), 6.46 (1H, d, J = 3.3 Hz), 4.59-4.49 (1H, m), 3.08-2.47 (5H, m), 1.07 (3H, d, J = 5.4 Hz).<br>MS (ESI) m/z 432 (M + H)+ |
| A-47 | 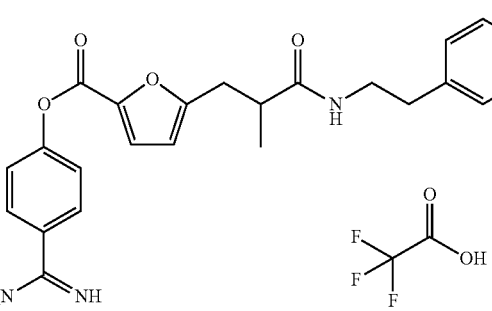 | 1H-NMR (300 MHz, DMSO-d6) δ 9.32 (2H, s), 9.00 (2H, s), 8.00 (1H, t, J = 5.4 Hz), 7.87 (2H, d, J = 8.7 Hz), 7.52 (2H, m),<br>7.30-7.10 (6H, m), 6.40 (1H, d, J = 3.3 Hz), 3.30-3.20 (2H, m),<br>3.00-2.90 (1H, m), 2.70-2.60 (4H, m), 1.01 (3H, d, J = 6.6 Hz).<br>MS (ESI) m/z 420 (M + H)+ |
| A-48 | 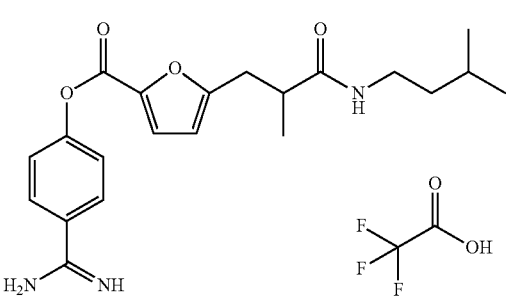 [SMILES: CC(C)CCNC(=O)C(C)Cc1ccc(C(=O)Oc2ccc(C(=N)N)cc2)o1 ; O=C(O)C(F)(F)F] | 1H-NMR (300 MHz, DMSO-d6) δ 9.20-9.05 (4H, br s), 7.92-7.82 (3H, m), 7.52 (3H, m), 6.45 (1H, d, J = 3.6 Hz), 3.30-3.20 (2H, m), 3.10-2.90 (1H, m), 2.75-2.65 (2H, m), 1.47 (1H, m), 1.24 (2H, m), 1.05 (3H, d, J = 6.6 Hz), 0.83 (6H, d, J = 6.6 Hz).<br>MS (ESI) m/z 386 (M + H)+ |

TABLE 2-12

| Compound No. | Structure | Analysis data |
| --- | --- | --- |
| A-49 | 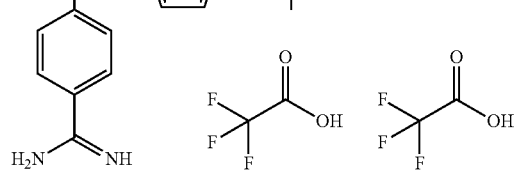 | 1H-NMR (300 MHz, DMSO-d6) δ 9.35 (2H, s), 9.19 (2H, s), 8.27 (1H, t, J = 5.4 Hz), 7.91 (2H, d, J = 9.0 Hz), 7.54 (3H, m), 6.50 (1H, d, J = 3.6 Hz), 3.18-2.98 (5H, m), 2.85-2.65 (8H, m), 1.08 (3H, d, J = 6.6 Hz).<br>MS (ESI) m/z 387 (M + H)+ |
| A-50 | 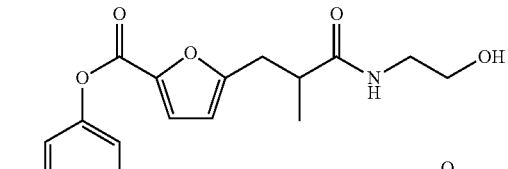 | 1H-NMR (300 MHz, DMSO-d6) δ 9.34 (2H, s), 9.02 (2H, s), 7.95 (1H, t, J = 5.4 Hz), 7.89 (2H, d, J = 8.7 Hz), 7.54 (3H, m), 6.47 (1H, d, J = 3.6 Hz), 3.30 (2H, m), 3.10 (2H, m), 2.98 (1H, m), 2.78-2.68 (2H, m), 1.06 (3H, d, J = 6.3 Hz).<br>MS (ESI) m/z 360 (M + H)+ |
| A-51 | 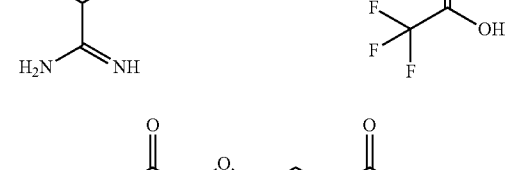 | 1H-NMR (300 MHz, DMSO-d6) δ 9.34 (2H, s), 8.93 (2H, s), 7.89 (2H, d, J = 9.0 Hz), 7.54 (3H, m), 6.47 (1H, d, J = 3.6 Hz), 3.60-3.00 (5H, m), 2.72 (2H, m), 1.90-1.70 (4H, m), 1.07 (3H, d, J = 5.7 Hz).<br>MS (ESI) m/z 370 (M + H)+ |
| A-52 | 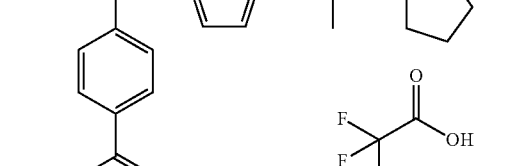 | 1H-NMR (400 MHz, DMSO-d6) δ 9.34 (2H, s), 8.98 (2H, s), 7.89 (2H, m), 7.55 (3H, m), 6.48 (1H, d, J = 3.2 Hz), 3.90-3.80 (2H, m), 3.55-3.25 (2H, m), 3.08-2.98 (2H, m), 2.80-2.70 (2H, m), 2.10-1.20 (4H, m), 1.07 (3H, d, J = 6.4 Hz).<br>MS (ESI) m/z 428 (M + H)+ |
| A-53 | 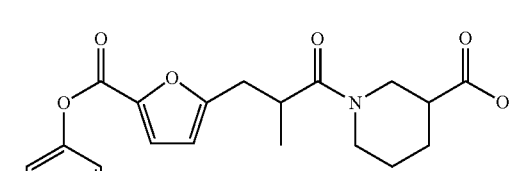 | 1H-NMR (400 MHz, DMSO-d6) δ 9.35 (2H, s), 9.01 (2H, s), 8.37 (1H, d, J = 8.0 Hz), 7.57 (1H, d, J = 2.0 Hz), 7.52-7.44 (3H, m), 6.47 (1H, d, J = 2.0 Hz), 4.55 (1H, m), 3.88 (3H, s), 2.97 (2H, t, J = 7.6 Hz), 2.68-2.55 (4H, m).<br>MS (ESI) m/z 448 (M + H)+ |

TABLE 2-12-continued
| Compound No. | Structure | Analysis data |
|---|---|---|
| A-54 | 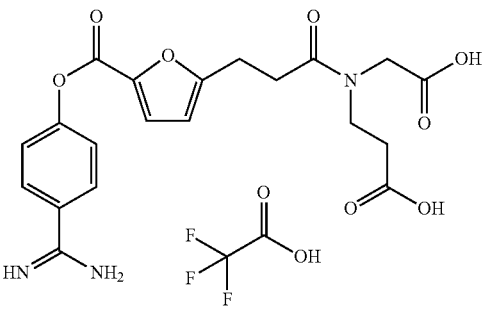 [SMILES: N=C(N)c1ccc(OC(=O)c2ccc(CCC(=O)N(CCC(=O)O)CC(=O)O)o2)cc1 ; O=C(O)C(F)(F)F] | 1H-NMR (400 MHz, DMSO-d6) δ 9.34 (2H, s), 8.96 (2H, s) 7.89 (2H, dd, J = 6.8, 2.0 Hz), 7.54 (3H, m), 6.52 (0.5H, d, J = 3.6 Hz), 6.48 (0.5H, d, J = 3.6 Hz), 4.23 (1H, s), 3.96 (1H, s), 3.60 (1H, t, J = 6.8 Hz), 3.46 (1H, t, J = 6.8 Hz), 2.98-2.85 (2H, m), 2.70-2.40 (2H, m).<br>MS (ESI) m/z 418 (M + H)+ |
| A-55 | 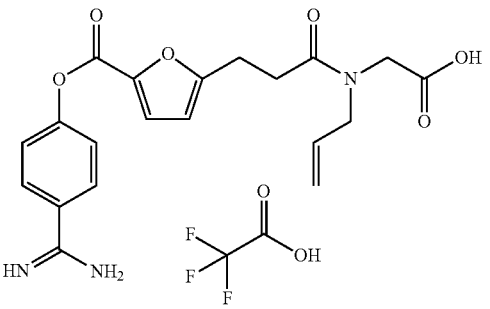 | 1H-NMR (400 MHz, DMSO-d6) δ 9.35 (1H, br s), 9.26-9.02 (2H, m), 7.95-7.86 (2H, m), 7.58-7.51 (2H, m), 6.52-6.47 (3H, m), 5.94-5.62 (1H, m), 5.23-5.03 (2H, m), 4.13-3.88 (4H, m), 3.04-2.91 (2H, m), 2.83-2.65 (2H, m).<br>MS (ESI) m/z 400 (M + H)+ |
| A-56 | 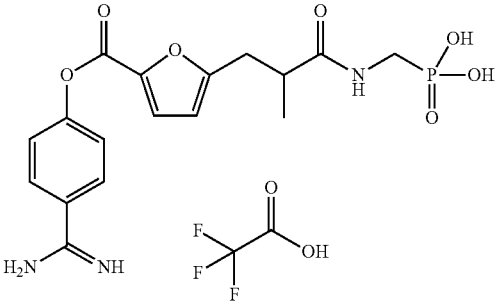 [SMILES: CC(Cc1ccc(C(=O)Oc2ccc(C(=N)N)cc2)o1)C(=O)NCP(=O)(O)O ; O=C(O)C(F)(F)F] | MS (ESI) m/z 410 (M + H)+ |
TABLE 2-13
| Compound No. | Structure | Analysis data |
|---|---|---|
| A-57 | 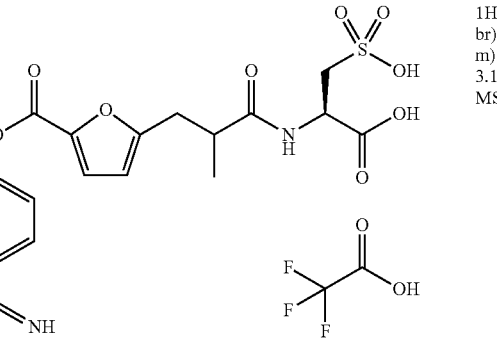 | 1H-NMR (300 MHz, DMSO-d6) δ 8.89 (2H, br), 8.89 (1H, br), 8.26-8.21 (1H, m), 7.89 (2H, d, J = 8.5 Hz), 7.59-7.56 (2H, m), 7.51-7.49 (1H, m), 6.57-6.55 (1H, m), 4.38-4.34 (1H, m), 3.12-2.72 (5H, m), 1.08 (3H, d, J = 6.5 Hz).<br>MS (ESI) m/z 468 (M + H)+ |

TABLE 2-13-continued

| Compound No. | Structure | Analysis data |
|---|---|---|
| A-58 | 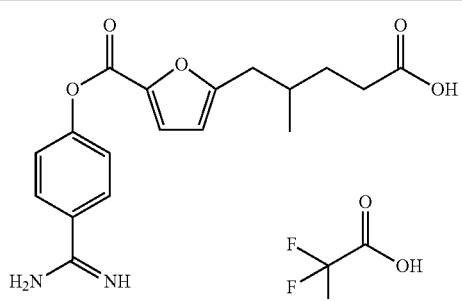 | 1H-NMR (300 MHz, DMSO-d6) δ 9.23 (4H, br s), 7.88 (2H, d, J = 8.7 Hz), 7.55 (1H, d, J = 3.4 Hz), 7.54 (2H, d, J = 8.7 Hz), 6.52 (1H, d, J = 3.4 Hz), 1.73-2.37 (7H, m), 0.89 (3H, d, J = 6.7 Hz).<br>MS (ESI) m/z 345 (M + H)+ |
| A-59 | 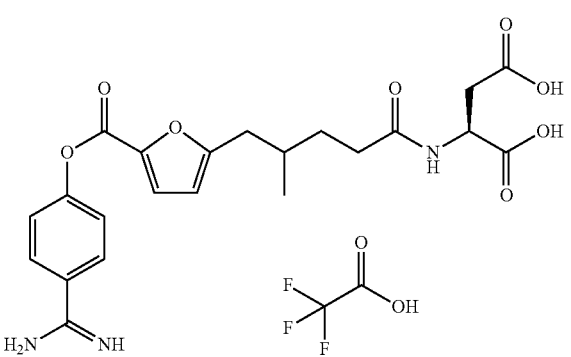 [SMILES: CC(CCC(=O)N[C@@H](CC(=O)O)C(=O)O)Cc1ccc(C(=O)Oc2ccc(C(=N)N)cc2)o1 ; O=C(O)C(F)(F)F] | 1H-NMR (300 MHz, DMSO-d6) δ 9.33 (2H, br s), 9.10 (2H, br s), 8.10 (1H, d, J = 7.6 Hz), 7.89 (2H, d, J = 8.8 Hz), 7.56 (2H, d, J = 8.8 Hz), 7.55 (1H, d, J = 3.5 Hz), 6.53-6.51 (1H, m), 4.50-4.43 (1H, m), 2.75 (1H, dd, J = 15.0, 6.2 Hz), 2.69-2.47 (3H, m), 2.25-2.11 (2H, m), 1.88-1.81 (1H, m), 1.63-1.57 (1H, m), 1.41-1.34 (1H, m), 0.89 (3H, d, J = 6.6 Hz).<br>MS (ESI) m/z 460 (M + H)+ |
| A-60 | 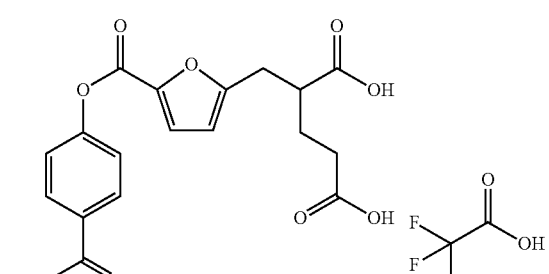 | 1H-NMR (300 MHz, DMSO-d6) δ 9.31(2H, br s), 9.26 (2H, br s), 7.90 (2H, d, J = 8.7 Hz), 7.55 (3H, m), 6.51 (1H, d, J = 3.6 Hz), 3.00 (1H, m), 2.90 (1H, m), 2.73 (1H, m), 2.28 (2H, m), 1.77 (2H, m).<br>MS (ESI) m/z 375 (M + H)+ |
| A-61 | 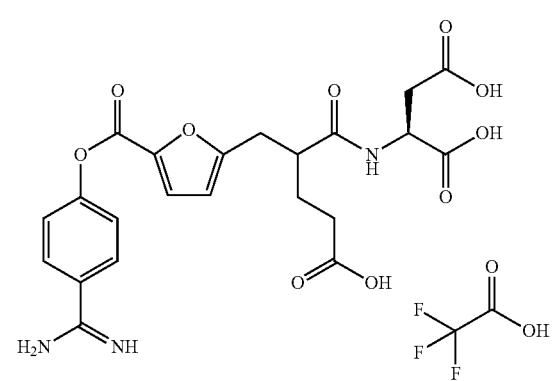 | 1H-NMR (300 MHz, DMSO-d6) δ 9.34 (2H, s), 9.06 (2H, s), 8.40 (1H, m), 8.89 (2H, d, J = 8.7 Hz), 7.55 (2H, d, J = 8.7 Hz), 7.50 (1H, d, J = 3.3 Hz), 6.48 (1H, m), 4.50 (1H, m), 2.95-2.40 (5H, m), 2.22 (2H, m), 1.80-1.60 (2H, m).<br>MS (ESI) m/z 490 (M + H)+ |

TABLE 2-13-continued

| Compound No. | Structure | Analysis data |
|---|---|---|
| A-62 | 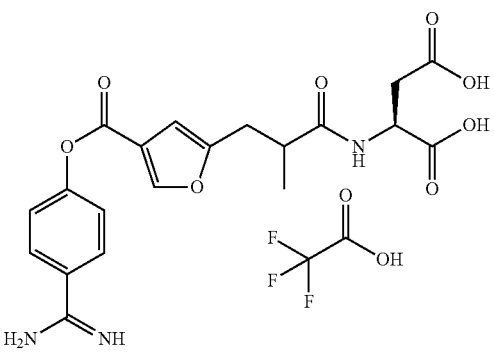 | 1H-NMR (300 MHz, DMSO-d6) δ 9.33 (2H, s), 9.05 (2H, s), 8.51 (1H, s), 8.24 (0.5H, d, J = 7.8 Hz), 8.26 (0.5H, d, J = 7.8 Hz), 7.89 (2H, d, J = 8.7 Hz), 7.52 (2H, d, J = 8.7 Hz), 6.61 (0.5H, s), 6.58 (0.5H, s), 4.54 (1H, m), 3.10-2.80 (5H, m), 1.02 (3H, m). MS (ESI) m/z 432 (M + H)+ |
| A-63 | 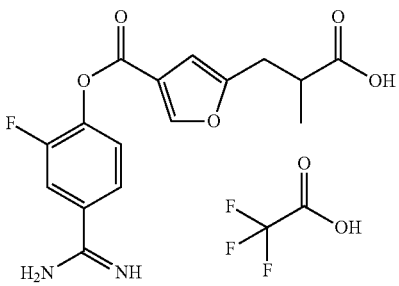 | 1H-NMR (400 MHz, DMSO-d6) δ 12.35 (1H, br s), 9.41 (2H, br s), 9.18 (2H, br s), 8.62 (1H, d, J = 0.8 Hz), 7.92 (1H, dd, J = 11.6, 1.6 Hz), 7.76-7.70 (2H, m), 6.63 (1H, d, J = 0.8 Hz), 2.99 (1H, dd, J = 15.0, 6.6 Hz), 2.83-2.72 (2H, m), 1.11 (3H, d, J = 6.8 Hz). MS (ESI) m/z 335 (M + H) |
| A-64 | 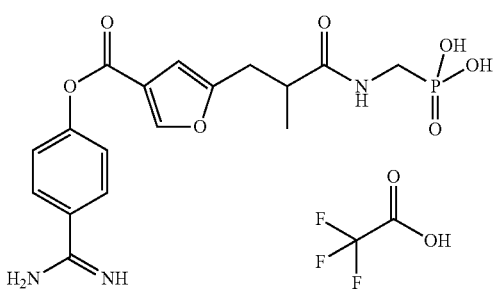 [SMILES: CC(Cc1cc(C(=O)Oc2ccc(C(=N)N)cc2)co1)C(=O)NCP(=O)(O)O ; O=C(O)C(F)(F)F] | 1H-NMR (400 MHz, DMSO-d6) δ 9.33 (2H, s), 8.94 (2H, s), 8.52 (1H, s), 8.09 (1H, t, J = 6.8 Hz), 7.89 (2H, d, J = 6.8 Hz), 7.52 (2H, d, J = 6.8 Hz), 6.59 (1H, s), 2.92 (1H, dd, J = 14.8, 6.8 Hz), 2.79 (2H, m), 2.67 (2H, m), 1.03 (3H, d, J = 6.8 Hz). MS (ESI) m/z 410 (M + H)+ |

TABLE 2-14

| Compound No. | Structure | Analysis data |
|---|---|---|
| A-65 | 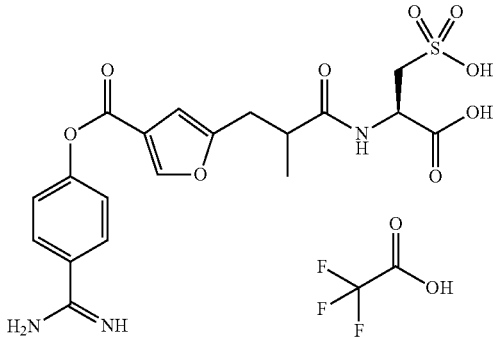 [SMILES: CC(Cc1cc(C(=O)Oc2ccc(C(=N)N)cc2)co1)C(=O)N[C@@H](CS(=O)(=O)O)C(=O)O ; O=C(O)C(F)(F)F] | 1H-NMR (400 MHz, DMSO-d6) δ 9.33 (2H, s), 8.91 (2H, s), 8.50 (1H, s), 8.19 (1H, t, J = 7.2 Hz), 7.88 (2H, d, J = 6.4 Hz), 7.55 (2H, m), 6.65 (0.5H, s), 6.62 (0.5H, s), 4.35 (1H, m), 2.91 (1H, m), 2.80 (2H, m), 2.65 (2H, m), 1.05 (3H, d, J = 6.8 Hz). MS (ESI) m/z 468 (M + H)+ |

TABLE 2-14-continued

| Compound No. | Structure | Analysis data |
|---|---|---|
| A-66 | 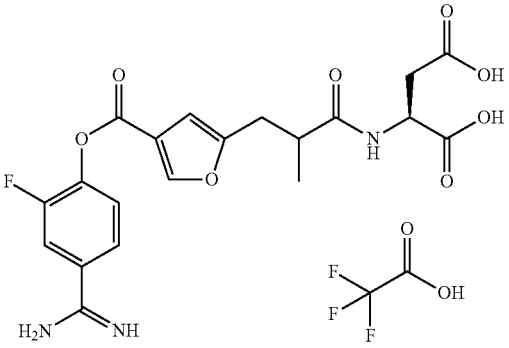 [SMILES: CC(Cc1cc(C(=O)Oc2ccc(C(=N)N)cc2F)co1)C(=O)N[C@@H](CC(=O)O)C(=O)O ; O=C(O)C(F)(F)F] | 1H-NMR (400 MHz, DMSO-d6) δ 9.40 (2H, br s), 9.07 (2H, br s), 8.61 (1H, d, J = 0.8 Hz), 8.29 (1H, m), 7.92 (1H, dd, J = 11.6, 2.0 Hz), 7.75-7.69 (2H, m), 6.59 (1H, m), 4.52 (1H, m), 2.90 (1H, m), 2.75-2.55 (4H, m), 1.02 (3H, m).<br>MS (ESI) m/z 450 (M + H)+ |
| A-67 | 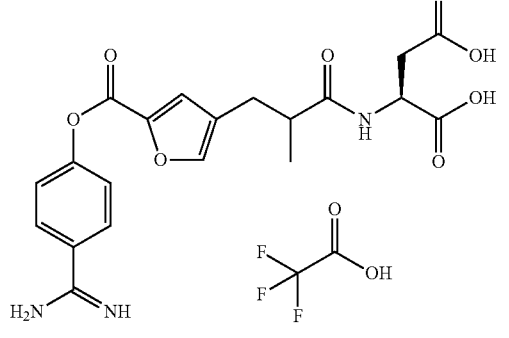 | 1H-NMR (300 MHz, DMSO-d6) δ 9.33 (2H, s), 8.97 (2H, s), 8.23 (1H, m), 7.90-7.80 (3H, m), 7.55 (2H, d, J = 8.4 Hz), 7.47 (1H, s), 4.48 (1H, m), 3.10-2.90 (3H, m), 2.70-2.50 (2H, m), 1.02 (3H, m).<br>MS (ESI) m/z 432 (M + H)+ |
| A-68 | 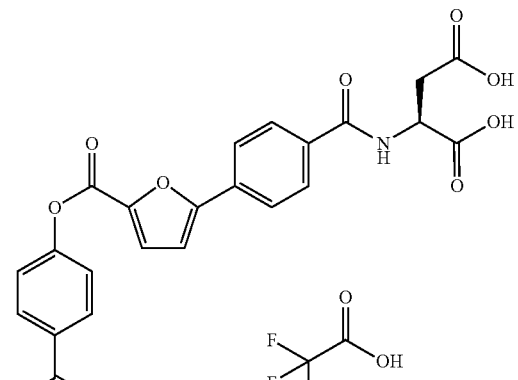 | 1H-NMR (400 MHz, DMSO-d6) δ 9.36 (2H, br s), 8.98 (2H, br s), 8.88 (1 H, d, J = 8.0 Hz), 8.01 (4H, s), 7.93 (2H, d, J = 8.8 Hz), 7.79 (1H, d, J = 3.6 Hz), 7.62 (2H, d, J = 8.8 Hz), 7.48 (1H, d, J = 3.6 Hz), 4.80-4.75 (1H, m), 2.87 (1H, dd, J = 16.0, 5.6 Hz), 2.73 (1H, dd, J = 16.0, 8.0 Hz).<br>MS (ESI) m/z 466 (M + H)+ |
| A-69 | 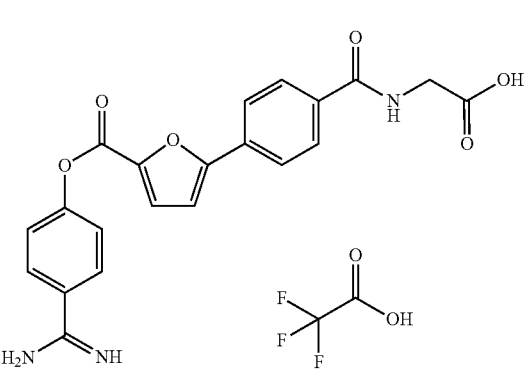 [SMILES: N=C(N)c1ccc(OC(=O)c2ccc(-c3ccc(C(=O)NCC(=O)O)cc3)o2)cc1 ; O=C(O)C(F)(F)F] | 1H-NMR (400 MHz, DMSO-d6) δ 12.62 (1H, br s), 9.36 (2H, br s), 9.00 (2H, br s), 8.97 (1H, t, J = 6.0 Hz), 8.04-8.01 (4H, m), 7.92 (2H, d, J = 8.8 Hz), 7.78 (1H, d, J = 3.6 Hz), 7.76 (2H, d, J = 8.8 Hz), 7.47 (1H, d, J = 3.6 Hz), 3.95 (2H, d, J = 6.0 Hz).<br>MS (ESI) m/z 408 (M + H)+ |

TABLE 2-14-continued
| Compound No. | Structure | Analysis data |
|---|---|---|
| A-70 | 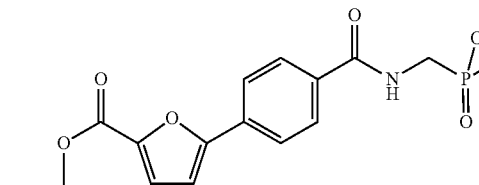 | 1H-NMR (400 MHz, DMSO-d6) δ 9.31 (2H, br s), 9.20 (2H, br s), 8.66 (1H, t, J = 5.6 Hz), 8.03 (2H, d, J = 8.4 Hz), 7.96 (2H, d, J = 8.4 Hz), 7.90 (2H, d, J = 8.8 Hz), 7.77 (1H, d, J = 4.0 Hz), 7.60 (2H, d, J = 8.8 Hz), 7.45 (1H, d, J = 4.0 Hz), 3.56 (2H, dd, J = 12.2, 5.6 Hz).<br>MS (ESI) m/z 444 (M + H)+ |
| A-71 | 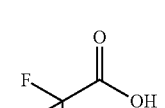 | MS (ESI) m/z 466 (M + H)+ |
TABLE 2-15
| Compound No. | Structure | Analysis data |
|---|---|---|
| A-72 | 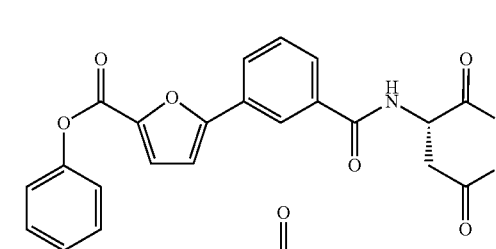 | 1H-NMR (300 MHz, DMSO-d6) δ 9.34 (2H, br s), 9.01 (2H, br s), 7.89 (2H, d, J = 8.7 Hz), 7.56 (2H, d, J = 8.7 Hz), 7.54 (1H, s), 6.61-6.49 (1H, m), 5.28-2.19 (1H, m), 3.39-2.60 (5H, m), 1.24-1.04 (3H, m).<br>MS (ESI) m/z 433 (M + H)+ |
| A-73 | 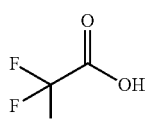 | 1H-NMR (400 MHz, DMSO-d6) δ 9.34 (2H, s), 9.15 (2H, s), 7.93-7.87 (2H, m), 7.59-7.51 (3H, m), 6.54 (1H, d, J = 3.6 Hz), 4.37-4.28 (1H, m), 3.21-3.03 (2H, m), 3.01-2.62 (3H, m), 1.25-1.13 (3H, m).<br>MS (ESI) m/z 449 (M + H)+ |

TABLE 2-15-continued

| Compound No. | Structure | Analysis data |
|---|---|---|
| A-74 | 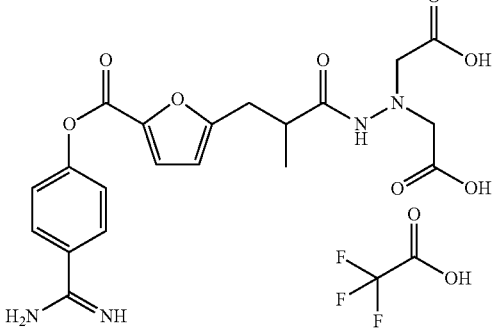 | 1H-NMR (400 MHz, DMSO-d6) δ 12.50 (2H, br s), 9.59 (1H, s), 9.34 (2H, br s), 9.04 (2H, br s), 7.89 (2H, d, J = 8.7 Hz), 7.54 (2H, d, J = 8.7 Hz), 7.49 (1H, d, J = 3.5 Hz), 6.45 (1H, d, J = 3.5 Hz), 3.70 (4H, s), 2.93 (1H, dd, J = 14.6, 7.8 Hz), 2.78-2.70 (2H, m), 1.03 (3H, d, J = 6.6 Hz). MS (ESI) m/z 447 (M + H)+ |

TABLE 2-16

| Compound No. | Structure | Analysis data |
|---|---|---|
| B-25 | 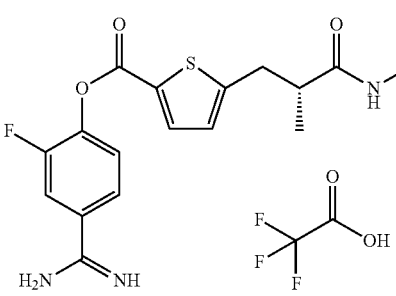 | 1H-NMR (400 MHz, DMSO-d6) δ 9.41 (2H, s), 9.12 (2H, s), 8.32 (1H, d, J = 8.0 Hz), 7.93 (2H, m), 7.74 (2H, m), 7.09 (1H, d, J = 3.6 Hz), 4.50 (1H, m), 3.16 (1H, dd, J = 14.8, 7.6 Hz), 2.90 (1H, dd, J = 14.8, 6.4 Hz), 2.75-2.65 (2H, m), 2.55 (1H, dd, J = 8.4, 1.2 Hz). 1.05 (3H, 6.8 Hz). MS (ESI) m/z 466 (M + H)+ |
| B-26 | 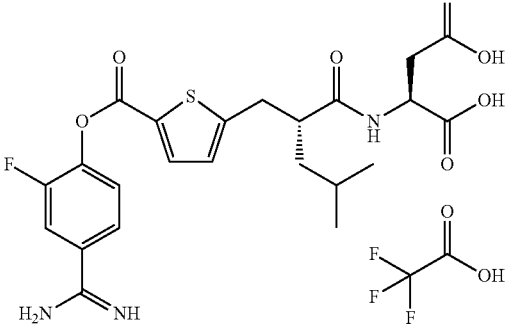 | 1H-NMR (400 MHz, DMSO-d6) δ 9.41 (2H, s), 9.15 (2H, s), 8.39 (1H, d, J = 8.0 Hz), 7.93 (2H, m), 7.75 (2H, m), 7.10 (1H, d, J = 4.0 Hz), 4.51 (1H, m), 3.07 (1H, dd, J = 14.8, 8.0 Hz), 2.92 (1H, dd, J = 14.8, 6.4 Hz), 2.80-2.65 (2H, m), 2.55 (1H, m), 1.50 (2H, m), 1.13 (1H, m), 0.80 (6H, m). MS (ESI) m/z 508 (M + H)+ |
| B-27 | 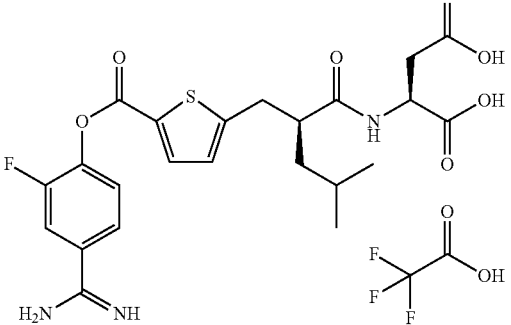 | 1H-NMR (400 MHz, DMSO-d6) δ 9.41 (2H, s), 9.08 (2H, s), 8.33 (1H, d, J = 8.0 Hz), 7.92 (2H, m), 7.73 (2H, m), 7.07 (1H, d, J = 4.4 Hz), 4.53 (1H, m), 3.06 (1H, dd, J = 14.8, 8.4 Hz), 2.93 (1H, dd, J = 14.8, 6.0 Hz), 2.80-2.50 (3H, m), 1.55 (2H, m), 1.15 (1H, m), 0.88 (3H, d, J = 6.8 Hz), 0.81 (3H, d, J = 6.8 Hz). MS (ESI) m/z 508 (M + H)+ |

TABLE 2-16-continued

| Compound No. | Structure | Analysis data |
|---|---|---|
| B-28 | 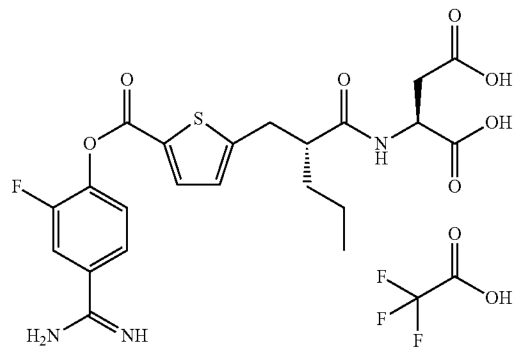 | 1H-NMR (400 MHz, DMSO-d6) δ 9.41 (2H, s), 9.09 (2H, s), 8.33 (1H, m), 7.90 (2H, m), 7.74 (2H, m), 7.09 (1H, d, J = 3.6 Hz), 4.48 (1H, m), 3.10 (1H, dd, J = 14.8, 8.4 Hz), 2.93 (1H, dd, J = 14.8, 6.0 Hz), 2.75-2.60 (2H, m), 2.55 (1H, m), 1.55-1.20 (4H, m), 0.82 (3H, t, J = 6.8 Hz). MS (ESI) m/z 494 (M + H)+ |
| B-29 | 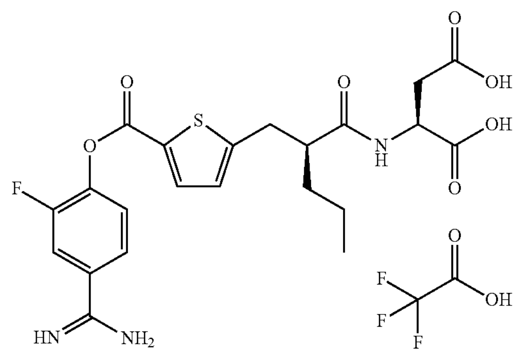 | 1H-NMR (400 MHz, DMSO-d6) δ 9.41 (2H, s), 9.10 (2H, s), 8.29 (1H, m), 7.90 (2H, m), 7.74 (2H, m), 7.06 (1H, d, J = 4.0 Hz), 4.53 (1H, m), 3.10 (1H, dd, J = 14.8, 6.4 Hz), 2.94 (1H, dd, J = 14.8, 5.6 Hz), 2.75-2.50 (3H, m), 1.55-1.20 (4H, m), 0.85 (3H, t, J = 7.2 Hz). MS (ESI) m/z 494 (M + H)+ |
| B-30 | 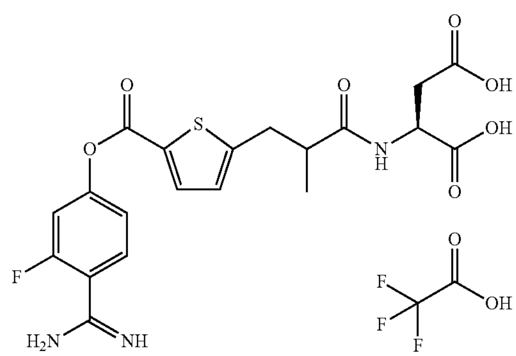 | 1H-NMR (300 MHz, DMSO-d6) δ 9.48 (2H, br s), 9.20 (2H, br s), 8.20 (1H, br s), 7.88 (1H, d, J = 3.8 Hz), 7.79 (1H, dd, J = 8.4, 8.2 Hz), 7.62 (1H, d, J = 10.9 Hz), 7.40 (1H, dd, J = 8.4, 2.0 Hz), 7.08 (0.5H, d, J = 3.8 Hz), 7.05 (0.5H, d, J = 3.8 Hz), 4.44 (1H, br m), 1.40-3.45 (5H, m), 1.07 (1.5H, d, J = 7.1 Hz), 1.05 (1.5H, d, J = 7.9 Hz). MS (ESI) m/z 466 (M + H)+ |
| B-31 | 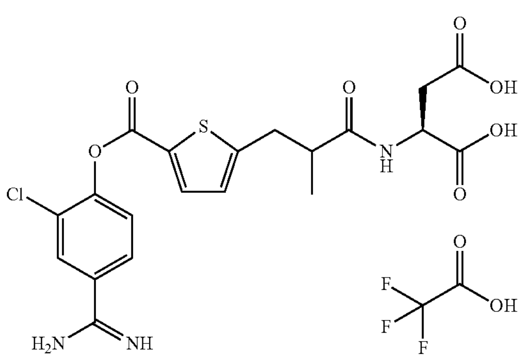 | 1H-NMR (300 MHz, DMSO-d6) δ 9.42 (2H, br s), 9.10 (2H, br s), 821 (1H, br s), 8.10 (1H, d, J = 2.2 Hz), 7.92 (1H, d, J = 3.8 Hz), 7.86 (1H, dd, J = 8.5, 2.2 Hz), 7.77 (1H, d, J = 8.5 Hz), 7.10 (0.5H, d, J = 3.8 Hz), 7.08 (0.5H, d, J = 3.8 Hz), 4.45 (1H, br m), 2.51-3.42 (5H, m), 1.08 (1.5H, d, J = 7.0 Hz), 1.06 (1.5H, d, J = 8.2 Hz). MS (ESI) m/z 466 (M + H)+ |

TABLE 2-16-continued

| Compound No. | Structure | Analysis data |
|---|---|---|
| B-32 | 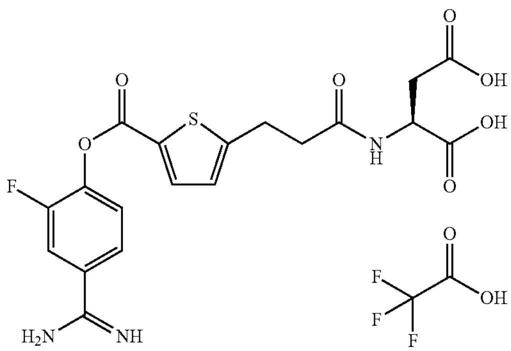 | 1H-NMR (400 MHz, DMSO-d6) δ 9.41 (2H, s), 9.11 (2H, s), 8.33 (1H, d, J = 8.0 Hz), 7.93 (2H, m), 7.73 (2H, m), 7.12 (1H, d, J = 3.6 Hz), 4.55 (1H, m), 3.13 (2H, t, J = 7.2 Hz), 2.68 (1H, dd, J = 12.4, 6.0 Hz), 2.62-2.55 (3H, m).<br>MS (ESI) m/z 452 (M + H)+ |

TABLE 2-17

| Compound No. | Structure | Analysis data |
|---|---|---|
| B-33 | 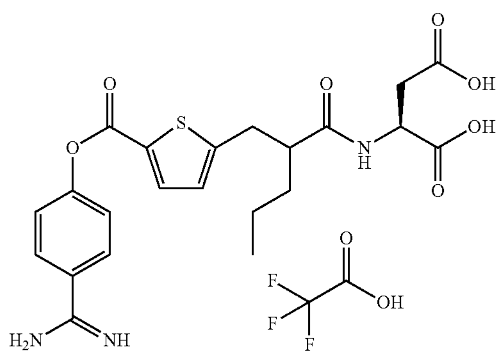 | 1H-NMR (300 MHz, DMSO-d6) δ 9.34 (2H, s), 9.04 (2H, s), 8.35 (0.5H, d, J = 7.8 Hz), 8.29 (0.5H, d, J = 7.8 Hz), 7.91-7.82 (3H, m), 7.55 (2H, d, J = 7.2 Hz), 7.05 (1H, m), 4.53 (1H, m), 3.15-2.90 (2H, m), 2.75-2.50 (3H, m), 1.55-1.18 (4H, m), 0.85 (3H, m).<br>MS (ESI) m/z 476 (M + H)+ |
| B-34 | 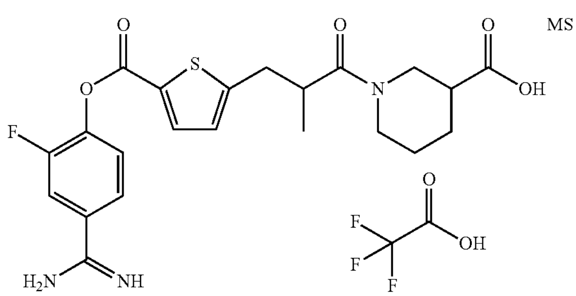 | MS (ESI) m/z 462 (M + H)+ |
| B-35 | 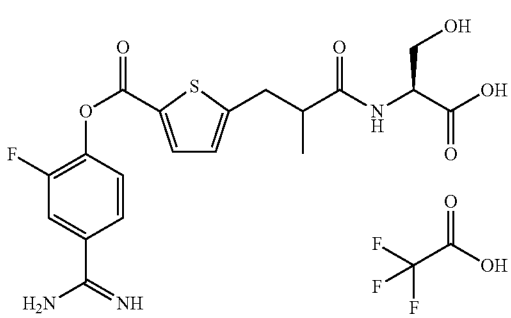 | 1H-NMR (300 MHz, DMSO-d6) δ 9.41 (2H, s), 9.21 (2H, s), 8.15 (1H, m), 7.96-7.91 (2H, m), 7.72 (2H, m), 7.10 (1H, m), 4.26 (1H, m), 3.75-3.60 (2H, m), 3.22-3.10 (1H, m), 2.96-2.75 (2H, m), 1.07 (3H, m).<br>MS (ESI) m/z 438 (M + H)+ |

TABLE 2-17-continued

| Compound No. | Structure | Analysis data |
| --- | --- | --- |
| B-36 | 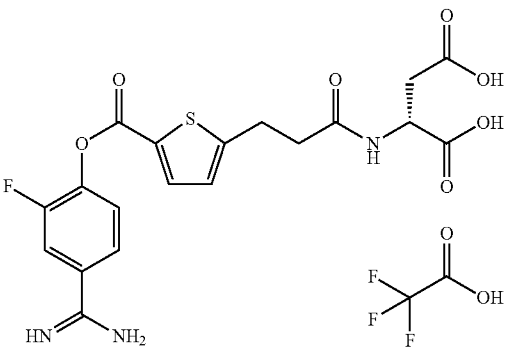 | 1H-NMR (400 MHz, DMSO-d6) δ 9.41 (2H, s), 9.07 (2H, s), 8.33 (1H, d, J = 8.0 Hz), 7.93 (2H, m), 7.73 (2H, m), 7.12 (1H, d, J = 3.6 Hz), 4.55 (1H, m), 3.13 (1H, t, J = 7.6 Hz), 2.68 (1H, dd, J = 12.0, 5.6 Hz), 2.60-2.50 (4H, m).<br>MS (ESI) m/z 452 (M + H)+ |
| B-37 | 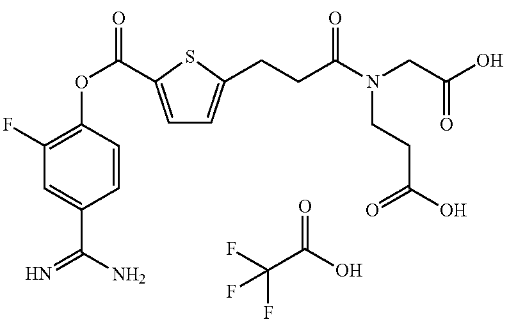 [SMILES: N=C(N)c1ccc(OC(=O)c2ccc(CCC(=O)N(CCC(=O)O)CC(=O)O)s2)c(F)c1 ; O=C(O)C(F)(F)F] | 1H-NMR (400 MHz, DMSO-d6) δ 9.42 (2H, s), 9.15 (2H, s), 7.93 (2H, m), 7.75 (2H, m), 7.16 (0.5H, d, J = 4.0 Hz), 7.13 (0.5H, d, J = 4.0 Hz), 4.21 (1H, s), 3.97 (1H, s), 3.60-3.40 (2H, m), 3.14 (2H, t, J = 6.8 Hz), 2.90 (1H, t, J = 6.8 Hz), 2.66 (1H, t, J = 6.8 Hz), 2.54 (1H, t, J = 6.8 Hz), 2.46 (1H, t, J = 6.8 Hz).<br>MS (ESI) m/z 466 (M + H)+ |
| B-38 | 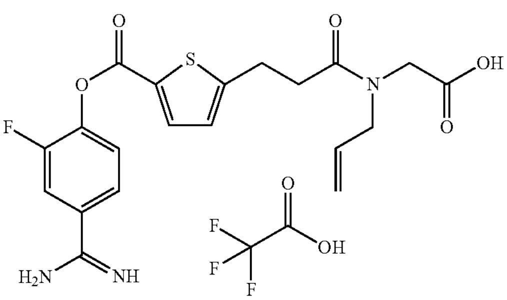 | 1H-NMR (400 MHz, DMSO-d6) δ 9.41 (2H, br s), 9.07 (2H, br), 7.96-7.89 (2H, m), 7.79-7.70 (2H, m), 7.14 (1H, d, J = 3.6 Hz), 5.92-5.62 (1H, m), 5.23-5.06 (2H, m), 4.11-3.90 (4H, m), 3.21-3.09 (2H, m), 2.84-2.62 (2H, m).<br>MS (ESI) m/z 434 (M + H)+ |
| B-39 | 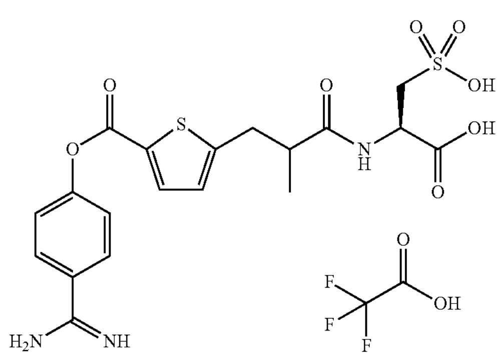 | 1H-NMR (400 MHz, DMSO-d6) δ 9.34 (2H, br), 8.89 (2H, br), 8.22-8.18 (1H, m), 7.90-7.86 (3H, m), 7.60-7.56 (2H, m), 7.12-7.11 (1H, m), 4.39-4.33 (1H, m), 3.22-2.60 (5H, m), 1.09-1.06 (3H, m).<br>MS (ESI) m/z 484 (M + H)+ |

TABLE 2-17-continued

| Compound No. | Structure | Analysis data |
|---|---|---|
| B-40 | 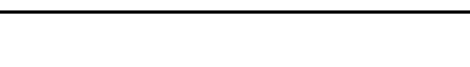 | 1H-NMR (400 MHz, DMSO-d6) δ 9.45 (2H, br s), 9.20 (2H, br s), 7.98 (1H, br s), 7.85-7.87 (3H, m), 7.50 (1H, br s), 7.08 (1H, d, J = 3.0 Hz), 3.17-2.75 (5H, m), 1.05 (3H, d, J = 6.6 Hz).<br>MS (ESI) m/z 426 (M + H)+ |

TABLE 2-18

| Compound No. | Structure | Analysis data |
|---|---|---|
| B-41 | 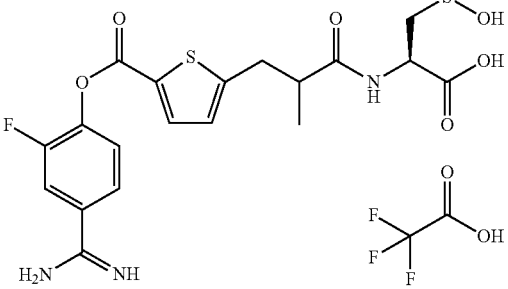 | 1H-NMR (400 MHz, DMSO-d6) δ 9.39 (2H, br), 9.09 (2H, br), 8.20 (1H, t, J = 4.7 Hz), 7.94 (1H, d, J = 1.5 Hz), 7.91 (1H, d, J = 3.0 Hz), 7.81-7.72 (2H, m), 7.14 (1H, dd, J = 2.9, 1.1 Hz) 4.39-4.33 (1H, m), 3.22-2.63 (5H, m), 1.09-1.06 (3H, m).<br>MS (ESI) m/z 502 (M + H)+ |
| B-42 | 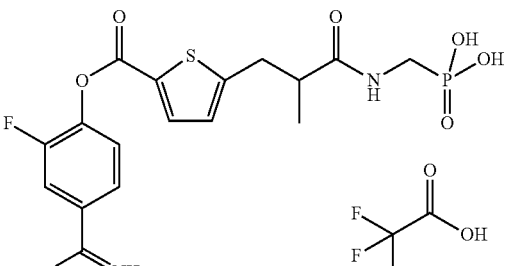 | 1H-NMR (400 MHz, DMSO-d6) δ 9.43 (2H, br s), 9.34 (2H, br s), 8.09 (1H, br s), 7.93-7.90 (2H, m), 7.75-7.73 (2H, m), 7.10 (1H, d, J = 3.0 Hz), 3.26-3.12 (3H, m), 2.88 (1H, dd, J = 11.0, 5.0 Hz), 2.84-2.75 (1H, m), 1.05 (3H, d, J = 6.8 Hz).<br>MS (ESI) m/z 444 (M + H)+ |
| B-43 | 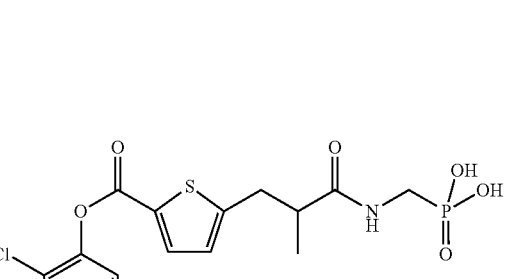 | 1H-NMR (400 MHz, DMSO-d6) δ 9.42 (2H, s), 9.08 (2H, s), 8.10 (2H, m), 7.93 (1H, d, J = 3.6 Hz), 7.86 (1H, dd, J = 8.4, 2.4 Hz), 7.76 (1H, d, J = 8.4 Hz), 7.09 (1H, d, J = 3.6 Hz), 3.20-3.10 (1H, m), 2.92 (1H, d, J = 14.4 Hz), 2.87 (1H, d, J = 14.4 Hz), 2.79 (2H, m), 1.06 (3H, d, J = 6.8).<br>MS (ESI) m/z 460 (M + H)+ |

TABLE 2-18-continued

| Compound No. | Structure | Analysis data |
| --- | --- | --- |
| B-44 | 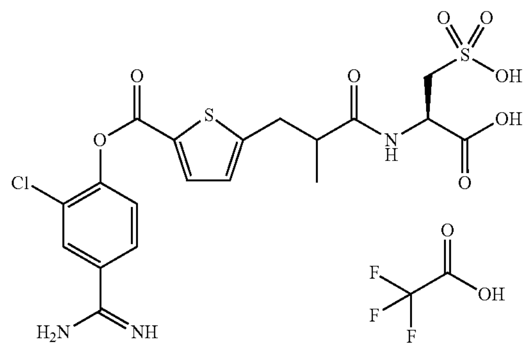 | 1H-NMR (400 MHz, DMSO-d6) δ 9.03 (2H, s), 8.23 (2H, s), 8.20 (1H, t, J = 8.4 Hz), 8.09 (1H, d, J = 1.6 Hz), 7.91 (1H, d, J = 3.6 Hz), 7.92-7.77 (2H, m), 7.13 (1H, d, J = 1.6 Hz), 4.37 (1H, m), 3.20-3.10 (1H, m), 2.95-2.75 (3H, m), 2.65 (1H, m), 1.08 (3H, m).<br>MS (ESI) m/z 518 (M + H)+ |
| B-45 | 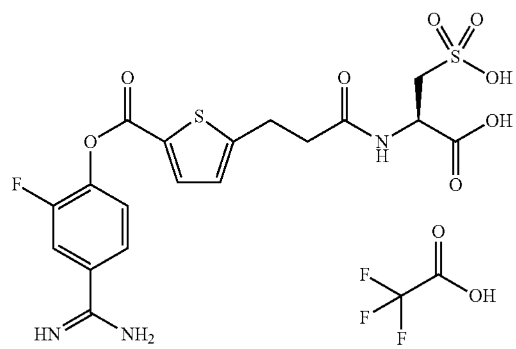 | MS (ESI) m/z 502 (M + H)+ |
| B-46 | Chiral | MS (ESI) m/z 444 (M + H)+ |
| B-47 | 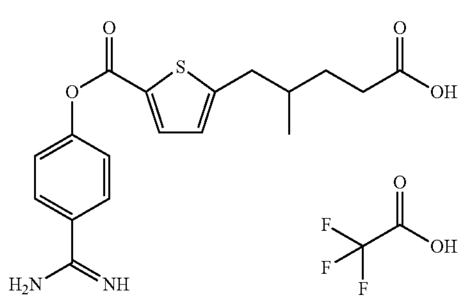 [SMILES: CC(CCC(=O)O)Cc1ccc(C(=O)Oc2ccc(C(=N)N)cc2)s1 ; O=C(O)C(F)(F)F] | 1H-NMR (400 MHz, DMSO-d6) δ 12.04 (1H, br s), 9.35 (2H, br s), 9.02 (2H, br s), 7.92 (1H, d, J = 3.8 Hz), 7.90 (2H, d, J = 8.7 Hz), 7.57 (2H, d, J = 8.7 Hz), 7.08 (1H, d, J = 3.8 Hz), 2.91 (1H, dd, J = 14.6, 6.3 Hz), 2.77 (1H, dd, J = 14.6, 7.7 Hz), 2.35-2.19 (2H, m), 1.85-1.76 (1H, m), 1.67-1.58 (1H, m), 1.44-1.35 (1H, m), 0.90 (3H, d, J = 6.6 Hz).<br>MS (ESI) m/z 361(M + H)+ |

TABLE 2-19

| Compound No. | Structure | Analysis data |
|---|---|---|
| B-48 | 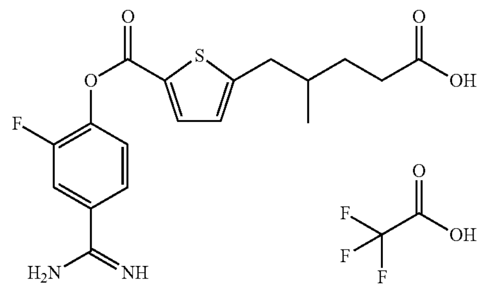 [SMILES: CC(CCC(=O)O)Cc1ccc(C(=O)Oc2ccc(C(=N)N)cc2F)s1 ; O=C(O)C(F)(F)F] | 1H-NMR (400 MHz, DMSO-d6) δ 12.05 (1H, br s), 9.42 (2H, br s), 9.17 (2H, br s), 7.97 (1H, d, J = 3.8 Hz), 7.93 (1H, dd, J = 10.8, 1.6 Hz), 7.79-7.73 (2H, m), 7.11 (1H, d, J = 3.8 Hz), 2.93 (1H, dd, J = 14.6, 6.3 Hz), 2.78 (1H, dd, J = 14.6, 7.5 Hz), 2.35-2.20 (2H, m), 1.85-1.77 (1H, m), 1.67-1.58 (1H, m), 1.44-1.35 (1H, m), 0.90 (3H, d, J = 6.6 Hz). MS (ESI) m/z 379 (M + H)+ |
| B-49 | 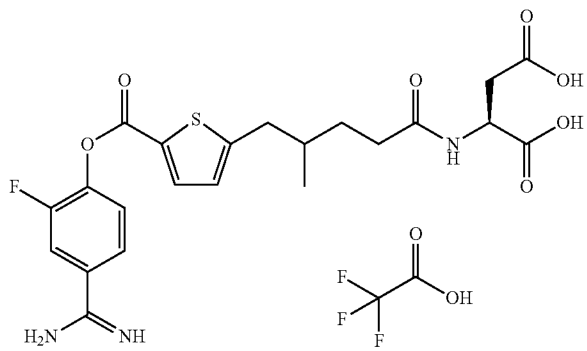 [SMILES: CC(CCC(=O)N[C@@H](CC(=O)O)C(=O)O)Cc1ccc(C(=O)Oc2ccc(C(=N)N)cc2F)s1 ; O=C(O)C(F)(F)F] | MS (ESI) m/z 494 (M + H)+ |
| B-50 | 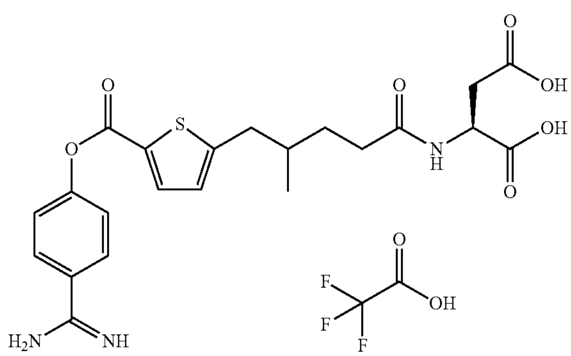 [SMILES: CC(CCC(=O)N[C@@H](CC(=O)O)C(=O)O)Cc1ccc(C(=O)Oc2ccc(C(=N)N)cc2)s1 ; O=C(O)C(F)(F)F] | MS (ESI) m/z 476 (M + H)+ |
| B-51 | 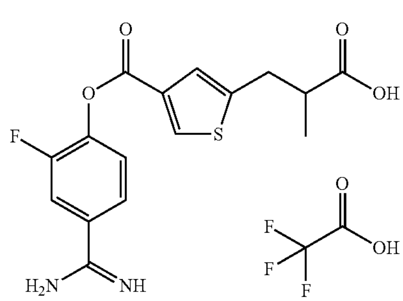 [SMILES: CC(Cc1cc(C(=O)Oc2ccc(C(=N)N)cc2F)cs1)C(=O)O ; O=C(O)C(F)(F)F] | 1H-NMR (400 MHz, DMSO-d6) δ 12.37 (1H, br s), 9.41 (2H, br s), 9.18 (2H, br s), 8.53 (1 H, d, J = 1.2 Hz), 7.93 (1H, dd, J = 10.6, 1.0 Hz), 7.74-7.75 (2H, m), 7.38 (1H, d, J = 1.2 Hz), 3.12 (1H, dd, J = 15.3, 7.8 Hz), 2.98 (1H, dd, J = 15.3, 6.0 Hz), 2.71 (1H, m), 1.13 (3H, d, J = 7.2 Hz). MS (ESI) m/z 351 (M + H)+ |

TABLE 2-19-continued

| Compound No. | Structure | Analysis data |
|---|---|---|
| B-52 | 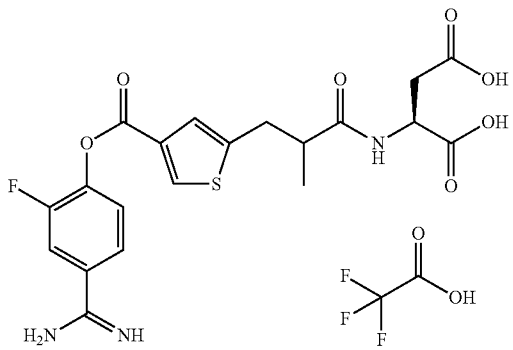 | 1H-NMR (400 MHz, DMSO-d6) δ 9.41 (2H, br s), 9.19 (2H, br s), 8.50 (1H, d, J = 1.6 Hz), 8.30 (1H, m), 7.91 (1H, dd, J = 11.6, 1.6 Hz), 7.73 (2H, m), 7.35 (1H, d, J = 3.6 Hz), 4.55-4.45 (1H, m), 3.10-3.00 (1H, m), 2.88-2.50 (4H, m), 1.07 (3H, m).<br>MS (ESI) m/z 466 (M + H)+ |
| B-53 | 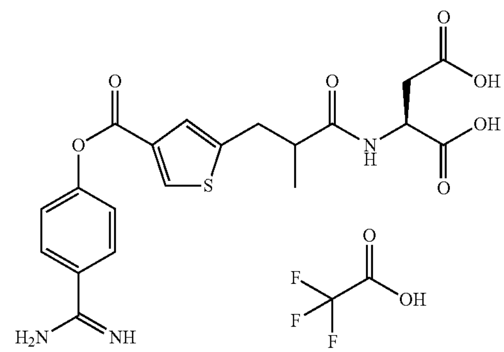 [SMILES: CC(Cc1cc(C(=O)Oc2ccc(C(=N)N)cc2)cs1)C(=O)N[C@@H](CC(=O)O)C(=O)O ; O=C(O)C(F)(F)F] | 1H-NMR (400 MHz, DMSO-d6) δ 9.33 (2H, s), 9.50 (2H, s), 8.42 (1H, d, J = 3.2 Hz), 8.32-8.26 (1H, m), 7.88 (2H, d, J = 6.8 Hz), 7.54 (2H, d, J = 6.8 Hz), 7.34 (1H, d, J = 8.4 Hz), 4.50 (1H, m), 3.10-3.00 (1H, m), 2.88-2.80 (1H, m), 2.70-2.55 (3H, m), 1.03 (3H, m).<br>MS (ESI) m/z 448 (M + H)+ |
| B-54 | 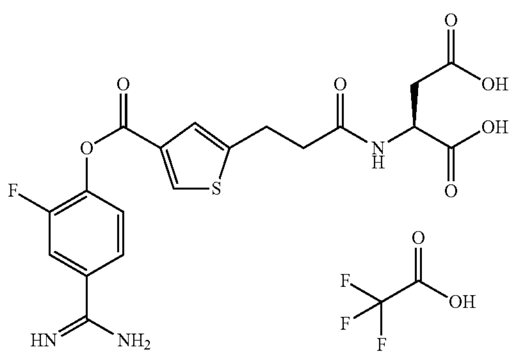 | 1H-NMR (400 MHz, DMSO-d6) δ 9.40 (2H, br s), 9.09 (2H, br s), 8.49 (1H, s), 8.30 (1H, d, J = 8.0 Hz), 7.92 (1H, d, J = 8.0 Hz), 7.73 (2H, m), 7.38 (1H, s), 4.55 (1H, m), 3.07 (2H, t, J = 7.6 Hz), 2.70-2.55 (4H, m).<br>MS (ESI) m/z 452 (M + H)+ |

TABLE 2-20

| Compound No. | Structure | Analysis data |
|---|---|---|
| B-55 | 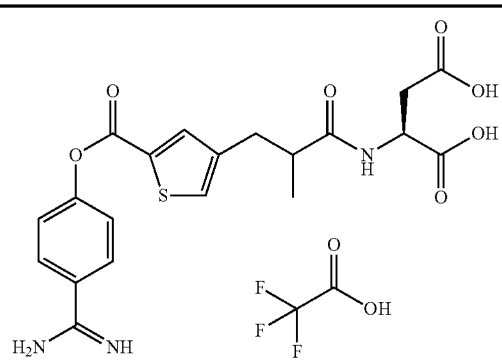 | 1H-NMR (300 MHz, DMSO-d6) δ 9.35 (2H, br s), 9.06 (2H, br s), 8.22 (1H, m), 7.90 (3H, m), 7.73 (1H, d, J = 7.8 Hz), 7.56 (2H, d, J = 7.8 Hz), 4.55 (1H, m), 2.95-2.80 (1 H, m), 2.78-2.55 (4H, m), 1.00 (3H, m).<br>MS (ESI) m/z 448 (M + H)+ |

TABLE 2-20-continued

| Compound No. | Structure | Analysis data |
|---|---|---|
| B-56 | 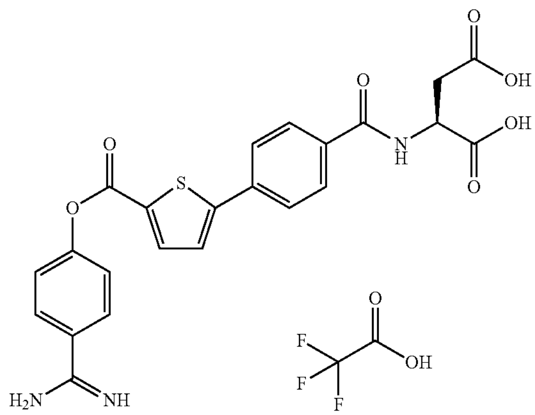 [SMILES: N=C(N)c1ccc(OC(=O)c2ccc(-c3ccc(C(=O)N[C@@H](CC(=O)O)C(=O)O)cc3)s2)cc1 ; O=C(O)C(F)(F)F] | MS (ESI) m/z 482 (M + H)+ |
| B-57 | 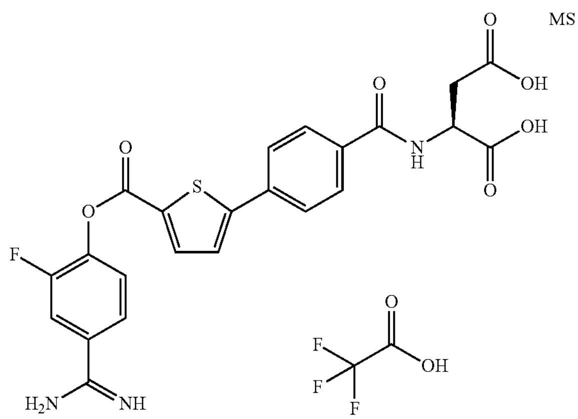 | MS (ESI) m/z 500 (M + H)+ |
| B-58 | 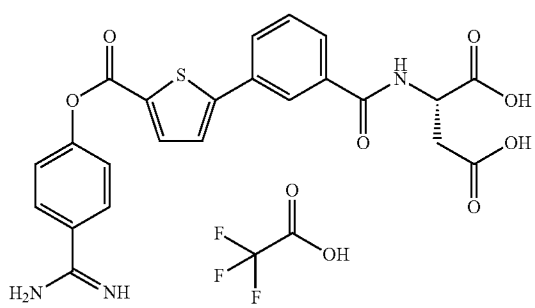 [SMILES: N=C(N)c1ccc(OC(=O)c2ccc(-c3cccc(C(=O)N[C@@H](CC(=O)O)C(=O)O)c3)s2)cc1 ; O=C(O)C(F)(F)F] | MS (ESI) m/z 482 (M + H)+ |
| B-59 | 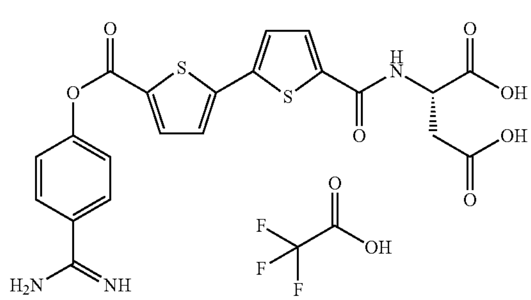 | MS (ESI) m/z 488 (M + H)+ |

TABLE 2-20-continued

| Compound No. | Structure | Analysis data |
|---|---|---|
| B-60 | 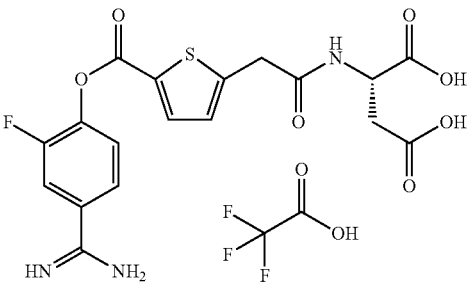 | 1H-NMR (400 MHz, DMSO-d6) δ 9.41 (2H, br s), 9.10 (2H, br s), 8.64 (1H, d, J = 4.0 Hz), 7.98 (2H, m), 7.75 (2H, m), 7.14 (1H, d, J = 3.6 Hz), 4.55 (1H, m), 3.90 (2H, s), 3.08-2.98 (1H, m), 2.70-2.60 (1H, m).<br>MS (ESI) m/z 438 (M + H)+ |

TABLE 2-21

| Compound No. | Structure | Analysis data |
|---|---|---|
| B-61 | 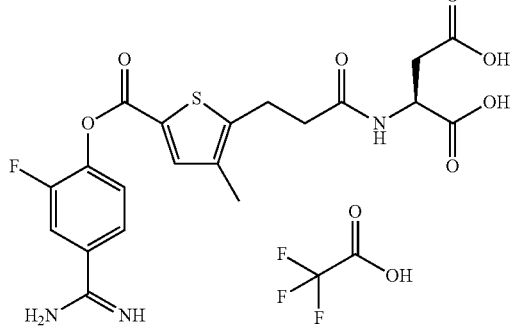 | 1H-NMR (400 MHz, DMSO-d6) δ 9.40 (2H, br s), 9.11 (2H, br s), 8.29 (1H, d, J = 7.2 Hz), 7.92 (1H, d, J = 11.2 Hz), 7.84 (1 H, s), 7.77-7.71 (2H, m), 4.57-4.46 (1H, m), 3.03 (2H, t, J = 7.6 Hz), 2.71-2.49 (4H, m), 2.21 (3H, s).<br>MS (ESI) m/z 466 (M + H)+ |
| B-62 | 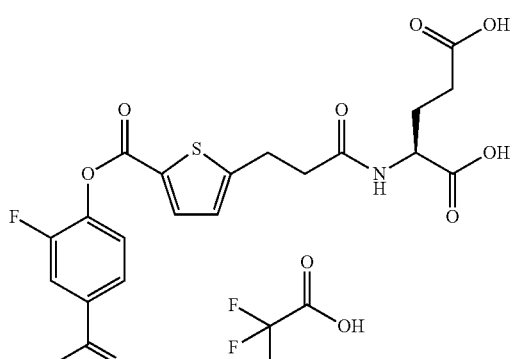 | 1H-NMR (400 MHz, DMSO-d6) δ 9.52-9.28 (2H, br s), 9.28-9.03 (2H, br s), 8.22 (1H, d, J = 8.0 Hz), 7.96-7.89 (2H, m), 7.78-7.71 (2H, m), 7.12 (1H, d, J = 8.0 Hz), 4.22 (1H, td, J = 8.0, 4.2 Hz), 3.15 (2H, t, J = 5.4 Hz), 2.63-2.51 (2H, m), 2.29-2.18 (2H, m), 2.01-1.87 (1H, m), 1.82-1.69 (1H, m).<br>MS (ESI) m/z 466 (M + H)+ |
| B-63 | 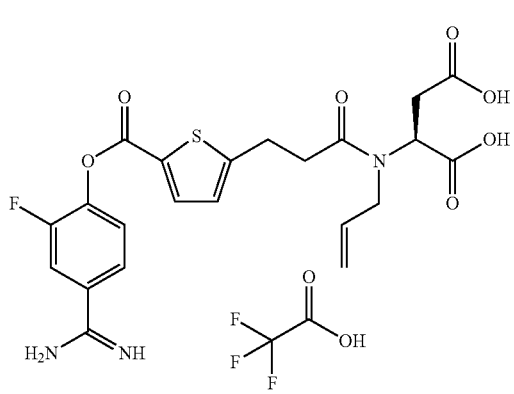 | 1H-NMR (400 MHz, DMSO-d6) δ 9.56-9.10 (4H, m), 7.98-7.89 (2H, m), 7.79-7.70 (2H, m), 718-7.09 (1H, m), 5.95-5.65 (1H, m), 5.46-4.95 (2H, m), 4.61-4.48 (1H, m), 4.18-3.84 (2H, m), 3.71-2.41 (6H, m).<br>MS (ESI) m/z 492 (M + H)+ |

TABLE 2-21-continued

| Compound No. | Structure | Analysis data |
|---|---|---|
| B-64 | 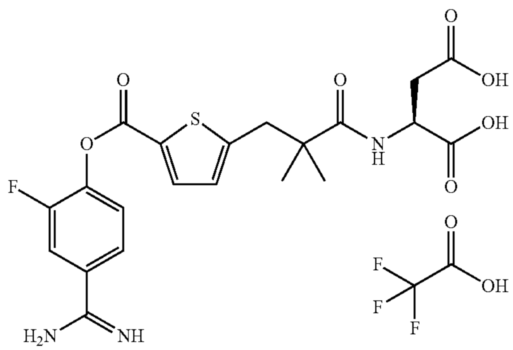 | 1H-NMR (400 MHz, DMSO-d6) δ 9.41 (2H, br s), 9.10 (2H, br s), 7.96-7.89 (3H, m), 7.79-7.71 (2H, m), 7.07 (1H, d, J = 4.0 Hz), 4.57 (1H, dt, J = 7.2, 6.8 Hz), 3.13 (2H, s), 2.76 (1H, dd, J = 16.4, 6.8 Hz), 2.58 (1H, dd, J = 16.4, 6.8 Hz), 1.14 (3H, s), 1.13 (3H, s).<br>MS (ESI) m/z 480 (M + H)+ |
| B-65 | 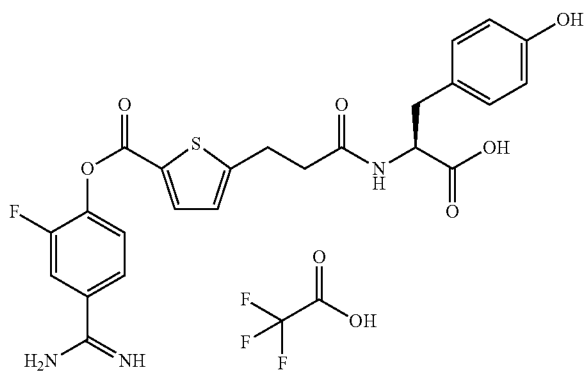 [SMILES: N=C(N)c1ccc(OC(=O)c2ccc(CCC(=O)N[C@@H](Cc3ccc(O)cc3)C(=O)O)s2)c(F)c1 ; O=C(O)C(F)(F)F] | 1H-NMR (400 MHz, DMSO-d6) δ 9.42 (2H, br s), 9.24 (1H, br s), 9.16 (2H, br s), 8.24 (1H, d, J = 8.0 Hz), 7.96-7.88 (2H, m), 7.79-7.71 (2H, m), 7.00 (1H, d, J = 4.8 Hz), 6.98 (2H, d, J = 8.4 Hz), 6.64 (2H, d, J = 8.4 Hz), 4.37 (1H, ddd, J = 9.2, 8.0, 4.8 Hz), 3.07 (2H, t, J = 7.2 Hz), 2.93 (1H, dd, J = 14.0, 4.8 Hz), 2.73 (1H, dd, J = 14.0, 9.2 Hz), 2.52 (3H, t, J = 7.2 Hz).<br>MS (ESI) m/z 500 (M + H)+ |
| B-66 | 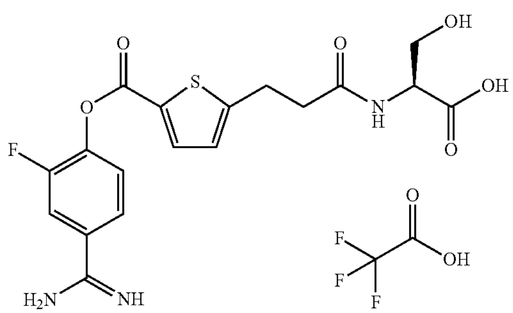 | 1H-NMR (400 MHz, DMSO-d6) δ 9.41 (2H, s), 9.11 (2H, s), 8.17 (1H, d, J = 7.6 Hz), 7.93 (2H, m), 7.75 (2H, m), 7.13 (1H, d, J = 3.6 Hz), 4.31 (1H, m), 3.71-3.66 (1H, m), 3.63-3.58 (1H, m), 3.14 (2H, t, J = 7.2 Hz), 2.62 (2H, t, J = 7.2 Hz).<br>MS (ESI) m/z 424 (M + H)+ |

TABLE 2-22

| Compound No. | Structure | Analysis data |
|---|---|---|
| C-4 | 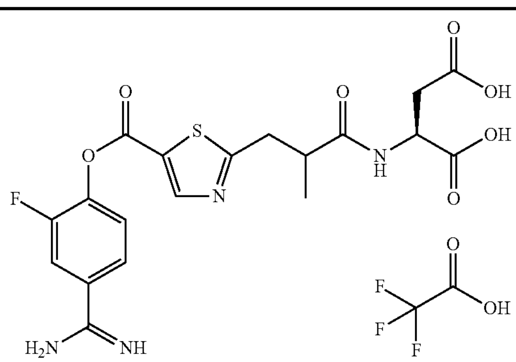 | 1H-NMR (400 MHz, DMSO-d6) δ 9.42 (2H, s), 9.16 (2H, s), 8.62 (1H, s), 8.36 (1H, m), 7.95 (1H, dd, J = 11.0, 2.0 Hz), 7.76 (2H, m), 4.50 (1H, m), 3.30 (1H, m), 3.10-2.85 (1H, m), 2.75-2.55 (3H, m), 1.10 (3H, m).<br>MS (ESI) m/z 467 (M + H)+ |

TABLE 2-22-continued

| Compound No. | Structure | Analysis data |
|---|---|---|
| C-5 | 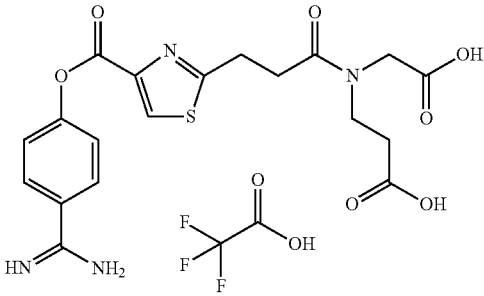 [SMILES: N=C(N)c1ccc(OC(=O)c2csc(CCC(=O)N(CCC(=O)O)CC(=O)O)n2)cc1 ; O=C(O)C(F)(F)F] | 1H-NMR (400 MHz, DMSO-d6) δ 9.35 (2H, s), 9.02 (2H, s), 8.72 (1H, s), 7.91 (2H, d, J = 8.4 Hz), 7.57 (2H, d, J = 8.4 Hz), 4.22 (1H, s), 3.97 (1H, s), 3.65-3.30 (4H, m), 2.95 (1H, t, J = 6.8 Hz), 2.75 (1H, t, J = 6.8 Hz), 2.55 (1H, t, J = 6.8 Hz), 2.45 (1H, t, J = 6.8 Hz).<br>MS (ESI) m/z 449 (M + H)+ |

Experimental Example 1

Measurement of Trypsin Inhibitory Activity

Using a 96 well plate (#3915, Costar), a test compound (25 μL) was mixed with 20 μM fluorescence enzyme substrate (Boc-Phe-Ser-Arg-AMC, 50 μL) mixed with 200 mM Tris-HCl buffer (pH 8.0), and human trypsin (Sigma, 25 μL) was added. Using a fluorescence plate reader fmax (Molecular Devices, Inc.), the reaction rate was measured from the time-course changes at excitation wavelength 355 nm and fluorescence wavelength 460 nm. The Ki value was calculated from the concentration of the test compound, reciprocal of reaction rate, and Km value of the enzyme substrate, and by using Dixon plot. The results are shown in Table 3.

Experimental Example 2

Measurement of Enteropeptidase Inhibitory Activity

Using a 96 well plate (#3915, Costar), a test compound (25 μL), 400 mM Tris-HCl buffer (pH 8.0, 25 μL) and 0.5 mg/mL fluorescence enzyme substrate (Gly-Asp-Asp-Asp-Asp-Lys-β-Naphtylamide, 25 μL) were mixed, and recombinant human enteropeptidase (R&D Systems, Inc., 25 μL) was added. Using a fluorescence plate reader fmax (Molecular Devices, Inc.), the reaction rate was measured from the time-course changes at excitation wavelength 320 nm and fluorescence wavelength 405 nm. The Ki value was calculated from the concentration of the test compound, reciprocal of reaction rate, and Km value of the enzyme substrate, and by using Dixon plot. The results are shown in Table 3.

TABLE 3

| Compound No. | Enteropeptidase inhibitory activity Ki (nM) | Trypsin inhibitory activity Ki (nM) |
|---|---|---|
| A-1 | 2.27 | 0.52 |
| A-2 | 1.97 | 0.44 |
| A-3 | 1.15 | 0.69 |
| A-4 | 2.68 | 1.26 |
| A-5 | 1.37 | 1.13 |
| A-6 | 0.62 | 1.53 |
| A-7 | 1.49 | 1.01 |
| A-9 | 3.17 | 7.32 |
| A-10 | 6.73 | 9.15 |
| A-12 | 3.31 | 1.13 |
| A-14 | 3.52 | 0.48 |
| A-15 | 1.63 | 1.16 |
| A-16 | 1.88 | 1.84 |
| A-17 | 2.43 | 1.76 |
| A-18 | 0.61 | 1.07 |
| A-19 | 1.91 | 2.92 |
| A-20 | 2.54 | 1.88 |
| A-21 | 4.81 | 3.25 |
| A-22 | 0.95 | 2.0 |
| A-23 | 2.0 | 1.3 |
| A-24 | 1.9 | 2.4 |
| A-25 | 2.1 | 2.0 |
| A-26 | 0.68 | 2.29 |
| A-27 | 0.57 | 0.95 |
| A-28 | 0.42 | 0.75 |
| A-29 | 0.82 | 1.67 |
| A-30 | 1.03 | 1.28 |
| A-31 | 0.50 | 0.62 |
| A-32 | 0.62 | 2.89 |
| A-33 | 0.65 | 0.79 |
| A-34 | 0.98 | 1.65 |
| A-35 | 0.25 | 0.38 |
| A-36 | 0.58 | 1.33 |
| A-37 | 0.64 | 1.46 |
| A-38 | 0.57 | 0.86 |
| A-39 | 0.67 | 1.60 |
| A-41 | 0.50 | 0.89 |
| A-42 | 0.71 | 3.8 |
| A-43 | 0.40 | 0.52 |
| A-44 | 0.33 | 0.62 |
| A-45 | 0.46 | 0.97 |
| A-46 | 0.35 | 0.47 |
| A-47 | 1.9 | 5.7 |
| A-48 | 1.3 | 4.5 |
| A-49 | 7.6 | 3.4 |
| A-50 | 4.4 | 2.3 |
| A-51 | 4.9 | 3.6 |
| A-52 | 2.5 | 1.2 |
| A-54 | 0.60 | 1.3 |
| A-55 | 1.3 | 1.4 |
| A-56 | 1.1 | 1.7 |
| A-57 | 0.39 | 2.0 |
| A-58 | 0.70 | 0.72 |
| A-59 | 0.35 | 0.12 |
| A-60 | 0.31 | 6.7 |
| A-61 | 0.42 | 3.7 |
| A-62 | 2.1 | 4.2 |
| A-63 | 0.53 | 0.92 |
| A-64 | 2.5 | 3.1 |
| A-65 | 1.0 | 4.5 |
| A-66 | 0.32 | 0.44 |
| A-67 | 0.52 | 0.20 |
| A-68 | 2.2 | 0.23 |
| A-69 | 4.7 | 0.62 |
| A-70 | 2.7 | 0.30 |
| A-71 | 1.6 | 0.054 |
| A-72 | 0.68 | 2.3 |
| A-73 | 0.88 | 0.53 |
| A-74 | 2.6 | 3.8 |

TABLE 3-continued

| Compound No. | Enteropeptidase inhibitory activity Ki (nM) | Trypsin inhibitory activity Ki (nM) |
|---|---|---|
| B-2 | 9.29 | 6.34 |
| B-3 | 5.72 | 4.76 |
| B-6 | 1.44 | 7.19 |
| B-7 | 2.15 | 7.36 |
| B-8 | 0.84 | 0.22 |
| B-11 | 1.41 | 2.39 |
| B-12 | 2.21 | 5.75 |
| B-16 | 0.29 | 1.51 |
| B-17 | 0.42 | 1.76 |
| B-18 | 1.36 | 1.76 |
| B-19 | 0.42 | 0.91 |
| B-20 | 0.28 | 0.18 |
| B-21 | 0.56 | 0.15 |
| B-22 | 0.50 | 0.39 |
| B-23 | 1.47 | 1.54 |
| B-24 | 0.49 | 0.83 |
| B-25 | 0.79 | 0.19 |
| B-26 | 2.2 | 1.0 |
| B-27 | 0.95 | 1.3 |
| B-28 | 1.1 | 0.43 |
| B-29 | 0.58 | 1.3 |
| B-30 | 0.52 | 0.33 |
| B-31 | 0.33 | 0.66 |
| B-32 | 0.31 | 0.48 |
| B-33 | 2.8 | 3.6 |
| B-34 | 2.2 | 2.7 |
| B-35 | 0.40 | 0.97 |
| B-36 | 0.51 | 0.84 |
| B-37 | 0.50 | 4.5 |
| B-38 | 0.75 | 1.4 |
| B-39 | 0.95 | 2.2 |
| B-40 | 2.0 | 1.8 |
| B-41 | 0.27 | 0.21 |
| B-42 | 0.37 | 0.22 |
| B-43 | 0.42 | 0.49 |
| B-44 | 0.21 | 0.57 |
| B-45 | 0.48 | 1.1 |
| B-46 | 0.38 | 0.44 |
| B-47 | 2.5 | 1.8 |
| B-48 | 0.88 | 0.37 |
| B-49 | 0.41 | 0.18 |
| B-50 | 0.89 | 0.47 |
| B-51 | 0.72 | 1.6 |
| B-52 | 0.39 | 0.51 |
| B-53 | 4.8 | 8.5 |
| B-54 | 0.58 | 0.79 |
| B-55 | 0.98 | 5.0 |
| B-56 | 9.5 | 0.70 |
| B-57 | 3.0 | 0.27 |
| B-58 | 9.8 | 3.5 |
| B-59 | 8.2 | 4.4 |
| B-60 | 0.64 | 3.2 |
| B-61 | 0.13 | 0.5 |
| B-62 | 0.57 | 0.4 |
| B-63 | 0.55 | 0.9 |
| B-64 | 0.14 | 0.6 |
| B-65 | 3.20 | 3.7 |
| B-66 | 0.73 | 1.2 |
| C-2 | 5.67 | 0.39 |
| C-4 | 3.7 | 0.2 |

Thus, the compound of the present invention was confirmed to show superior enteropeptidase inhibitory activity and superior trypsin inhibitory activity. Therefore, it has been shown that the compound of the present invention having an inhibitory activity on enteropeptidase and trypsin decreases digestive capacity for protein, lipid, and carbohydrates, and is effective as a therapeutic and prophylactic drug for obesity and hyperlipidemia.

Experimental Example 3

Evaluation of Antidiabetic Action

KK-A$^y$/JCL mice (male, 5- to 7-week-old, CLEA Japan, Inc.) known to spontaneously develop obese type 2 diabetes were purchased and, after one week of preliminary rearing period, grouped (6 per group) with the body weight and non-fasting blood glucose levels as indices. The animals were individually housed in a polycarbonate cage and allowed to drink water freely from a watering bottle. During the test period, they were allowed to freely ingest a mixture of a test compound (B-18 hydrochloride, B-20 hydrochloride, A-28 hydrochloride, B-23 hydrochloride, or B-32 hydrochloride) (5.6 mg/100 g or 16.8 mg/100 g) and powder feed CRF-1 (Oriental Yeast Co., Ltd.). CRF-1 alone was given to the control group. After one week of dosing period, the blood (6 μL) was drawn from the tail vein of the animals, and the blood glucose level was measured by ACCU-CHEK Aviva (Roche Diagnostics K.K.). The results are shown in Table 4. A significant difference from the control group was detected by Dunnett's multiple comparison test or Student's t-test (significance level less than 5%). Thus, the test compound showed a significant hypoglycemic action. The compound of the present invention having an enteropeptidase inhibitory activity and a trypsin inhibitory activity was shown to have a blood glucose elevation suppressing or hypoglycemic action. In addition, it has also been shown that the compound of the present invention shows an insulin sensitizing activity and is also useful as a prophylactic or therapeutic agent for obesity, diabetic complications, or metabolic syndrome, since it shows a blood glucose elevation suppressing or hypoglycemic action.

TABLE 4

| | Dose (mg/100 g) | Mean blood glucose level (mg/dL) | Standard error | p value |
|---|---|---|---|---|
| Control group | | 447 | 22 | |
| B-18 hydrochloride | 5.6 | 217 | 40 | <0.001 |
| B-18 hydrochloride | 16.8 | 138 | 7 | <0.001 |
| Control group | | 415 | 27 | |
| B-20 hydrochloride | 5.6 | 197 | 27 | <0.001 |
| A-28 hydrochloride | 5.6 | 219 | 46 | <0.001 |
| B-23 hydrochloride | 5.6 | 198 | 23 | <0.001 |
| Control group | | 478 | 28 | |
| B-32 hydrochloride | 5.6 | 249 | 39 | <0.001 |

INDUSTRIAL APPLICABILITY

The trypsin and enteropeptidase inhibitory compound relating to the present invention can be used as an active ingredient of a therapeutic or prophylactic drug of diabetes or diabetic complications.

Where a numerical limit or range is stated herein, the endpoints are included. Also, all values and subranges within a numerical limit or range are specifically included as if explicitly written out.

Obviously, numerous modifications and variations of the present invention are possible in light of the above teachings.

It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the prophylaxis or treatment of type II diabetes or hyperglycemia, comprising administering an effective amount of a compound represented by formula (I):

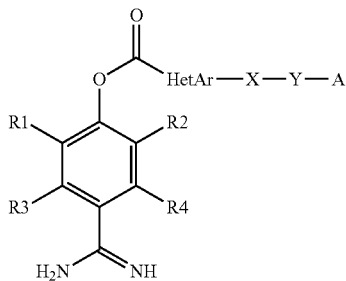

wherein

R1, R2, R3, and R4 may be the same or different and are each independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group;

HetAr is a furan ring optionally having substituent(s);

X is a lower alkylene group optionally having substituent(s), a lower alkenylene group optionally having substituent(s), a lower alkynylene group optionally having substituent(s), or a thiophenylene group;

Y is a carbonyl group, a thiocarbonyl group, or a sulfonyl group; and

A is a group of formula (II):

wherein R6 and R7 may be the same or different and are each independently a hydrogen atom, a hydroxyl group, a lower alkyl group optionally having substituent(s), a lower alkenyl group optionally having substituent(s), a lower alkynyl group optionally having substituent(s), or a lower alkoxyl group optionally having substituent(s), or R6 and R7 may be bonded to form a cyclic amino group optionally having substituent(s), or a pharmaceutically acceptable salt thereof, to a subject in need thereof.

2. A method for the prophylaxis or treatment of type II diabetes or hyperglycemia, comprising administering an effective amount of a compound represented by formula (I):

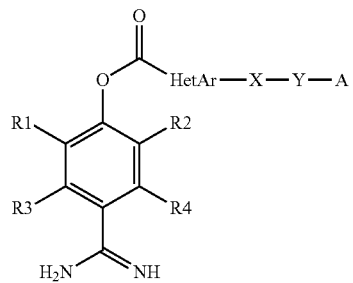

wherein

R1, R2, R3, and R4 may be the same or different and are each independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group;

HetAr is a furan ring optionally having substituent(s);

X is a lower alkylene group optionally having substituent(s), a lower alkenylene group optionally having substituent(s), or a lower alkynylene group optionally having substituent(s);

Y is a carbonyl group, a thiocarbonyl group, or a sulfonyl group; and

A is a group of formula (II):

wherein R6 and R7 may be the same or different and are each independently a hydrogen atom, a hydroxyl group, a lower alkyl group optionally having substituent(s), a lower alkenyl group optionally having substituent(s), a lower alkynyl group optionally having substituent(s), or a lower alkoxyl group optionally having substituent(s), or R6 and R7 may be bonded to form a cyclic amino group optionally having substituent(s), or a pharmaceutically acceptable salt thereof, to a subject in need thereof.

3. A method according to claim 1, wherein R1, R2, R3, and R4 are each independently a hydrogen atom, a nitro group, or a halogeno group.

4. A method according to claim 1, wherein -HetAr— is a heteroaromatic ring group represented by formula (III-1) or (III-2):

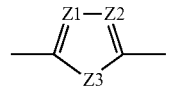

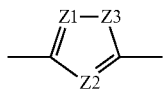

(III-2)

wherein Z1 and Z2 are each independently CRa, and Z3 is an oxygen atom, wherein each Ra may be the same or different and is independently a hydrogen atom, a nitro group, a halogeno group, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group.

5. A method according to claim 1, wherein X is a lower alkylene group optionally having substituent(s) or a lower alkenylene group optionally having substituent(s), wherein said substituent(s) is selected from the group consisting of a halogeno group, a hydroxyl group, an amino group, a lower alkyl group, a lower alkoxyl group, and a lower acyl group.

6. A method according to claim 1, wherein Y is a carbonyl group or a sulfonyl group.

7. A method according to claim 1, wherein A is a group of formula (IV):

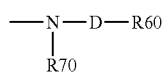

(IV)

wherein R60 is a carboxyl group, a sulfo group, a phosphono group, a lower alkoxycarbonyl group, or a hydroxyl group, D is a lower alkylene group optionally having substituent(s), a lower alkenylene group optionally having substituent(s), or a lower alkynylene group optionally having substituent(s), wherein said substituent(s) is selected from the group consisting of a nitro group, a halogeno group, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acylamino group, a lower acyloxy group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), and an oxo group, and R70 is a hydrogen atom, a hydroxyl group, a lower alkyl group optionally having substituent(s), or a lower alkoxyl group optionally having substituent(s), or R70 and D may be bonded to form a cyclic amino group optionally having substituent(s).

8. A method according to claim 7, wherein R60 is a carboxyl group, a sulfo group, a lower alkoxycarbonyl group, or a hydroxyl group, D is a lower alkylene group optionally having substituent(s), wherein said substituent(s) is selected from the group consisting of a halogeno group, a hydroxyl group, a thiol group, an amino group, a guanidino group, a carboxyl group, a sulfo group, a lower alkoxyl group, a lower alkylthio group, a lower alkylamino group, a lower acylamino group, a lower alkoxycarbonyl group, a carbamoyl group, a lower alkylcarbamoyl group, a lower alkylsulfonylamino group, an arylsulfonylamino group optionally having substituent(s), an aryl group optionally having substituent(s), a heterocyclic group optionally having substituent(s), and an oxo group, and R70 is a hydrogen atom, a hydroxyl group, a lower alkyl group optionally having substituent(s), or a lower alkoxyl group optionally having substituent(s), or R70 and D may be bonded to form a cyclic amino group optionally having substituent(s).

9. A method according to claim 1, wherein R1, R2, R3, and R4 are each independently a hydrogen atom, a nitro group, or a fluorine atom, and HetAr is furan optionally having substituent(s).

* * * * *